(12) United States Patent
Nugiel et al.

(10) Patent No.: US 6,407,103 B2
(45) Date of Patent: Jun. 18, 2002

(54) INDENO [1,2-C] PYRAZOL-4-ONES AND THEIR USES

(75) Inventors: David A. Nugiel, Cherry Hill, NJ (US); David J. Carini; Susan V. Di Meo, both of Wilmington, DE (US); Eddy W. Yue, Landenberg, PA (US)

(73) Assignee: Bristol-Myers Squibb Pharma Company, Wilmington, DE (US)

(*) Notice: Subject to any disclaimer, the term of this patent is extended or adjusted under 35 U.S.C. 154(b) by 0 days.

(21) Appl. No.: 09/731,304

(22) Filed: Dec. 6, 2000

Related U.S. Application Data

(63) Continuation-in-part of application No. 09/639,618, filed on Aug. 15, 2000, which is a continuation of application No. 09/295,078, filed on Apr. 20, 1999, now abandoned.
(60) Provisional application No. 60/082,476, filed on Apr. 21, 1998.

(51) Int. Cl.[7] .................. A61K 31/5377; A61K 31/416; A61P 35/00; C07D 231/54; C07D 413/14
(52) U.S. Cl. .................. 514/232.8; 514/403; 544/58.5; 544/58.6; 544/121; 544/130; 544/131; 544/140; 544/80; 544/357; 544/364; 544/371; 546/139; 546/199; 546/256; 546/269.7; 546/271.4; 546/272.1; 546/272.7; 546/275.7; 548/181; 548/236; 548/247; 548/311.7; 548/359.1
(58) Field of Search .................. 544/131, 140; 548/359.1; 514/232.8, 403

(56) References Cited

U.S. PATENT DOCUMENTS

| | | | |
|---|---|---|---|
| 2,989,538 | A | 6/1961 | Flores et al. |
| 6,107,305 | A | 8/2000 | Misra et al. |
| 6,114,365 | A | 9/2000 | Pevarello et al. |

FOREIGN PATENT DOCUMENTS

| | | |
|---|---|---|
| EP | 0203679 A2 | 3/1986 |
| GB | 2223946 A | 4/1990 |
| JP | 60-130521 | 7/1985 |
| JP | 62-099361 A2 | 5/1987 |

OTHER PUBLICATIONS

S. Mani et al, Pestell Exp. Opin. Invest. Drugs (2000) 9(8), 1849–1870.
A. M. Senderowicz et al, Sausville Journal of The National Cancer Institute (2000), 92, 5, 376–387.
Cancer Research, 57, 3375 (1997).
Pavletich, Nature 382:325–331, 1996.
J. Biochem., 117, 741–749, 1995.
Hrnciar and Svanygova Collect. Czech. Chem. Commun. 59:2734–40, 1994.
Kamb et al, Science 264:436–440, 1994.
Beach, Nature 336:701–704, 1993.
Jiang, Proc. Natl. Acad. Sci. USA 90:9026–9030, 1993.
Sherr, Cell 73:1059–1065, 1993.
H. Bumdgard, Advanced Drug Delivery Reviews, 8, p. 1–38, 1992.
Krogsgaard–Larsen and H. Bundgaard, ed., Chapter 5; "Design and Applications of Prodrugs" p. 113–191, 1991.
Draetta, Trends Biochem. Sci. 15:378–382, 1990.
Wang, Nature 343:555–557, 1990.
Skehan et al. J. Natl. Cancer Inst. 82:1107–12, 1990.
Quraishi, Farmaco 44:753–8, 1989.
Paradee, Science 246:603–608, (1989).
Journal of Pharmaceutical Sciences, 77, p. 285, 1988.
K. Widder et al, Methods in Enzymology, Ed., Academic Press, 42, p. 309–396, 1985.
N. Kakeya et al, Chem. Pharm. Bull., 32, p. 692, 1984.
Rappoport, J. Org. Chem. 49:2948–2953, 1984.
Chou and Talalay, Adv. Enzyme Regul. 22:27–55 (1984).
Lemke et al., J. Heterocyclic Chem. 19:1335–1340, 1982.
Zh. Organ. Khim. 9:2568–2570, 1973.
Rotberg and Oshkaya, Zh. Organ. Khim. 8:86–88, 1972.
Mosher and Soeder, J. Heterocyclic Chem. 8:855–59, 1971.

*Primary Examiner*—Robert W. Ramsuer
(74) *Attorney, Agent, or Firm*—Rena Patel

(57) ABSTRACT

The present invention relates to the synthesis of a new class of indeno[1,2-c]pyrazol-4-ones of formula (I):

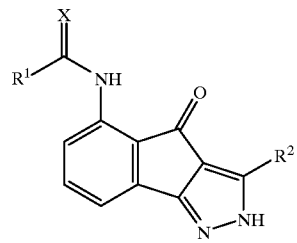

(I)

that are potent inhibitors of the class of enzymes known as cyclin dependent kinases, which relate to the catalytic subunits cdk1–9 and their regulatory subunits know as cyclins A–H.

This invention also provides a novel method of treating cancer or other proliferative diseases by administering a therapeutically effective amount of one of these compounds or a pharmaceutically acceptable salt form thereof. Alternatively, one can treat cancer or other proliferative diseases by administering a therapeutically effective combination of one of the compounds of the present invention and one or more other known anti-cancer or anti-proliferative agents.

57 Claims, No Drawings

INDENO [1,2-C] PYRAZOL-4-ONES AND THEIR USES

This application is a continuation-in-part of U.S. Ser. No. 09/639,618, filed Aug. 15, 2000, currently pending, which is a continuation of U.S. Ser. No. 09/295 078, filed Apr. 20, 1999, now abandoned, which in turn claims the benefit of U.S. Provisional application No. 60/082,476, filed Apr. 21, 1998.

FIELD OF THE INVENTION

This invention relates generally to novel 5-substituted-indeno[1,2-c]pyrazol-4-ones which are useful as cyclin dependent kinase (cdk) inhibitors, pharmaceutical compositions comprising the same, methods for using the same for treating proliferative diseases, and intermediates and processes for making the same.

BACKGROUND OF THE INVENTION

One of the most important and fundamental processes in biology is the division of cells mediated by the cell cycle. This process ensures the controlled production of subsequent generations of cells with defined biological function. It is a highly regulated phenomenon and responds to a diverse set of cellular signals both within the cell and from external sources. A complex network of tumor promoting and suppressing gene products are key components of this cellular signaling process. Over expression of the tumor promoting components or the subsequent loss of the tumor suppressing products will lead to unregulated cellular proliferation and the generation of tumors (Pardee, Science 246:603–608, 1989).

Cyclin dependent kinases (cdks) play a key role in regulating the cell cycle machinery. These complexes consist of two components: a catalytic subunit (the kinase) and a regulatory subunit (the cyclin). To date, nine kinase subunits (cdk 1–9) have been identified along with several regulatory subunits (cyclins A–H).(A. M. Senderowicz and E. A. Sausville Journal of the National Cancer Institute (2000), 92 (5), 376–387; and S. Mani; C. Wang; K. Wu; R. Francis; R. Pestell Exp. Opin. Invest. Drugs (2000) 9(8), 1849–1870).

Each kinase associates with a specific regulatory partner and together make up the active catalytic moiety. Each transition of the cell cycle is regulated by a particular cdk complex: G1l/S by cdk2/cyclin E, cdk4/cyclin D1 and cdk6/cyclinD2; S/G2 by cdk2/cyclin A and cdkl/cyclin A; G2/M by cdk1/B. The coordinated activity of these kinases guides the individual cells through the replication process and ensures the vitality of each subsequent generation (Sherr, Cell 73:1059–1065, 1993; Draetta, Trends Biochem. Sci. 15:378–382, 1990)

An increasing body of evidence has shown a link between tumor development and cdk related malfunctions. Over expression of the cyclin regulatory proteins and subsequent kinase hyperactivity have been linked to several types of cancers (Jiang, Proc. Natl. Acad. Sci. USA 90:9026–9030, 1993; Wang, Nature 343:555–557, 1990). More recently, endogenous, highly specific protein inhibitors of cdks were found to have a major affect on cellular proliferation (Kamb et al, Science 264:436–440, 1994; Beach, Nature 336:701–704, 1993). These inhibitors include p16$^{INK4}$ (an inhibitor of cdk4/D1), p21$^{CIP1}$ (a general cdk inhibitor), and p27$^{KIP1}$ (a specific cdk2/E inhibitor). A recent crystal structure of p27 bound to cdk2/A revealed how these proteins effectively inhibit the kinase activity through multiple interactions with the cdk complex (Pavletich, Nature 382:325–331, 1996). These proteins help to regulate the cell cycle through specific interactions with their corresponding cdk complexes. Cells deficient in these inhibitors are prone to unregulated growth and tumor formation.

Protein kinases, in particular, CDK, play a role in the regulation of cellular proliferation. Therefore, CDK inhibitors could be useful in the treatment of cell proliferative disorders such as cancer, familial adenomatosis polyposis, neuro-fibromatosis, psoriasis, fungal infections, endotoxic shock, trasplantaion rejection, vascular smooth cell proliferation associated with atherosclerosis, pulmonary fibrosis, arthritis glomerulonephritis and post-surgical stenosis and restenosis (U.S. Pat. No. 6,114,365). CDKs are also known to play a role in apoptosis.

Therefore CDK inhibitors, could be useful in the treatment of useful of cancer; viral infections, for example, herpevirus, poxyirus, Epstein-Barr virus, Sindbis virus and adenovirus; prevention of AIDS development in HIV-infected individuals; autoimmune diseases, for example, systemic lupus, erythematosus, autoimmune mediated glomerulonephritis, rheumatoid arthritis, psoriasis, inflammatory bowel disease, and autoimmune diabetes mellitus; neurodegenerative disorders, for example, Alzheimer's disease, AIDS-related dementia, Parkinson's disease, amyotrophic lateral sclerosis, retinitis pigmentosa, spinal muscular atrophy and cerebellar degeneration; myelodysplastic syndromes, aplastic anemia, ischemic injury associated with myocardial infarctions, stroke and reperfusion injury, arrhythmia, atherosclerosis, toxin-induced or alcohol related liver diseases, hematological diseases, for example, chronic anemia and aplastic anemia; degenerative diseases of the musculoskeletal system, for example, osteoporosis and arthritis, aspirin-sensitive rhinosinusitis, cystic fibrosis, multiple sclerosis, kidney diseases and cancer pain (U.S. Pat. No. 6,107,305).

It has also been discovered that some cyclin-dependent kinase inhibitors can be used in combination therapy with some other anticancer agents. For example, the cytotoxic activity of the cyclin-dependent kinase inhibitor, flavopiridol, has been used with other anticancer agents in cancer combination therapy. Cancer Research, 57, 3375 (1997).

Also, it has recenly been disclosed that CDK inhibitors may be useful in the chemoprevention of cancer. Chemoprevention is defined as inhibiting the development of invasive cancer by either blocking the initiating mutagenic event or by blocking the progression of pre-malignant cells that have already suffered an insult or inhibiting tumor relapse (U.S. Pat. No. 6,107,305).

Furthermore, it has recently been discovered that cdk5 is involved in the phosphorylation of tau protein, and therefore CDK inhibitors may be useful in the treatment of Alzheimer's disease (J. Biochem., 117, 741–749, 1995).

This body of evidence has led to an intense search for small molecule inhibitors of the cdk family as an approach to cancer chemotherapy. There are no known examples of molecules related to the current invention which describe 5-substituted-indeno[1,2-c]pyrazoles as cdk inhibitors. There is one case describing indeno[1,2-c]pyrazoles having anticancer activity. There are two other examples which describe indeno[1,2-c]pyrazoles having unrelated utilities and structures.

A series of indeno[1,2-c]pyrazoles having anticancer activity are described in JP 60130521 and JP 62099361 with the following generic structure:

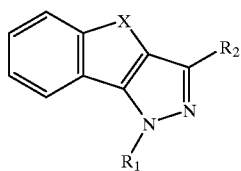

No substitution is claimed on the indenophenyl portion of the molecule and the molecules are not indicated to be cdk inhibitors. In addition, we discovered that substitution at the 5-position was critical for cdk inhibitory activity.

A series of indeno[1,2-c]pyrazoles having herbicidal activity are described in GB 2223946 with the following generic structure:

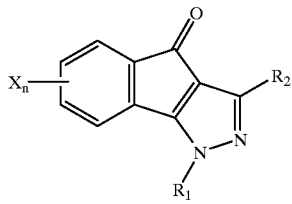

The above compounds differ from the presently claimed invention in $X_n$ is defined as halo, alkyl, haloalkyl, and haloalkoxy; n=0–2. In addition, $R_1$ is defined as acyl and $R_2$ is defined as alkyl or cycloalkyl.

A series of 1-(6'-substituted-4'-methylquinol-2'-yl)-3-methylindeno[1,2-c]pyrazoles having CNS activity are described by Quraishi, Farmaco 44:753–8, 1989 with the following generic structure:

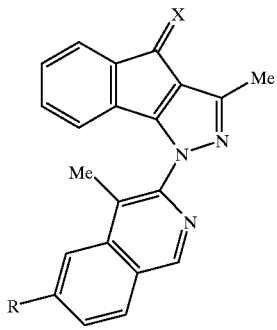

Compounds of this series are not considered to be part of the presently claimed invention.

SUMMARY OF THE INVENTION

The present invention describes a novel class of indeno[1,2-c]pyrazol-4-ones or pharmaceutically acceptable salt forms thereof that are potent inhibitors of the class of enzymes known as cyclin dependent kinases, which relate to the catalytic subunits cdk 1–9 and their regulatory subunits know as cyclins A–H.

It is another object of this invention to provide a novel method of treating proliferative diseases associated with CDK activity by administering a therapeutically effective amount of one of the compounds of the invention or a pharmaceutically acceptable salt form thereof.

It is another object of this invention to provide a novel method of treating cancer associated with CDK activity by administering a therapeutically effective amount of one of the compounds of the invention or a pharmaceutically acceptable salt form thereof.

It is another object of this invention to provide a novel method of treating a proliferative disease, which comprises administering a therapeutically effective combination of one of the compounds of the present invention and one or more other known anti-cancer treatments such as radiation therapy, chemotoxic or chemostatic agents.

These and other objectives have been achieved by the inventors' discovery that compounds of formula (I):

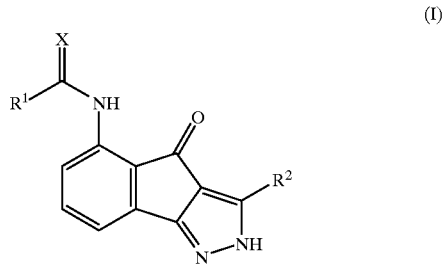

wherein $R_1$, $R_2$ and X are defined below or pharmaceutically acceptable salts thereof are cyclin dependent kinase inhibitors.

DETAILED DESCRIPTION OF PREFERRED EMBODIMENTS

The invention pertains to novel cyclin dependent kinase inhibitors (cdks) and specifically, but not exclusively, as inhibitors of cdk/cyclin complexes. The inhibitors of this invention are indeno[1,2-c]pyrazol-4-one analogs. Certain analogs were selective for their activity against cdks and their cyclin bound complexes and were less active against other known serine/threonine kinases such as Protein Kinase A (PKA) and Protein Kinase C (PKC).

As described herein, the inhibitors of this invention are capable of inhibiting the cell-cycle machinery and consequently would be useful in modulating cell-cycle progression, which would ultimately control cell growth and differentiation. Such compounds would be useful for treating subjects having disorders associated with excessive cell proliferation, such as the treatment of cancer, psoriasis, immunological disorders involving unwanted leukocyte proliferation, in the treatment of restinosis and other smooth muscle cell disorders, and the like.

[1] The present invention, in a first embodiment, describes novel compounds of formula (I):

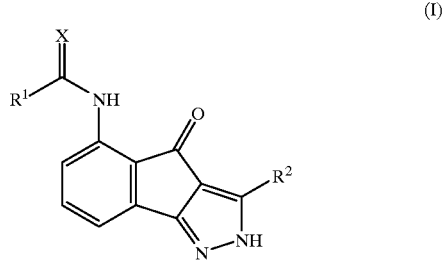

or stereoisomers, pharmaceutically acceptable salts, and prodrugs thereof, wherein:

X is selected from the groups: O, S, and NR;

R is selected from the groups: H, $C_{1-4}$ alkyl, and $NR^5R^{5a}$;

R¹ is selected from the groups: H, $C_{1-10}$ alkyl substituted with 0–3 $R^c$, $C_{2-10}$ alkenyl substituted with 0–3 $R^c$, $C_{2-10}$ alkynyl substituted with 0–3 $R^c$, —NHR⁴, $C_{3-10}$ membered carbocycle substituted with 0–5 $R^a$, and 3–10 membered heterocycle containing from 1–4 heteroatoms selected from O, N, and S and substituted with 0–5 $R^b$;

$R^a$ is independently selected from the groups: $R^5 R^{5a}N(CR^6R^{6a})_m$, $R^5O(CR^6R^{6a})_m$, halo, —CN, $N_3$, $NO_2$, $C_{1-4}$ alkyl, $C_{1-4}$ haloalkyl, $NR^3R^{3a}$, =O, $OR^3$, $SR^3$, $COR^3$, $CO_2R^3$, $CONR^3R^{3a}$, $NHC(O)NR^3R^{3a}$, $NHC(S)NR^3R^{3a}$, $NR^3C(O)OR^3$, $NR^3C(O)R^3$, $SO_2NR^3R^{3a}$, $SO_2R^{3b}$, and 5–10 membered heterocycle containing from 1–4 heteroatoms selected from O, N, and S;

alternatively, when two Ra's are present on adjacent carbon atoms they combine to form —OCH₂O— or —OCH₂CH₂O—;

$R^b$ is independently selected from the groups: halo, —CN, $NO_2$, $C_{1-4}$ alkyl, $C_{1-4}$ haloalkyl, $NR^3R^{3a}$, $NR^3C(O)OR^3$, $NR^3C(O)R^3$, $OR^3$, $COR^3$, $CO_2R^3$, $CONR^3R^{3a}$, $CON(R^6)((CH_2)_mR^7)$, $CO(CH_2)_mR^7$, $NHC(O)NR^3R^{3a}$, $NHC(S)NR^3R^{3a}$, $SO_2NR^3R^{3a}$, and $SO_2R^{3b}$;

$R^c$ is independently selected from the groups: halo, —CN, $NO_2$, $C_{1-4}$ alkyl, $C_{1-4}$ haloalkyl, $NR^3R^{3a}$, $NR^5NR^5R^{5a}$, $NR^3C(O)OR^3$, $NR^3C(O)R^3$, =O, $OR^3$, $COR^3$, $CO_2R^3$, $CONR^3R^{3a}$, $NHC(O)NR^3R^{3a}$, $NHC(S)NR^3R^{3a}$, $SO_2N^3R^{3a}$, $SO_2R^{3b}$, $C_{3-10}$ membered carbocycle substituted with 0–5 $R^a$, and 5–10 membered heterocycle containing from 1–4 heteroatoms selected from O, N, and S, substituted with 0–3 $R^3$;

R² is selected from the groups: H, $C_{1-10}$ alkyl substituted with 0–3 $R^c$, $C_{2-10}$ alkenyl substituted with 0–3 $R^c$, $C_{2-10}$ alkynyl substituted with 0–3 $R^c$, —$(CF_2)_mCF_3$, $C_{3-10}$ membered carbocycle substituted with 0–5 $R^a$, and 3–10 membered heterocycle containing from 1–4 heteroatoms selected from O, N, and S and substituted with 0–5 $R^b$;

R³ is independently selected from the groups: H, halo, —CN, $NO_2$, $C_{1-4}$ haloalkyl, $R^5R^{5a}N(CR^6R^{6a})m$, $NR^5NR^5R^{5a}$, $NR^5C(O)OR^5$, $NR^5C(O)R^5$, =O, $R^5O(CR^6R^{6a})m$, $COR^5$, $CO_2R^5$, $CONR^5R^{5a}$, $NHC(O)NR^5R^{5a}$, $NHC(S)NR^5R^{5a}$, $SO_2NR^5R^{5a}$, $SO_2R^{5b}$, $C_{1-4}$ alkyl, phenyl, and benzyl;

$R^{3a}$ is independently selected from the groups: H, $C_{1-4}$ alkyl, phenyl, and benzyl;

alternatively, R³ and $R^{3a}$, together with the atoms to which they are attached, form a heterocycle having 4–8 atoms in the ring and containing an additional 0–1 N, S, or O atom and substituted with 0–3 $R^{3c}$;

$R^{3b}$ is independently selected from the groups: H, $C_{1-4}$ alkyl, phenyl, and benzyl;

$R^{3c}$ is independently selected from the groups: halo, —CN, $N_3$, $NO_2$, $C_{1-4}$ alkyl, $C_{3-8}$ cycloalkyl, $C_{4-10}$ cycloalkylalkyl, $C_{1-4}$ haloalkyl, $NR^3R^{3b}$, $R^5R^{5a}N(CR^6R^{6a})m$, =O, $OR^3$, $R^5O(CR^6R^{6a})m$, $COR^3$, $CO_2R^3$, $CONR^3R^{3b}$, $NHC(O)NR^3R^{3b}$, $NHC(S)NR^3R^{3b}$, $NR^3C(O)OR^3$, $NR^3C(O)R^3$, $C(=NR^5)R^{5a}$, $C(=NR^5)NR^{5a}R^{5b}$, $SO_2NR^3R^{3b}$, $SO_2R^{3b}$, and 5–10 membered heterocycle containing from 1–4 heteroatoms selected from O, N, and S;

R⁴ is independently selected from the groups: H, —CN, $C_{1-4}$ alkyl, $C_{1-4}$ haloalkyl, $NR^3R^{3a}$, $NR^3C(O)OR^3$, $NR^3C(O)R^3$, $OR^3$, $COR^3$, $CO_2R^3$, $CONR^3R^{3a}$, $NHC(O)NR^3R^{3a}$, $NHC(S)NR^3R^{3a}$, $SO_2NR^3R^{3a}$, $SO_2R^{3b}$, $C_{3-10}$ membered carbocycle substituted with 0–5 $R^a$, and 5–10 membered heterocycle containing from 1–4 heteroatoms selected from O, N, and S, substituted with 0–3 $R^3$;

R⁵ is independently selected from the groups: H, $C_{1-4}$ alkyl, phenyl and benzyl;

$R^{5a}$ is independently selected from the groups: H, $C_{1-4}$ alkyl, phenyl and benzyl;

alternatively, R⁵ and $R^{5a}$, together with the atoms to which they are attached, form a heterocycle having 4–8 atoms in the ring and containing an additional 0–1 N, S, or O atom;

$R^{5b}$ is independently selected from the groups: H, $C_{1-4}$ alkyl, phenyl and benzyl;

R⁶ is idependently selected from the groups: H, $C_{1-4}$ alkyl;

$R^{6a}$ is independently selected from the groups: H, $C_{1-4}$ alkyl;

R⁷ is independently selected from the groups: $NR^3R^{3a}$, membered carbocycle substituted with 0–3 $R^3$, and 5–10 membered heterocycle containing from 1–4 heteroatoms selected from O, N, and S, substituted with 0–3 $R^3$; and m is independently selected from 0, 1, 2, 3, and 4;

provided that: when R² is a $C_{1-4}$ unsubstituted, branched alkyl then R¹ is not $CH_3$; or when R¹ is NHR⁴ and R⁴ is $NR^3R^{3a}$ then R³ and $R^{3a}$ can not both be phenyl.

[2] In another embodiment, the invention describes novel compounds of formula (I):

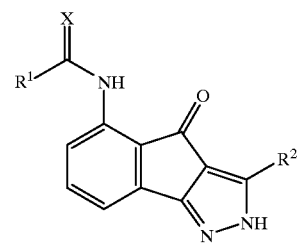

(I)

or stereoisomers, pharmaceutically acceptable salts, and prodrugs thereof, wherein:

X is selected from the groups: O, S, and NR;

R is selected from the groups: H, $C_{1-4}$ alkyl, and $NR^5R^{5a}$;

R¹ is selected from the groups: H, $C_{1-10}$ alkyl substituted with 0–3 $R^c$, $C_{2-10}$ alkenyl substituted with 0–3 $R^c$, $C_{2-10}$ alkynyl substituted with 0–3 $R^c$, —NHR⁴, $C_{3-10}$ membered carbocycle substituted with 0–5 $R^a$, and 3–10 membered heterocycle containing from 1–4 heteroatoms selected from O, N, and S and substituted with 0–5 $R^b$;

$R^a$ is independently selected from the groups: halo, —CN, $N^3$, $NO_2$, $C_{1-4}$ alkyl, $C_{1-4}$ haloalkyl, $NR^3R^{3a}$, =O, $OR^3$, $COR^3$, $CO_2R^3$, $CONR^3R^{3a}$, $NHC(O)NR^3R^{3a}$, $NHC(S)NR^3R^{3a}$, $NR^3C(O)OR^3$, $NR^3C(O)R^3$, $SO_2NR^3R^{3a}$, $SO_2R^{3b}$, and 5–10 membered heterocycle containing from 1–4 heteroatoms selected from O, N, and S;

alternatively, when two $R^a$'s are present on adjacent carbon atoms they combine to form —OCH₂O— or —OCH₂CH₂O—;

$R^b$ is independently selected from the groups: halo, —CN, $NO_2$, $C_{1-4}$ alkyl, $C_{1-4}$ haloalkyl, $NR^3R^{3a}$, $NR^3C(O)OR^3$, $NR^3C(O)R^3$, $OR^3$, $COR^3$, $CO_2R^3$, $CONR^3R^{3a}$, CON($R^6$)(($CH_2$)$_m R^7$), CO($CH_2$)$_m R^7$, NHC(O)$NR^3 R^{3a}$, NHC(S)$NR^3 R^{3a}$, $SO_2 NR^3 R^{3a}$, and $SO_2 R^{3b}$;

$R^c$ is independently selected from the groups: halo, —CN, $NO_2$, $C_{1-4}$ alkyl, $C_{1-4}$ haloalkyl, $NR^3 R^{3a}$, $NR^5 NR^5 R^{5a}$, $NR^3 C(O)OR^3$, $NR^3 C(O)R^3$, =O, $OR^3$, $COR^3$, $CO_2 R^3$, $CONR^3 R^{3a}$, NHC(O)$NR^3 R^{3a}$, NHC(S)$NR^3 R^{3a}$, $SO_2 NR^3 R^{3a}$, $SO_2 R^{3b}$, $C_{3-10}$ membered carbocycle substituted with 0–5 $R^a$, and 5–10 membered heterocycle containing from 1–4 heteroatoms selected from O, N, and S, substituted with 0–3 $R^3$;

$R^2$ is selected from the groups: H, $C_{1-10}$ alkyl substituted with 0–3 $R^c$, $C_{2-10}$ alkenyl substituted with 0–3 $R^c$, $C_{2-10}$ alkynyl substituted with 0–3 $R^c$, —(CF$_2$)$_m$CF$_3$, $C_{3-10}$ membered carbocycle substituted with 0–5 $R^a$, and 3–10 membered heterocycle containing from 1–4 heteroatoms selected from O, N, and S and substituted with 0–5 $R^b$;

$R^3$ is independently selected from the groups: H, halo, —CN, $NO_2$, $C_{1-4}$ haloalkyl, $R^5 R^{5a} N(CR^6 R^{6a})m$, $NR^5 NR^5 R^{5a}$, $NR^5 C(O)OR^5$, $NR^5 C(O)R^5$, =O, $R^5 O (CR^5 R^{6a})m$, $COR^5$, $CO_2 R^5$, $CONR^5 R^{5a}$, NHC(O)$NR^5 R^{5a}$, NHC(S)$NR^5 R^{5a}$, $SO_2 NR^5 R^{5a}$, $SO_2 R^{5b}$, $C_{1-4}$ alkyl, phenyl, and benzyl;

$R^{3a}$ is independently selected from the groups: H, $C_{1-4}$ alkyl, phenyl, and benzyl;

alternatively, $R^3$ and $R^{3a}$, together with the atoms to which they are attached, form a heterocycle having 4–8 atoms in the ring and containing an additional 0–1 N, S, or O atom and substituted with 0–3 $R^{3c}$;

$R^{3b}$ is independently selected from the groups: H, $C_{1-4}$ alkyl, phenyl, and benzyl;

$R^{3c}$ is independently selected from the groups: halo, —CN, $N_3$, $NO_2$, $C_{1-4}$ alkyl, $C_{3-8}$ cycloalkyl, $C_{4-10}$ cycloalkylalkyl, $C_{1-4}$ haloalkyl, $NR^3 R^{3b}$, $R^5 R^{5a} N (CR^6 R^{6a})m$, =O, $OR^3$, $R^5 O(CR^6 R^{6a})m$, $COR^3$, $CO_2 R^3$, $CONR^3 R^{3b}$, NHC(O)$NR^3 R^{3b}$, NHC(S)$NR^3 R^{3b}$, $NR^3 C(O)OR^3$, $NR^3 C(O)R^3$, C(=$NR^5$)$R^{5a}$, C(=$NR^5$)$NR^{5a} R^{5b}$, $SO_2 NR^3 R^{3b}$, $SO_2 R^{3b}$, and 5–10 membered heterocycle containing from 1–4 heteroatoms selected from O, N, and S;

$R^4$ is independently selected from the groups: H, —CN, $C_{1-4}$ alkyl, $C_{1-4}$ haloalkyl, $NR^3 R^{3a}$, $NR^3 C(O)OR^3$, $NR^3 C(O)R^3$, $OR^3$, $COR^3$, $CO_2 R^3$, $CONR^3 R^{3a}$, NHC(O)$NR^3 R^{3a}$, NHC(S)$NR^3 R^{3a}$, $SO_2 NR^3 R^{3a}$, $SO_2 R^{3b}$, $C_{3-10}$ membered carbocycle substituted with 0–5 $R^a$, and 5–10 membered heterocycle containing from 1–4 heteroatoms selected from O, N, and S, substituted with 0–3 $R^3$;

$R^5$ is independently selected from the groups: H, $C_{1-4}$ alkyl, phenyl and benzyl;

$R^{5a}$ is independently selected from the groups: H, $C_{1-4}$ alkyl, phenyl and benzyl;

alternatively, $R^5$ and $R_{5a}$, together with the atoms to which they are attached, form a heterocycle having 4–8 atoms in the ring and containing an additional 0–1 N, S, or O atom;

$R_{5b}$ is independently selected from the groups: H, $C_{1-4}$ alkyl, phenyl and benzyl;

$R^6$ is independently selected from the groups: H, $C_{1-4}$ alkyl;

$R^{6a}$ is independently selected from the groups: H, $C_{1-4}$ alkyl;

$R^7$ is independently selected from the groups: $NR^3 R^{3a}$, $C_{3-10}$ membered carbocycle substituted with 0–3 $R^3$, and 5–10 membered heterocycle containing from 1–4 heteroatoms selected from O, N, and S, substituted with 0–3 $R^3$; and m is independently selected from 0, 1, 2, 3, and 4; provided that:

1) when $R^2$ is a $C_{1-4}$ unsubstituted, branched alkyl then $R^1$ is not $CH_3$; or 2) when $R^1$ is $NHR^4$ and $R^4$ is $NR^3 R^{3a}$ then $R^3$ and $R^{3a}$ can not both be phenyl.

$R^3$ and $R^{3a}$ can not both be phenyl.

[3] In another embodiment, the invention describes novel compounds of embodiment [1], wherein X is O or S;

$R^1$ is H, $C_{1-10}$ alkyl substituted with 0–3 $R^c$, —$NHR^4$, $C_{3-10}$ membered carbocycle substituted with 0–5 , or 3–10 membered heterocycle containing from 1–4 heteroatoms selected from O, N, and S and substituted with 0–5;

$R^c$ is independently selected from the groups: halo, $C_{3-10}$ membered carbocycle substituted with 0–5 $R^a$, 5–10 membered heterocycle containing from 1–4 heteroatoms selected from O, N, and S, substituted with 0–3 $R^3$, $NR^3 R^{3a}$;

$R^3$ is H, $C_{1-4}$ alkyl, phenyl, benzyl, or together with the atoms to which they are attached, form a heterocycle having 4–8 atoms in the ring and containing an additional 0–1 N, S, or O atom and substituted with 0–3 $R^{3c}$;

R4 is H, $C_{1-4}$ alkyl, $NR^3 R^{3a}$, $C_{3-10}$ membered carbocycle substituted with 0–5 $R^a$, and 5–10 membered heterocycle containing from 1–4 heteroatoms selected from O, N, and S, substituted with 0–3 $R^3$;

$R^2$ is selected from the groups: $C_{3-10}$ membered carbocycle substituted with 0–5 $R^a$, and 3–10 membered heterocycle containing from 1–4 heteroatoms selected from O, N, and S and substituted with 0–5 $R^b$, and $C_{1-10}$ alkyl substituted with 0–3 $R^c$.

[4] In another embodiment, the invention describes novel compounds of embodiment [1], wherein X is O or S;

$R^1$ is $C_{1-4}$ alkyl substituted with 0–3 $R^c$, wherein $R^c$ is independently selected from the group consisting of: $C_{3-6}$ membered carbocycle substituted with 0–5 $R^a$, 5–6 membered heterocycle substituted with 0–3 $R^3$, $NR^3 R^{3a}$, and $OR^3$; $C_{3-6}$ membered carbocycle substituted with 0–5 $R^a$, wherein $R^a$ is independently selected from the group consisting of:
$R^5 R^{5a} N(CR^6 R^{6a})m$—, $R^5 O(CR^6 R^{6a})m$—, $OR^3$, halo, $C_{1-4}$ alkyl, —$NR^3 O(O)R^3$, $COR^3$, $CO_2 R^3$, $N_3$, $NR^3 C(O)OR^3$, $NR^3 R^{3a} CONR^3 R^{3a}$, and 5–6 membered heterocycle; or when two $R^a$'s are present on adjacent carbon atoms they combine to form —$OCH_2 O$— or —$OCH_2 CH_2 O$—; or 5–6 membered heterocycle and substituted with 0–5 $R^b$, wherein $R^b$ is independently selected from the group:
$OR^3$, halo, $COR^3$, $C_{1-4}$ alkyl, $CO_2 R^3$, $NR^3 C(O)R^3$, $NR^3 C(O)OR^3$, $NR^3 R^{3a}$, and $CONR^3 R^{3a}$;

$R^2$ is $C_{3-6}$ membered carbocycle substituted with 0–5 $R^a$, wherein $R^a$ is independently selected from the groups: $R^5 R^{5a} N(CR^6 R^{6a})m$, $R^5 O(CR^6 R^{6a})m$, $OR^3$, halo, $C_{1-4}$ alkyl, $NR^3 C(O)R^3$, $COR^3$, $CO_2 R^3$, $N^3$, $NR^3 C(O)OR^3$, $NR^3 R^{3a}$, $CONR^3 R^{3a}$, and 5–6 membered heterocycle, or when two $R^a$'s are present on adjacent carbon atoms they combine to form —$OCH_2 O$— or —$OCH_2 CH_2 O$—; 3–6 membered heterocycle containing from 1–4 heteroatoms selected from O, N, and S and substituted with 0–5 $R^b$, wherein $R^b$ is independently selected from the group:

OR$^3$, halo, COR$^3$, C$_{1-4}$ alkyl, CO$_2$R$^3$, NR$^3$C(O)R$^3$, NR$^3$C(O)OR$^3$, NR$^3$R$^{3a}$, and CONR$^3$R$^{3a}$; or C$_{1-10}$ alkyl substituted with 0–3 R$^c$, wherein R$^c$ is independently selected from the groups:

C$_{3-6}$ membered carbocycle substituted with 0–5 R$^a$, 5–6 membered heterocycle substituted with 0–3 R$^3$, NR$^3$R$^{3a}$, and OR$^3$.

[5] In another embodiment, the invention describes novel compounds of embodiment [1], wherein X is O or S;

R$^1$ is selected from the groups: H, —NHR$^4$, C$_{1-4}$ alkyl substituted with 0–3 R$^c$, C$_{3-6}$ membered carbocycle substituted with 0–5 R$^a$, and 5–6 membered heterocycle and substituted with 0–5 R$^b$;

R$^2$ is selected from the group: C$_{3-6}$ membered carbocycle substituted with 0–5 R$^a$, 3–10 membered heterocycle containing from 1–4 heteroatoms selected from O, N, and S and substituted with 0–5 R$^b$, and C$_{1-10}$ alkyl substituted with 0–3 R$^c$, C$_{2-10}$ alkenyl substituted with 0–3 R$^c$;

R$^4$ is independently selected from the groups: H, C$_{1-4}$ alkyl, NR$^3$R$^{3a}$, C$_{3-6}$ membered carbocycle substituted with 0–5 R$^a$, and 5–6 membered heterocycle substituted with 0–5 R$^3$;

R$^3$ is independently selected from the group: H, halo, COR$^5$, CO$_2$R$^5$, R$^5$R$^{5a}$N(CR$^6$R$^{6a}$)m, R$^5$O(CR$^6$R$^{6a}$)m, CONR$^5$R$^{5a}$, NR$^5$C(O)OR$^5$, NR$^5$C(O)R$^5$, C$_{1-4}$ alkyl, phenyl, and benzyl;

R$^{3a}$ is independently selected from the group: H, C$_{1-4}$ alkyl, phenyl, and benzyl; or R$^3$ and R$^{3a}$, together with the atoms to which they are attached, form a 5–6 membered heterocycle containing an additional 0–1 N, S, or O atom and substituted with 0–3 R$^{3c}$;

R$^c$ is independently selected from the groups: C$_{3-6}$ membered carbocycle substituted with 0–5 R$^a$, 5–6 membered heterocycle substituted with 0–3 R$^3$, NR$^3$R$^{3a}$, and OR$^3$;

R$^a$ is independently selected from the groups: R$^5$ R$^{5a}$N(CR$^6$R$^6$)m, R$^5$O(CR$^6$R$^{6a}$)m, OR$^3$, halo, C$_{1-4}$ alkyl, NR$^3$C(O)R$^3$, COR$^3$, CO$_2$R$^3$, N$_3$, NR$^3$C(O)OR$^3$, NR$^3$R$^{3a}$, CONR$^3$R$^{3a}$, 5–6 membered heterocycle; or when two R$^a$'s are present on adjacent carbon atoms they combine to form —OCH$_2$O— or —OCH$_2$CH$_2$O—;

R$^b$ is independently selected from the group: OR$^3$, halo, COR$^3$, C$_{1-4}$ alkyl, CO$_2$R$^3$, NR$^3$C(O)R$^3$, NR$^3$C(O)OR$^3$, NR$^3$R$^{3a}$, CONR$^3$R$^{3a}$;

R$^{3c}$ is independently selected from the groups: OR$^3$, halo, COR$^3$, R$^5$R$^{5a}$N(CR$^6$R$^{6a}$)m—, R$^5$O(CR$^6$R$^{6a}$)m—, CO$_2$R$^3$, N$_3$, NR$^3$R$^{3b}$, C$_{1-4}$ alkyl, NR$^3$C(O)R$^3$, NR$^3$C(O)OR$^3$, N$^3$, NR$^3$R$^{3b}$, CONR$^3$R$^{3b}$, and 5–6 membered heterocycle; and m is independently selected from the group consisting of 1 2, 3 and 4.

[6] In another embodiment, the invention describes novel compounds of embodiment [1], wherein R$^1$ is selected from the group: —NHR$^4$ and C$_{1-2}$ alkyl substituted with 1 R$^c$.

[7] In another embodiment, the invention describes novel compounds of embodiment [1], wherein X is O or S; and R$^1$ is selected from the group: H, C$_{1-4}$ alkyl substituted with 0–3 R$^c$, C$_{2-4}$ alkenyl substituted with 0–3 R$^c$, C$_{2-4}$ alkynyl substituted with 0–3 R$^c$, —NHR$^4$, C$_{3-6}$ carbocycle substituted with 0–5 R$^a$, and 3–6 membered heterocycle containing from 1–4 heteroatoms selected from O, N, and S and substituted with 0–5 R$^b$.

[8] In another embodiment, the invention describes novel compounds of embodiment [1], wherein X is O or S; and R$^1$ is selected from the group: H, C$_{1-4}$ alkyl substituted with 0–3 R$^c$, C$_{2-4}$ alkenyl substituted with 0–3 R$^c$, C$_{2-4}$ alkynyl substituted with 0–3 R$^c$, —NHR$^4$, C$_{3-6}$ carbocycle substituted with 0–5 R$^a$, and 3–6 membered heterocycle containing from 1–4 heteroatoms selected from O, N, and S and substituted with 0–5 R$^b$;

R$^a$ is independently at each occurrence selected from the group: —CH$_2$N(CH$_3$)$_2$, —CH$_2$NH$_2$, —SH, —SCH$_3$, —NR$^3$C(O)R$^3$, —N$_3$, halo, C$_{1-4}$ alkyl, NR$^3$R$^{3a}$, and OR$^3$; alternatively, when two R$^a$'s are present on adjacent carbon atoms they combine to form —OCH$_2$O— or —OCH$_2$CH$_2$O—;

R$^b$ is independently at each occurrence selected from the group: halo, C$_{1-4}$ alkyl, NR$^3$R$^{3a}$, OR$^3$, COR$^3$, and CO$_2$R$^3$;

R$^c$ is independently at each occurrence selected from the group: halo, C$_{1-4}$ alkyl, NR$^3$R$^{3a}$, C$_{3-6}$ carbocycle substituted with 0–5 R$^a$, and 5–7 membered heterocycle containing from 1–4 heteroatoms selected from O, N, and S, substituted with 0–3 R$^3$;

R$^{3a}$ is H or C$_{1-4}$ alkyl; and

R$^3$ is selected from the group: H, —CH$_2$CH$_2$OH, —C(O)CH$_2$NH$_2$, —C(O)CH$_2$N(CH3)2, —NR$^5$R$^{5a}$, —C$_{1-4}$alkyl-NR$^5$R$^{5a}$, C$_{1-4}$ alkyl, phenyl, and benzyl.

[9] In another embodiment, the invention describes novel compounds of embodiment [1], wherein X is O or S;

R$^1$ is selected from the group: H, C$_{1-4}$ alkyl substituted with 0–3 R$^c$, —NHR$^4$, C$_{3-6}$ carbocycle substituted with 0–5 R$^a$, and 3–6 membered heterocycle containing from 1–4 heteroatoms selected from O, N, and S and substituted with 0–5 R$^b$;

R$^a$ is independently at each occurrence selected from the group: —CH$_2$N(CH$_3$)$_2$, —CH$_2$NH$_2$, —SH, —SCH$_3$, halo, C$_{1-4}$ alkyl, NR$^3$R$^{3a}$, and OR$^3$; alternatively, when two R$^a$'s are present on adjacent carbon atoms they combine to form —OCH$_2$O— or —OCH$_2$CH$_2$O—;

R$^b$ is independently at each occurrence selected from the group: halo, C$_{1-4}$ alkyl, NR$^3$R$^{3a}$, OR$^3$, COR$^3$, and CO$_2$R$^3$;

R$^c$ is independently at each occurrence selected from the group: —OH, chloro, C$_{1-4}$ alkyl, —NH2, —NHCH3, —NHCH2CH3, —NHCH2CH2CH3,—NHCH2CH2OH, —N(CH3)2, phenyl substituted with 0–5 R$^a$, and 5–7 membered heterocycle containing from 1–4 heteroatoms selected from O, N, and S, substituted with 0–3 R$^3$.

[10] In another embodiment, the invention describes novel compounds of embodiment [1], wherein R$^1$ is selected from the group: H, C$_{1-10}$ alkyl substituted with 0–3 R$^c$, C$_{2-10}$ alkenyl substituted with 0–3 R$^c$, C$_{2-10}$ alkynyl substituted with 0–3 R$^c$;

R$^2$ is selected from the group: H, —(CF$_2$)$_m$CF$_3$, C$_{3-10}$ carbocycle substituted with 0–5 R$^a$, and 3–10 membered heterocycle containing from 1–4 heteroatoms selected from O, N, and S and substituted with 0–5 R$^b$; and R$^c$ is independently at each occurrence selected from the group: phenyl substituted with 0–5 R$^a$, and thiophenyl or pyridyl, which is substituted with 0–3 R$^3$.

[11] In another embodiment, the invention describes novel compounds of embodiment [1], wherein $R^1$ is selected from the group: H, $C_{1-10}$ alkyl substituted with 0–3 $R^c$, $C_{2-10}$ alkenyl substituted with 0–3 $R^c$, $C_{2-10}$ alkynyl substituted with 0–3 $R^c$;

$R^2$ is selected from the group: H, —(CF$_2$)$_m$CF$_3$, $C_{3-10}$ carbocycle substituted with 0–5 $R^a$, and 3–10 membered heterocycle containing from 1–4 heteroatoms selected from O, N, and S and substituted with 0–5 $R^b$; and $R^c$ is independently at each occurrence selected from the group: thiophenyl, piperazinyl, piperidinyl, thiomorpholinyl, morpholinyl, pyrrolidinyl, and pyridyl, which is substituted with 0–3 substituents indepently selected from the group consiting of CH3, CH2CH2OH, CH2CH2NH2, —C(=O)NH2, —OCH3, CH2NH2, NHCH2CH3,OH, NH2, halo, —CH2N(CH3)2, —OCH2CH2O—, —OCH2O—, —N(CH3)2, uridomethyl, and pyridyl.

[12] In another embodiment, the invention describes novel compounds of embodiment [1], wherein $R^1$ is selected from the group: H, $C_{1-10}$ alkyl substituted with 0–3 $R^c$, $C_{2-10}$ alkenyl substituted with 0–3 $R^c$, $C_{2-10}$ alkynyl substituted with 0–3 $R^c$;

$R^2$ is selected from the group: H, —(CF$_2$)$_m$CF$_3$, $C_{3-10}$ carbocycle substituted with 0–5 $R^a$, and 3–10 membered heterocycle containing from 1–4 heteroatoms selected from O, N, and S and substituted with 0–5 $R^b$; and $R^c$ is phenyl substituted with 0–5 substituents indepently selected from the group consiting of CH3, CH2CH2OH, CH2CH2NH2, —C(=O)NH2, —OCH3, CH2NH2, NHCH2CH3,OH, NH2, halo, —CH2N(CH3)2, —OCH2CH2O—, —OCH2O—, —N(CH3)2, uridomethyl, and pyridyl.

[13] In another embodiment, the invention describes novel compounds of embodiment [1], wherein X is O or S;

$R^1$ is —NHR$^4$ or methylene substituted with 0–3 $R^c$;

$R^c$ is NR$^3$ R$^{3a}$;

$R^4$ is selected from the group consisting of H, C1–4 alkyl, and NR$^3$ R$^{3a}$; and $R^3$ and $R^{3a}$, are independently hydrogen or C1–4alkyl, or $R^3$ and $R^{3a}$, together with the nitrogen atom to which they are attached, form a 4–8 membered heterocycle containing an additional 0–1 N, S, or O atom and substituted with 0–3 $R^{3c}$.

[14] In another embodiment, the invention describes novel compounds of embodiment [1], wherein X is O or S;

$R^1$ is —NHR$^4$ or methylene substituted with 0–3 $R^c$;

$R^c$ is NR$^3$R$^{3a}$;

$R^4$ is selected from the group consisting of H, C1–4 alkyl, and NR$^3$R$^{3a}$; and $R^3$ and $R^{3a}$, are independently hydrogen or C1–4alkyl, or $R^3$ and $R^{3a}$, together with the nitrogen atom to which they are attached, form a 4–8 membered heterocycle containing an additional 0–1 N, S, or O atom and substituted with with 0–3 substituents independently selected from the group consisting of methyl, —CH$_2$OCH$_3$, —C(CH$_3$)$_2$OCH$_3$, —CH$_2$CH$_2$OH, —CH$_2$OH, —CH$_2$OCH$_2$Phenyl, —CH$_2$CH$_2$NH$_2$, —CH$_2$NH$_2$, —C(=NH)CH$_3$, and NH$_2$.

[15] In another embodiment, the invention describes novel compounds of embodiment [1], wherein X is O or S; and $R^1$ is selected from the group: methylene substituted with a substituent selected from the group consisting of: halo, NR$^3$R$^{3a}$, $C_{3-6}$ carbocycle substituted with 0–5 $R^a$, and 5–7 membered heterocycle containing from 1–4 heteroatoms selected from O, N, and S, substituted with 0–3 $R^3$.

[16] In another embodiment, the invention describes novel compounds of embodiment [1], wherein X is O or S;

$R^1$ is selected from the group: methylene substituted with NR$^3$R$^{3a}$; and $R^3$ and $R^{3a}$, together with the nitrogen atom to which they are attached, form pyrrolyl, pyrrolinyl, pyrrolidinyl, imidazolyl, imidazolinyl, imidazolidinyl, pyrazolyl, pyrazolinyl, pyrazolidinyl, thiomorpholinyl, pymorpholinyl, piperidinyl, piperazinyl, or piperadinyl, which is substituted with 0–3 $R^{3c}$.

[17] In another embodiment, the invention describes novel compounds of embodiment [1], wherein $R^1$ is —NHR$^4$;

$R^4$ is NR3R3a; and $R^3$ and $R^{3a}$, together with the nitrogen atom to which they are attached, form pyrrolyl, pyrrolinyl, pyrrolidinyl, imidazolyl, imidazolinyl, imidazolidinyl, pyrazolyl, pyrazolinyl, pyrazolidinyl, thiomorpholinyl, pymorpholinyl, piperidinyl, piperazinyl, or piperadinyl, which is substituted with 0–3 $R^{3c}$.

[18] In another embodiment, the invention describes novel compounds of embodiment [1], wherein $R^1$ is —NHR$^4$;

$R^4$ is NR3R3a; and $R^3$ and $R^3$a, together with the nitrogen atom to which they are attached, form pyrrolyl, pyrrolinyl, pyrrolidinyl, imidazolyl, imidazolinyl, imidazolidinyl, pyrazolyl, pyrazolinyl, pyrazolidinyl, thiomorpholinyl, pymorpholinyl, piperidinyl, piperazinyl, or piperadinyl, which is substituted with 0–3 substituents independently selected from the group consisting of methyl, —CH$_2$OCH$_3$, —C(CH$_3$)$_2$OCH$_3$, —CH$_2$CH$_2$OH, —CH$_2$OH, —CH$_2$OCH$_2$Phenyl, —CH$_2$CH$_2$NH$_2$, —CH$_2$NH$_2$, —C(=NH)CH$_3$, and NH2.

[19] In another embodiment, the invention describes novel compounds of embodiment [1], wherein $R^2$ is selected from the group: 5- to 7- membered monocyclic saturated, or partially saturated, heterocyclic ring substituted with 0–5 $R^b$.

[20] In another embodiment, the invention describes novel compounds of embodiment [1], wherein $R^2$ is selected from the group: 5- to 7- membered monocyclic aromatice heterocyclic ring substituted with 0–5 $R^b$.

[21] In another embodiment, the invention describes novel compounds of embodiment [1], wherein $R^2$ is selected from the group: $C_{1-10}$ alkyl substituted with 0–3 $R^c$, $C_{3-10}$ carbocycle substituted with 0–5 $R^a$, and 3–10 membered heterocycle containing from 1–4 heteroatoms selected from O, N, and S and substituted with 0–5 $R^b$.

[22] In another embodiment, the invention describes novel compounds of embodiment [1], wherein $R^2$ is selected from the group: $C_{1-6}$ alkyl substituted with 0–3 $R^c$, $C_{3-6}$ carbocycle substituted with 0–5 $R^a$, and 3–7 membered heterocycle containing from 1–4 heteroatoms selected from O, N, and S and substituted with 0–5 $R^b$.

[23] In another embodiment, the invention describes novel compounds of embodiment [1], wherein $R^2$ is selected from the group: $C_{1-6}$ alkyl substituted with $C_{3-10}$ carbocycle substituted with 0–5 $R^a$, and $C_{1-6}$ alkyl substituted with 5–10 membered heterocycle containing from 1–4 heteroatoms selected from O, N, and S.

[24] In another embodiment, the invention describes novel compounds of embodiment [1], wherein $R^2$ is selected from the group: phenyl substituted with 0–5 $R^a$, and cyclopropyl or cyclohexyl substituted with 0–2 $R^a$; and $R^a$ is independently at each occurrence selected from the group: —$CH_2N(CH_3)_2$, —$CH_2NH_2$, —$SR_3$ halo, —CN, $N_3$, $NO_2$, $C_{1-4}$ alkyl, $C_{1-4}$ haloalkyl, $NR^3R^{3a}$, =O, $OR^3$, $COR^3$, $CO_2R^3$, $CONR^3R^{3a}$, NHC(O)$NR^3R^{3a}$, NHC(S)$NR^3R^{3a}$, $NR^3C(O)OR^3$, $NR^3C(O)R^3$, $SO_2NR^3R^{3a}$, $SO_2R^{3b}$, and 5–10 membered heterocycle containing from 1–4 heteroatoms selected from O, N, and S.

[25] In another embodiment, the invention describes novel compounds of embodiment [1], wherein $R^2$ is selected from the group: phenyl substituted with 0–5 $R^a$, and cyclopropyl or cyclohexyl substituted with 0–2 $R^a$; and $R^a$ is independently at each occurrence selected from the group: $C_{1-4}$ alkyl, $COR^3$, $CO_2R^3$, and $CONR^3R^{3a}$;

$R^{3a}$ is H or $C_{1-4}$ alkyl.

[26] In another embodiment, the invention describes novel compounds of embodiment [1], wherein $R^2$ is selected from the group: phenyl substituted with 0–5 $R^a$, and cyclopropyl or cyclohexyl substituted with 0–2 $R^a$;

$R^a$ is independently at each occurrence selected from the group: $C_{1-4}$ alkyl, $COR^3$, $CO_2R^3$, and $CONR^3R^{3a}$;

$R^{3a}$ is H or $C_{1-4}$ alkyl;

$R^3$ is $C_{1-4}$alkyl, $C_{1-4}$alkyl-NR5R5a; and $R^5$ and $R^{5a}$, together with the atoms to which they are attached, form a heterocycle having 4–8 atoms in the ring and containing an additional 0–1 N, S, or O atom.

[27] In another embodiment, the invention describes novel compounds of embodiment [1], wherein $R^2$ is selected from the group: phenyl substituted with 0–5 $R^a$, and cyclopropyl or cyclohexyl substituted with 0–2 $R^a$;

$R^a$ is independently at each occurrence selected from the group: $C_{1-4}$ alkyl, $COR^3$, $CO_2R^3$, and $CONR^3R^{3a}$; and $R^{3a}$ is H or $C_{1-4}$ alkyl.

[28] In another embodiment, the invention describes novel compounds of embodiment [1], wherein $R^2$ is phenyl substituted with $NR^3R^{3a}$, wherein $R^3$ and $R^{3a}$ together with the nitrogen atom to which they are attached, form a 4–8 membered heterocycle containing an additional 0–1 N, S, or O atom and substituted with 0–3 $R^{3c}$.

[29] In another embodiment, the invention describes novel compounds of embodiment [1], wherein $R^2$ is phenyl substituted with $NR^3R^{3a}$; and $R^3$ and $R^{3a}$, together with the nitrogen atom to which they are attached, form a pyrrolinyl, pyrrolidinyl, imidazolidinyl, pyrazolidinyl, pyrazolinyl, piperidinyl, morpholinyl, thiomorpholinyl, homopiperazinyl or piperazinyl group, substituted with 0–3 $R^{3c}$.

[30] In another embodiment, the invention describes novel compounds of embodiment [1], wherein $R^2$ is phenyl substituted with $NR^3R^{3a}$, wherein $R^3$ and $R^{3a}$, together with the nitrogen atom to which they are attached, form a piperidinyl, homopiperazinyl or piperazinyl group, substituted with 0–3 $R^{3c}$.

[31] In another embodiment, the invention describes novel compounds of embodiment [1], wherein $R^2$ is phenyl substituted with $NR^3R^{3a}$; and $R^3$ and $R^{3a}$, together with the nitrogen atom to which they are attached, form a piperidinyl, homopiperazinyl or piperazinyl group, substituted with 0–3 substituents independently selected from the group consisting of: —C(=NH)$CH_3$, pyrrolinyl, pyrrolidinyl, imidazolinyl, pyrazolidinyl, pyrazolinyl, piperidinyl, morpholinyl, thiomorpholinyl, homopiperazinyl or piperazinyl group, pyridyl, $C_{1-4}$ alkyl, —$NR^3R^{3b}$.

[32] In another embodiment, the invention describes novel compounds of embodiment [1], which is selected from Table 1.

[33] In another embodiment, the invention describes novel compounds of embodiment [1], which is selected from Table 2.

[34] In another embodiment, the invention describes novel compounds of embodiment [1], which is selected from Table 3.

[35] In another embodiment, the invention describes novel compounds of embodiment [1], which is selected from Table 4.

[36] In another embodiment, the invention describes novel compounds of embodiment [1], selected from:

3-(4-methoxyphenyl)-5-(acetamido)indeno[1,2-c]pyrazol-4-one;

3-phenyl-5-(acetamido)indeno[1,2-c]pyrazol-4-one;

3-(4-methylthiophenyl)-5-(acetamido)indeno[1,2-c]pyrazol-4-one;

3-(4-methanesulfonylphenyl)-5-(acetamido)indeno[1,2-c]pyrazol-4-one;

3-(4-(N,N-dimethylamino)phenyl)-5-(acetamido)indeno[1,2-c]pyrazol-4-one;

3-(3-pyridyl)-5-(acetamido)indeno[1,2-c]pyrazol-4-one;

3-(4-methoxyphenyl)-5-(formamido)indeno[1,2-c]pyrazol-4-one;

3-(4-hydroxyphenyl)-5-(acetamido)indeno[1,2-c]pyrazol-4-one;

3-(4-piperidinophenyl)-5-(acetamido)indeno[1,2-c]pyrazol-4-one;

3-(4-morpholinophenyl)-5-(acetamido)indeno[1,2-c]pyrazol-4-one;

3-(4-ethoxyphenyl)-5-(acetamido) indeno[1,2-c]pyrazol-4-one;

3-(4-butylphenyl)-5-(acetamido)indeno[1,2-c]pyrazol-4-one;

3-(4-ethylphenyl)-5-(acetamido)indeno[1,2-c]pyrazol-4-one;

3-(4-n-propylphenyl)-5-(acetamido)indeno[1,2-c]pyrazol-4-one;

3-(4-methoxyphenyl)-5-((4-aminophenyl)acetamido)indeno[1,2-c]pyrazol-4-one;

3-(4-pyridyl)-5-(formamido)indeno[1,2-c]pyrazol-4-one;

3-(4-pyridyl)-5-(acetamido)indeno[1,2-c]pyrazol-4-one;

3-(4-methoxyphenyl)-5-((4-aminophenyl)acetamido)indeno[1,2-c]pyrazol-4-one;

3-(4-methoxyphenyl)-5-((4-azidophenyl)acetamido)indeno[1,2-c]pyrazol-4-one;

3-(4-methoxyphenyl)-5-((4-(methoxycarbonylamino)phenyl)acetamido)indeno[1,2-c]pyrazol-4-one;

3-(4-methoxyphenyl)-5-((4-(aminomethylcarbonylamino)phenyl)acetamido)indeno[1,2-c]pyrazol-4-one;

3-(4-methoxyphenyl)-5-((4-((N,N-dimethylamino)methylcarbonylamino)phenyl)acetamido)indeno[1,2-c]pyrazol-4-one;
3-(4-methoxyphenyl)-5-((4-acetamidophenyl)acetamido)indeno[1,2-c]pyrazol-4-one;
3-(4-methoxyphenyl)-5-(pyrrolidinoacetamido)indeno[1,2-c]pyrazol-4-one;
3-(4-methoxyphenyl)-5-(morpholinoacetamido)indeno[1,2-c]pyrazol-4-one;
3-(4-methoxyphenyl)-5-(thiomnorpholinoacetainido)indeno[1,2-c]pyrazol-4-one;
3-(4-methoxyphenyl)-5-(ethylaminoacetamido)indeno[1,2-c]pyrazol-4-one;
3-(4-mnethoxyphenyl)-5-(piperidinoacetamido)indeno[1,2-c]pyrazol-4-one;
3-(4-mnethoxyphenyl)-5-(4-(aminomethyl)piperidinoacetamnido)indeno[1,2-c]pyrazol-4-one;
3-(4-methoxyphenyl)-5-(piperazinoacetamido)indeno[1,2-c]pyrazol-4-one;
3-(4-methoxyphenyl)-5-(4-methylpiperazinoacetamnido)indeno[1,2-c]pyrazol-4-one;
3-(4-methoxyphenyl)-5-(4-(2-hydroxyethyl)piperazinoacetamnido)indeno[1,2-c]pyrazol-4-one;
3-(4-methoxyphenyl)-5-(N,N-dimnethylaminoacetamnido)indeno [1,2-c]pyrazol-4-one;
3-(4-methoxyphenyl)-5-((2-hydroxyethyl)aminoacetamnido)indeno [1,2-c]pyrazol-4-one;
3-(4-methoxyphenyl)-5-(amninoacetamido)indeno[1,2-c]pyrazol-4-one;
3-(4-methoxyphenyl)-5-((2-chlorophenyl)acetamnido)indeno[1,2-c]pyrazol-4-one;
3-(4-methoxyphenyl)-5-((2,4-dichlorophenyl)acetamido)indeno[1,2-c]pyrazol-4-one;
3-(4-methoxyphenyl)-5-((3, 4-dichlorophenyl) acetamido)indeno[1,2-c]pyrazol-4-one;
3-(4-methoxyphenyl)-5-((2-methoxyphenyl) acetamido)indeno[1,2-c]pyrazol-4-one;
3-(4-dimethoxyphenyl)-5-(3-thienylacetamido)indeno[1,2-c]pyrazol-4-one;
3-(4-methoxyphenyl)-5-((3,4-methylenedioxyphenyl)acetamido)indeno[1,2-c]pyrazol-4-one;
3-(3,4-dimethoxyphenyl)-5-(acetamido)indeno[1,2-c]pyrazol-4-one;
3-(2-methoxyphenyl)-5-(acetamido)indeno[1,2-c]pyrazol-4-one;
3-(4-methoxyphenyl)-5-((2,5-dimethoxyphenyl)acetamido)indeno[1,2-c]pyrazol-4-one;
3-(4-methoxyphenyl)-5-((3,4-dimethoxyphenyl)acetamido)indeno[1,2-c]pyrazol-4-one;
3-(4-methoxyphenyl)-5-((4-methoxyphenyl)acetamido)indeno[1,2-c]pyrazol-4-one;
3-(4-methoxyphenyl)-5-((3-methoxyphenyl)acetamido)indeno[1,2-c]pyrazol-4-one;
3-(4-methoxyphenyl)-5-((4-chlorophenyl)acetamido)indeno[1,2-c]pyrazol-4-one;
3-(4-methoxyphenyl)-5-((butylcarbamoyl)amino)indeno[1,2-c]pyrazol-4-one;
3-(4-methoxyphenyl)-5-((4-aminobenzylcarbamoyl)amino)indeno[1,2-c]pyrazol-4-one;
3-(4-methoxyphenyl)-5-((4-pyridylcarbamoyl) amino)indeno[1,2-c]pyrazol-4-one;
3-(4-methoxyphenyl)-5-((phenylcarbamoyl)amino)indeno[1,2-c]pyrazol-4-one;
3-(4-methoxyphenyl)-5-(cyclobutanecarboxamido)indeno[1,2-c]pyrazol-4-one;
3-(4-methoxyphenyl)-5-(cyclopentanecarboxamido)indeno[1,2-c]pyrazol-4-one;
3-(4-methoxyphenyl)-5-(butanamido)indeno[1,2-c]pyrazol-4-one;
3-(4-methoxyphenyl)-5-(propanamido)indeno[1,2-c]pyrazol-4-one;
3-(4-methoxyphenyl)-5-(phenylacetamido)indeno[1,2-c]pyrazol-4-one;
3-(4-methoxyphenyl)-5-(2-methylpropanamido)indeno[1,2-c]pyrazol-4-one;
3-(4-methoxyphenyl)-5-(cyclopropanecarboxamido)indeno[1,2-c]pyrazol-4-one;
3-(4-methoxyphenyl)-5-(chloroacetamido)indeno[1,2-c]pyrazol-4-one;
3-(4-methoxyphenyl)-5-(4-(aminomethyl)piperidinoacetamido)-indeno[1,2-c]pyrazol-4-one;
3-(4-(N,N-dimethylamino)phenyl)-5-(morpholinoacetamido)indeno[1,2-c]pyrazol-4-one;
3-(4-(N,N-dimethylamino)phenyl)-5-(N,N-dimethylaminoacetamido)indeno[1,2-c]pyrazol-4-one;
3-(4-(trifluoromethyl)phenyl)-5-(acetamido)indeno[1,2-c]pyrazol-4-one;
3-(4-(N,N-dimethylamino)phenyl)-5-(4-methyl-piperazinoacetamido)indeno[1,2-c]pyrazol-4-one;
3-(4-(N,N-dimethylamino)phenyl)-5-(4-(aminomethyl)-piperidinoacetamido)indeno[1,2-c]pyrazol-4-one;
3-(4-(N,N-dimethylamino)phenyl)-5-(4-hydroxy-piperidinoacetamido)indeno[1,2-c]pyrazol-4-one;
3-(4-morpholinophenyl)-5-(morpholinoacetamido)indeno[1,2-c]pyrazol-4-one;
3-(4-morpholinophenyl)-5-(4-methylpiperazinoacetamido)indeno[1,2-c]pyrazol-4-one;
3-(4-morpholinophenyl)-5-(4-hydroxy-piperidinoacetamido)indeno[1,2-c]pyrazol-4-one;
3-(4-morpholinophenyl)-5-(4-(aminomethyl)-piperidinoacetamido)indeno[1,2-c]pyrazol-4-one;
3-(4-piperazinophenyl)-5-(morpholinoacetamido)indeno[1,2-c]pyrazol-4-one;
3-(4-piperazinophenyl)-5-((N,N-dimethylamino)acetamido)indeno[1,2-c]pyrazol-4-one;
3-(4-piperazinophenyl)-5-(4-methylpiperazinoacetamido)indeno[1,2-c]pyrazol-4-one;
3-(4-piperazinophenyl)-5-(4-(aminomethyl)-piperidinoacetamido)indeno[1,2-c]pyrazol-4-one;
3-(4-piperazinophenyl)-5-(carbamoylamino)indeno[1,2-c]pyrazol-4-one;
3-(4-piperazinophenyl)-5-(aminocarbamoylamino)indeno[1,2-c]pyrazol-4-one;
3-(4-piperazinophenyl)-5-(morpholinocarbamoylamino)-indeno[1,2-c]pyrazol-4-one;
3-(4-(4-methylpiperazino)phenyl)-5-(morpholinocarbamoylamino)indeno[1,2-c]pyrazol-4-one;
3-(4-(4-ethylpiperazino)phenyl)-5-(morpholinocarbamoylamino)indeno[1,2-c]pyrazol-4-one;
3-(4-(4-isopropylpiperazino)phenyl)-5-(morpholinocarbamoylamino)indeno[1,2-c]pyrazol-4-one;
3-(4-(4-t-butoxycarbonylpiperazino)phenyl)-5-(morpholinocarbamoylamino)indeno[1,2-c]pyrazol-4-one;
3-(4-(N,N-dimethylamino)phenyl)-5-((4-methylpiperazino)-carbamoylamino)indeno[1,2-c]pyrazol-4-one;
3-(c-propyl)-5-(acetamido)indeno[1,2-c]pyrazol-4-one;
3-(2-thienyl)-5-(acetamido)indeno[1,2-c]pyrazol-4-one;
3-(3-methyl-2-thienyl)-5-(acetamido)indeno[1,2-c]pyrazol-4-one;

3-(ethyl)-5-(carbamoylamino)indeno[1,2-c]pyrazol-4-one;
3-(n-propyl)-5-(carbamoylamino)aminoindeno[1,2-c]pyrazol-4-one;
3-(i-propyl)-5-(carbamoylamino)indeno[1,2-c]pyrazol-4-one;
3-(c-propyl)-5-(carbamoylamino)indeno[1,2-c]pyrazol-4-one;
3-(c-hexyl)-5-(carbamoylamino)indeno[1,2-c]pyrazol-4-one;
3-(2-thienyl)-5-(carbamoylamino)indeno[1,2-c]pyrazol-4-one;
3-(3-methyl-2-thienyl)-5-(carbamoylamino)indeno[1,2-c]pyrazol-4-one;
3-(5-methyl-2-thienyl)-5-(carbamoylamino)indeno[1,2-c]pyrazol-4-one;
3-(5-carboethoxy-2-thienyl)-5-(carbamoylamino)indeno[1,2-c]pyrazol-4-one;
3-(3-thienyl)-5-(carbamoylamino)indeno[1,2-c]pyrazol-4-one;
3-(1-methyl-3-pyrrolyl)-5-(carbamoylamino)indeno[1,2-c]pyrazol-4-one;
3-(2,5-dimethyl-3-thienyl)-5-(carbamoylamino)indeno[1,2-c]pyrazol-4-one;
3-(2-furanyl)-5-(carbamoylamino)indeno[1,2-c]pyrazol-4-one;
3-(i-propyl)-5-((N,N-dimethylaminocarbamoyl)amino)indeno[1,2-c]pyrazol-4-one;
3-(c-propyl)-5-((N,N-dimethylaminocarbamoyl)amino)indeno[1,2-c]pyrazol-4-one;
3-(c-hexyl)-5-((N,N-dimethylaminocarbamoyl)amino)indeno[1,2-c]pyrazol-4-one;
3-(2-thienyl)-5-((N,N-dimethylaminocarbamoyl)amino)indeno[1,2-c]pyrazol-4-one;
3-(5-methoxy-2-thienyl)-5-((N,N-dimethylaminocarbamoyl)amino)indeno[1,2-c]pyrazol-4-one;
3-(5-methyl-2-thienyl)-5-((N,N-dimethylaminocarbamoyl)amino)indeno[1,2-c]pyrazol-4-one;
3-(5-carboethoxy-2-thienyl)-5-((N,N-dimethylaminocarbamoyl)amino)indeno[1,2-c]pyrazol-4-one;
3-(3-thienyl)-5-((N,N-dimethylaminocarbamoyl)amino)indeno[1,2-c]pyrazol-4-one;
3-(5-chloro-3-thienyl)-5-((N,N-dimethylaminocarbamoyl)amino)indeno[1,2-c]pyrazol-4-one;
3-(2,5-dimethyl-3-thienyl)-5-((N,N-dimethylaminocarbamoyl)amino)indeno[1,2-c]pyrazol-4-one;
3-(2-furanyl)-5-((N,N-dimethylaminocarbamoyl)amino)indeno[1,2-c]pyrazol-4-one;
3-(i-propyl)-5-((4-carbamoylpiperidino)acetamido)indeno[1,2-c]pyrazol-4-one;
3-(c-hexyl)-5-((4-carbamoylpiperidino)acetamido)indeno[1,2-c]pyrazol-4-one;
3-(ethyl)-5-(4-(aminomethyl)piperidinoacetamido)indeno[1,2-c]pyrazol-4-one;
3-(i-propyl)-5-(4-(aminomethyl)piperidinoacetamido)indeno[1,2-c]pyrazol-4-one;
3-(c-propyl)-5-(4-(aminomethyl)piperidinoacetamido)indeno[1,2-c]pyrazol-4-one;
3-(c-hexyl)-5-(4-(aminomethyl)piperidinoacetamido)indeno[1,2-c]pyrazol-4-one;
3-(i-propyl)-5-((4-methylpiperazino)-carbamoylamino)indeno[1,2-c]pyrazol-4-one;
3-(5-carboethoxy-2-thienyl)-5-((4-methylpiperazino)-carbamoylamino)indeno[1,2-c]pyrazol-4-one;
3-(5-carboxyl-2-thienyl)-5-((4-methylpiperazino)-carbamoylamino)indeno[1,2-c]pyrazol-4-one;
3-(2,5-dimethyl-3-thienyl)-5-((4-methylpiperazino)-carbamoylamino)indeno[1,2-c]pyrazol-4-one;
3-(i-propyl)-5-(morpholinocarbamoylamino)indeno[1,2-c]pyrazol-4-one;
3-(1-methoxycarbonyl-4-piperidinyl)-5-(morpholinocarbamoylamino)indeno[1,2-c]pyrazol-4-one;
3-(5-methyl-2-thienyl)-5-(morpholinocarbamoylamino)indeno[1,2-c]pyrazol-4-one;
3-(5-chloro-3-thienyl)-5-(morpholinocarbamoylamino)indeno[1,2-c]pyrazol-4-one;
3-(2,5-dimethyl-3-thienyl)-5-(morpholinocarbamoylamino)indeno[1,2-c]pyrazol-4-one;
3-(5-carboethoxy-2-thienyl)-5-(morpholinylcarbamoylamino)indeno[1,2-c]pyrazol-4-one;
3-(5-carboxyl-2-thienyl)-5-(morpholinylcarbamoylamino)indeno[1,2-c]pyrazol-4-one;
3-(5-(benzylaminocarbonyl)-2-thienyl)-5-(morpholinocarbamoylamino)indeno[1,2-c]pyrazol-4-one;
3-(5-((4-methylpiperazino)carbonyl)-2-thienyl)-5-(morpholinocarbamoylamino)indeno[1,2-c]pyrazol-4-one;
3-(5-((2-(1-methyl-2-pyrrolidinyl)ethyl)aminocarbonyl)-2-thienyl)-5-(morpholinocarbamoylamino)indeno[1,2-c]pyrazol-4-one;
3-(5-((N,N-dimethylamino)aminocarbonyl)-2-thienyl-5-(morpholinocarbamoylamino)indeno[1,2-c]pyrazol-4-one;
3-(5-((2-(N,N-dimethylamino)ethyl)aminocarbonyl)-2-thienyl-5-(morpholinocarbamoylamino)indeno[1,2-c]pyrazol-4-one;
3-(5-(2-pyrrolidinoethyl)aminocarbonyl)-2-thienyl-5-(morpholinocarbamoylamino)indeno[1,2-c]pyrazol-4-one;
3-(5-(2-morpholinoethyl)aminocarbonyl)-2-thienyl)-5-(morpholinocarbamoylamino)indeno[1,2-c]pyrazol-4-one;
3-(5-(morpholinocarbonyl)-2-thienyl)-5-(morpholinocarbamoylamino)indeno[1,2-c]pyrazol-4-one;
3-(5-((3-(2-pyrrolidon-1-yl)propyl)aminocarbonyl)-2-thienyl-5-(morpholinocarbamoylamino)indeno[1,2-c]pyrazol-4-one;
3-(5-((2-(3-pyridyl)ethyl)aminocarbonyl)-2-thienyl)-5-(morpholinocarbamoylamino)indeno[1,2-c]pyrazol-4-one;
3-(5-((3-(1-imidazolyl)propyl)aminocarbonyl)-2-thienyl)-5-(morpholinocarbamoylamino)indeno[1,2-c]pyrazol-4-one;
3-(5-((2-(2-pyridyl)ethyl)aminocarbonyl)-2-thienyl)-5-(morpholinocarbamoylamino)indeno[1,2-c]pyrazol-4-one;
3-(5-((2-pyridyl)methyl)aminocarbonyl)-2-thienyl)-5-(morpholinocarbamoylamino)indeno[1,2-c]pyrazol-4-one;
3-(5-((2-piperidinoethyl)aminocarbonyl)-2-thienyl)-5-(morpholinocarbamoylamino)indeno[1,2-c]pyrazol-4-one;
3-(4-piperazinophenyl)-5-((N,N-dimethylamino)carbamoylamino)-indeno[1,2-c]pyrazol-4-one;
3-(4-(4-methylpiperazino)phenyl)-5-((N,N-dimethylamino)-carbamoylamino)indeno[1,2-c]pyrazol-4-one;
3-(4-piperazinophenyl)-5-((4-methylpiperazino)carbamoylamino)-indeno[1,2-c]pyrazol-4-one;

3-(4-(4-methylpiperazino)phenyl)-5-((4-methylpiperazino)-carbamoylamino)indeno[1,2-c]pyrazol-4-one;

3-(4-(4-ethylpiperazino)phenyl)-5-((4-methylpiperazino)-carbamoylamino)indeno[1,2-c]pyrazol-4-one;

3-(4-(4-isopropylpiperazino)phenyl)-5-((4-methylpiperazino)-carbamoylamino)indeno[1,2-c]pyrazol-4-one;

3-(4-piperazinophenyl)-5-((2,6-dimethylpiperidino)-carbamoylamino)indeno[1,2-c]pyrazol-4-one;

3-(4-piperazinophenyl)-5-((4-(2-hydroxyethyl)piperazino)-carbamoylamino)indeno[1,2-c]pyrazol-4-one;

3-(4-piperazinophenyl)-5-((2(R)-(methoxymethyl)pyrrolidino)-carbamoylamino)indeno[1,2-c]pyrazol-4-one;

3-(4-piperazinophenyl)-5-((2(S)-(methoxymethyl)pyrrolidino)-carbamoylamino)indeno[1,2-c]pyrazol-4-one;

3-(4-piperazinophenyl)-5-((2(R)-(1-methoxy-1-methylethyl)-pyrrolidino)carbamoylamino)indeno[1,2-c]pyrazol-4-one;

3-(4-piperazinophenyl)-5-((2(S)-(1-methoxy-1-methylethyl)-pyrrolidino)carbamoylamino)indeno[1,2-c]pyrazol-4-one;

3-(4-piperazinophenyl)-5-((2(R)-(hydroxymethyl)-pyrrolidino)carbamoylamino)indeno[1,2-c]pyrazol-4-one;

3-(4-piperazinophenyl)-5-((2(S)-(hydroxymethyl)-pyrrolidino)carbamoylamino)indeno[1,2-c]pyrazol-4-one;

3-(4-piperazinophenyl)-5-((2(R)-(benzyloxymethyl)-pyrrolidino)carbamoylamino)indeno[1,2-c]pyrazol-4-one;

3-(4-piperazinophenyl)-5-((2(S)-(benzyloxymethyl)-pyrrolidino)carbamoylamino)indeno[1,2-c]pyrazol-4-one;

3-(4-(3-methylpiperazino)phenyl)-5-(morpholinocarbamoylamino)indeno[1,2-c]pyrazol-4-one;

3-(4-(cis-3,5-dimethylpiperazino)phenyl)-5-(morpholinocarbamoylamino)indeno[1,2-c]pyrazol-4-one;

3-(4-(cis-3,4,5-trimethylpiperazino)phenyl)-5-(morpholinocarbamoylamino)indeno[1,2-c]pyrazol-4-one;

3-(4-(4-isopropylpiperazino)-2-methylphenyl)-5-(morpholinocarbamoylamino)indeno[1,2-c]pyrazol-4-one;

3-(4-homopiperazinophenyl)-5-(morpholinocarbamoylamino)-indeno[1,2-c]pyrazol-4-one;

3-(4-(4-methylhomopiperazino)phenyl)-5-(morpholinocarbamoylamino)indeno[1,2-c]pyrazol-4-one;

3-(4-(4-ethylhomopiperazino)phenyl)-5-(morpholinocarbamoylamino)indeno[1,2-c]pyrazol-4-one;

3-(4-(4-isopropylhomopiperazino)phenyl)-5-(morpholinocarbamoylamino)indeno[1,2-c]pyrazol-4-one;

3-(4-homopiperazino-2-methylphenyl)-5-(morpholinocarbamoylamino)indeno[1,2-c]pyrazol-4-one;

3-(4-(4-ethylhomopiperazino)-2-methylphenyl)-5-(morpholinocarbamoylamino)indeno[1,2-c]pyrazol-4-one;

3-(4-(4-isopropylhomopiperazino)-2-methylphenyl)-5-(morpholinocarbamoylamino)indeno[1,2-c]pyrazol-4-one;

3-(4-(4-(N,N-dimethylamino)piperidino)phenyl)-5-(morpholinocarbamoylamino)indeno[1,2-c]pyrazol-4-one;

3-(4-(4-(N,N-diethylamino)piperidino)phenyl)-5-(morpholinocarbamoylamino)indeno[1,2-c]pyrazol-4-one;

3-(4-(4-piperidinopiperidino)phenyl)-5-(morpholinocarbamoylamino)indeno[1,2-c]pyrazol-4-one;

3-(4-(4-pyrrolidinopiperidino)phenyl)-5-(morpholinocarbamoylamino)indeno[1,2-c]pyrazol-4-one;

3-(4-(4-(N,N-diethylamino)piperidino)phenyl)-5-(morpholinocarbamoylamino)indeno[1,2-c]pyrazol-4-one;

3-(4-methoxyphenyl)-5-((4-methylpiperazino)-thionocarbamoylamino)indeno[1,2-c]pyrazol-4-one;

3-(1-methyl-3-pyrrolyl)-5-(carbamoylamino)indeno[1,2-c]pyrazol-4-one;

3-(5-pyrrolidinoaminocarbonyl-2-thienyl)-5-(morpholinocarbamoylamino)indeno[1,2-c]pyrazol-4-one;

3-(5-piperidinoaminocarbonyl-2-thienyl)-5-(morpholinocarbamoylamino)indeno[1,2-c]pyrazol-4-one;

3-(5-piperidinocarbonyl-2-thienyl)-5-(morpholinocarbamoylamino)indeno[1,2-c]pyrazol-4-one;

3-(5-piperazinocarbonyl-2-thienyl)-5-(morpholinocarbamoylamino)indeno[1,2-c]pyrazol-4-one;

3-(5-(4-methylpiperazinocarbonyl)-2-thienyl)-5-(morpholinocarbamoylamino)indeno[1,2-c]pyrazol-4-one;

3-(5-(4-ethylpiperazinocarbonyl)-2-thienyl)-5-(morpholinocarbamoylamino)indeno[1,2-c]pyrazol-4-one;

3-(5-(4-(2-hydroxyethyl)piperazinocarbonyl)-2-thienyl)-5-(morpholinocarbamoylamino)indeno[1,2-c]pyrazol-4-one;

3-(5-(4-(cyclopropylmethyl)piperazinocarbonyl)-2-thienyl)-5-(morpholinocarbamoylamino)indeno[1,2-c]pyrazol-4-one;

3-(5-(4-(t-butoxycarbonyl)piperazinocarbonyl)-2-thienyl)-5-(morpholinocarbamoylamino)indeno[1,2-c]pyrazol-4-one;

3-(5-(4-(2-pyridyl)piperazinocarbonyl)-2-thienyl)-5-(morpholinocarbamoylamino)indeno[1,2-c]pyrazol-4-one;

3-(5-(((1S,4S)-(+)-2,5-diazabicyclo[2.2.1]heptyl)carbonyl)-2-thienyl)-5-(morpholinocarbamoylamino)indeno[1,2-c]pyrazol-4-one;

3-(5-(((1S,4S)-(+)-2-methyl-2,5-diazabicyclo[2.2.1]heptyl)carbonyl)-2-thienyl)-5-(morpholinocarbamoylamino)indeno[1,2-c]pyrazol-4-one;

3-(5-(4-(N,N-dimethylamino)piperidinocarbonyl)-2-thienyl)-5-(morpholinocarbamoylamino)indeno[1,2-c]pyrazol-4-one;

3-(5-(4-pyrrolidinopiperidinocarbonyl)-2-thienyl)-5-(morpholinocarbamoylamino)indeno[1,2-c]pyrazol-4-one;

3-(5-(4-piperidinopiperidinocarbonyl)-2-thienyl)-5-(morpholinocarbamoylamino)indeno[1,2-c]pyrazol-4-one;

3-(5-cyclohexylaminocarbonyl-2-thienyl)-5-(morpholinocarbamoylamino)indeno[1,2-c]pyrazol-4-one;

3-(5-(4-piperidylaminocarbonyl)-2-thienyl)-5-(morpholinocarbamoylamino)indeno[1,2-c]pyrazol-4-one;

3-(5-((1-(t-butoxycarboxyl)piperidin-4-yl)aminocarbonyl)-2-thienyl)-5-(morpholinocarbamoylamino)indeno[1,2-c]pyrazol-4-one;

3-(5-(4-(1-methylpiperidin-4-yl)methylaminocarbonyl)-2-thienyl)-5-(morpholinocarbamoylamino)indeno[1,2-c]pyrazol-4-one;

3-(5-(3-(N,N-dimethylamino)piperidinocarbonyl)-2-thienyl)-5-(morpholinocarbamoylamino)indeno[1,2-c]pyrazol-4-one;

3-(5-(3-p-toluenesulfonylamino)piperidinocarbonyl-2-thienyl)-5-(morpholinocarbamoylamino)indeno[1,2-c]pyrazol-4-one;

3-(5-(3-hydroxypiperidinocarbonyl)-2-thienyl)-5-(morpholinocarbamoylamino)indeno[1,2-c]pyrazol-4-one;

3-(5-((3-piperidyl)aminocarbonyl)-2-thienyl)-5-(morpholinocarbamoylamino)indeno[1,2-c]pyrazol-4-one;

3-(5-((3-quinuclidyl)aminocarbonyl)-2-thienyl)-5-(morpholinocarbamoylamino)indeno[1,2-c]pyrazol-4-one;

3-(5-((3-aminocyclohexyl)aminocarbonyl)-2-thienyl)-5-(morpholinocarbamoylamino)indeno[1,2-c]pyrazol-4-one;

3-(5-((3-(t-butoxycarbonylamino)cyclohexyl)aminocarbonyl)-2-thienyl)-5-(morpholinocarbamoylamino)indeno[1,2-c]pyrazol-4-one;

3-(5-(2-(N,N-dimethylaminomethyl)piperidinocarbonyl)-2-thienyl)-5-(morpholinocarbamoylamino)indeno[1,2-c]pyrazol-4-one;

3-(5-(2-(N,N-diethylaminomethyl)piperidinocarbonyl)-2-thienyl)-5-(morpholinocarbamoylamino)indeno[1,2-c]pyrazol-4-one;

3-(5-pyrrolidinocarbonyl-2-thienyl)-5-(morpholinocarbamoylamino)indeno[1,2-c]pyrazol-4-one;

3-(5-(3-aminopyrrolidinocarbonyl)-2-thienyl)-5-(morpholinocarbamoylamino)indeno[1,2-c]pyrazol-4-one;

3-(5-(3(S)-N-methylamino)pyrrolidinocarbonyl-2-thienyl)-5-(morpholinocarbamoylamino)indeno[1,2-c]pyrazol-4-one;

3-(5-(3(S)-acetamidopyrrolidinocarbonyl)-2-thienyl)-5-(morpholinocarbamoylamino)indeno[1,2-c]pyrazol-4-one;

3-(5-(3(S)-(N-methylacetamido)pyrrolidinocarbonyl)-2-thienyl)-5-(morpholinocarbamoylamino)indeno[1,2-c]pyrazol-4-one;

3-(5-(3(S)-(N-methyl-t-butoxycarbonylamino)pyrrolidinocarbonyl)-2-thienyl)-5-(morpholinocarbamoylamino)indeno[1,2-c]pyrazol-4-one;

3-(5-(3-(N,N-dimethylamino)pyrrolidinocarbonyl)-2-thienyl)-5-(morpholinocarbamoylamino)indeno[1,2-c]pyrazol-4-one;

3-(5-(3(R)-(N,N-dimethylamino)pyrrolidinocarbonyl)-2-thienyl)-5-(morpholinocarbamoylamino)indeno[1,2-c]pyrazol-4-one;

3-(5-(3(S)-(N,N-dimethylamino)pyrrolidinocarbonyl)-2-thienyl)-5-(morpholinocarbamoylamino)indeno[1,2-c]pyrazol-4-one;

3-(5-((1-methylpyrrolidin-3-yl)methylaminocarbonyl)-2-thienyl)-5-(morpholinocarbamoylamino)indeno[1,2-c]pyrazol-4-one;

3-(5-(2(R)-(pyrrolidinomethyl)pyrrolidinocarbonyl)-2-thienyl)-5-(morpholinocarbamoylamino)indeno[1,2-c]pyrazol-4-one;

3-(5-(2(S)-(hydroxymethyl)pyrrolidinocarbonyl)-2-thienyl)-5-(morpholinocarbamoylamino)indeno[1,2-c]pyrazol-4-one;

3-(5-(2(R)-(methoxymethyl)pyrrolidinocarbonyl)-2-thienyl)-5-(morpholinocarbamoylamino)indeno[1,2-c]pyrazol-4-one;

3-(5-(2(S)-(phenylaminomethyl)pyrrolidinocarbonyl)-2-thienyl)-5-(morpholinocarbamoylamino)indeno[1,2-c]pyrazol-4-one;

3-(5-(2(R)-(methoxymethyl)pyrrolidinoaminocarbonyl)-2-thienyl)-5-(morpholinocarbamoylamino)indeno[1,2-c]pyrazol-4-one;

3-(5-homopiperidinocarbonyl-2-thienyl)-5-(morpholinocarbamoylamino)indeno[1,2-c]pyrazol-4-one;

3-(5-homopiperazinocarbonyl-2-thienyl)-5-(morpholinocarbamoylamino)indeno[1,2-c]pyrazol-4-one;

3-(5-(4-methylhomopiperazinocarbonyl)-2-thienyl)-5-(morpholinocarbamoylamino)indeno[1,2-c]pyrazol-4-one;

3-(5-(4-ethylhomopiperazinocarbonyl)-2-thienyl)-5-(morpholinocarbamoylamino)indeno[1,2-c]pyrazol-4-one;

3-(5-(4-(cyclopropylmethyl)homopiperazinocarbonyl)-2-thienyl)-5-(morpholinocarbamoylamino)indeno[1,2-c]pyrazol-4-one;

3-(5-(4-(t-butoxycarbonyl)homopiperazinocarbonyl)-2-thienyl)-5-(morpholinocarbamoylamino)indeno[1,2-c]pyrazol-4-one;

3-(5-(4-acetylhomopiperazinocarbonyl)-2-thienyl)-5-(morpholinocarbamoylamino)indeno[1,2-c]pyrazol-4-one;

3-(5-((4-methylaminophenyl)aminocarbonyl)-2-thienyl)-5-(morpholinocarbamoylamino)indeno[1,2-c]pyrazol-4-one;

3-(5-((4-acetamidophenyl)aminocarbonyl)-2-thienyl)-5-(morpholinocarbamoylamino)indeno[1,2-c]pyrazol-4-one;

3-(5-(4-(diethylamino)phenylaminocarbonyl)-2-thienyl)-5-(morpholinocarbamoylamino)indeno[1,2-c]pyrazol-4-one;

3-(5-((1-methyl-3-cyclopropylpyrazo-5-yl)aminocarbonyl)-2-thienyl)-5-(morpholinocarbamoylamino)indeno[1,2-c]pyrazol-4-one;

3-(1-methyl-3-pyrrolyl)-5-(morpholinocarbamoylamino)indeno[1,2-c]pyrazol-4-one;

3-(5-carboethoxy-2-thienyl)-5-(2(R)-(methoxymethyl)pyrrolidinocarbamoylamino)indeno[1,2-c]pyrazol-4-one;

3-(5-carboxyl-2-thienyl)-5-(2(R)-(methoxymethyl)pyrrolidinocarbamoylamino)indeno[1,2-c]pyrazol-4-one;

3-(5-(4-methylpiperazinocarbonyl)-2-thienyl)-5-(2(R)-(methoxymethyl)pyrrolidinocarbamoylamino)indeno[1,2-c]pyrazol-4-one;

3-(5-piperazinocarbonyl-2-thienyl)-5-(2(R)-(methoxymethyl)pyrrolidinocarbamoylamino)indeno[1,2-c]pyrazol-4-one;

3-(5-(4-(t-butoxycarbonyl)piperazinocarbonyl)-2-thienyl)-5-(2(R)-(methoxymethyl)pyrrolidinocarbamoylamino)indeno[1,2-c]pyrazol-4-one;

3-(5-(4-methylhomopiperazinocarbonyl)-2-thienyl)-5-(2(R)-(methoxymethyl)pyrrolidinocarbamoylamino)indeno[1,2-c]pyrazol-4-one;

3-(5-homopiperazinocarbonyl-2-thienyl)-5-(2(R)-(methoxymethyl)pyrrolidinocarbamoylamino)indeno[1,2-c]pyrazol-4-one;

3-(5-(4-(t-butoxycarbonyl)homopiperazinocarbonyl)-2-thienyl)-5-(2(R)-(methoxymethyl)pyrrolidinocarbamoylamino)indeno[1,2-c]pyrazol-4-one;
3-(c-propyl)-5-(4-carbamoylpiperidinoacetamido)indeno[1,2-c]pyrazol-4-one;
3-ethyl-5-(4-methylpiperazinocarbamoylamino)indeno[1,2-c]pyrazol-4-one;
3-(c-propyl)-5-(4-methylpiperazinocarbamoylamino)indeno[1,2-c]pyrazol-4-one;
3-(c-hexyl)-5-(4-methylpiperazinocarbamoylamino)indeno[1,2-c]pyrazol-4-one;
3-ethyl-5-(morpholinocarbamoylamino)indeno[1,2-c]pyrazol-4-one;
3-(c-propyl)-5-(morpholinocarbamoylamino)indeno[1,2-c]pyrazol-4-one;
3-(c-hexyl)-5-(morpholinocarbamoylamino)indeno[1,2-c]pyrazol-4-one;
3-(1-ethoxycarbonylpiperidin-4-yl)-5-(morpholinocarbamoylamino)indeno[1,2-c]pyrazol-4-one;
3-(1-phenoxycarbonylpiperidin-4-yl)-5-(morpholinocarbamoylamino)indeno[1,2-c]pyrazol-4-one;
3-(1-(imidazol-1-ylcarbonyl)piperidin-4-yl)-5-(morpholinocarbamoylamino)indeno[1,2-c]pyrazol-4-one;
3-(1-(2-thienylcarbonyl)piperidin-4-yl)-5-(morpholinocarbamoylamino)indeno[1,2-c]pyrazol-4-one;
3-(1-carbamoylpiperidin-4-yl)-5-(morpholinocarbamoylamino)indeno[1,2-c]pyrazol-4-one;
3-(1-(ethylcarbamoyl)piperidin-4-yl)-5-(morpholinocarbamoylamino)indeno[1,2-c]pyrazol-4-one;
3-(1-(2-(1-methylpyrrolidin-2-yl)ethylaminocarbamoyl)piperidin-4-yl)-5-(morpholinocarbamoylamino)indeno[1,2-c]pyrazol-4-one;
3-(1-(4-(dimethylamino)piperidinocarbonyl)piperidin-4-yl)-5-(morpholinocarbamoylamino)indeno[1,2-c]pyrazol-4-one;
3-(1-(piperazinocarbonyl)piperidin-4-yl)-5-(morpholinocarbamoylamino)indeno[1,2-c]pyrazol-4-one;
3-(1-(4-(t-butoxycarbonyl)piperazinocarbonyl)piperidin-4-yl)-5-(morpholinocarbamoylamino)indeno[1,2-c]pyrazol-4-one;
3-(1-(((1S,4S)-(+)-2,5-diazabicyclo[2.2.1]hept-2-yl)carbonyl)piperidin-4-yl)-5-(morpholinocarbamoylamino)indeno[1,2-c]pyrazol-4-one;
3-(1-(((1S,4S)-(+)-5-methyl-2,5-diazabicyclo[2.2.1]hept-2-yl)carbonyl)piperidin-4-yl)-5-(morpholinocarbamoylamino)indeno[1,2-c]pyrazol-4-one;
3-(1-(3-aminopropylcarbonyl)piperidin-4-yl)-5-(morpholinocarbamoylamino)indeno[1,2-c]pyrazol-4-one;
3-(1-(3-(dimethylamino)propylcarbonyl)piperidin-4-yl)-5-(morpholinocarbamoylamino)indeno[1,2-c]pyrazol-4-one;
3-(1-(3-(t-butoxycarbonylamino)propylcarbonyl)piperidin-4-yl)-5-(morpholinocarbamoylamino)indeno[1,2-c]pyrazol-4-one;
3-(1-(4-aminobutylcarbonyl)piperidin-4-yl)-5-(morpholinocarbamoylamino)indeno[1,2-c]pyrazol-4-one;
3-(1-(4-(dimethylamino)butylcarbonyl)piperidin-4-yl)-5-(morpholinocarbamoylamino)indeno[1,2-c]pyrazol-4-one;
3-(1-(4-(t-butoxycarbonylamino)butylcarbonyl)piperidin-4-yl)-5-(morpholinocarbamoylamino)indeno[1,2-c]pyrazol-4-one;
3-(1-((1-methylpiperidin-4-yl)carbonyl)piperidin-4-yl)-5-(morpholinocarbamoylamino)indeno[1,2-c]pyrazol-4-one;
3-(1-((1-(t-butoxycarbonyl)piperidin-4-yl)carbonyl)piperidin-4-yl)-5-(morpholinocarbamoylamino)indeno[1,2-c]pyrazol-4-one;
3-(1-(cis-4-aminocyclohexylcarbonyl)piperidin-4-yl)-5-(morpholinocarbamoylamino)indeno[1,2-c]pyrazol-4-one;
3-(1-(4-aminocyclohexylcarbonyl)piperidin-4-yl)-5-(morpholinocarbamoylamino)indeno[1,2-c]pyrazol-4-one;
3-(1-(cis-4-(dimethylamino)cyclohexylcarbonyl)piperidin-4-yl)-5-(morpholinocarbamoylamino)indeno[1,2-c]pyrazol-4-one;
3-(1-(4-(t-butoxycarbonylamino)cyclohexylcarbonyl)piperidin-4-yl)-5-(morpholinocarbamoylamino)indeno[1,2-c]pyrazol-4-one;
3-(1-(trans-4-(t-butoxycarbonylamino)cyclohexylcarbonyl)piperidin-4-yl)-5-(morpholinocarbamoylamino)indeno[1,2-c]pyrazol-4-one;
3-(1-(piperidin-3-ylcarbonyl)piperidin-4-yl)-5-(morpholinocarbamoylamino)indeno[1,2-c]pyrazol-4-one;
3-(1-(1-methylpiperidin-3-ylcarbonyl)piperidin-4-yl)-5-(morpholinocarbamoylamino)indeno[1,2-c]pyrazol-4-one;
3-(1-(1-(t-butoxycarbonyl)piperidin-3-ylcarbonyl)piperidin-4-yl)-5-(morpholinocarbamoylamino)indeno[1,2-c]pyrazol-4-one;
3-(1-(3-aminocyclohexylcarbonyl)piperidin-4-yl)-5-(morpholinocarbamoylamino)indeno[1,2-c]pyrazol-4-one;
3-(1-(3-(dimethylamino)cyclohexylcarbonyl)piperidin-4-yl)-5-(morpholinocarbamoylamino)indeno[1,2-c]pyrazol-4-one;
3-(1-(trans-4-methoxycyclohexylcarbonyl)piperidin-4-yl)-5-(morpholinocarbamoylamino)indeno[1,2-c]pyrazol-4-one;
3-(1-(cis-4-methoxycyclohexylcarbonyl)piperidin-4-yl)-5-(morpholinocarbamoylamino)indeno[1,2-c]pyrazol-4-one;
3-(1-(4-aminobenzylcarbonyl)piperidin-4-yl)-5-(morpholinocarbamoylamino)indeno[1,2-c]pyrazol-4-one;
3-(1-(4-(dimethylamino)benzylcarbonyl)piperidin-4-yl)-5-(morpholinocarbamoylamino)indeno[1,2-c]pyrazol-4-one;
3-(1-(4-(t-butoxycarbonylamino)benzylcarbonyl)piperidin-4-yl)-5-(morpholinocarbamoylamino)indeno[1,2-c]pyrazol-4-one;
3-(1-(4-aminophenylcarbonyl)piperidin-4-yl)-5-(morpholinocarbamoylamino)indeno[1,2-c]pyrazol-4-one;
3-(1-(4-(dimethylamino)phenylcarbonyl)piperidin-4-yl)-5-(morpholinocarbamoylamino)indeno[1,2-c]pyrazol-4-one;
3-(1-(4-(t-butoxycarbonylamino)phenylcarbonyl)piperidin-4-yl)-5-(morpholinocarbamoylamino)indeno[1,2-c]pyrazol-4-one;
3-(trans-4-carboxylcyclohexyl)-5-(morpholinocarbamoylamino)indeno[1,2-c]pyrazol-4-one;
3-(trans-4-(methoxycarbonyl)cyclohexyl)-5-(morpholinocarbamoylamino)indeno[1,2-c]pyrazol-4-one;

3-(trans-4-(3-(dimethylamino)pyrrolidinocarbonyl) cyclohexyl)-5-(morpholinocarbamoylamino)indeno[1,2-c]pyrazol-4-one;

3-(trans-4-(piperazinocarbonyl)cyclohexyl)-5-(morpholinocarbamoylamino)indeno[1,2-c]pyrazol-4-one;

3-(trans-4-(4-methylpiperazinocarbonyl)cyclohexyl)-5-(morpholinocarbamoylamino)indeno[1,2-c]pyrazol-4-one;

3-(trans-4-(homopiperazinocarbonyl)cyclohexyl)-5-(morpholinocarbamoylamino)indeno[1,2-c]pyrazol-4-one;

3-(trans-4-(4-methylhomopiperazinocarbonyl)cyclohexyl)-5-(morpholinocarbamoylamino)indeno[1,2-c]pyrazol-4-one; or pharmaceutically acceptable salt form thereof.

[37] In another embodiment, the invention describes novel compounds of embodiment [1], selected from:

3-(4-piperazinophenyl)-5-(morpholinocarbamoylamino)-indeno[1,2-c]pyrazol-4-one;

3-(4-(4-methylpiperazino)phenyl)-5-(morpholinocarbamoylamino)indeno[1,2-c]pyrazol-4-one;

3-(4-(4-ethylpiperazino)phenyl)-5-(morpholinocarbamoylamino)indeno[1,2-c]pyrazol-4-one;

3-(4-(4-isopropylpiperazino)phenyl)-5-(morpholinocarbamoylamino)indeno[1,2-c]pyrazol-4-one;

3-(4-piperazinophenyl)-5-((N,N-dimethylamino) carbamoylamino)-indeno[1,2-c]pyrazol-4-one;

3-(4-(4-methylpiperazino)phenyl)-5-((N,N-dimethylamino)-carbamoylamino)indeno[1,2-c]pyrazol-4-one;

3-(4-piperazinophenyl)-5-((4-methylpiperazino) carbamoylamino)-indeno[1,2-c]pyrazol-4-one;

3-(4-(4-methylpiperazino)phenyl)-5-((4-methylpiperazino)-carbamoylamino)indeno[1,2-c]pyrazol-4-one;

3-(4-(4-ethylpiperazino)phenyl)-5-((4-methylpiperazino)-carbamoylamino)indeno[1,2-c]pyrazol-4-one;

3-(4-(4-isopropylpiperazino)phenyl)-5-((4-methylpiperazino)-carbamoylamino)indeno[1,2-c] pyrazol-4-one;

3-(4-piperazinophenyl)-5-((2(R)-(methoxymethyl) pyrrolidino)-carbamoylamino)indeno[1,2-c]pyrazol-4-one;

3-(4-piperazinophenyl)-5-((2(R)-(1-methoxy-1-methylethyl)-pyrrolidino)carbamoylamino)indeno[1,2-c] pyrazol-4-one;

3-(4-homopiperazinophenyl)-5-(morpholinocarbamoylamino)indeno[1,2-c]pyrazol-4-one;

3-(4-(4-methylhomopiperazino)phenyl)-5-(morpholinocarbamoylamino)indeno[1,2-c]pyrazol-4-one;

3-(4-(4-ethylhomopiperazino)phenyl)-5-(morpholinocarbamoylamino)indeno[1,2-c]pyrazol-4-one;

3-(4-(4-isopropylhomopiperazino)phenyl)-5-(morpholinocarbamoylamino)indeno[1,2-c]pyrazol-4-one;

3-(4-(4-(N,N-dimethylamino)piperidino)phenyl)-5-(morpholinocarbamoylamino)indeno[1,2-c]pyrazol-4-one;

3-(4-(4-(N,N-diethylamino)piperidino)phenyl)-5-(morpholinocarbamoylamino)indeno[1,2-c]pyrazol-4-one;

3-(4-(4-piperidinopiperidino)phenyl)-5-(morpholinocarbamoylamino)indeno[1,2-c]pyrazol-4-one;

3-(4-(4-pyrrolidinopiperidino)phenyl)-5-(morpholinocarbamoylamino)indeno[1,2-c]pyrazol-4-one;

3-(2,4-dimethylthiazol-5-yl)-5-(carbamoylamino)indeno[1,2-c]pyrazol-4-one;

3-(2,4-dimethylthiazol-5-yl)-5-(morpholinocarbamoylamino)indeno[1,2-c]pyrazol-4-one;

3-(2,4-dimethylthiazol-5-yl)-5-((1-methyl-1-phenylamino) carbamoylamino)indeno[1,2-c]pyrazol-4-one;

3-(2,4-dimethylthiazol-5-yl)-5-((2,6-dimethylpiperidino) carbamoylamino)indeno[1,2-c]pyrazol-4-one; and 3-(2,4-dimethylthiazol-5-yl)-5-((4-methylpiperazino) carbamoylamino)indeno[1,2-c]pyrazol-4-one; or pharmaceutically acceptable salt form thereof.

[38] In another embodiment, the invention describes a pharmaceutical composition, comprising a pharmaceutically acceptable carrier, a compound according to embodiment [1] or a pharmaceutically acceptable salt or prodrug form thereof, and a cytostatic or cytotoxic agent.

[39] In another embodiment, the invention describes a method of treating a cell proliferative disease associated with CDK activity in a patient in need thereof, comprising administrering to said patient a pharmaceutically effective amount of a compound according to embodiment [1], or a pharmaceutically acceptable salt or prodrug form thereof, wherein the proliferative diseases is selected from the group consisting of: Alzheimer's disease, viral infections, autoimmune diseases, fungal disease, cancer, psoriasis, vascular smooth cell proliferation associated with atherosclerosis, pulmonary fibrosis, arthritis glomerulonephritis, neurodegenerative disorders and post-surgical stenosis and restenosis.

[40] In another embodiment, the invention describes a method of treating cancer associated with CDK activity in a patient in need thereof, comprising administrering to said patient a pharmaceutically effective amount of a compound according to embodiment [1], or a pharmaceutically acceptable salt or prodrug form thereof, wherein the cancer is selected from the group consisting of: carcinoma such as bladder, breast, colon, kidney, liver, lung, including small cell lung cancer, esophagus, gall-bladder, ovary, pancreas, stomach, cervix, thyroid, prostate, and skin, including squamous cell carcinoma; hematopoietic tumors of lymphoid lineage, including leukemia, acute lymphocytic leukemia, acute lymphoblastic leukemia, B-cell lymphoma, T-cell-lymphoma, Hodgkin's lymphoma, non-Hodgkin's lymphoma, hairy cell lymphoma and Burkett's lymphoma; hematopoietic tumors of myeloid lineage, including acute and chronic myelogenous leukemias, myelodysplastic syndrome and promyelocytic leukemia; tumors of mesenchymal origin, including fibrosarcoma and rhabdomyosarcoma; tumors of the central and peripheral nervous system, including astrocytoma, neuroblastoma, glioma and schwannomas; other tumors, including melanoma, seminoma, teratocarcinoma, osteosarcoma, xenoderoma pigmentosum, keratoctanthoma, thyroid follicular cancer and Kaposi's sarcoma.

[41] In another embodiment, the invention describes a method of treating a disease associated with apoptosis in a patient in need thereof, comprising administrering to said patient a pharmaceutically effective amount of a compound according to embodiment [1], or a pharmaceutically acceptable salt or prodrug form thereof, wherein the disease associated with apoptosis is selected from the group consisting of: cancer, viral infections, autoimmune diseases and neurodegenerative disorder.

[42] In another embodiment, the invention describes a method of inhibiting tumor angiogenesis and metastasis in a patient in need thereof, comprising administrering to said patient a pharmaceutically effective amount of a compound according to embodiment [1], or a pharmaceutically acceptable salt or prodrug form thereof.

[43] In another embodiment, the invention describes a method of modulating the level of cellular RNA and DNA synthesis in a patient in need thereof, comprising administering to said patient a CDK inhibitory effective amount of a compound according to embodiment [1], or a pharmaceutically acceptable salt or prodrug form thereof.

[44] In another embodiment, the invention describes a method of treating viral infections in a patient in need thereof, comprising administering to said patient a CDK inhibitory effective amount of a compound according to embodiment [1], or a pharmaceutically acceptable salt or prodrug form thereof, wherein the viral infections is selected from the group consiting of HIV, human papilloma virus, herpesvirus, poxvirus, Epstein-Barr virus, Sindbis virus and adenovirus.

[45] In another embodiment, the invention describes a method of chemopreventing cancer in a patient, comprising administering to said patient in need thereof, a CDK inhibitory effective amount of a compound according to embodiment [1], or a pharmaceutically acceptable salt or prodrug form thereof.

[46] In another embodiment, the invention describes a method of inhibiting CDK activity comprising combining an effective amount of a compound according to embodiment [1], with a composition containing CDK.

[47] In another embodiment, the invention describes a method of treating cancer associated with CDK activity in a patient in need thereof, comprising administrering to said patient a pharmaceutically effective amount of a compound according to embodiment [1], or a pharmaceutically acceptable salt or prodrug form thereof, in combination (administered together or sequentially) with known anti-cancer treatments such as radiation therapy or with cytostatic or cytotoxic agents, wherein such agents are selected from the group consisting of: DNA interactive agents, such as cisplatin or doxorubicin; topoisomerase II inhibitors, such as etoposide; topoisomerase I inhibitors such as CPT-11 or topotecan; tubulin interacting agents, such as paclitaxel, docetaxel or the epothilones; hormonal agents, such as tamoxifen; thymidilate synthase inhibitors, such as 5-fluorouracil; and anti-metabolites, such as methoxtrexate.

[48] In another embodiment, the invention describes a method treating cell proliferative diseases associated with CDK activity in a patient in need thereof, comprising administrering to said patient a pharmaceutically effective amount of a compound according to embodiment [1], or a pharmaceutically acceptable salt or prodrug form thereof, in combination (administered together or sequentially) with known anti-proliferating agents selected from the group consisting of:, altretamine, busulfan, chlorambucil, cyclophosphamide, ifosfamide, mechlorethamine, melphalan, thiotepa, cladribine, fluorouracil, floxuridine, gemcitabine, thioguanine, pentostatin, methotrexate, 6-mercaptopurine, cytarabine, carmustine, lomustine, streptozotocin, carboplatin, cisplatin, oxaliplatin, iproplatin, tetraplatin, lobaplatin, JM216, JM335, fludarabine, aminoglutethimide, flutamide, goserelin, leuprolide, megestrol acetate, cyproterone acetate, tamoxifen, anastrozole, bicalutamide, dexamethasone, diethylstilbestrol, prednisone, bleomycin, dactinomycin, daunorubicin, doxirubicin, idarubicin, mitoxantrone, losoxantrone, mitomycin-c, plicamycin, paclitaxel, docetaxel, CPT-11, epothilones, topotecan, irinotecan, 9-amino camptothecan, 9-nitro camptothecan, GS-211, etoposide, teniposide, vinblastine, vincristine, vinorelbine, procarbazine, asparaginase, pegaspargase, methoxtrexate, octreotide, estramustine, and hydroxyurea.

[49] In another embodiment, the invention describes a method of inhibiting CDK1 activity, comprising adminsitering to a patient in need thereof an efective CDK1 inhibitory amount of a compound according to embodiment [1], or a pharmaceutically acceptable salt or prodrug form thereof.

[50] In another embodiment, the invention describes a method of inhibiting CDK2 activity, comprising adminsitering to a patient in need thereof an efective CDK2 inhibitory amount of a compound according to embodiment [1], or a pharmaceutically acceptable salt or prodrug form thereof.

[51] In another embodiment, the invention describes a method of inhibiting CDK3 activity, comprising adminsitering to a patient in need thereof an efective CDK3 inhibitory amount of a compound according to embodiment [1], or a pharmaceutically acceptable salt or prodrug form thereof.

[52] In another embodiment, the invention describes a method of inhibiting CDK4 activity, comprising adminsitering to a patient in need thereof an efective CDK4 inhibitory amount of a compound according to embodiment [1], or a pharmaceutically acceptable salt or prodrug form thereof.

[53] In another embodiment, the invention describes a method of inhibiting CDK5 activity, comprising adminsitering to a patient in need thereof an efective CDK5 inhibitory amount of a compound according to embodiment [1], or a pharmaceutically acceptable salt or prodrug form thereof.

[54] In another embodiment, the invention describes a method of inhibiting CDK6 activity, comprising adminsitering to a patient in need thereof an efective CDK6 inhibitory amount of a compound according to embodiment [1], or a pharmaceutically acceptable salt or prodrug form thereof.

[55] In another embodiment, the invention describes a method of inhibiting CDK7 activity, comprising adminsitering to a patient in need thereof an efective CDK7 inhibitory amount of a compound according to embodiment [1], or a pharmaceutically acceptable salt or prodrug form thereof.

[56] In another embodiment, the invention describes a method of inhibiting CDK8 activity, comprising adminsitering to a patient in need thereof, an efective CDK8 inhibitory amount of a compound according to embodiment [1], or a pharmaceutically acceptable salt or prodrug form thereof.

[57] In another embodiment, the invention describes a method of inhibiting CDK9 activity, comprising adminsitering to a patient in need thereof an efective CDK9 inhibitory amount of a compound according to embodiment [1], or a pharmaceutically acceptable salt or prodrug form thereof.

[58] In another embodiment, the invention describes a pharmaceutical kit for treating a cell proliferative disease associated with CDK activity, said kit comprising a plurality of separate containers, wherein at least one of said containers contains a compound accordig to embodiment [1],, or a pharmaceutically acceptable salt or prodrug form thereof, and at least another of said containers contains one or more compounds selected from the group consisting of cytostatic or cytotoxic agents, such as for example, but not limited to, DNA interactive agents, such as carboplatin, cisplatin or doxorubicin; topoisomerase II inhibitors, such as etoposide; topoisomerase I inhibitors such as CPT-11 or topotecan; tubulin interacting agents, such as paclitaxel, taxane, docetaxel or the epothilones; hormonal agents, such as tamoxifen; thymidilate synthase inhibitors, such as 5-fluorouracil; and anti-metabolites, such as methoxtrexate, and said containers optionally contain a pharmaceutical carrier, which kit may be effectively utilized for carrying out combination therapies according to the invention.

It is a further object of the invention to provide a method of treating a patient having a disorder associated with excessive cell proliferation, comprising administering to the patient a therapeutically effective amount of a compound of embodiment [1], such that the excessive cell proliferation in the patient is reduced.

It is appreciated that certain feactures of the invention, which are, for clarity, described in the context of separate embodiments, may also be provided in combination in a single embodiment. For example, $R^1$ of embodiment [6] may be combined with R2 of embodiment [19] to form a single embodiment. Conversely, various feactures of the invention which are, for brevity, described in the context of a single embodiment, may also be provided seperately or in any suitable subcombination.

DETAILED DESCRIPTION OF THE INVENTION

As used above, and throughout the description of the invention, the following terms, unless otherwise indicated, shall be understood to have the following meanings:

Definitions

As used herein, the following terms and expressions have the indicated meanings.

The term "compounds of the invention", and equivalent expressions, are meant to embrace compounds of the invention as herein before described i.e. compounds of formula (I), which expression includes the prodrugs, the pharmaceutically acceptable salts, and the solvates, e.g. hydrates, where the context so permits. Similarly, reference to intermediates, whether or not they themselves are claimed, is meant to embrace their salts, and solvates, where the context so permits. For the sake of clarity, particular instances when the context so permits are sometimes indicated in the text, but these instances are purely illustrative and it is not intended to exclude other instances when the context so permits.

The term "derivative" means a chemically modified compound wherein the modification is considered routine by the ordinary skilled chemist, such as an ester or an amide of an acid, protecting groups, such as a benzyl group for an alcohol or thiol, and tert-butoxycarbonyl group for an amine.

The term "effective amount" means an amount of a compound/composition according to the present invention effective in producing the desired therapeutic effect.

The term "amine protecting group" means an easily removable group which is known in the art to protect an amino group against undesirable reaction during synthetic procedures and to be selectively removable. The use of amine protecting groups is well known in the art for protecting groups against undesirable reactions during a synthetic procedure and many such protecting groups are known, for example, T. H. Greene and P. G. M. Wuts, Protective Groups in Organic Synthesis, 2nd edition, John Wiley & Sons, New York (1991), incorporated herein by reference. Preferred amine protecting groups are acyl, including formyl, acetyl, chloroacetyl, trichloroacetyl, o-nitrophenylacetyl, o-nitrophenoxyacetyl, trifluoroacetyl, acetoacetyl, 4-chlorobutyryl, isobutyryl, o-nitrocinnamoyl, picolinoyl, acylisothiocyanate, aminocaproyl, benzoyl and the like, and acyloxy including methoxycarbonyl, 9-fluorenylmethoxycarbonyl, 2,2,2-trifluoroethoxycarbonyl, 2-trimethylsilylethxoycarbonyl, vinyloxycarbonyl, allyloxycarbonyl, t-butyloxycarbonyl (BOC), 1,1-dimethylpropynyloxycarbonyl, benzyloxycarbonyl (CBZ), p-nitrobenzyloxycarbony, 2,4-dichlorobenzyloxycarbonyl, and the like.

The term "acid labile amine protecting group" means an amine protecting group as defined above which is readily removed by treatment with acid while remaining relatively stable to other reagents. A preferred acid labile amine protecting group is tert-butoxycarbonyl (BOC).

The term "hydrogenation labile amine protecting group" means an amine protecting group as defined above which is readily removed by hydrogenation while remaining relatively stable to other reagents. A preferred hydrogenation labile amine protecting group is benzyloxycarbonyl (CBZ).

The term "hydrogenation labile acid protecting group" means an acid protecting group as defined above which is readily removed by hydrogenation while remaining relatively stable to other reagents. A preferred hydrogenation labile acid protecting group is benzyl.

The term "analogue" means a compound which comprises a chemically modified form of a specific compound or class thereof, and which maintains the pharmaceutical and/or pharmacological activities characteristic of said compound or class.

The term "patient" includes both human and other mammals.

The term "pharmaceutical composition" means a composition comprising a compound of formula (I) and at least one component selected from the group comprising pharmaceutically acceptable carriers, diluents, adjuvants, excipients, or vehicles, such as preserving agents, fillers, disintegrating agents, wetting agents, emulsifying agents, suspending agents, sweetening agents, flavoring agents, perfuming agents, antibacterial agents, antifungal agents, lubricating agents and dispensing agents, depending on the nature of the mode of administration and dosage forms. Examples of suspending agents include ethoxylated isostearyl alcohols, polyoxyethylene sorbitol and sorbitan esters, microcrystalline cellulose, aluminum metahydroxide, bentonite, agar-agar and tragacanth, or mixtures of these substances. Prevention of the action of microorganisms can be ensured by various antibacterial and antifungal agents, for example, parabens, chlorobutanol, phenol, sorbic acid, and the like. It may also be desirable to include isotonic agents, for example sugars, sodium chloride and the like. Prolonged absorption of the injectable pharmaceutical form can be brought about by the use of agents delaying absorption, for example, aluminum monosterate and gelatin. Examples of suitable carriers, diluents, solvents or vehicles include water, ethanol, polyols, suitable mixtures thereof, vegetable oils (such as olive oil) and injectable organic esters such as ethyl oleate. Examples of excipients include lactose, milk sugar, sodium citrate, calcium carbonate, dicalcium phosphate phosphate. Examples of disintegrating agents include starch, alginic acids and certain complex silicates. Examples of lubricants include magnesium stearate, sodium lauryl sulphate, talc, as well as high molecular weight polyethylene glycols.

The term "solvate" means a physical association of a compound of this invention with one or more solvent molecules. This physical association includes hydrogen bonding. In certain instances the solvate will be capable of isolation, for example when one or more solvent molecules are incorporated in the crystal lattice of the crystalline solid. "Solvate" encompasses both solution-phase and isolable solvates. Exemplary solvates include hydrates, ethanolates, methanolates, and the like.

The term "alkyl" is intended to include both branched and straight-chain saturated aliphatic hydrocarbon groups having the specified number of carbon atoms. Examples of alkyl include, but are not limited to, methyl, ethyl, n-propyl, i-propyl, n-butyl, s-butyl, t-butyl, n-pentyl, and s-pentyl. In addition, the term is intended to include both unsubstituted and substituted alkyl groups, the latter referring to alkyl moieties having one or more hydrogen substituents replaced by, but not limited to halogen, hydroxyl, carbonyl, alkoxy, ester, ether, cyano, phosphoryl, amino, imino, amido, sulfhydryl, alkythio, thioester, sulfonyl, nitro, heterocyclo, aryl or heteroaryl. It will also be understood by those skilled in the art that the substituted moieties themselves can be substituted as well when appropriate.

The terms "halo" or "halogen" as used herein refer to fluoro, chloro, bromo and iodo. The term "aryl" is intended to mean an aromatic moiety containing the specified number of carbon atoms, such as, but not limited to phenyl, indanyl or naphthyl. The terms "cycloalkyl" and "bicycloalkyl" are intended to mean any stable ring system, which may be saturated or partially unsaturated. Examples of such include, but are not limited to, cyclopropyl, cyclopentyl, cyclohexyl, norbornyl, bicyclo[2.2.2]nonane, adamantly, or tetrahydronaphthyl (tetralin).

As used herein, "carbocycle" or "carbocyclic residue" is intended to mean any stable 3- to 7-membered monocyclic or bicyclic or 7- to 13-membered bicyclic or tricyclic, any of which may be saturated, partially unsaturated, or aromatic. Examples of such carbocycles include, but are not limited to, cyclopropyl, cyclobutyl, cyclopentyl, cyclohexyl, cycloheptyl, adamantyl, cyclooctyl,; [3.3.0]bicyclooctane, [4.3.0]bicyclononane, [4.4.0]bicyclodecane (decalin), [2.2.2]bicyclooctane, fluorenyl, phenyl, naphthyl, indanyl, adamantyl, or tetrahydronaphthyl (tetralin).

As used herein, the term "heterocycle" or "heterocyclic system" is intended to mean a stable 5- to 7- membered monocyclic or bicyclic or 7- to 10-membered bicyclic heterocyclic ring which is saturated partially unsaturated or unsaturated (aromatic), and which consists of carbon atoms and from 1 to 4 heteroatoms independently selected from the group consisting of N, O and S and including any bicyclic group in which any of the above-defined heterocyclic rings is fused to a benzene ring. The nitrogen and sulfur heteroatoms may optionally be oxidized. The heterocyclic ring may be attached to its pendant group at any heteroatom or carbon atom which results in a stable structure. The heterocyclic rings described herein may be substituted on carbon or on a nitrogen atom if the resulting compound is stable. If specifically noted, a nitrogen in the heterocycle may optionally be quaternized. It is preferred that when the total number of S and O atoms in the heterocycle exceeds 1, then these heteroatoms are not adjacent to one another. It is preferred that the total number of S and O atoms in the heterocycle is not more than 1. As used herein, the term "aromatic heterocyclic system" is intended to mean a stable 5- to 7- membered monocyclic or bicyclic or 7- to 10-membered bicyclic heterocyclic aromatic ring which consists of carbon atoms and from 1 to 4 heterotams independently selected from the group consisting of N, O and S. It is preferred that the total number of S and O atoms in the aromatic heterocycle is not more than 1.

Examples of heterocycles include, but are not limited to, 1H-indazole, 2-pyrrolidonyl, 2H,6H-1,5,2-dithiazinyl, 2H-pyrrolyl, 3H-indolyl, 4-piperidonyl, 4aH-carbazole, 4H-quinolizinyl, 6H-1,2,5-thiadiazinyl, acridinyl, azocinyl, benzimidazolyl, benzofuranyl, benzothiofuranyl, benzothiophenyl, benzoxazolyl, benzthiazolyl, benztriazolyl, benztetrazolyl, benzisoxazolyl, benzisothiazolyl, benzimidazalonyl, carbazolyl, 4aH-carbazolyl, b-carbolinyl, chromanyl, chromenyl, cinnolinyl, decahydroquinolinyl, 2H,6H-1,5,2-dithiazinyl, dihydrofuro[2,3-b]tetrahydrofuran, furanyl, furazanyl, imidazolidinyl, imidazolinyl, imidazolyl, 1H-indazolyl, indolenyl, indolinyl, indolizinyl, indolyl, isobenzofuranyl, isochromanyl, isoindazolyl, isoindolinyl, isoindolyl, isoquinolinyl, isothiazolyl, isoxazolyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl., oxazolyl, oxazolidinylperimidinyl, phenanthridinyl, phenanthrolinyl, phenarsazinyl, phenazinyl, phenothiazinyl, phenoxathiinyl, phenoxazinyl, phthalazinyl, piperazinyl, piperidinyl, pteridinyl, piperidonyl, 4-piperidonyl, pteridinyl, purinyl, pyranyl, pyrazinyl, pyrazolidinyl, pyrazolinyl, pyrazolyl, pyridazinyl, pyridooxazole, pyridoimidazole, pyridothiazole, pyridinyl, pyridyl, pyrimidinyl, pyrrolidinyl, pyrrolinyl, pyrrolyl, quinazolinyl, quinolinyl, 4H-quinolizinyl, quinoxalinyl, quinuclidinyl, carbolinyl, tetrahydrofuranyl, tetrahydroisoquinolinyl, tetrahydroquinolinyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thienothiazolyl, thienooxazolyl, thienoimidazolyl, thiophenyl, triazinyl, 1,2,3-triazolyl, 1,2,4-triazolyl, 1,2,5-triazolyl, 1,3,4-triazolyl, xanthenyl. Preferred heterocycles include, but are not limited to, pyridinyl, furanyl, thienyl, pyrrolyl, pyrazolyl, imidazolyl, indolyl, benzimidazolyl, 1H-indazolyl, oxazolidinyl, benzotriazolyl, benzisoxazolyl, oxindolyl, benzoxazolinyl, or isatinoyl. Also included are fused ring and spiro compounds containing, for example, the above heterocycles.

As used herein, "pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of basic residues such as amines; alkali or organic salts of acidic residues such as carboxylic acids; and the like. The pharmaceutically acceptable salts include the conventional non-toxic salts or the quaternary ammonium salts of the parent compound formed, for example, from non-toxic inorganic or organic acids. For example, such conventional non-toxic salts include those derived from inorganic acids such as hydrochloric, hydrobromic, sulfuric, sulfamic, phosphoric, nitric and the like; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, isethionic, and the like.

The pharmaceutically acceptable salts of the present invention can be synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, nonaqueous media like ether, ethyl acetate, ethanol, isopropanol, or acetonitrile are preferred. Lists of suitable salts are found in Remington's Pharmaceutical Sciences, 18th ed., Mack Publishing Company, Easton, Pa., 1990, p. 1445, the disclosure of which is hereby incorporated by reference.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication commensurate with a reasonable benefit/risk ratio.

The term "Pharmaceutically acceptable prodrugs" as used herein means those prodrugs of the compounds useful according to the present invention which are, within the scope of sound medical judgment, suitable for use in contact with the tissues of humans and lower animals with undue toxicity, irritation, allergic response, and the like, commensurate with a reasonable benefit/risk ratio, and effective for their intended use, as well as the zwitterionic forms, where possible, of the compounds of the invention.

The term "Prodrugs", as the term is used herein, are intended to include any covalently bonded carriers which release an active parent drug of the present invention in vivo when such prodrug is administered to a mammalian subject. Since prodrugs are known to enhance numerous desirable qualities of pharmaceuticals (i.e., solubility, bioavailability, manufacturing, etc.) the compounds of the present invention may be delivered in prodrug form. Thus, the present invention is intended to cover prodrugs of the presently claimed compounds, methods of delivering the same, and compositions containing the same. Prodrugs of the present invention are prepared by modifying functional groups present in the compound in such a way that the modifications are cleaved, either in routine manipulation or in vivo, to the parent compound. The transformation in vivo may be, for example, as the result of some metabolic process, such as chemical or enzymatic hydrolysis of a carboxylic, phosphoric or sulphate ester, or reduction or oxidation of a susceptible functionality. Prodrugs include compounds of the present invention wherein a hydroxy, amino, or sulfhydryl group is bonded to any group that, when the prodrug of the present invention is administered to a mammalian subject, it cleaves to form a free hydroxyl, free amino, or free sulfydryl group, respectively. Functional groups which may be rapidly transformed, by metabolic cleavage, in vivo form a class of groups reactive with the carboxyl group of the compounds of this invention. They include, but are not limited to such groups as alkanoyl (such as acetyl, propionyl, butyryl, and the like), unsubstituted and substituted aroyl (such as benzoyl and substituted benzoyl), alkoxycarbonyl (such as ethoxycarbonyl), trialkylsilyl (such as trimethyl- and triethysilyl), monoesters formed with dicarboxylic acids (such as succinyl), and the like. Because of the ease with which the metabolically cleavable groups of the compounds useful according to this invention are cleaved in vivo, the compounds bearing such groups act as pro-drugs. The compounds bearing the metabolically cleavable groups have the advantage that they may exhibit improved bioavailability as a result of enhanced solubility and/or rate of absorption conferred upon the parent compound by virtue of the presence of the metabolically cleavable group. A thorough discussion of prodrugs is provided in the following: Design of Prodrugs, H. Bundgaard, ed., Elsevier, 1985; Methods in Enzymology, K. Widder et al, Ed., Academic Press, 42, p.309-396, 1985; A Textbook of Drug Design and Development, Krogsgaard-Larsen and H. Bundgaard, ed., Chapter 5; "Design and Applications of Prodrugs" p.113–191, 1991; Advanced Drug Delivery Reviews, H. Bundgard, 8, p.1–38, 1992; Journal of Pharmaceutical Sciences, 77, p. 285, 1988; Chem. Pharm. Bull., N. Nakeya et al, 32, p. 692, 1984; Pro-drugs as Novel Delivery Systems, T. Higuchi and V. Stella, Vol. 14 of the A.C.S. Symposium Series, and Bioreversible Carriers in Drug Design, Edward B. Roche, ed., American Pharmaceutical Association and Pergamon Press, 1987, which are incorporated herein by reference.

"Substituted" is intended to indicate that one or more hydrogens on the atom indicated in the expression using "substituted" is replaced with a selection from the indicated group(s), provided that the indicated atom's normal valency is not exceeded, and that the substitution results in a stable compound. When a substituent is keto (i.e., $=O$) group, then 2 hydrogens on the atom are replaced.

The term "Treating" refers to:
(i) preventing a disease, disorder or condition from occurring in an animal which may be predisposed to the disease, disorder and/or condition but has not yet been diagnosed as having it;
(ii) inhibiting the disease, disorder or condition, i.e., arresting its development; and
(iii) relieving the disease, disorder or condition, i.e., causing regression of the disease, disorder and/or condition.

Preparation of Comounds of the Invention

It will be apparent to those skilled in the art that certain compounds of formula (I) can exhibit isomerism, for example geometrical isomerism, e.g., E or Z isomerism, and optical isomerism, e.g., R or S configurations. Geometrical isomers include the cis and trans forms of compounds of the invention having alkenyl moieties. It is well known in the art how to prepare optically active forms, such as by resolution of racemic forms or by synthesis from optically active starting materials. All chiral, diastereomeric, racemic forms and all geometric isomeric forms of a structure are intended, unless the specific stereochemistry or isomer form is specifically indicated.

Such isomers can be separated from their mixtures, by the application or adaptation of known methods, for example chromatographic techniques and recrystallization techniques, or they are separately prepared from the appropriate isomers of their intermediates, for example by the application or adaptation of methods described herein.

The compounds of the present invention are useful in the form of the free base or acid or in the form of a pharmaceutically acceptable salt thereof. All forms are within the scope of the invention.

Where the compound of the present invention is substituted with a basic moiety, acid addition salts are formed and are simply a more convenient form for use; and in practice, use of the salt form inherently amounts to use of the free base form. The acids which can be used to prepare the acid addition salts include preferably those which produce, when combined with the free base, pharmaceutically acceptable salts, that is, salts whose anions are non-toxic to the patient in pharmaceutical doses of the salts, so that the beneficial inhibitory effects on CDK inherent in the free base are not vitiated by side effects ascribable to the anions. Although pharmaceutically acceptable salts of said basic compounds are preferred, all acid addition salts are useful as sources of the free base form even if the particular salt, per se, is desired only as an intermediate product as, for example, when the salt is formed only for purposes of purification, and identification, or when it is used as intermediate in preparing a pharmaceutically acceptable salt by ion exchange procedures.

According to a further feature of the invention, acid addition salts of the compounds of this invention are prepared by reaction of the free base with the appropriate acid, by the application or adaptation of known methods. For example, the acid addition salts of the compounds of this invention are prepared either by dissolving the free base in aqueous or aqueous-alcohol solution or other suitable solvents containing the appropriate acid and isolating the salt by evaporating the solution, or by reacting the free base and acid in an organic solvent, in which case the salt separates directly or can be obtained by concentration of the solution.

The acid addition salts of the compounds of this invention can be regenerated from the salts by the application or adaptation of known methods. For example, parent compounds of the invention can be regenerated from their acid addition salts by treatment with an alkali, e.g. aqueous sodium bicarbonate solution or aqueous ammonia solution.

Where the compound of the invention is substituted with an acidic moiety, base addition salts may be formed and are simply a more convenient form for use; and in practice, use of the salt form inherently amounts to use of the free acid form. The bases which can be used to prepare the base addition salts include preferably those which produce, when combined with the free acid, pharmaceutically acceptable salts, that is, salts whose cations are non-toxic to the animal organism in pharmaceutical doses of the salts, so that the beneficial inhibitory effects on CDK inherent in the free acid are not vitiated by side effects ascribable to the cations. Pharmaceutically acceptable salts, including for example alkali and alkaline earth-metal salts, within the scope of the invention are those derived from the following bases: sodium hydride, sodium hydroxide, potassium hydroxide, calcium hydroxide, aluminum hydroxide, lithium hydroxide, magnesium hydroxide, zinc hydroxide, ammonia, ethylenediamine, N-methyl-glucamine, lysine, arginine, ornithine, choline, N,N'-dibenzylethylenediamine, chloroprocaine, diethanolamine, procaine, N-benzylphenethylamine, diethylamine, piperazine, tris(hydroxymethyl)-aminomethane, tetramethylammonium hydroxide, and the like.

Metal salts of compounds of the present invention may be obtained by contacting a hydride, hydroxide, carbonate or similar reactive compound of the chosen metal in an aqueous or organic solvent with the free acid form of the compound. The aqueous solvent employed may be water or it may be a mixture of water with an organic solvent, preferably an alcohol such as methanol or ethanol, a ketone such as acetone, an aliphatic ether such as tetrahydrofuran, or an ester such as ethyl acetate. Such reactions are normally conducted at ambient temperature but they may, if desired, be conducted with heating.

Amine salts of compounds of the present invention may be obtained by contacting an amine in an aqueous or organic solvent with the free acid form of the compound. Suitable aqueous solvents include water and mixtures of water with alcohols such as methanol or ethanol, ethers such as tetrahydrofuran, nitrites such as acetonitrile, or ketones such as acetone. Amino acid salts may be similarly prepared.

The base addition salts of the compounds of this invention can be regenerated from the salts by the application or adaptation of known methods. For example, parent compounds of the invention can be regenerated from their base addition salts by treatment with an acid, e.g. hydrochloric acid.

Pharmaceutically acceptable salts also include quaternary lower alkyl ammonium salts. The quaternary salts are prepared by the exhaustive alkylation of basic nitrogen atoms in compounds, including nonaromatic and aromatic basic nitrogen atoms, according to the invention, i.e., alkylating the non-bonded pair of electrons of the nitrogen moieties with an alkylating agent such as methylhalide, particularly methyl iodide, or dimethyl sulfate. Quaternarization results in the nitrogen moiety becoming positively charged and having a negative counter ion associated therewith.

As will be self-evident to those skilled in the art, some of the compounds of this invention do not form stable salts. However, acid addition salts are more likely to be formed by compounds of this invention having a nitrogen-containing heteroaryl group and/or wherein the compounds contain an amino group as a substituent. Preferable acid addition salts of the compounds of the invention are those wherein there is not an acid labile group.

As well as being useful in themselves as active compounds, salts of compounds of the invention are useful for the purposes of purification of the compounds, for example by exploitation of the solubility differences between the salts and the parent compounds, side products and/or starting materials by techniques well known to those skilled in the art.

Compounds according to the invention, for example, starting materials, intermediates or products, are prepared as described herein or by the application or adaptation of known methods, by which is meant methods used heretofore or described in the literature.

Compounds useful according to the invention may be prepared by the application or adaptation of known methods, by which is meant methods used heretofore or described in the literature, for example those described by R. C. Larock in Comprehensive Organic Transformations, VCH publishers, 1989.

In the reactions described hereinafter it may be necessary to protect reactive functional groups, for example hydroxy, amino, imino, thio or carboxy groups, where these are desired in the final product, to avoid their unwanted participation in the reactions. Conventional protecting groups may be used in accordance with standard practice, for examples see T. W. Green and P. G. M. Wuts in "Protective Groups in Organic Chemistry" John Wiley and Sons, 1991; J. F. W. McOmie in "Protective Groups in Organic Chemistry" Plenum Press, 1973.

Preferred methods of synthesizing the compounds of the invention include, but are not limited to, those methods described below. Each of the references cited below are hereby incorporated herein by reference.

SCHEME 1

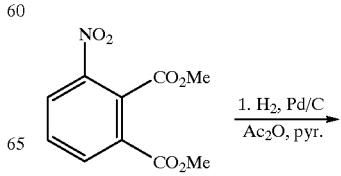

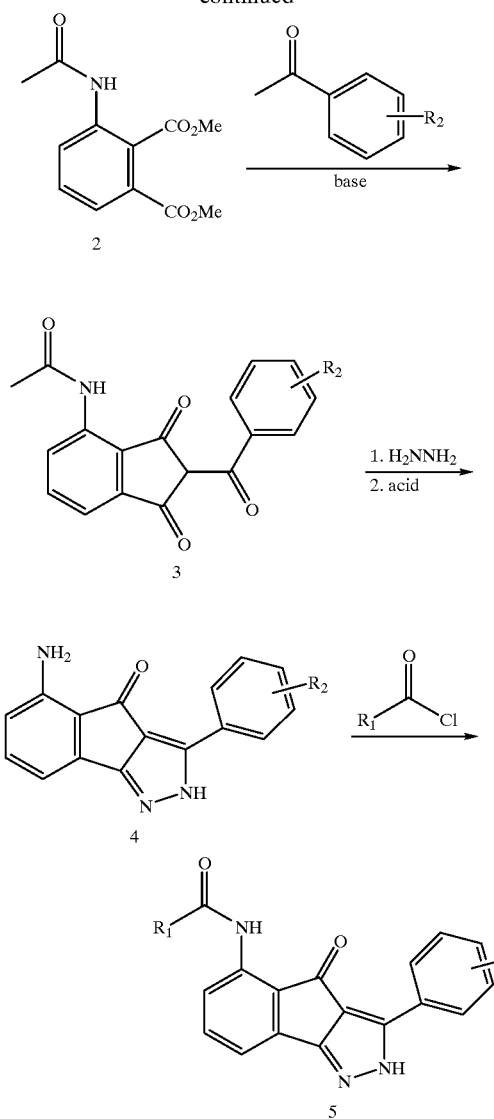

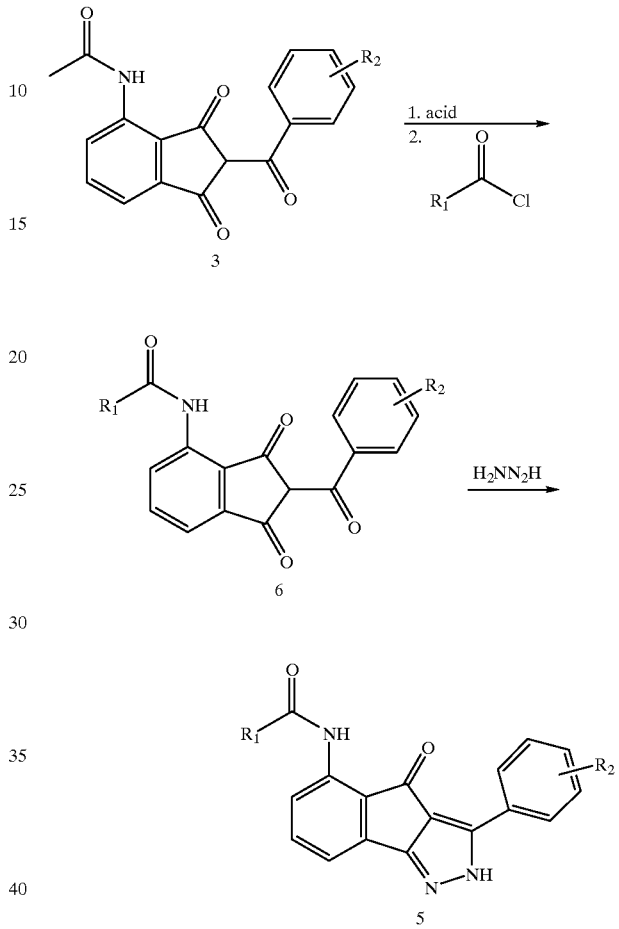

An approach to preparing indeno[1,2-c]pyrazol-4-ones is presented in Scheme 1 and can be used to prepare compounds of the present invention. The nitro group of dimethyl 3-nitrophthalate was reduced to the amine using catalytic hydrogenation. The aniline was acylated using acetic anhydride and pyridine as a base. A mixture of the resulting acetamide 2 and an acetophenone were treated with a strong base in an appropriate solvent at elevated temperature to give the desired triketone 3. Additional means of preparing triketones are known to one skilled in the art as described in Kilgore et al, Industrial and Engineering Chemistry 34:494–497, 1946, the contents of which are hereby incorporated herein by reference. The triketone was treated with hydrazine at elevated temperature in an appropriate solvent to give the indeno[1,2-c]pyrazol-4-one ring system. Additional means of preparing indeno[1,2-c]pyrazol-4-ones are known to one skilled in the art as described in Lemke et al., J. Heterocyclic Chem. 19:1335–1340, 1982; Mosher and Soeder, J. Heterocyclic Chem. 8:855–59, 1971;Hrnciar and Svanygova Collect. Czech. Chem. Commun. 59:2734–40, 1994 the contents of which are hereby incorporated herein by reference. The amide was deacetylated by heating with a strong acid in an appropriate solvent to give aniline 4. This aniline was acylated under standard conditions using an acid chloride in an appropriate solvent to give the desired product 5.

An alternative method for making compounds of the present invention is shown in Scheme 2. The intermediate triketone 3 can be deacetylated with strong acid and reacylated with an appropriate acid chloride using methods known to those skilled in the art. Subsequently, triketone 6 can be converted to the indeno[1,2-c]pyrazol-4-ones using the same conditions described previously in Scheme 1.

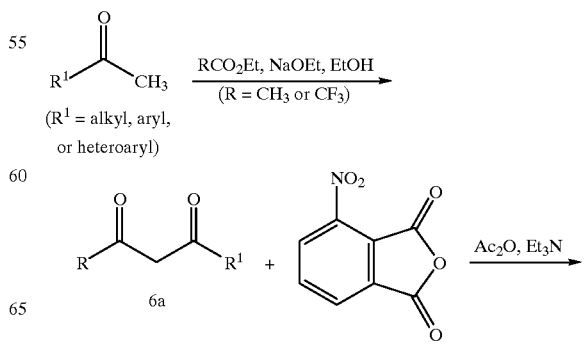

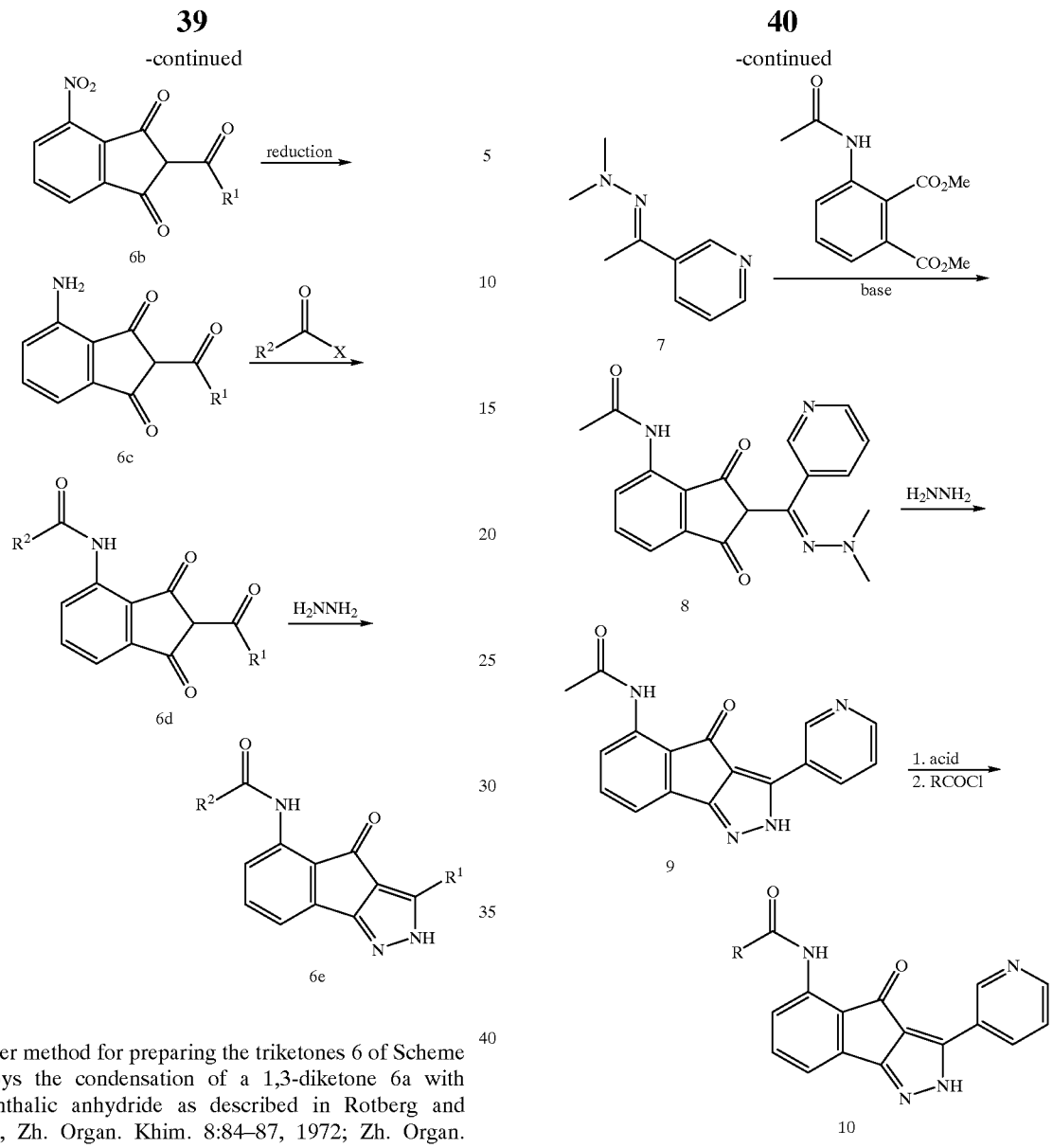

Another method for preparing the triketones 6 of Scheme 2 employs the condensation of a 1,3-diketone 6a with 3-nitrophthalic anhydride as described in Rotberg and Qshkaya, Zh. Organ. Khim. 8:84–87, 1972; Zh. Organ. Khim. 9:2548-2550, 1973, the contents of which are hereby incorporated herein by reference. The 1,3-diketones, when not commercially available can be readily prepared by one skilled in the art by the acetylation or trifluoroacetylation of the requisite methyl ketone, $R^1COCH_3$. Reduction of the nitro derivative 6b to the aniline 6c can be accomplished in a variety of ways including catalyic hydrogenation, treatment with zinc or iron under acidic conditions, or treatment with other reducing agents such as sodium dithionite or stannous chloride. Subsequently the aniline 6c can be converted to the indeno[1,2-c]pyrazol-4-ones of this invention by acylation followed by treatment with hydrazine as described previously in Scheme 2.

SCHEME 4

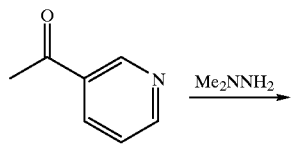

Another method for making the indeno[1,2-c]pyrazol-4-one ring system is exemplified in Scheme 4. Dimethyl hydrazine was reacted with 3-acetylpyridine with no solvent to give the hydrazone 7. This was treated in a similar fashion as described in Scheme 1 to give the desired intermediate 8. Additional means of preparing similar intermediates are known to one skilled in the art as described in Rappoport, J. Org. Chem. 49:2948–2953, 1984, the contents of which are hereby incorporated herein by reference. This intermediate was carried through the sequence in a similar fashion as described in Scheme 1.

The ureas and semicarbazides ($R^1$=$NHR^4$, X=O) of this invention can be prepared by treating the aniline intermediates in Schemes 1–4, for example 4 or 6c, with an isocyanate (RNCO) or an aminoisocyanate (RR'NNCO). These reagents are readily prepared in advance by one skilled in the art, or they can be generated in situ employing a precursor, such as an O-phenylcarbamate ($RNHCO_2Ph$ or $RR'NNHCO_2Ph$), in the presense of base. Alternatively, the ureas and semicarbazides can be prepared by treatment of the anilines intermediates above with phenyl chloroformate in the presense of base to give an intermediate phenyl carbamate, followed by exposure of the phenyl carbamate to an amine or a hydrazine at elevated temperatures in an appropriate solvent.

The thioureas and thiosemicarbazides (X=S) of this invention can be prepared as described above by treating the aniline intermediates with phenyl thionochloroformate, followed by exposure of the resulting phenyl thiocarbamate to the appropriate amine or hydrazine derivative. The thioamides, thioureas, and thiosemicarbazides can also be prepared from the corresponding amides, ureas, and semicarbazides by treatment with a reagent such as phosphorous pentasulfide or Lawesson's reagent.

The amidines and guanidines (X=NR) of this invention can be prepared as described in Schemes 1–4 by treatment of the intermediate anilines with a wide variety of reagents known to one skilled in the art. These reagents include, but are not limited to, imidates and iminoyl chlorides for the production of amidines and isothioures and carbodiimides for the production of guanidines. Alternatively, the amidines and guanidines of this invention can be prepared from the corresponding thioamides, thioureas, and thiosemicarbazides. For example, a thiourea can be S-alkylated by treatment with an akylating agent such as methyl iodide or methyl triflate to provide the corresponding isothiourea. Treatment of this intermediate with the requisite amine or hydrazine at elevated temperatures in an appropriate solvent then provides the desired quanidine derivative.

Many of the compounds of this invention are synthesized from the indeno[1,2-c]pyrazol-4-ones prepared in Schemes 1–4 by the further synthetic elaboration of the $R^1$ and $R^2$ groups. As required the pyrazole ring can be protected by a wide range of protecting groups known to one skilled in the art with the selection of a protecting depending on the chemistry to be employed.

Other features of the invention will become apparent during the following descriptions of exemplary embodiments which are given for illustration of the invention and are not intended to be limiting thereof.

EXAMPLES

Abbreviations used in the Examples are defined as follows: "°C." for degrees Celsius, "CIMS" for chemical ionization mass spectroscopy, "eq" for equivalent or equivalents, "g" for gram or grams, "h" for hour or hours, "mg" for milligram or milligrams, "mL" for milliliter or milliliters, "mmol" for millimolar, "M" for molar, "min" for minute or minutes, "p-TsOH" for para-toluenesulphonic acid, "DMF" for dimethylformamide, and "TFA" for trifluoroacetic acid.

Example I

Preparation of 3-(4-methoxyphenyl)-5-(acetamido) indeno[1,2-c]pyrazol-4-one

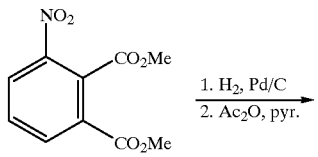

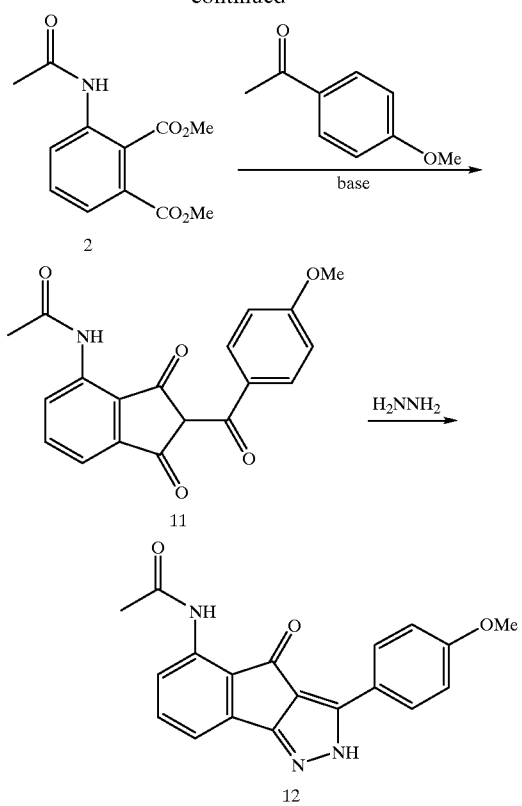

Step 1. Synthesis of 2 from Dimethyl 3-nitrophthalate.

A solution of dimethyl 3-nitrophthalate (25 g, 105 mmol) in methanol (100 mL) was treated with 5% Pd/C (2.5 g) and hydrogenated on a Parr Shaker at 50 psi for 2 h. The solution was filtered (Celite), the filtrate collected and the solvent removed at reduced pressure. The residue was dissolved in acetic anhydride (20 mL) treated with pyridine (0.05 mL) and heated to 80° C. for 1 min. The reaction was cooled and stirred at 25° C. for 2 h. The solvent was removed at reduced pressure and the residue recrystallized from ethanol to give the product as a white solid (21 g, 79%). mp 104–105° C.; CIMS m/e calc'd for $C_{12}H_{14}NO_5$: 252.0872, found 252.0888; Analysis calc'd for $C_{12}H_{13}NO_5$: C, 57.37; H, 5.22; N, 5.58; found: C, 57.67; H, 5.29; N, 5.77.

Step 2. Synthesis of Triketone 11 from 2.

A solution of 2 (1 g, 4.0 mmol) in dry DMF (2 mL) was treated with sodium hydride (0.15 g, 60% suspension in oil, 0.4 mmol) in one portion. After 1 h, 4-methoxyacetophenone (0.6 g, 4.0 mmol) was added in one portion and the reaction heated to 90° C. A second portion of sodium hydride (0.15 g, 60% suspension in oil, 0.4 mmol) was added and the exothermic reaction turns deep red. After 20 min, the reaction was cooled to 25° C., diluted with water (20 mL), extracted with EtOAc (10 mL) and the aqueous phase separated. The aqueous phase was acidified with 2 N HCl to pH 2 and the crude product collected. Recrystalization with ethanol gave the desired product as a yellow solid (0.4 g, 30%). mp 174–175° C.; CIMS m/e calc'd for $C_{19}H_{16}NO_5$: 338.1028, found 338.1022; Analysis calc'd for $C_{19}H_{15}NO_5$: C, 67.65;H, 4.48; N, 4.15; found: C, 67.87;H, 4.29; N, 3.99.

Step 3. Synthesis of 12 from 11.

A solution of 11 (0.2 g, 0.6 mmol) in EtOH (5 mL) was treated with hydrazine hydrate (0.1 mL, 1.8 mmol) and p-TsOH (3 mg). The reaction was heated to reflux and stirred for 2 h. The reaction was cooled to 25° C. and the product collected as a yellow solid (0.1 g, 50%). mp 268° C.; CIMS m/e calc'd for $C_{19}H_{16}N_3O_3$: 334.1192, found: 334.1168; Analysis calc'd for $C_{19}H_{15}N_3O_3$: C, 68.46;H, 4.54; N, 12.61; found: C, 68.81;H, 4.39; N, 12.45.

Example II

Preparation of 3-(4-methoxyphenyl)-5-(chloroacetamido)indeno[1,2-c]pyrazol-4-one

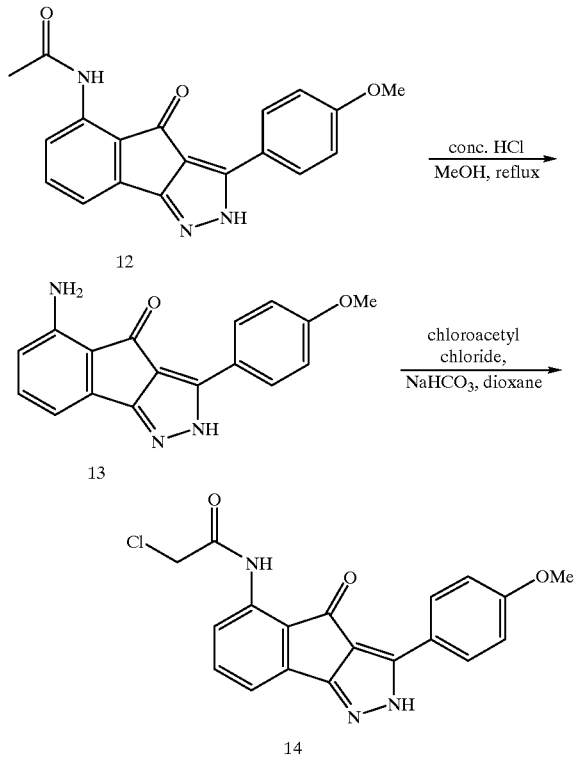

Step 1. Synthesis of 13 from 12.

A suspension of 12 (1.0 g, 3.0 mmol) in MeOH (10 mL) was treated with conc. HCl (1 mL) and heated to reflux. After 2 h, the reaction was cooled and the product was collected as a greenish solid (0.7 g, 81%). mp 273° C.; CIMS m/e calc'd for $C_{17}H_{14}N_3O_2$: 292.1086, found: 292.1080; Analysis calc'd for $C_{17}H_{13}N_3O_2$: C, 69.85;H, 4.83; N, 14.37; found: C, 69.99;H, 4.59; N, 14.44.

Step 2. Synthesis of 14 from 13.

A suspension of 13 (20 mg, 0.07 mmol) in dioxane (2 mL) was treated with aqueous sat. NaHCO3 (1 mL) and chloroacetyl chloride (30 mL, 0.21 mmol). The reaction was heated to 50° C. and stirred for 2 h. The reaction was cooled, poured into water (2 mL), extracted with EtOAc (10 mL), the organic layer separated, dried (MgSO$_4$) and the solvent removed at reduced pressure. The solid residue was recrystallized from EtOH to give the product as a yellow solid (9 mg, 35%). mp 274° C.; CIMS m/e calc'd for $C_{19}H_{15}N_3O_3Cl$: 368.0802, found: 368.0818.

Example III

Preparation of 3-(4-methoxyphenyl)-5-(cyclopropanecarboxamido)indeno[1,2-c]pyrazol-4-one Prepared in a similar fashion as described for example II using cyclopropanecarboxoyl chloride as the starting material. mp 289° C.; CIMS m/e calc'd for $C_{21}H_{18}N_3O_3$: 360.1348, found: 360.1330.

Example IV

Preparation of 3-(4-methoxyphenyl)-5-(2-methylpropanamido)indeno[1,2-c]pyrazol-4-one Prepared in a similar fashion as described for example II using 2-methylpropanoyl chloride as the starting material. mp 288° C.; CIMS m/e calc'd for $C_{21}H_{20}N_3O_3$: 362.1505, found: 362.1535.

Example V

Preparation of 3-(4-methoxyphenyl)-5-(propanamido)indeno[1,2-c]pyrazol-4-one

Prepared in a similar fashion as described for example II using propionyl chloride as the starting material. mp 287° C.; CIMS m/e calc'd for $C_{20}H_{18}N_3O_3$: 348.1348, found: 348.1313.

Example VI

Preparation of 3-(4-methoxyphenyl)-5-(cyclopentanecarboxamido)indeno[1,2-c]pyrazol-4-one Prepared in a similar fashion as described for example II using cyclopentanecarboxoyl chloride as the starting material. mp 267° C.; CIMS m/e calc'd for $C_{23}H_{22}N_3O_3$: 388.1661, found: 388.1626.

Example VII

Preparation of 3-(4-methoxyphenyl)-5-(cyclobutanecarboxamido)indeno[1,2-c]pyrazol-4-one Prepared in a similar fashion as described for example II using cyclobutanecarboxoyl chloride as the starting material. mp 297° C.; CIMS m/e calc'd for $C_{22}H_{20}N_3O_3$: 374.1505, found: 374.1530.

Example VIII

Preparation of 3-(4-methoxyphenyl)-5-(phenylacetamido)indeno[1,2-c]pyrazol-4-one Prepared in a similar fashion as described for example II using phenylacetyl chloride as the starting material. mp 280° C.; CIMS m/e calc'd for $C_{25}H_{20}N_3O_3$: 410.1505, found: 410.1533.

Example IX

Preparation of 3-(4-methoxyphenyl)-5-(butanamido)indeno[1,2-c]pyrazol-4-one

Prepared in a similar fashion as described for example II using butyryl chloride as the starting material. mp 282° C.; CIMS m/e calc'd for $C_{21}H_{20}N_3O_3$: 362.1505, found: 362.1500.

Example X

Preparation of 3-(4-methoxyphenyl)-5-((4-chlorophenyl)acetamido)indeno[1,2-c]pyrazol-4-one Prepared in a similar fashion as described for example II using 4-chlorophenylacetyl chloride as the starting material.

mp 238° C.; CIMS m/e calc'd for $C_{25}H_{19}N_3O_3Cl$: 444.1115, found: 444.1110.

Example XI

Preparation of 3-(4-methoxyphenyl)-5-((3-methoxyphenyl)acetamido)indeno[1,2-c]pyrazol-4-one Prepared in a similar fashion as described for example II using 3-methoxyphenylacetyl chloride as the starting material. mp >300° C.; CIMS m/e calc'd for $C_{26}H_{22}N_3O_4$: 440.1610, found: 440.1620.

Example XII

Preparation of 3-(4-methoxyphenyl)-5-((4-methoxyphenyl)acetamido)indeno[1,2-c]pyrazol-4-one Prepared in a similar fashion as described for example II using 4-methoxyphenylacetyl chloride as the starting material. mp 280° C.; CIMS m/e calc'd for $C_{26}H_{22}N_3O_4$: 440.1610, found: 440.1630.

Example XIII

Preparation of 3-(4-methoxyphenyl)-5-((3,4-dimethoxyphenyl)acetamido)indeno[1,2-c]pyrazol-4-one Prepared in a similar fashion as described for example II using 3,4-dimethoxyphenylacetyl chloride as the starting material. mp >300° C.; CIMS m/e calc'd for $C_{27}H_{24}N_3O_5$: 470.1716, found: 470.1731.

Example XIV

Preparation of 3-(4-methoxyphenyl)-5-((2,5-dimethoxyphenyl)acetamido)indeno[1,2-c]pyrazol-4-one Prepared in a similar fashion as described for example II using 2,5-dimethoxyphenylacetyl chloride as the starting material. mp 226° C.; CIMS m/e calc'd for $C_{27}H_{24}N_3O_5$: 470.1716, found: 470.1739.

Example XV

Preparation of 3-(2-methoxyphenyl)-5-(acetamido)indeno[1,2-c]pyrazol-4-one

Prepared in a similar fashion as described for example I using 2-methoxyacetophenone as the starting material. mp 276° C.; CIMS m/e calc'd for $C_{19}H_{16}N_3O_3$: 334.1192, found: 334.1169.

Example XVI

Preparation of 3-(3,4-dimethoxyphenyl)-5-(acetamido)indeno[1,2-c]pyrazol-4-one

Prepared in a similar fashion as described for example I using 3,4-dimethoxyacetophenone as the starting material. mp >300° C.; CIMS m/e calc'd for $C_{20}H_{18}N_3O_4$: 364.1297, found: 364.1288.

Example XVII

Preparation of 3-(4-methoxyphenyl)-5-((3,4-methylenedioxyphenyl)acetamido)indeno[1,2-c]pyrazol-4-one

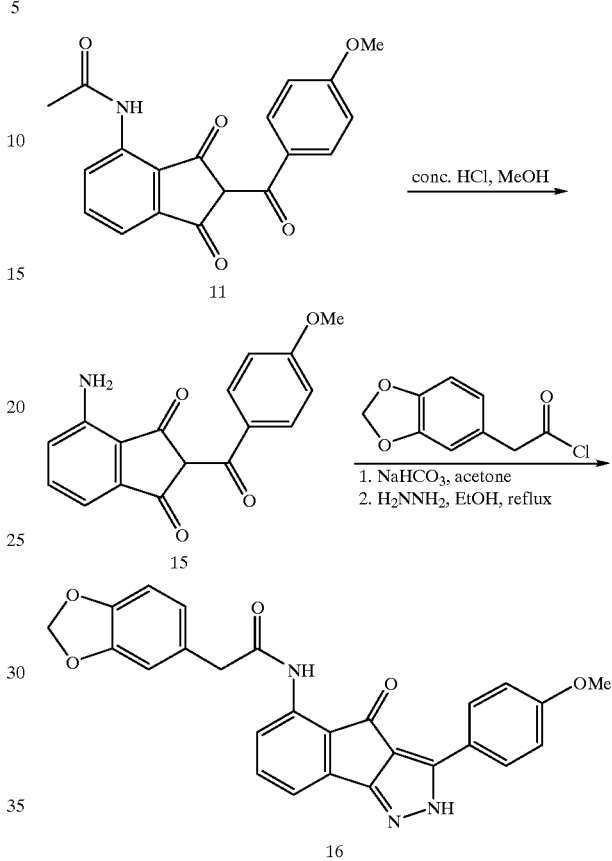

Step 1. Synthesis of 15 from 11.

A suspension of 11 (5 g, 14.8 mmol) in MeOH (50 mL) was treated with conc. HCl (3 mL) and heated to reflux. After stirring for 2 h, the reaction was cooled to 0° C. and the product collected as a yellow solid (4.2 g, 96%). mp 173° C.; CIMS m/e calc'd for $C_{17}H_{14}NO_4$: 296.0923, Found: 296.0901.

Step 2. Synthesis of 16 from 15.

A suspension of 15 (20 mg, 0.07 mmol) in acetone (2 mL) was treated with $NaHCO_3$ (10 mg) and the acid chloride of (3,4-methylenedioxyphenyl)acetic acid (prepared by heating the acid in a benzene:thionyl chloride 4:1 mixture at 50° C. for 2 h, removing the volatile components at reduced pressure, and using the crude acid chloride without further purification). The reaction was heated to 50° C. and stirred for 2 h. The reaction was cooled, poured into water (4 mL), extracted with EtOAc (10 mL), dried ($MgSO_4$), filtered and concentrated. The crude triketone was suspended in EtOH (2 mL), treated with hydrazine hydrate (0.05 mL) and p-TsOH (1 mg) and heated to reflux for 2 h. The reaction was cooled to 0° C. and the product filtered to give a yellow solid (6.5 mg, 20%). mp 297° C.; CIMS m/e calc'd for $C_{26}H_{20}N_3O_5$: 454.1403, Found: 454.1398.

Example XVIII

Preparation of 3-(4-dimethoxyphenyl)-5-(3-thienylacetamido)indeno[1,2-c]pyrazol-4-one Prepared in a similar fashion as described for example XVII using the acid chloride of 3-thiopheneacetic acid as the starting material. mp 293° C.; CIMS m/e calc'd for $C_{23}H_{18}N_3O_3S$: 416.1069, found: 416.1088.

Example XIX

Preparation of 3-(4-methoxyphenyl)-5-((2-methoxyphenyl)acetamido)indeno[1,2-c]pyrazol-4-one Prepared in a similar fashion as described for example XVII using the acid chloride of 2-methoxyphenylacetic acid as the starting material. mp 255° C.; CIMS m/e calc'd for $C_{26}H_{22}N_3O_4$: 440.1610, found: 440.1622.

Example XX

Preparation of 3-(4-methoxyphenyl)-5-((3,4-dichlorophenyl)acetamido)indeno[1,2-c]pyrazol-4-one Prepared in a similar fashion as described for example XVII using the acid chloride of 3,4-dichlorophenylacetic acid as the starting material. mp 299° C.; CIMS m/e calc'd for $C_{25}H_{18}N_3O_3Cl_2$: 478.0725, found: 478.0744.

Example XXI

Preparation of 3-(4-methoxyphenyl)-5-((2,4-dichlorophenyl)acetamido)indeno[1,2-c]pyrazol-4-one Prepared in a similar fashion as described for example XVII using the acid chloride of 2,4-dichlorophenylacetic acid as the starting material. mp 286° C.; CIMS m/e calc'd for $C_{25}H_{18}N_3O_3Cl_2$: 478.0725, found: 478.0734.

Example XXII

Preparation of 3-(4-methoxyphenyl)-5-((2-chlorophenyl)acetamido)indeno[1,2-c]pyrazol-4-one Prepared in a similar fashion as described for example XVII using the acid chloride of 2-chlorophenylacetic acid as the starting material. mp 300° C.; CIMS m/e calc'd for $C_{25}H_{19}N_3O_3Cl$: 444.1115, found: 444.1111.

Example XXIII

Preparation of 3-(4-methoxyphenyl)-5-(aminoacetamido)indeno[1,2-c]pyrazol-4-one

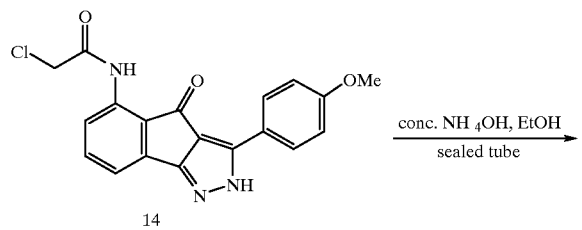

14 conc. NH$_4$OH, EtOH
sealed tube

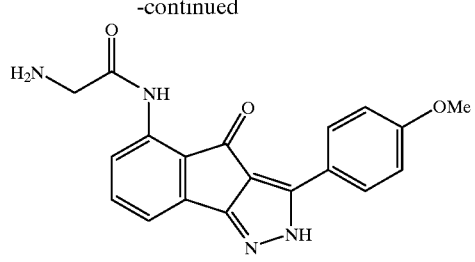

17

A suspension of 14 (15 mg, 0.04 mmol) in EtOH (1 mL) was treated with conc. NH$_4$OH (1 mL), placed in a sealed tube and heated to 80° C. for 3 h. The reaction was cooled and the solvent removed at reduced pressure. The residue was recrystallized from EtOH to give the product as a yellow solid (9 mg, 62%). mp >300° C.; CIMS m/e calc'd for $C_{20}H_{19}N_4O_3$: 363.1457, Found: 363.1431.

Example XXIV

Preparation of 3-(4-methoxyphenyl)-5-((2-hydroxyethyl)aminoacetamido)indeno[1,2-c]pyrazol-4-one Prepared in a similar fashion as described for example XXIII using hydroxylamine as the starting material. mp 243° C.; CIMS m/e calc'd for $C_{21}H_{21}N_4O_4$: 393.1563, found: 393.1539.

Example XXV

Preparation of 3-(4-methoxyphenyl)-5-(N,N-dimethylaminoacetamido)indeno[1,2-c]pyrazol-4-one Prepared in a similar fashion as described for example XXIII using dimethylamine as the starting material. mp 279° C.; CIMS m/e calc'd for $C_{21}H_{21}N_4O_3$: 377.1614, found: 377.1640.

Example XXVI

Preparation of 3-(4-methoxyphenyl)-5-(piperazinoacetamido)indeno[1,2-c]pyrazol-4-one Prepared in a similar fashion as described for example XXIII using piperazine as the starting material. mp 277° C.; CIMS m/e calc'd for $C_{23}H_{24}N_5O_3$: 418.1879, found: 418.1899.

Example XXVII

Preparation of 3-(4-methoxyphenyl)-5-(4-methylpiperazinoacetamido)indeno[1,2-c]pyrazol-4-one Prepared in a similar fashion as described for example XXIII using 4-methylpiperizine as the starting material. mp >300° C.; CIMS m/e calc'd for $C_{24}H_{26}N_5O_3$: 432.2036, found: 432.2030.

Example XXVIII

Preparation of 3-(4-methoxyphenyl)-5-(4-(2-hydroxyethyl)piperazinoacetamido)indeno[1,2-c]pyrazol-4-one Prepared in a similar fashion as described for example XXIII using 4-hydroxyethylpiperizine as the starting material. mp >300° C.; CIMS m/e calc'd for $C_{25}H_{28}N_5O_4$: 462.2141, found: 462.2128.

Example XXIX

Preparation of 3-(4-methoxyphenyl)-5-(piperidinoacetamido)indeno[1,2-c]pyrazol-4-one Prepared in a similar fashion as described for example XXIII using piperidine as the starting material. mp 291° C.; CIMS m/e calc'd for $C_{24}H_{25}N_4O_3$: 417.1927, found: 417.1955.

Example XXX

Preparation of 3-(4-methoxyphenyl)-5-(4-(aminomethyl)piperidinoacetamido)indeno[1,2-c]pyrazol-4-one Prepared in a similar fashion as described for example XXIII using 4-aminomethylpiperidine as the starting material. mp >300° C.; CIMS m/e calc'd for $C_{25}H_{28}N_5O_3$: 446.2192, found: 446.2166.

Example XXXI

Preparation of 3-(4-methoxyphenyl)-5-(ethylaminoacetamido)indeno[1,2-c]pyrazol-4-one Prepared in a similar fashion as described for example XXIII using ethylamine as the starting material. mp 250° C.; CIMS m/e calc'd for $C_{21}H_{21}N_4O_3$: 377.1614, found: 377.1644.

Example XXXII

Preparation of 3-(4-methoxyphenyl)-5-(thiomorpholinoacetamido)indeno[1,2-c]pyrazol-4-one Prepared in a similar fashion as described for example XXIII using thiomorpholine as the starting material. mp 298° C.; CIMS m/e calc'd for $C_{23}H_{23}N_4O_3S$: 435.1491, found: 435.1477.

Example XXXIII

Preparation of 3-(4-methoxyphenyl)-5-(morpholinoacetamido)indeno[1,2-c]pyrazol-4-one Prepared in a similar fashion as described for example XXIII using morpholine as the starting material. mp 295° C.; CIMS m/e calc'd for $C_{23}H_{23}N_4O_4$: 419.1719, found: 419.1744.

Example XXXIV

Preparation of 3-(4-methoxyphenyl)-5-(pyrrolidinoacetamido)indeno[1,2-c]pyrazol-4-one Prepared in a similar fashion as described for example XXIII using pyyrolidine as the starting material. mp 279° C.; CIMS m/e calc'd for $C_{23}H_{23}N_4O_3$: 403.1770, found: 403.1761.

Example XXXV

Preparation of 3-(4-methoxyphenyl)-5-((4-pyridinylmethylaminoacetamido)indeno[1,2-c]pyrazol-4-one Prepared in a similar fashion as described for example XXIII using 4-aminomethylpyridine as the starting material. mp >300° C.; CIMS m/e calc'd for $C_{25}H_{22}N_5O_3$: 440.1723, found: 440.1762.

Example XXXVI

Preparation of 3-(4-methoxyphenyl)-5-((4-acetamidophenyl)acetamido)indeno[1,2-c]pyrazol-4-one

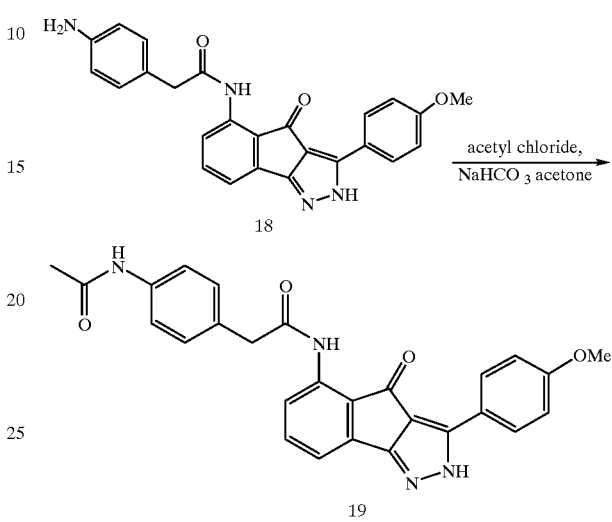

A suspension of 18 (10 mg, 0.02 mmol) in dioxane (1 mL) was treated with aqueous sat. NaHCO$_3$ (0.5 mL) and acetyl chloride (0.01 mL) and heated at 50° C. for 1 h. The reaction was cooled, poured into water (5 mL), extracted with EtOAc (10 mL), the organic layer separated, dried (MgSO$_4$) and the solvent removed at reduced pressure. The residue was recrystallized from EtOH to give the product as a yellow solid (5.6 mg, 61%). mp 268° C.; CIMS m/e calc'd for $C_{27}H_{23}N_4O_4$: 467.1719, Found: 467.1730.

Example XXXVII

Preparation of 3-(4-methoxyphenyl)-5-((4-(methoxycarbonylamino)phenyl)acetamido) indeno [1,2-c]pyrazol-4-one Prepared in a similar fashion as described for example XXXII using methylchloroformate as the starting material. mp 257° C.; CIMS m/e calc'd for $C_{27}H_{23}N_4O_5$: 483.1668, found: 483.1633.

Example XXXVIII

Preparation of 3-(4-methoxyphenyl)-5-((4-(aminomethylcarbonylamino)phenyl)acetamido) indeno[1,2-c]pyrazol-4-one Prepared in a similar fashion as described for example XXIII and XXXII using chloroacetyl chloride and conc. NH$_4$OH as the starting materias. mp 228° C.; CIMS m/e calc'd for $C_{27}H_{24}N_5O_4$: 482.1828, found: 482.1844.

Example XXXIX

Preparation of 3-(4-methoxyphenyl)-5-((4-((N,N-dimethylamino)methylcarbonylamino)phenyl) acetamido) indeno[1,2-c]pyrazol-4-one Prepared in a similar fashion as described for example XXIII and XXXII using chloroacetyl chloride and dimethyl amine as the starting materias. mp >300° C.; CIMS m/e calc'd for $C_{29}H_{28}N_5O_4$: 510.2141, found: 510.2121.

Example XL

Preparation of 3-(4-methoxyphenyl)-5-((4-azidophenyl)acetamido)indeno[1,2-c]pyrazol-4-one A solution of example XXXVI (20 mg, 0.04 mmol) in DMF (2 mL) was treated with 5% palladium on carbon (5 mg) and hydrogentaed at atmospheric pressure using a hydrogen baloon. After 2 h, the solution was filtered (Celite), and the solvent removed at reduced pressure. The residue was recrystallized from EtOH to give the product as a yellow solid (15 mg, 78%). mp >300° C.; CIMS m/e calc'd for $C_{25}H_{19}N_6O_3$: 451.1519, found: 451.1544.

Example XLI

Preparation of 3-(4-methoxyphenyl)-5-((4-aminophenyl)acetamido)indeno[1,2-c]pyrazol-4-one Prepared in a similar fashion as described for example XXVII using the acid chloride of 4-azidophenylacetic acid as the starting material. mp 283° C.; CIMS m/e calc'd for $C_{25}H_{21}N_4O_3$: 425.1614, found: 425.1643.

Example XLII

Preparation of 3-(4-methoxyphenyl)-5-((phenylcarbamoyl)amino)indeno [1,2-c]pyrazol-4-one

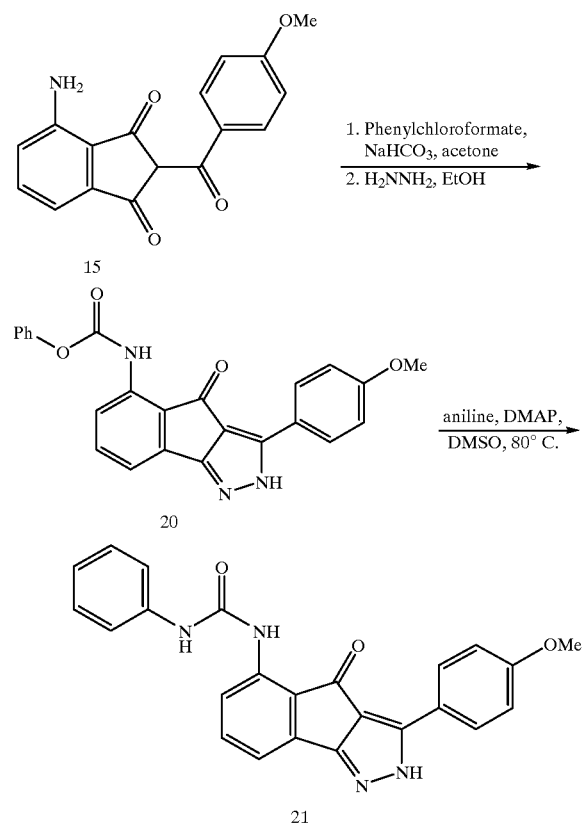

Step 1. Synthesis of 20 from 15.
A suspension of 15 (0.5 g, 1.7 mmol) in acetone (10 mL) was treated with NaHCO₃ (0.5 g) and phenyl chloroformate. The mixture was heated to 50° C. for 2 h. The reaction was cooled, poured into water (20 mL), extracted with EtOAc (40 mL), the organic layer separated, dried (MgSO₄) and the solvent removed at reduced pressure. The residue was suspended in EtOH (10 mL) and treated with hydrazine hydrate (0.16 mL, 5.1 mmol) and p-TsOH (10 mg). The mixture was heated to reflux and stirred for 3 h. The reaction was cooled to 0° C. and the product collected as a yellow solid (0.25 g, 36%). mp 195° C.; CIMS m/e calc'd for $C_{24}H_{18}N_3O_4$: 412.1297, Found: 412.1308.
Step 2. Synthesis of 21 from 20.
A solution of 20 (20 mg, 0.05 mmol) in DMSO (2 mL) was treated with aniline (20 mL, mmol) and dimethylaminopyridine (1 mg). The mixture was heated to 80° C. for 2 h. The reaction was cooled, poured into water (4 mL), extracted with EtOAc (15 mL), the organic layer separated, dried (MgSO₄) and the solvent removed at reduced pressure. The residue was recrystallized from EtOH to give the product as a yellow solid (9 mg, 44%). mp >300° C.; CIMS m/e calc'd for $C_{24}H_{19}N_4O_3$: 411.1457, Found: 411.1432.

Example XLIII

Preparation of 3-(4-methoxyphenyl)-5-((butylcarbamoyl)amino)indeno[1,2-c]pyrazol-4-one Prepared in a similar fashion as described for example XLII using butyl amine as the starting material. mp 252° C.; CIMS m/e calc'd for $C_{21}H_{21}N_4O_3$: 377.1614, found: 377.1633.

Example XLIV

Preparation of 3-((4-methoxyphenyl)-5-(4-aminobenzylcarbamoyl)amino)indeno[1,2-c]pyrazol-4-one Prepared in a similar fashion as described for example XLII using 4-aminobenzyl amine as the starting material. mp >300° C.; CIMS m/e calc'd for $C_{25}H_{22}N_5O_3$: 440.1723, found: 440.1700.

Example XLV

Preparation of 3-(4-methoxyphenyl)-5-((4-pyridylcarbamoyl)amino)indeno[1,2-c]pyrazol-4-one Prepared in a similar fashion as described for example XLII using 4-aminomethylpyridine as the starting material. mp >300° C.; CIMS m/e calc'd for $C_{24}H_{20}N_5O_3$: 426.1566, found: 426.1533.

Example XLVI

Preparation of 3-(4-hydroxyphenyl)-5-(acetamido)indeno[1,2-c]pyrazol-4-one

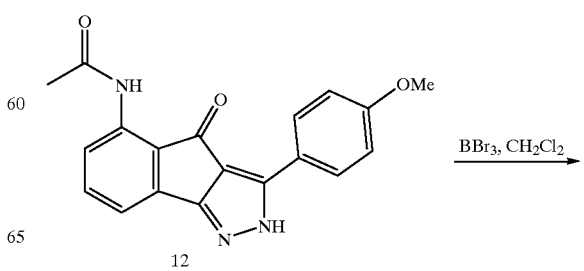

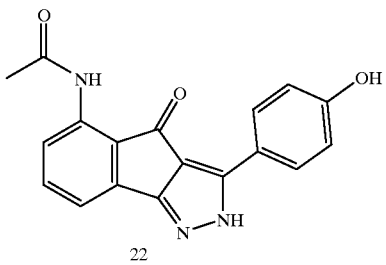

A suspension of 12 (20 mg, 0.07 mmol) in CH$_2$Cl$_2$ (2 mL) was treated with excess BBr$_3$ (1.0 mL, 1.0 M in CH$_2$Cl$_2$) and stirred for 20 h. The reaction was slowly poured into aqueous sat. NaHCO$_3$ (5 mL), extracted with EtOAc (10 mL), dried (MgSO$_4$) and concentrated. The residue was recrystallized from EtOH to give the desired product as a yellow solid (7.5 mg, 33%). mp >300° C.; CIMS m/e calc'd for C$_{18}$H$_{14}$N$_3$O$_3$: 320.1035, Found: 320.1050.

Example XLVII

Preparation of 3-(4-methoxyphenyl)-5-(formamido)indeno[1,2-c]pyrazol-4-one

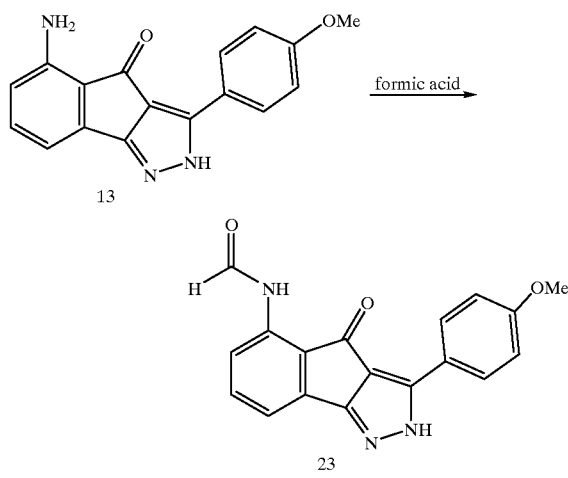

A suspension of 13 (20 mg, 0.06 mmol) in formic acid (2 mL) was heated to 100° C. for 2 h. The reaction mixture was cooled and the solvent removed at reduced pressure. The residue was recrystallized from EtOH to give the desired product as a yellow solid (12 mg, 63%). mp 280° C.; CIMS m/e calc'd for C$_{18}$H$_{14}$N$_3$O$_3$: 320.1035, Found: 320.1040.

Example XLVIII

Preparation of 3-(3-pyridyl)-5-(acetamido)indeno[1,2-c]pyrazol-4-one

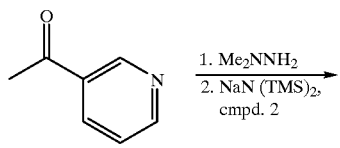

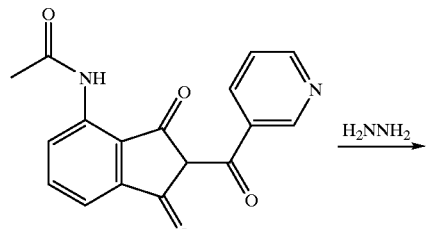

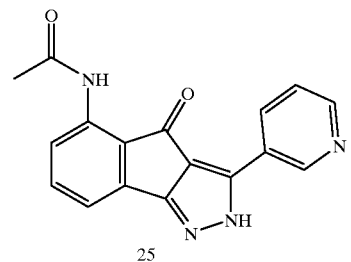

Step 1. Synthesis of 24 from 3-acetylpyridine.
A solution of 3-acetylpyridine (1.0 g, 8.3 mmol) in benzene (3 mL) was treated with 1,1-dimethylhydrazine (0.62 mL, 8.3 mmol) and p-TsOH (5 mg). The mixture was heated to 85° C. and stirred for 3 h. The reaction was cooled and the solvent removed at reduced pressure. This crude hydrazone was treated with 1.0 M NaN(TMS)$_2$ in THF (16.6 mL, 16.6 mmol) at 25° C. over 5 min. After 30 min dimethyl 3-acetamidophthalate (2.1 g, 8.3 mmol) was added in one portion and the reaction heated to reflux. Stirring was continued for 6 h. The reaction was cooled and quenched by the slow addition of TFA. The solvent was removed at reduced pressure and the residue chromatographed (silica, 2.5–5% MeOH/CH$_2$Cl$_2$) to give the product as a yellow solid (0.35 g, 14%). mp 265° C.; CIMS m/e calc'd for C$_{17}$H$_{13}$N$_2$O$_4$: 309.0875, Found: 309.0888.
Step 2. Synthesis of 25 from 24.
A suspension of 24 (30 mg, 0.09 mmol) in EtOH (2 mL) was treated with hydrazine hydrate (0.05 mL) and p-TsOH (1 mg) and heated to reflux. After stirring for 2 h. the reaction was cooled and the product filtered to give a yellow solid (12 mg, 44%). mp >300° C.; CIMS m/e calc'd for C$_{17}$H$_{13}$N$_4$O$_2$: 305.1039, Found: 305.1048.

Example XLIX

Preparation of 3-(4-pyridyl)-5-(acetamido)indeno[1,2-c]pyrazol-4-one

Prepared in a similar fashion as described for example XLVIII using 4-acetylpyridine as the starting material. mp >300° C.; CIMS m/e calc'd for C$_{17}$H$_{13}$N$_4$O$_2$: 305.1039, found: 305.1046.

Example L

Preparation of 3-(4-pyridyl)-5-(formamido)indeno[1,2-c]pyrazol-4-one

Prepared in a similar fashion as described for example XLVII using 4-acetylpyridine as the starting material. mp >300° C.; CIMS m/e calc'd for C$_{16}$H$_{11}$N$_4$O$_2$: 291.0882, found: 291.0882.

Example LI

Preparation of 3-phenyl-5-(acetamido)indeno [1,2-c]pyrazol-4-one

Prepared in a similar fashion as described for example I using acetophenone as the starting material. mp >300° C.; CIMS m/e calc'd for C$_{18}$H$_{13}$N$_3$O$_2$: 304.1065, found: 304.1086.

Example LII

Preparation of 3-(4-methylthiophenyl)-5-(acetamido)indeno[1,2-c]pyrazol-4-one

Prepared in a similar fashion as described for example I using 4'-methylthioacetophenone as the starting material. mp 283° C.; CIMS m/e calc'd for $C_{19}H_{15}N_3O_2S$: 350.0956, found: 350.0963.

Example LIII

Preparation of 3-(4-methanesulphonylphenyl)-5-(acetamido)indeno[1,2-c]pyrazol-4-one Prepared by oxidation of the product of example LII. mp >300° C.; CIMS m/e calc'd for $C_{19}H_{15}N_3O_4S$: 382.0860, found: 382.0862.

Example LIV

Preparation of 3-(4-(N,N-dimethylamino)phenyl)-5-(acetamido)indeno[1,2-c]pyrazol-4-one Prepared in a similar fashion as described for example I using 4'-(N,N-dimethylamino)acetophenone as the starting material. mp >300° C.; CIMS m/e calc'd for $C_{20}H_{18}N_4O_2$: 347.1496, found: 347.1508.

Example LV

Preparation of 3-(4-(N,N-dimethylamino)phenyl)-5-(morpholinoacetamido)indeno[1,2-c]pyrazol-4-one Prepared in a similar fashion as described for examples II and XXIII employing the product of example LIV and morpholine as the starting materials. mp >300° C.; CIMS m/e calc'd for $C_{24}H_{26}N_5O_3$: 432.2036, found: 432.2020.

Example LVI

Preparation of 3-(4-(N,N-dimethylamino)phenyl)-5-(N,N-dimethylaminoacetamido)indeno[1,2-c]pyrazol-4-one Prepared in a similar fashion as described for examples II and XXIII employing the product of example LIV and dimethylamine as the starting materials. mp >300° C.; CIMS m/e calc'd for $C_{22}H_{24}N_5O_2$: 390.1930, found: 390.1948.

Example LVII

Preparation of 3-(4-piperidinophenyl)-5-(acetamido)indeno[1,2-c]pyrazol-4-one

Prepared in a similar fashion as described for example I using 4'-(1-piperidinyl)acetophenone as the starting material. mp 291° C.; CIMS m/e calc'd for $C_{23}H_{22}N_4O_2$: 387.1801, found: 387.1821.

Example LVIII

Preparation of 3-(4-morpholinophenyl)-5-(acetamido)indeno[1,2-c]pyrazol-4-one

Prepared in a similar fashion as described for example I using 4'-morpholinylacetophenone as the starting material. mp >300° C.; CIMS m/e calc'd for $C_{22}H_{20}N_4O_3$: 388.1528, found: 388.1535.

Example LIX

Preparation of 3-(4-ethoxyphenyl)-5-(acetamido)indeno[1,2-c]pyrazol-4-one

Prepared in a similar fashion as described for example I using 4'-ethoxyacetophenone as the starting material. mp 288° C.; CIMS m/e calc'd for $C_{20}H_{17}N_3O_3$: 348.1325, found: 348.1348.

Example LX

Preparation of 3-(4-butylphenyl)-5-(acetamido)indeno[1,2-c]pyrazol-4-one

Prepared in a similar fashion as described for example I using 4'-butylacetophenone as the starting material. mp 259° C.; CIMS m/e calc'd for $C_{22}H_{21}N_3O_2$: 360.1701, found: 360.1712.

Example LXI

Preparation of 3-(4-ethylphenyl)-5-(acetamido)indeno[1,2-c]pyrazol-4-one

Prepared in a similar fashion as described for example I using 4'-ethylacetophenone as the starting material. mp 294° C.; CIMS m/e calc'd for $C_{20}H_{17}N_3O_2$: 331.1310, found: 331.1321.

Example LXII

Preparation of 3-(4-n-propylphenyl)-5-(acetamido)indeno[1,2-c]pyrazol-4-one

Prepared in a similar fashion as described for example I using 4'-n-propylacetophenone as the starting material. mp 269° C.; CIMS m/e calc'd for $C_{21}H_{19}N_3O_2$: 346.1555, found: 346.1554.

Example LXIII

Preparation of 3-(4-methoxyphenyl)-5-(carbamoylamino)indeno[1,2-c]pyrazol-4-one

Prepared in a similar fashion as described for example XLII using concentrated ammonium hydroxide as the starting material. mp >300° C.; CIMS m/e calc'd for $C_{18}H_{15}N_4O_3$: 335.1144, found: 335.1113.

Example LXIV

Preparation of 3-(4-methoxyphenyl)-5-((N,N-dimethylaminocarbamoyl)amino)indeno[1,2-c]pyrazol-4-one Prepared in a similar fashion as described for example XLII using dimethylamino hydrazine as the starting material. mp >300° C.; CIMS m/e calc'd for $C_{20}H_{20}N_5O_3$: 378.1566, found: 378.1555.

Example LXV

Preparation of 3-(4-methoxyphenyl)-5-((methylcarbamoyl)amino)indeno[1,2-c]pyrazol-4-one Prepared in a similar fashion as described for example XLII using methylamine as the starting material. mp >300° C.; CIMS m/e calc'd for $C_{19}H_{17}N_4O_3$: 349.1300, found: 349.1311.

Example LXVI

Preparation of 3-(4-methoxyphenyl)-5-((morpholinocarbamoyl)amino)indeno[1,2-c]pyrazol-4-one Prepared in a similar fashion as described for example XLII using N-aminomorpholine as the starting material. mp >300° C.; CIMS m/e calc'd for $C_{22}H_{22}N_5O_4$: 420.1671, found: 420.1655.

Example LXVII

Preparation of 3-(4-methoxyphenyl)-5-((cis-2-aminocyclohexylcarbamoyl)amino)indeno[1,2-c]pyrazol-4-one Prepared in a similar fashion as described for example XLII using cis-1,2-diaminocyclohexane as the starting material. mp >300° C.; CIMS m/e calc'd for $C_{24}H_{26}N_5O_3$: 432.2035, found: 432.2020.

Example LXVIII

Preparation of 3-(4-methoxyphenyl)-5-((4-methylpiperazinocarbamoyl)amino)indeno[1,2-c]pyrazol-4-one Prepared in a similar fashion as described for example XLII using (4-amino)methylpiperazine as the starting material. mp >300° C.; CIMS m/e calc'd for $C_{23}H_{25}N_6O_3$: 433.1987, found: 433.1999.

Example LXIX

Preparation of 3-(4-methoxyphenyl)-5-(4-(uridomethyl)piperidinoacetamido)indeno[1,2-c]pyrazol-4-one Prepared in a similar fashion as described for example XXIII using example XXX as the starting material. mp >300° C.; CIMS m/e calc'd for $C_{26}H_{29}N_6O_4$: 489.2250, found: 489.2209.

Example LXX

Preparation of 3-(4-methoxyphenyl)-5-(4-(2-pyridyl)piperazinoacetamido)indeno[1,2-c]pyrazol-4-one Prepared in a similar fashion as described for example XXIII using 4-(2-pyridyl)piperazine as the starting material. mp >300° C.; CIMS m/e calc'd for $C_{28}H_{27}N_6O_3$: 495.2144, found: 495.2111.

Example LXXI

Preparation of 3-(4-methoxyphenyl)-5-(4-(aminoethyl)piperazinoacetamido)indeno[1,2-c]pyrazol-4-one Prepared in a similar fashion as described for example XXIII using 4-(aminoethyl)piperazine as the starting material. mp >300° C.; CIMS m/e calc'd for $C_{25}H_{29}N_6O_3$: 461.2300, found: 461.2333.

Example LXXII

Preparation of 3-(4-methoxyphenyl)-5-(4-carbamoylpiperidinoacetamido)indeno[1,2-c]pyrazol-4-one Prepared in a similar fashion as described for example XXIII using isonipecotamide as the starting material. mp >300° C.; CIMS m/e calc'd for $C_{25}H_{26}N_5O_4$: 460.1984, found: 460.1998.

Example LXXIII

Preparation of 3-(4-methoxyphenyl)-5-(4-hydroxypiperidinoacetamido)indeno[1,2-c]pyrazol-4-one Prepared in a similar fashion as described for example XXIII using 4-hydroxypiperidine as the starting material. mp >300° C.; CIMS m/e calc'd for $C_{24}H_{25}N_4O_4$: 433.1875, found: 433.1844.

Example LXXIV

Preparation of 3-(4-methoxyphenyl)-5-(4-(hydroxmethyl)piperidinoacetamido)indeno[1,2-c]pyrazol-4-one Prepared in a similar fashion as described for example XXIII using 4-(hydroxmethyl)piperidine as the starting material. mp >300° C.; CIMS m/e calc'd for $C_{25}H_{27}N_4O_4$: 447.2032, found: 447.2002.

Example LXXV

Preparation of 3-(4-methoxyphenyl)-5-(4-amidopiperazinylacetamido)indeno[1,2-c]pyrazol-4-one Prepared in a similar fashion as described for example XXIII using 4-amidopiperazine as the starting material. mp >300° C.; CIMS m/e calc'd for $C_{24}H_{25}N_6O_6$: 493.1835, found: 493.1802.

Example LXXVI

Preparation of 3-(4-methoxyphenyl)-5-(4-(N,N-dimethylamino)piperidinoacetamido)indeno[1,2-c]pyrazol-4-one Prepared in a similar fashion as described for example XXIII using 4-dimethylaminopiperidine as the starting material. mp >300° C.; CIMS m/e calc'd for $C_{26}H_{30}N_5O_5$: 492.2246, found: 492.2220.

Example LXXVII

Preparation of 3-(4-methoxyphenyl)-5-(4-aminopiperidinoacetamido)indeno[1,2-c]pyrazol-4-one Prepared in a similar fashion as described for example XXIII using 4-aminopiperidine as the starting material. mp >300° C.; CIMS m/e calc'd for $C_{24}H_{26}N_5O_5$: 464.1933, found: 464.1975.

Example LXXVIII

Preparation of 3-(4-(dimethylamino)phenyl)-5-((4-methylpiperazino)acetamido)indeno[1,2-c]pyrazol-4-one Prepared in a similar fashion as described for examples II and XXIII employing the product of example LIV and 1-methylpiperazine as the starting materials. mp >300° C.; ESI-MS m/e calc'd for $C_{25}H_{29}N_6O_2$: 445.2352, found: 445.2359.

Example LXXIX

Preparation of 3-(4-(N,N-dimethylamino)phenyl)-5-(4-(aminomethyl)piperidinoacetamido)indeno[1,2-c]pyrazol-4-one Prepared in a similar fashion as described for examples II and XXIII employing the product of example LIV and 4-(aminomethyl)piperidine as the starting materials. ESI-MS m/e calc'd for $C_{26}H_{31}N_6O_2$: 459.2508, found: 459.2508.

Example LXXX

Preparation of 3-(4-(N,N-dimethylamino)phenyl)-5-(4-hydroxypiperidinoacetamido)indeno[1,2-c]pyrazol-4-one Prepared in a similar fashion as described for examples II and XXIII employing the product of example LIV and 4-hydroxypiperidine as the starting materials. mp 267° C.; ESI-MS m/e calc'd for $C_{25}H_{28}N_5O_3$: 446.2192, found: 446.2206.

Example LXXXI

Preparation of 3-(4-morpholinophenyl)-5-(morpholinoacetamido)indeno[1,2-c]pyrazol-4-one Prepared in a similar fashion as described for examples II and XXIII employing the product of example LVIII and morpholine as the starting materials. mp 258° C.; ESI-MS m/e calc'd for $C_{26}H_{28}N_5O_4$: 474.2141, found: 474.2151.

Example LXXXII

Preparation of 3-(4-morpholinophenyl)-5-((4-methylpiperazinoacetamido)indeno[1,2-c]pyrazol-4-one Prepared in a similar fashion as described for examples II and XXIII employing the product of example LVIII and 1-methylpiperazine as the starting materials. mp 258° C.; ESI-MS m/e calc'd for $C_{27}H_{31}N_6O_3$: 487.2457, found: 487.2447.

Example LXXXIII

Preparation of 3-(4-(4-morpholinyl)phenyl)-5-((4-hydroxy-1-piperidinyl)acetamido)indeno[1,2-c]pyrazol-4-one Prepared in a similar fashion as described for examples II and XXIII employing the product of example LVIII and 4-hydroxypiperidine as the starting materials. mp 245° C.; ESI-MS m/e calc'd for $C_{27}H_{30}N_5O_4$: 488.2298, found: 488.2290.

Example LXXXIV

Preparation of 3-(4-morpholinophenyl)-5-(4-(aminomethyl)piperidinoacetamido)indeno[1,2-c]pyrazol-4-one Prepared in a similar fashion as described for examples II and XXIII employing the product of example LVIII and 4-(aminomethyl)piperidine as the starting materials. mp 240° C.; ESI-MS m/e calc'd for $C_{28}H_{33}N_6O_3$: 501.2614, found: 501.2619.

Example LXXXV

Preparation of 3-(4-(N,N-dimethylamino)phenyl)-5-(4-methylpiperazinocarbamoylamino)indeno[1,2-c]pyrazol-4-one Prepared in a similar fashion as described for examples I, XXVII, and XLII employing the 4-(dimethylamino)acetophenone and 1-amino-4-methylpiperazine as the starting materials. mp >300° C.; ESI-MS m/e calc'd for $C_{24}H_{28}N_7O_2$: 446.2304, found: 446.2310.

Example LXXXVI

Preparation of 3-(4-methoxyphenyl)-5-((4-methylpiperazino)thionocarbamoylamino)indeno[1,2-c]pyrazol-4-one Prepared in a similar fashion as described for example XLII using phenylthionochloroformate and 1-amino-4-methylpiperazine as the starting materials. mp >300° C.; CIMS m/e calc'd for $C_{23}H_{25}N_6O_2S$: 449.1760, found: 449.1777.

Example LXXXVII

Preparation of 3-(2-thienyl)-5-(acetamido)indeno[1,2-c]pyrazol-4-one

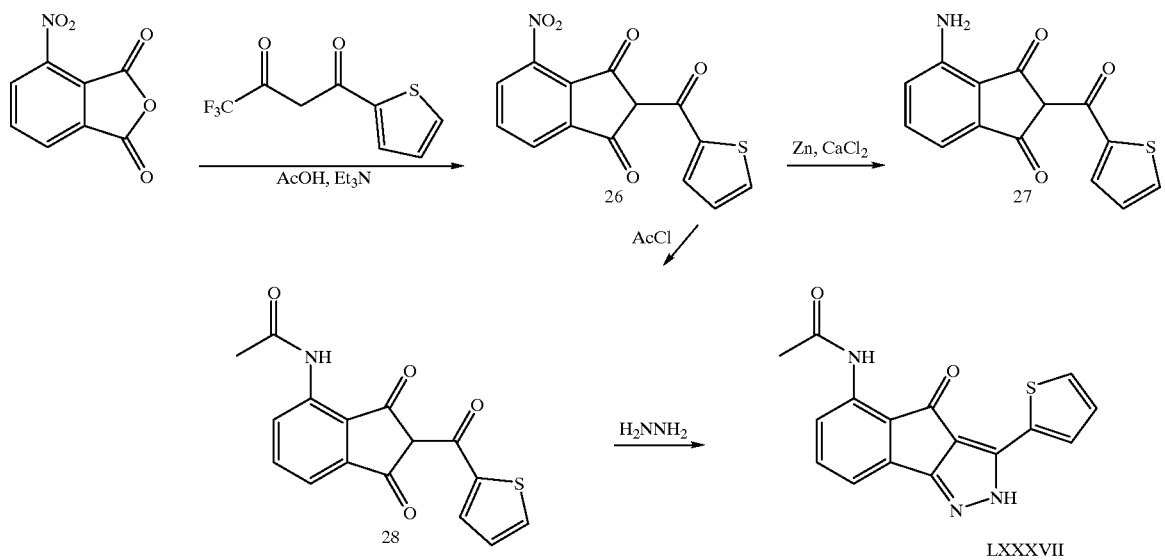

Step 1. Synthesis of 26 from 3-nitrophthalic anhydride.

A solution of 3-nitrophthalic anhydride (2.5 g, 13 mmol) and 2-thenoyltrifluoroacetone (2.87 g, 13 mmol) in acetic anhydride (7.3 mL, 78 mmol) was treated with triethylamine (3.6 mL, 26 mmol) and stirred at 25° C. for 12 h. The solution was diluted with 1 N HCl (25 mL) and the precipate collected and washed with 0.1 M HCl (2×25 mL) and hexane (3×25 mL) to give the product as a yellow solid (1.5 g, 38%). mp 140–141° C.; APIMS (M+H) calc'd for $C_{14}H_8NO_5S$: 302.29, found: 302.20.

Step 2. Synthesis of Triketone 27 from 26.

A solution of 26 (1 g, 3.3 mmol) in EtOH (12 mL) and water (12 mL) was treated with zinc (7.1 g, 110 mmol) and calcium chloride (240 mg, 2.2 mmol) and heated to reflux for 1.5 h. The reaction was filtered (Celite) and washed with EtOH/$H_2O$ (1:1, 3×200 mL), EtOAc (3×100 mL), MeOH (2×100 mL), and i-PrOH (2×100 mL). The filtrate was concentrated at reduced pressure to give an aqueous residue which was extracted with EtOAc (4×200 mL). The combined organic extracts were separated, dried ($Na_2SO_4$), filtered, and concentrated at reduced pressure to give a reddish foam (~0.9 g, 100%). mp >300° C.; ESIMS (M–H) calc'd for $C_{14}H_8NO_3S$: 270.29, found: 270.20.

Step 3. Synthesis of 28 from 27.

A solution of 27 (900 mg, 3.3 mmol) in acetic anhydride (20 mL) was refluxed for 1.5 h. The reaction mixture was treated heptane and the solvents were concentrated at reduced pressure to give a dark residue which was diluted with EtOAc (100 mL) and washed with $H_2O$ (3×75 mL) and brine (2×50 mL). The organic layer was separated, dried ($Na_2SO_4$), filtered, and concentrated at reduced pressure to give a reddish-brown foam. Purification ($SiO_2$, 1:1 EtOAc/hexane) gave the product as a red oil (600 mg, 58%). mp >300° C.; ESIMS (M–H) calc'd for $C_{16}H_{10}NO_4S$: 313.33, found: 313.10.

Step 4. Synthesis of LXXXVII from 28.

A solution of 28 (200 mg, 0.64 mmol) in EtOH (2 mL) was treated with hydrazine hydrate (0.04 mL, 1.3 mmol) and p-TsOH (6 mg, 0.032 mmol). The reaction was heated to reflux and stirred for 12 h. The reaction was cooled to 25° C. and the solid filtered. Purification by reverse phase HPLC ($CH_3CN/H_2O$) gave the product (16 mg, 9%). mp 269° C.; CIMS (M+H) calc'd for $C_{16}H_{12}N_3O_2S$: 310.0650, found: 310.0635.

Example LXXXVIII

Preparation of 3-(c-propyl)-5-(acetamido)indeno[1,2-c]pyrazol-4-one

Prepared in a similar fashion as described for example LXXXVII using 1-cyclopropyl-4,4,4-trifluoro-1,3-butanedione as the starting material. mp 220–221° C.; CIMS (M+H) calc'd for $C_{15}H_{14}N_3O_2$: 268.1086, found: 268.1078.

Example LXXXVIX

Preparation of 3-(1-methyl-3-pyrrolyl)-5-(carbamoylamino)indeno[1,2-c]pyrazol-4-one Prepared in a similar fashion as described for example LXXXVII and XLII using ammonia and the 1-methyl-3-pyrrolyl analog of 15 as the starting materials. mp >300° C.; ESIMS (M+H) calc'd for $C_{16}H_{14}N_5O_2$: 308.1148, found: 308.1166.

Example XC

Preparation of 3-(3-methyl-2-thienyl)-5-(acetamido)indeno[1,2-c]pyrazol-4-one

Prepared in a similar fashion as described for example LXXXVII and XLII using the 3-methyl-2-thienyl analog of 26 as the starting material. mp 275° C.; ESIMS (M+H) calc'd for $C_{17}H_{14}N_3O_2S$: 324.0811, found: 324.0807.

Example XCI

Preparation of 3-(ethyl)-5-(carbamoylamino)indeno[1,2-c]pyrazol-4-one

Prepared in a similar fashion as described for example LXXXVII and XLII using ammonia and the ethyl analog of 15 as the starting materials. mp >250° C.; CIMS (M+H) calc'd for $C_{13}H_{13}N_4O_2$: 257.1039, found: 257.1033.

Example XCII

Preparation of 3-(n-propyl)-5-(carbamoylamino)indeno[1,2-c]pyrazol-4-one

Prepared in a similar fashion as described for example LXXXVII and XLII using ammonia and the n-propyl analog of 15 as the starting materials. mp 187–189° C.; CIMS (M+H) calc'd for $C_{14}H_{15}N_4O_2$: 271.1195, found: 271.1187.

Example XCIII

Preparation of 3-(i-propyl)-5-(carbamoylamino)indeno[1,2-c]pyrazol-4-one

Prepared in a similar fashion as described for example LXXXVII and XLII using ammonia and the i-propyl analog of 15 as the starting materials. mp >250° C.; CIMS (M+H) calc'd for $C_{14}H_{15}N_4O_2$: 271.1195, found: 271.1196.

Example XCIV

Preparation of 3-(c-propyl)-5-(carbamoylamino)indeno[1,2-c]pyrazol-4-one

Prepared in a similar fashion as described for example LXXXVII and XLII using ammonia and the c-propyl analog of 15 as the starting materials. mp 252–253° C.; ESIMS (M–H) calc'd for $C_{14}H_{11}N_4O_2$: 267.0881, found: 267.0884.

Example XCV

Preparation of 3-(c-hexyl)-5-(carbamoylamino)indeno[1,2-c]pyrazol-4-one

Prepared in a similar fashion as described for example LXXXVII and XLII using ammonia and the c-hexyl analog of 15 as the starting materials. mp 178–179° C.; ESIMS (M+H) calc'd for $C_{17}H_{19}N_4O_2$: 311.1507, found: 311.1500.

Example XCVI

Preparation of 3-(2-thienyl)-5-(carbamoylamino)indeno[1,2-c]pyrazol-4-one

Prepared in a similar fashion as described for example LXXXVII and XLII using ammonia and the 2-thienyl analog of 15 as the starting materials. mp 214° C.; CIMS m+ calc'd for $C_{15}H_{10}N_4O_2S$: 310.0517, found: 310.0524.

Example XCVII

Preparation of 3-(3-methyl-2-thienyl)-5-(carbamoylamino)indeno[1,2-c]pyrazol-4-one Prepared in a similar fashion as described for example LXXXVII and XLII using ammonia and the 3-methyl-2-thienyl analog of 15 as the starting materials. mp 270° C.; ESIMS (M+H) calc'd for $C_{16}H_{13}N_4O_2S$: 325.0759, found: 325.0744.

Example XCVIII

Preparation of 3-(5-methyl-2-thienyl)-5-(carbamoylamino)indeno[1,2-c]pyrazol-4-one Prepared in a similar fashion as described for example LXXXVII and XLII using ammonia and the 5-methyl-2-thienyl analog of 15 as the starting materials. mp >280° C.; ESIMS (M+H) calc'd for $C_{16}H_{13}N_4O_2S$: 325.0759, found: 325.0761.

Example XCIX

Preparation of 3-(5-carboethoxy-2-thienyl)-5-(carbamoylamino)indeno[1,2-c]pyrazol-4-one Prepared in a similar fashion as described for example LXXXVII and XLII using ammonia and the 5-ethylcarboxyl-2-thienyl analog of 15 as the starting materials. mp >280° C.; ESIMS (M+H) calc'd for $C_{18}H_{15}N_4O_4S$: 383.0813, found: 383.0788.

Example C

Preparation of 3-(3-thienyl)-5-(carbamoylamino)indeno[1,2-c]pyrazol-4-one

Prepared in a similar fashion as described for example LXXXVII and XLII using ammonia and the 3-thienyl analog of 15 as the starting materials. mp >280° C.; ESIMS (M+H) calc'd for $C_{15}H_{11}N_4O_2S$: 311.0603, found: 311.0594.

Example CI

Preparation of 3-(5-chloro-3-thienyl)-5-(carbamoylamino)indeno[1,2-c]pyrazol-4-one Prepared in a similar fashion as described for example LXXXVII and XLII using ammonia and the 5-chloro-3-thienyl analog of 15 as the starting materials. mp >300° C.; ESIMS (M+H) calc'd for $C_{15}H_{10}N_4O_2SCl$: 345.0209, found: 345.0213.

Example CII

Preparation of 3-(2,5-dimethyl-3-thienyl)-5-(carbamoylamino)indeno[1,2-c]pyrazol-4-one Prepared in a similar fashion as described for example LXXXVII and XLII using ammonia and the 2,5-dimethyl-3-thienyl analog of 15 as the starting materials. mp >280° C.; ESIMS (M+H) calc'd for $C_{17}H_{15}N_4O_2S$: 339.0916, found: 339.0905.

Example CIII

Preparation of 3-(2-furanyl)-5-(carbamoylamino)indeno[1,2-c]pyrazol-4-one

Prepared in a similar fashion as described for example LXXXVII and XLII using ammonia and the 2-furanyl analog of 15 as the starting materials. mp 278° C.; ESIMS (M+H) calc'd for $C_{15}H_{11}N_4O_3$: 295.0831, found: 295.0838.

Example CIV

Preparation of 3-(i-propyl)-5-((N,N-dimethylaminocarbamoyl)amino)indeno [1,2-c]pyrazol-4-one Prepared in a similar fashion as described for example LXXXVII and XLII using 1,1-dimethylhydrazine and the i-propyl analog of 15 as the starting materials. mp 231–233° C.; ESIMS (M+H) calc'd for $C_{16}H_{20}N_5O_2$: 314.1616, found: 314.1599.

Example CV

Preparation of 3-(c-propyl)-5-((N,N-dimethylaminocarbamoyl)amino)indeno [1,2-c]pyrazol-4-one Prepared in a similar fashion as described for example LXXXVII and XLII using 1,1-dimethylhydrazine and the c-propyl analog of 15 as the starting materials. mp XXX° C.; ESIMS (M+H) calc'd for $C_{16}H_{18}N_5O_2$: 312.1460, found: 312.1487.

Example CVI

Preparation of 3-(c-hexyl)-5-((N,N-dimethylaminocarbamoyl)amino)indeno [1,2-c]pyrazol-4-one Prepared in a similar fashion as described for example LXXXVII and XLII using 1,1-dimethylhydrazine and the c-hexyl analog of 15 as the starting materials. mp 229–231° C.; ESIMS (M+H) calc'd for $C_{19}H_{24}N_5O_2$: 354.1929, found: 354.1932.

Example CVII

Preparation of 3-(2-thienyl)-5-((N,N-dimethylaminocarbamoyl)amino)indeno [1,2-c]pyrazol-4-one Prepared in a similar fashion as described for example LXXXVII and XLII using 1,1-dimethylhydrazine and the 2-thienyl analog of 15 as the starting materials. mp 279° C.; ESIMS (M+H) calc'd for $C_{17}H_{16}N_5O_2S$: 354.1024, found: 354.1025.

Example CVIII

Preparation of 3-(5-methoxy-2-thienyl)-5-((N,N-dimethylaminocarbamoyl)amino)indeno [1,2-c]pyrazol-4-one Prepared in a similar fashion as described for example LXXXVII and XLII using 1,1-dimethylhydrazine and the 5-methoxy-2-thienyl analog of 15 as the starting materials. mp 280° C.; ESIMS (M+H) calc'd for $C_{18}H_{18}N_5O_3S$: 384.1130, found: 384.1119.

Example CIX

Preparation of 3-(5-methyl-2-thienyl)-5-((N,N-dimethylaminocarbamoyl)amino)indeno [1,2-c]pyrazol-4-one Prepared in a similar fashion as described for example LXXXVII and XLII using 1,1-dimethylhydrazine and the 5-methyl-2-thienyl analog of 15 as the starting materials. mp >280° C.; ESIMS (M+H) calc'd for $C_{18}H_{18}N_5O_2S$: 368.1181, found: 368.1171.

Example CX

Preparation of 3-(5-carboethoxy-2-thienyl)-5-((N,N-dimethylaminocarbamoyl)amino)indeno [1,2-c]pyrazol-4-one Prepared in a similar fashion as described for example LXXXVII and XLII using 1,1-dimethylhydrazine and the 5-ethylcarboxyl-2-thienyl analog of 15 as the starting materials. mp 252° C.; ESIMS (M+H) calc'd for $C_{20}H_{20}N_5O_4S$: 426.1236, found: 426.1251.

Example CXI

Preparation of 3-(3-thienyl)-5-((N,N-dimethylaminocarbamoyl)amino)indeno [1,2-c]pyrazol-4-one Prepared in a similar fashion as described for example LXXXVII and XLII using 1,1-dimethylhydrazine and the 3-thienyl analog of 15 as the starting materials. mp 202° C.; ESIMS (M+H) calc'd for $C_{17}H_{16}N_5O_2S$: 354.1025, found: 354.1031.

Example CXII

Preparation of 3-(1-methyl-3-pyrrolyl)-5-(carbamoylamino)indeno[1,2-c]pyrazol-4-one Prepared in a similar fashion as described for example LXXXVII and XLII using ammonia and the 1-methyl-3-pyrrolyl analog of 15 as the starting materials. mp >300° C.; ESIMS (M+H) calc'd for $C_{16}H_{14}N_5O_2$: 308.1147, found: 308.1166.

Example CXIII

Preparation of 3-(2,5-dimethyl-3-thienyl)-5-((N,N-dimethylaminocarbamoyl)amino)indeno [1,2-c] pyrazol-4-one Prepared in a similar fashion as described for example LXXXVII and XLII using 1,1-dimethylhydrazine and the 2,5-dimethyl-3-thienyl analog of 15 as the starting materials. mp 252° C.; ESIMS (M+H) calc'd for $C_{19}H_{20}N_5O_2S$: 382.1338, found: 382.1357.

Example CXIV

Preparation of 3-(2-furanyl)-5-((N,N-dimethylaminocarbamoyl)amino)indeno [1,2-c] pyrazol-4-one Prepared in a similar fashion as described for example LXXXVII and XLII using 1,1-dimethylhydrazine and the 2-furanyl analog of 15 as the starting materials. mp 202° C.; ESIMS (M+H) calc'd for $C_{17}H_{16}N_5O_3$: 338.1253, found: 338.1248.

Example CXV

Preparation of 3-(i-propyl)-5-((4-carbamoylpiperidino)acetamido)indeno [1,2-c] pyrazol-4-one Prepared in a similar fashion as described for example XXIII using isonipecotamide and the i-propyl analog of 14 as the starting materials. mp 224–225° C.; ESIMS (M+H) calc'd for $C_{21}H_{26}N_5O_3$: 396.2035, found: 396.2036.

Example CXVI

Preparation of 3-(c-hexyl)-5-((4-carbamoylpiperidino)acetamido)indeno [1,2-c] pyrazol-4-one Prepared in a similar fashion as described for example XXIII using isonipecotamide and the c-hexyl analog of 14 as the starting materials. mp 228–229° C.; ESIMS (M+H) calc'd for $C_{24}H_{30}N_5O_3$: 436.2348, found: 436.2345.

Example CXVII

Preparation of 3-(ethyl)-5-(4-(aminomethyl) piperidinoacetamido)indeno [1,2-c]pyrazol-4-one Prepared in a similar fashion as described for example XXIII using 4-(aminomethyl)piperidine and the ethyl analog of 14 as the starting materials. mp 174–176° C.; ESIMS (M+H) calc'd for $C_{20}H_{26}N_5O_2$: 368.2086, found: 368.2078.

Example CXVIII

Preparation of 3-(i-propyl)-5-(4-(aminomethyl) piperidinoacetamido)indeno [1,2-c]pyrazol-4-one Prepared in a similar fashion as described for example XXIII using 4-(aminomethyl)piperidine and the i-propyl analog of 14 as the starting materials. mp 218–220° C.; ESIMS (M+H) calc'd for $C_{21}H_{28}N_5O_2$: 382.2242, found: 382.2227.

Example CXIX

Preparation of 3-(c-propyl)-5-(4-(aminomethyl) piperidinoacetamido)indeno [1,2-c]pyrazol-4-one Prepared in a similar fashion as described for example XXIII using 4-(aminomethyl)piperidine and the c-propyl analog of 14 as the starting materials. mp 138–140° C.; ESIMS (M+H) calc'd for $C_{21}H_{26}N_5O_2$: 380.2086, found: 380.2079.

Example CXX

Preparation of 3-(c-hexyl)-5-(4-(aminomethyl) piperidinoacetamido)indeno [1,2-c]pyrazol-4-one Prepared in a similar fashion as described for example XXIII using 4-(aminomethyl)piperidine and the c-hexyl analog of 14 as the starting materials. mp 196–198° C.; ESIMS (M+H) calc'd for $C_{24}H_{32}N_5O_2$: 422.2555, found: 422.2540.

Example CXXI

Preparation of 3-(i-propyl)-5-((4-methylpiperazino) carbamoylamino)indeno [1,2-c]pyrazol-4-one Prepared in a similar fashion as described for example LXXXVII and XLII using 1-amino-4-methylpiperazine and the i-propyl analog of 15 as the starting materials. mp 231–233 ° C.; ESIMS (M+H) calc'd for $C_{19}H_{25}N_6O_2$: 369.2038, found: 369.2039.

Example CXXII

Preparation of 3-(5-carboethoxy-2-thienyl)-5-((4-methylpiperazino)carbamoylamino)indeno [1,2-c] pyrazol-4-one Prepared in a similar fashion as described for example LXXXVII and XLII using 1-amino-4-methylpiperazine and the 5-ethylcarboxyl-2-thienyl analog of 15 as the starting materials. mp 249° C.; ESIMS (M+H) calc'd for $C_{23}H_{25}N_6O_4S$: 481.1657, found: 481.1642.

Example CXXIII

Preparation of 3-(5-carboxyl-2-thienyl)-5-((4-methylpiperazino)carbamoylamino)indeno [1,2-c] pyrazol-4-one

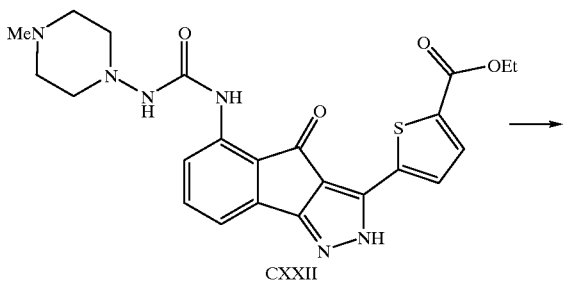

CXXII

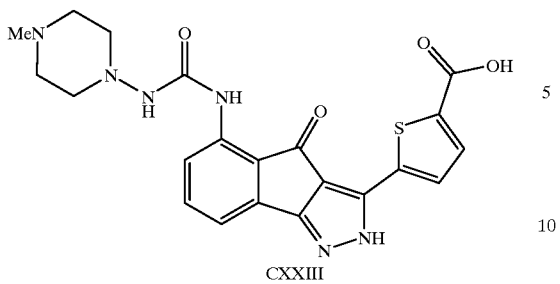

CXXIII

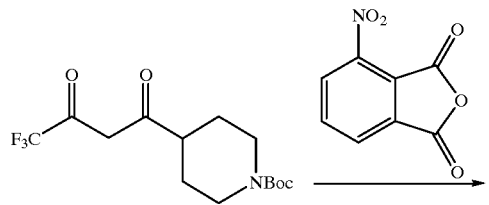

29A

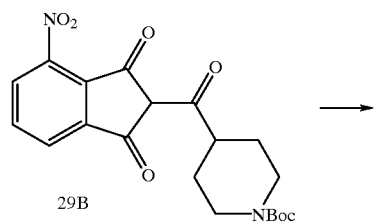

29B

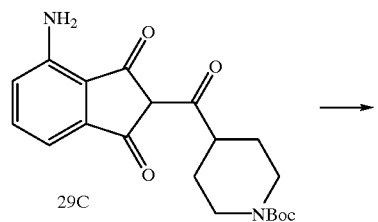

29C

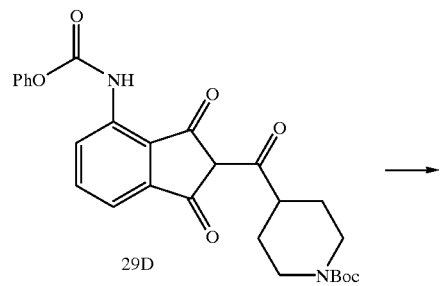

29D

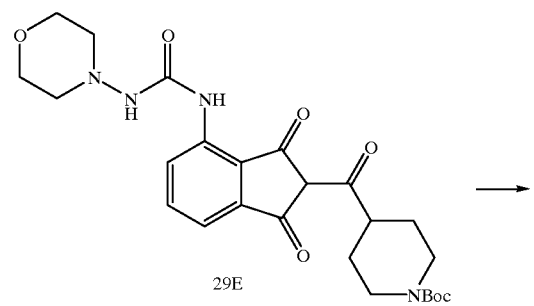

29E

A solution of CXXII (30 mg, 0.05 mmol) in 3:1 THF/water (2 mL) was treated with LiOH (23 mg, 0.5 mmol) and the reaction was stirred at 25° C. for 12 h and then heated to reflux for 1 h. The organic solvent was removed at reduced pressure and the residue was partioned between EtOAc (5 mL) and water (5 mL). The organic layer was separated and the aqueous phase was adjusted to pH=2 with 1 M HCl and re-extracted with EtOAc (5 mL). The combined organic layers were dried (Na2SO4), filtered and concentrated at reduced pressure to give a crude residue. Purification by reverse phase HPLC gave the product as a yellow solid (10.4 mg, 46%). mp 270° C.; ESIMS (M+H) calc'd for $C_{21}H_{21}N_6O_4S$: 453.1344, found: 453.1353.

Example CXXIV

Preparation of 3-(2,5-dimethyl-3-thienyl)-5-((4-methylpiperazino)carbamoylamino)indeno [1,2-c] pyrazol-4-one Prepared in a similar fashion as described for example LXXXVI using 1-amino-4-methylpiperazine and the 2,5-dimethyl-3-thienyl analog of 15 as the starting materials. mp 250° C.; ESIMS (M+H) calc'd for $C_{22}H_{25}N_6O_2S$: 437.1760, found: 437.1771.

Example CXXV

Preparation of 3-(i-propyl)-5-(morpholinylcarbamoylamino)indeno [1,2-c] pyrazol-4-one Prepared in a similar fashion as described for example LXXXVI using 4-aminomorpholine and the i-propyl analog of 15 as the starting materials. mp 256–258° C.; ESIMS (M–H) calc'd for $C_{18}H_{20}N_5O_3$: 354.1566, found: 354.1543.

Example CXXVI

Preparation of 3-(1-methoxycarbonyl-4-piperidinyl)-5-(morpholinylcarbamoylamino)indeno [1,2-c] pyrazol-4-one

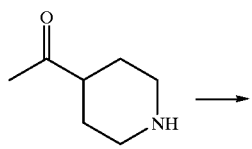

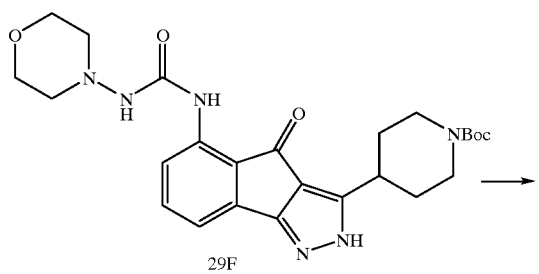

29F

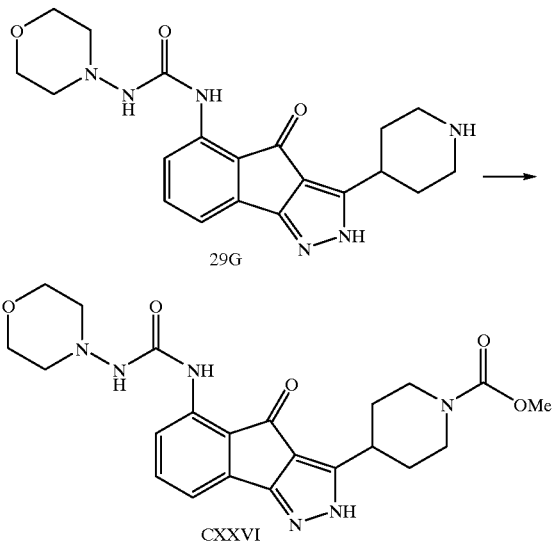

Step 1. Synthesis of 29A from 4-acetylpiperidine hydrochloride.

A solution of 4-acetylpiperidine hydrochloride (8.18 g, 0.05 mol) in THF (100 mL) at 0° C. was treated with triethylamine (13.93 mL, 0.1 mol) and stirred for 15 min. The reaction mixture was treated with a solution of di-t-butyldicarbonate (10.91 g, 0.05 mol) in THF (50 mL) and stirred at 25° C. for 1 h. The reaction mixture was diluted with water (100 mL) and extracted with EtOAc (100 mL). The organic layer was separated, dried (MgSO$_4$), filtered, and concentrated at reduced pressure to give a pale yellow oil (10.7 g, 94%). The 4-acetyl-N-BOC-piperidine in EtOH (20 mL) was added dropwise to a solution of ethyl trifluoroacetate (6.25 g, 0.044 mol) and sodium ethoxide [freshly prepared from sodium (1.01 g, 0.044 mol) and EtOH (100 mL)] and stirred at 25° C. for 16 h. The solution was quenched with aqueous H$_2$SO$_4$ (50 mls, 0.044 mol) and extracted with EtOAc (200 mL). The organic layer was separated, dried (MgSO$_4$), filtered, and concentrated at reduced pressure to give a pale yellow liquid (14.8 g, 92%). CI-MS (M+H) calc'd for C$_{14}$H$_{20}$F$_3$NO$_4$: 323.1344, found: 323.1337.

Step 2. Synthesis of 29B from 29A.

Prepared in a similar fashion as described for example LXXXVII, Step 1, using 3-nitrophthalic anhydride and 29A as the starting materials. mp 132–134° C.; ESI-MS (M+H) calc'd for C$_{20}$H$_{23}$N$_2$O$_7$: 403.1505, found: 403.1521.

Step 3. Synthesis of 29C from 29B.

Prepared in a similar fashion as described for example LXXXVII, Step 2, using 29B as the starting material. mp 187– 189° C.; ESI-MS (M+H) calc'd for C$_{20}$H$_{25}$N$_2$O$_5$: 373.1763, found: 373.1777.

Step 4. Synthesis of 29D from 29C.

A suspension of C (8.0 g, 21.5 mmol) in acetone (200 mL) was treated with NaHCO$_3$ (16.0 g) and phenyl chloroformate (4.04 g, 25.8 mmol) and heated to 50° C. for 16 h. The reaction mixture was cooled, poured into water (200 mL), and extracted with EtOAc (400 mL). The organic layer was separated, dried (MgSO$_4$), filtered, and concentrated at reduced pressure to give a crude residue. Trituration with hexane gave the product as a pale yellow solid (1.1 g, 79%). mp 121–123° C.; ESI-MS (M+H) calc'd for C$_{27}$H$_{29}$N$_2$O$_7$: 493.1975, found: 493.1982.

Step 5. Synthesis of 29E from 29D.

A solution of 29D (4.93 g, 0.01 mol) in dimethylsulfoxide (30 mL) was treated with 4-aminomorpholine (2.04 g, 0.02 mol) and heated to 90° C. in a sealed tube for 6 hours. The solvent was removed at reduced pressure and the residue was taken up in water (30 mL). The solid was filtered to give the product as a yellow solid (5.0 g, 99%). mp 164–166° C.; ESI-MS (M+H) calc'd for C$_{25}$H$_{33}$N$_4$O$_7$: 501.2349, found: 501.2357.

Step 6. Synthesis of 29F from 29E.

Prepared in a similar fashion as described for example LXXXVII, Step 4, using 29E (5.0 g, 0.01 mol) as the starting material to give the product as a yellow solid (3.8 g, 77%). mp 201–203° C.; ESI-MS (M–H) calc'd for C$_{25}$H$_{31}$N$_6$O$_5$: 495.2356, found: 495.2383.

Step 7. Synthesis of 29G from 29F.

A solution of 29F (1.8 g, 3.6 mmol) in methylene chloride (25 mL) was treated with trifluoroacetic acid (2.8 mL, 36 mmol) and stirred at 25° C. for 3 h. The organic solvent was removed at reduced pressure and rediluted with methylene chloride (25 mL). Removal of the organic solvent again at reduced pressure gave a solid which was treated with ether (25 mL) and stirred at 25° C. for 16 h. The solid was filtered to give the product as a yellow solid (1.8 g, 98%). mp 282–284° C.; ESI-MS (M+H) calc'd for C$_{20}$H$_{25}$N$_6$O$_3$: 397.1988, found: 397.1993.

Step 8. Synthesis of CXXVI from 29G.

A suspension of 29G (0.03 g, 0.059 mmol) in acetone (1 mL) was treated with NaHCO$_3$ (0.06 g) and methyl chloroformate (6.69 mg, 0.071 mmol) and heated to 50° C. for 2 h. The reaction was cooled, poured into water (20 mL), and extracted with EtOAc (40 mL). The organic layer was separated, dried (MgSO$_4$), filtered, and the concentrated at reduced pressure to give a yellow solid. Purification using reverse phase HPLC (CH$_3$CN/water) gave the product as an off-white solid (7.7 mg, 23%). mp 216–218° C.; ESI-MS (M+H) calc'd for C$_{22}$H$_{27}$N$_6$O$_5$: 455.2043, found: 455.2036.

Example CXXVII

Preparation of 3-(5-methyl-2-thienyl)-5 - (morpholinylcarbamoylamino)indeno [1,2-c] pyrazol-4-one Prepared in a similar fashion as described for example LXXXVII and XLII using 4-aminomorpholine and the 5-methyl-2-thienyl analog of 15 as the starting materials. mp 261° C.; ESIMS (M+H) calc'd for C$_{20}$H$_{20}$N$_5$O$_3$S: 410.1287, found: 410.1308.

Example CXXVIII

Preparation of 3-(5-chloro-3-thienyl)-5- (morpholinylcarbamoylamino)indeno [1,2-c] pyrazol-4-one Prepared in a similar fashion as described for example LXXXVII and XLII using 4-aminomorpholine and the 5-chloro-3-thienyl analog of 15 as the starting materials. mp 259° C.; ESIMS (M+H) calc'd for C$_{19}$H$_{17}$N$_5$O$_3$SCl: 430.0741, found: 430.0757.

Example CXXIX

Preparation of 3-(2,5-dimethyl-3-thienyl)-5- (morpholinylcarbamoylamino)indeno [1,2-c] pyrazol-4-one Prepared in a similar fashion as described for example LXXXVII and XLII using 4-aminomorpholine and the 2,5- dimethyl-3-thienyl analog of 15 as the starting materials. mp >280° C.; ESIMS (M+H) calc'd for $C_{21}H_{22}N_5O_3S$: 424.1443, found: 424.1431.

Example CXXX

Preparation of 3-(5-carboethoxy-2-thienyl)-5-(morpholinylcarbamoylamino)indeno [1,2-c]pyrazol-4-one Prepared in a similar fashion as described for example LXXXVII and XLII using 4-aminomorpholine and the 5-ethylcarboxyl-2-thienyl analog of 15 as the starting materials. mp 258° C.; ESIMS (M+H) calc'd for $C_{22}H_{22}N_5O_5S$: 468.1341, found: 468.1331.

Example CXXXI

Preparation of 3-(5-carboxyl-2-thienyl)-5-(morpholinylcarbamoylamino)indeno [1,2-c]pyrazol-4-one Prepared in a similar fashion as described for example CXXIII using CXXX as starting material. mp 273° C.; ESIMS (M+H) calc'd for $C_{20}H_{18}N_5O_5S$: 440.1028, found: 440.1026.

Example CXXXII

Preparation of 3-(5-benzylaminocarbonyl-2-thienyl)-5-(morpholinylcarbamoylamino)indeno [1,2-c]pyrazol-4-one

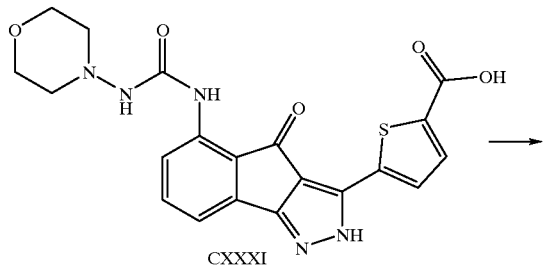

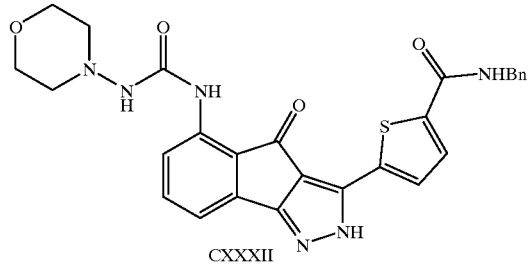

A solution of benzylamine (0.01 mL, 0.09 mmol) in DMF (1 mL) was treated with acid CXXXI (40 mg, 0.09 mmol) and stirred at 25° C. The reaction was treated with TBTU (29 mg, 0.09 mmol) and stirred at 25° C. for 30 min. Triethylamine (0.01 mL, 0.09 mmol) was added and the reaction stirred at 25° C. for 12 h. After adding more TBTU (15 mg, 0.045 mmol) and triethylamine (0.01 mL, 0.09 mmol) the reaction was stirred at 25° C. for an additional 4 h. The reaction was diluted with EtOAc (10 mL) and water (10 mL) and the aqueous layer was extracted with EtOAc (5×10 mL). The combined organic layers were dried (Na2SO4), filtered, and the solvent removed at reduced pressure. Purification of the residue using reverse phase HPLC gave the product as a yellow solid (21 mg, 42%). mp 275° C.; ESIMS (M+H) calc'd for $C_{27}H_{25}N_5O_4S$: 529.1659, found: 529.1682.

Example CXXXIII

Preparation of 3-(5-((4-methylpiperazino)carbonyl)-2-thienyl)-5-(morpholinylcarbamoyl)aminoindeno [1,2-c]pyrazol-4-one Prepared in a similar fashion as described for example CXXXII using CXXXI and 1-amino-4-methylpiperazine as the starting materials. mp 190° C. (TFA salt); ESIMS (M+H) calc'd for $C_{25}H_{29}N_8O_4S$: 537.2032, found: 537.2055.

Example CXXXIV

Preparation of 3-(5-((2-(1-methyl-2-pyrrolidinyl)ethyl) aminocarbonyl)-2-thienyl)-5-(morpholinylcarbamoylamino)indeno [1,2-c]pyrazol-4-one Prepared in a similar fashion as described for example CXXXII using CXXXI and 2-(2-aminoethyl)-1-methylpyrrolidine as the starting materials. mp 235° C. (TFA salt); ESIMS (M+H) calc'd for $C_{27}H_{32}N_7O_4S$: 550.2236, found: 550.2229.

Example CXXXV

Preparation of 3-(5-((N,N-dimethylamino) aminocarbonyl)-2-thienyl)-5-(morpholinylcarbamoylamino)indeno [1,2-c]pyrazol-4-one Prepared in a similar fashion as described for example CXXXII using CXXXI and 1,1-dimethylhydrazine as the starting materials. mp 201° C. (TFA salt); ESIMS (M+H) calc'd for $C_{22}H_{24}N_7O_4S$: 482.1610, found: 482.1588.

Example CXXXVI

Preparation of 3-(5-(2-((N,N-dimethylamino)ethyl) aminocarbonyl)-2-thienyl)-5-(morpholinylcarbamoylamino)indeno [1,2-c]pyrazol-4-one Prepared in a similar fashion as described for example CXXXII using CXXXI and N,N-dimethylethylenediamine as the starting materials. mp 190° C. (TFA salt); ESIMS (M+H) calc'd for $C_{24}H_{28}N_7O_4S$: 510.1923, found: 510.1922.

Example CXXXVII

Preparation of 3-(5-((2-pyrrolidinoethyl) aminocarbonyl)-2-thienyl)-5-(morpholinylcarbamoylamino)indeno [1,2-c]pyrazol-4-one Prepared in a similar fashion as described for example CXXXII using CXXXI and 1-(2-aminoethyl)pyrrolidine as the starting materials. mp 224° C. (TFA salt); ESIMS (M+H) calc'd for $C_{26}H_{30}N_7O_4S$: 536.2080, found: 536.2091.

Example CXXXVIII

Preparation of 3-(5-((2-morpholinoethyl) aminocarbonyl)-2-thienyl)-5-(morpholinylcarbamoylamino)indeno [1,2-c]pyrazol-4-one Prepared in a similar fashion as described for example CXXXII using CXXXI and 4-(2-aminoethyl)morpholine as the starting materials. mp 241° C. (TFA salt); ESIMS (M+H) calc'd for $C_{26}H_{30}N_7O_5S$: 552.2029, found: 552.2043.

Example CXXXIX

Preparation of 3-(5-(morpholinoaminocarbonyl)-2-thienyl)-5-(morpholinylcarbamoylamino)indeno [1,2-c]pyrazol-4-one Prepared in a similar fashion as described for example CXXXII using CXXXI and 4-aminomorpholine as the starting materials. mp 271° C. (TFA salt); ESIMS (M+H) calc'd for $C_{24}H_{26}N_7O_5S$: 524.1716, found: 524.1719.

Example CXL

Preparation of 3-(5-((3-(2-pyrrolidon-1-yl)propyl)aminocarbonyl)-2-thienyl)-5-(morpholinylcarbamoylamino)indeno [1,2-c]pyrazol-4-one Prepared in a similar fashion as described for example CXXXII using CXXXI and 1-(3-aminopropyl)-2-pyrrolidinone as the starting materials. mp 260° C. (TFA salt); ESIMS (M+H) calc'd for $C_{27}H_{30}N_7O_5S$: 564.2029, found: 564.2031.

Example CXLI

Preparation of 3-(5-((2-(3-pyridyl)ethyl)aminocarbonyl)-2-thienyl)-5-(morpholinylcarbamoylamino)indeno [1,2-c]pyrazol-4-one Prepared in a similar fashion as described for example CXXXII using CXXXI and 3-(2-aminoethyl)pyridine as the starting materials. mp 203° C. (TFA salt); ESIMS (M+H) calc'd for $C_{27}H_{26}N_7O_4S$: 544.1766, found: 544.1760.

Example CXLII

Preparation of 3-(5-((3-(1-imidazolyl)propyl)aminocarbonyl)-2-thienyl)-5-(morpholinylcarbamoylamino)indeno [1,2-c]pyrazol-4-one Prepared in a similar fashion as described for example CXXXII using CXXXI and 1-(3-aminopropyl)imidazole as the starting materials. mp 263° C. (TFA salt); ESIMS (M+H) calc'd for $C_{26}H_{27}N_8O_4S$: 547.1875, found: 547.1872.

Example CXLIII

Preparation of 3-(5-((2-(2-pyridyl)ethyl)aminocarbonyl)-2-thienyl)-5-(morpholinylcarbamoylamino)indeno [1,2-c]pyrazol-4-one Prepared in a similar fashion as described for example CXXXII using CXXXI and 2-(2-aminoethyl)pyridine as the starting materials. mp >280° C. (TFA salt); ESIMS (M+H) calc'd for $C_{27}H_{26}N_7O_4S$: 544.1767, found: 544.1778.

Example CXLIV

Preparation of 3-(5-(((2-pyridyl)methyl)aminocarbonyl)-2-thienyl)-5-(morpholinylcarbamoylamino)indeno [1,2-c]pyrazol-4-one Prepared in a similar fashion as described for example CXXXII using CXXXI and 2-(aminomethyl)pyridine as the starting materials. mp 239° C. (TFA salt); ESIMS (M+H) calc'd for $C_{26}H_{24}N_7O_4S$: 530.1610, found: 530.1603.

Example CXLV

Preparation of 3-(5-((2-piperidinoethyl)aminocarbonyl)-2-thienyl)-5-(morpholinylcarbamoylamino)indeno [1,2-c]pyrazol-4-one Prepared in a similar fashion as described for example CXXXII using CXXXI and 1-(2-aminoethyl)piperidine as the starting materials. mp 228° C. (TFA salt); ESIMS (M+H) calc'd for $C_{27}H_{32}N_7O_4S$: 550.2236, found: 550.2236.

Example CXLVI

Preparation of 3-(5-pyrrolidinoaminocarbonyl-2-thienyl)-5-(morpholinocarbamoylamino)indeno [1,2-c]pyrazol-4-one Prepared in a similar fashion as described for example CXXXII using CXXXI and 1-aminopyrrolidine as the starting materials. mp 213–215° C. (TFA salt); ESI-MS (M+H) calc'd for $C_{24}H_{26}N_7O_4S$: 508.1764, found: 508.1774.

Example CXLVII

Preparation of 3-(5-piperidinoaminocarbonyl-2-thienyl)-5-(morpholinocarbamoylamino)indeno [1,2-c]pyrazol-4-one Prepared in a similar fashion as described for example CXXXII using CXXXI and 1-aminopiperidine as the starting materials. mp 189–191° C. (TFA salt); ESI-MS (M+H) calc'd for $C_{25}H_{28}N_7O_4S$: 522.1923, found: 522.1920.

Example CXLVIII

Preparation of 3-(5-piperidinocarbonyl-2-thienyl)-5-(morpholinocarbamoylamino)indeno [1,2-c]pyrazol-4-one Prepared in a similar fashion as described for example CXXXII using CXXXI and piperidine as the starting materials. ESI-MS (M+H) calc'd for $C_{25}H_{27}N_6O_4S$: 507.1815, found: 507.1833.

Example CXLIX

Preparation of 3-(5-piperazinocarbonyl-2-thienyl)-5-(morpholinocarbamoylamino)indeno [1,2-c]pyrazol-4-one Prepared in a similar fashion as described for example CXXXII using CXXXI and piperazine as the starting materials. mp 241–242° C. (TFA salt); ESI-MS (M+H) calc'd for $C_{24}H_{26}N_7O_4S$: 508.5732, found: 508.1758.

Example CL

Preparation of 3-(5-(4-methylpiperazinocarbonyl)-2-thienyl)-5-(morpholinocarbamoylamino)indeno[1,2-c]pyrazol-4-one Prepared in a similar fashion as described for example CXXXII using CXXXI and 1-methylpiperazine as the starting materials. mp 186–187° C. (TFA salt); ESI-MS (M+H) calc'd for $C_{25}H_{28}N_7O_4S$: 522.1923, found: 522.1928.

Example CLI

Preparation of 3-(5-(4-ethylpiperazinocarbonyl)-2-thienyl)-5-(morpholinocarbamoylamino)indeno[1,2-c]pyrazol-4-one Prepared in a similar fashion as described for example CXXXII using CXXXI and 1-ethylpiperazine as the starting

Example CLII

Preparation of 3-(5-(4-(2-hydroxyethyl)piperazinocarbonyl)-2-thienyl)-5-(morpholinocarbamoylamino)indeno[1,2-c]pyrazol-4-one Prepared in a similar fashion as described for example CXXXII using CXXXI and 1-(2-hydroxyethyl)piperazine as the starting materials. mp 186–187° C. (TFA salt); ESI-MS (M+H) calc'd for $C_{26}H_{30}N_7O_5S$: 552.2029, found: 552.2032.

Example CLIII

Preparation of 3-(5-(4-(cyclopropylmethyl)piperazinocarbonyl)-2-thienyl)-5-(morpholinocarbamoylamino)indeno[1,2-c]pyrazol-4-one Prepared in a similar fashion as described for example CXXXII using CXXXI and 1-(cyclopropylmethyl)piperazine as the starting materials. mp 211–212° C. (TFA salt); ESI-MS (M+H) calc'd for $C_{28}H_{32}N_7O_4S$: 562.2236, found: 562.2249.

Example CLIV

Preparation of 3-(5-(4-(t-butoxycarbonyl)piperazinocarbonyl)-2-thienyl)-5-(morpholinocarbamoylamino)indeno[1,2-c]pyrazol-4-one Prepared in a similar fashion as described for example CXXXII using CXXXI and 4-t-butoxycarbonylpiperazine as the starting materials. mp 225–226° C. (TFA salt); ESI-MS (M+H) calc'd for $C_{29}H_{34}N_7O_6S$: 608.2290, found: 608.2320.

Example CLV

Preparation of 3-(5-(4-(2-pyridyl)piperazinocarbonyl)-2-thienyl)-5-(morpholinocarbamoylamino)indeno[1,2-c]pyrazol-4-one Prepared in a similar fashion as described for example CXXXII using CXXXI and 4-(2-pyridyl)piperazine as the starting materials. mp 201–202° C. (TFA salt); ESI-MS (M+H) calc'd for $C_{29}H_{29}N_8O_4S$: 585.2032, found: 585.2002.

Example CLVI

Preparation of 3-(5-(((1S,4S)-(+)-2,5-diazabicyclo[2.2.1]heptyl)carbonyl)-2-thienyl)-5-(morpholinocarbamoylamino)indeno [1,2-c]pyrazol-4-one Prepared in a similar fashion as described for example CXXXII using CXXXI and (1S,4S)-(+)-2,5-diazabicyclo[2.2.1]heptane as the starting materials. mp >300° C. (TFA salt); ESI-MS (M+H) calc'd for $C_{25}H_{26}N_7O_4S$: 520.1767, found: 520.1765.

Example CLVII

Preparation of 3-(5-(((1S,4S)-(+)-2-methyl-2,5-diazabicyclo[2.2.1]heptyl)carbonyl)-2-thienyl)-5-(morpholinocarbamoylamino)indeno[1,2-c]pyrazol-4-one Prepared in a similar fashion as described for example CXXXII using CXXXI and (1S,4S)-(+)-2-methyl-2,5-diazabicyclo[2.2.1]heptane as the starting materials. mp 224–225° C. (TFA salt); ESI-MS (M+H) calc'd for $C_{26}H_{28}N_7O_4S$: 534.1923, found: 534.1934.

Example CLVIII

Preparation of 3-(5-(4-(N,N-dimethylamino)piperidinocarbonyl)-2-thienyl)-5-(morpholinocarbamoylamino)indeno[1,2-c]pyrazol-4-one Prepared in a similar fashion as described for example CXXXII using CXXXI and 4-(N,N-dimethylamino)piperidine as the starting materials. mp 185–186° C. (TFA salt); ESI-MS (M+H) calc'd for $C_{27}H_{32}N_7O_4S$: 550.2240, found: 550.2250.

Example CLIX

Preparation of 3-(5-(4-pyrrolidinopiperidinocarbonyl)-2-thienyl)-5-(morpholinocarbamoylamino)indeno[1,2-c]pyrazol-4-one Prepared in a similar fashion as described for example CXXXII using CXXXI and 4-pyrrolidinopiperidine as the starting materials. mp 228° C. (TFA salt); ESI-MS (M+H) calc'd for $C_{29}H_{34}N_7O_4S$: 576.2393, found: 576.2410.

Example CLX

Preparation of 3-(5-(4-piperidinopiperidinocarbonyl)-2-thienyl)-5-(morpholinocarbamoylamino)indeno[1,2-c]pyrazol-4-one Prepared in a similar fashion as described for example CXXXII using CXXXI and 4-piperidinopiperidine as the starting materials. ESI-MS (M+H) calc'd for $C_{30}H_{36}N_7O_4S$: 590.2549, found: 590.2536.

Example CLXI

Preparation of 3-(5-cyclohexylaminocarbonyl-2-thienyl)-5-(morpholinocarbamoylamino)indeno[1,2-c]pyrazol-4-one Prepared in a similar fashion as described for example CXXXII using CXXXI and cyclohexylamine as the starting materials. mp 264–267° C. (TFA salt); ESI-MS (M+H) calc'd for $C_{26}H_{29}N_6O_4S$: 521.1971, found: 521.1971.

Example CLXII

Preparation of 3-(5-(4-piperidylaminocarbonyl)-2-thienyl)-5-(morpholinocarbamoylamino)indeno[1,2-c]pyrazol-4-one Prepared in a similar fashion as described for example CXXXII using CXXXI and 4-aminopiperidine as the starting materials. mp 224–226° C. (TFA salt); ESI-MS (M+H) calc'd for $C_{25}H_{28}N_7O_4S$: 522.1923, found: 522.1933.

Example CLXIII

Preparation of 3-(5-((1-(t-butoxycarboxyl)piperidin-4-yl)aminocarbonyl)-2-thienyl)-5-(morpholinocarbamoylamino)indeno[1,2-c]pyrazol-4-one Prepared in a similar fashion as described for example CXXXII using CXXXI and 4-amino-1-(t-butoxycarbonyl)

materials. mp 186–188° C. (TFA salt); ESI-MS (M+H) calc'd for $C_{26}H_{30}N_7O_4S$: 536.2080, found: 536.2081.

piperidine as the starting materials. mp 229–230° C. (TFA salt); ESI-MS (M+H) calc'd for $C_{30}H_{34}N_7O_4S$: 620.2291, found: 620.2304.

Example CLXIV

Preparation of 3-(5-(4-(1-methylpiperidin-4-yl) methylaminocarbonyl)-2-thienyl)-5-(morpholinocarbamoylamino)indeno[1,2-c]pyrazol-4-one Prepared in a similar fashion as described for example CXXXII using CXXXI and 1-methyl-4-(methylamino) piperidine as the starting materials. mp 230° C. (TFA salt); ESI-MS (M+H) calc'd for $C_{27}H_{32}N_7O_4S$: 550.2236, found: 550.2241.

Example CLXV

Preparation of 3-(5-(3-(N,N-dimethylamino) piperidinocarbonyl)-2-thienyl)-5-(morpholinocarbamoylamino)indeno[1,2-c]pyrazol-4-one Prepared in a similar fashion as described for example CXXXII using CXXXI and 3-(N,N-dimethylamino) piperidine as the starting materials. mp >300° C. (TFA salt); ESI-MS (M+H) calc'd for $C_{27}H_{32}N_7O_4S$: 550.2236, found: 550.2232.

Example CLXVI

Preparation of 3-(5-(3-p-toluenesulfonylamino) piperidinocarbonyl-2-thienyl)-5-(morpholinocarbamoylamino)indeno [1,2-c]pyrazol-4-one Prepared in a similar fashion as described for example CXXXII using CXXXI and 3-(p-toluenesulfonylamino) piperidine as the starting materials. mp 193–194° C. (TFA salt); ESI-MS (M+H) calc'd for $C_{32}H_{34}N_7O_6S$: 676.2018, found: 676.2025.

Example CLXVII

Preparation of 3-(5-(3-hydroxypiperidinocarbonyl)-2-thienyl)-5-(morpholinocarbamoylamino)indeno[1,2-c]pyrazol-4-one Prepared in a similar fashion as described for example CXXXII using CXXXI and 3-hydroxypiperidine as the starting materials. ESI-MS (M+H) calc'd for $C_{25}H_{27}N_6O_5S$: 523.1764, found: 523.1765.

Example CLXVIII

Preparation of 3-(5-((3-piperidyl)aminocarbonyl)-2-thienyl)-5-(morpholinocarbamoylamino)indeno[1,2-c]pyrazol-4-one Prepared in a similar fashion as described for example CXXXII using CXXXI and 3-aminopiperidine as the starting materials. mp >300° C. (TFA salt); ESI-MS (M+H) calc'd for $C_{25}H_{28}N_7O_4S$: 522.1923, found: 522.1934.

Example CLXIX

Preparation of 3-(5-((3-quinuclidyl)aminocarbonyl)-2-thienyl)-5-(morpholinocarbamoylamino)indeno[1,2-c]pyrazol-4-one Prepared in a similar fashion as described for example CXXXII using CXXXI and (S)-(−)-3-aminoquinuclidine as the starting materials. mp 245–246° C. (TFA salt); ESI-MS (M+H) calc'd for $C_{27}H_{30}N_7O_4S$: 548.2080, found: 548.2084.

Example CLXX

Preparation of 3-(5-((3-aminocyclohexyl) aminocarbonyl)-2-thienyl)-5-(morpholinocarbamoylamino)indeno[1,2-c]pyrazol-4-one Prepared in a similar fashion as described for example CXXXII using CXXXI and 1,3-diaminocyclohexane as the starting materials. mp >300° C. (TFA salt); ESI-MS (M+H) calc'd for $C_{26}H_{30}N_7O_4S$: 536.2080, found: 536.2078.

Example CLXXI

Preparation of 3-(5-((3-(t-butoxycarbonylamino) cyclohexyl)aminocarbonyl)-2-thienyl)-5-(morpholinocarbamoylamino)indeno[1,2-c]pyrazol-4-one Prepared in a similar fashion as described for example CXXXII using CXXXI and 1-amino-3-(t-butoxycarbonylamino)cyclohexane as the starting materials. mp >300° C. (TFA salt); ESI-MS (M+H) calc'd for $C_{31}H_{38}N_7O_6S$: 636.2604, found: 636.2625.

Example CLXXII

Preparation of 3-(5-(2-(N,N-dimethylaminomethyl) piperidinocarbonyl)-2-thienyl)-5-(morpholinocarbamoylamino)indeno[1,2-c]pyrazol-4-one Prepared in a similar fashion as described for example CXXXII using CXXXI and 2-(dimethylaminomethyl) piperidine as the starting materials. mp >300° C. (TFA salt); ESI-MS (M+H) calc'd for $C_{28}H_{34}N_7O_4S$: 564.2393, found: 564.2388.

Example CLXXIII

Preparation of 3-(5-(2-(N,N-diethylaminomethyl) piperidinocarbonyl)-2-thienyl)-5-(morpholinocarbamoylamino)indeno[1,2-c]pyrazol-4-one Prepared in a similar fashion as described for example CXXXII using CXXXI and 2-(diethylaminomethyl) piperidine as the starting materials. mp 210–212° C. (TFA salt); ESI-MS (M+H) calc'd for $C_{30}H_{38}N_7O_4S$: 592.2706, found: 592.2706.

Example CLXXIV

Preparation of 3-(5-pyrrolidinocarbonyl-2-thienyl)-5-(morpholinocarbamoylamino)indeno[1,2-c]pyrazol-4-one Prepared in a similar fashion as described for example CXXXII using CXXXI and pyrrolidine as the starting materials. mp >300° C. (TFA salt); ESI-MS (M+H) calc'd for $C_{24}H_{25}N_6O_4S$: 493.1658, found: 493.1679.

Example CLXXV

Preparation of 3-(5-(3-aminopyrrolidinocarbonyl)-2-thienyl)-5-(morpholinocarbamoylamino)indeno[1,2-c]pyrazol-4-one Prepared in a similar fashion as described for example CXXXII using CXXXI and 3-aminopyrrolidine as the starting materials. mp 201–202° C. (TFA salt); ESI-MS (M+H) calc'd for $C_{24}H_{26}N_7O_4S$: 508.5793, found: 508.1775.

Example CLXXVI

Preparation of 3-(5-(3(S)-N-methylamino) pyrrolidinocarbonyl-2-thienyl)-5-(morpholinocarbamoylamino)indeno [1,2-c]pyrazol-4-one Prepared in a similar fashion as described for example CXXXII using CXXXI and (S)-3-N-methylaminopyrrolidine as the starting materials. ESI-MS (M+H) calc'd for $C_{25}H_{28}N_7O_4S$: 522.1920, found: 522.1920.

Example CLXXVII

Preparation of 3-(5-(3(S)-acetamidopyrrolidinocarbonyl)-2-thienyl)-5-(morpholinocarbamoylamino)indeno[1,2-c]pyrazol-4-one Prepared in a similar fashion as described for example CXXXII using CXXXI and (S)-3-N-acetamidopiperidine as the starting materials. mp 264–265° C. (TFA salt); ESI-MS (M+H) calc'd for $C_{26}H_{28}N_7O_5S$: 550.1873, found: 550.1896.

Example CLXXVIII

Preparation of 3-(5-(3(S)-(N-methylacetamido) pyrrolidinocarbonyl)-2-thienyl)-5-(morpholinocarbamoylamino)indeno[1,2-c]pyrazol-4-one Prepared in a similar fashion as described for example CXXXII using CXXXI and (S)-3-(N-acetyl-N-methylamino)piperidine as the starting materials. mp >300° C. (TFA salt); ESI-MS (M+H) calc'd for $C_{27}H_{30}N_7O_5S$: 564.2029, found: 564.2054.

Example CLXXIX

Preparation of 3-(5-(3(S)-(N-methyl-t-butoxycarbonylamino)pyrrolidinocarbonyl)-2-thienyl)-5-(morpholinocarbamoylamino)indeno[1,2-c]pyrazol-4-one Prepared in a similar fashion as described for example CXXXII using CXXXI and (S)-3-(N-t-butoxycarbonyl-N-methylamino)piperidine as the starting materials. mp >300° C. (TFA salt); ESI-MS (M+H) calc'd for $C_{30}H_{36}N_7O_6S$: 622.2448, found: 622.2472.

Example CLXXX

Preparation of 3-(5-(3-(N,N-dimethylamino) pyrrolidinocarbonyl)-2-thienyl)-5-(morpholinocarbamoylamino)indeno[1,2-c]pyrazol-4-one Prepared in a similar fashion as described for example CXXXII using CXXXI and 3-(N,N-dimethylamino)pyrrolidine as the starting materials. mp 216–217° C. (TFA salt); ESI-MS (M+H) calc'd for $C_{26}H_{30}N_7O_4S$: 536.2079, found: 536.2070.

Example CLXXXI

Preparation of 3-(5-(3(R)-(N,N-dimethylamino) pyrrolidinocarbonyl)-2-thienyl)-5-(morpholinocarbamoylamino)indeno[1,2-c]pyrazol-4-one Prepared in a similar fashion as described for example CXXXII using CXXXI and (R)-3-(N,N-dimethylamino) pyrrolidine as the starting materials. mp 265° C. (TFA salt); ESI-MS (M+H) calc'd for $C_{26}H_{30}N_7O_4S$: 536.298, found: 536.2105.

Example CLXXXII

Preparation of 3-(5-(3(S)-(N,N-dimethylamino) pyrrolidinocarbonyl)-2-thienyl)-5-(morpholinocarbamoylamino)indeno[1,2-c]pyrazol-4-one Prepared in a similar fashion as described for example CXXXII using CXXXI and (S)-3-(N,N-dimethylamino) pyrrolidine as the starting materials. mp 264–265° C. (TFA salt); ESI-MS (M+H) calc'd for $C_{26}H_{30}N_7O_4S$: 536.2980, found: 536.2096.

Example CLXXXIII

Preparation of 3-(5-((1-methylpyrrolidin-3-yl) methylaminocarbonyl)-2-thienyl)-5-(morpholinocarbamoylamino)indeno[1,2-c]pyrazol-4-one Prepared in a similar fashion as described for example CXXXII using CXXXI and 1-methyl-3-(methylamino) pyrrolidine as the starting materials. mp 151–153° C. (TFA salt); ESI-MS (M+H) calc'd for $C_{26}H_{30}N_7O_4S$: 536.2080, found: 536.2088.

Example CLXXXIV

Preparation of 3-(5-(2(R)-(pyrrolidinomethyl) pyrrolidinocarbonyl)-2-thienyl)-5-(morpholinocarbamoylamino)indeno[1,2-c]pyrazol-4-one Prepared in a similar fashion as described for example CXXXII using CXXXI and (R)-2-(pyrrolidinomethyl) pyrrolidine as the starting materials. mp 166–167° C. (TFA salt); ESI-MS (M+H) calc'd for $C_{29}H_{34}N_7O_4S$: 536.2393, found: 576.2416.

Example CLXXXV

Preparation of 3-(5-(2(S)-(hydroxymethyl) pyrrolidinocarbonyl)-2-thienyl)-5-(morpholinocarbamoylamino)indeno[1,2-c]pyrazol-4-one Prepared in a similar fashion as described for example CXXXII using CXXXI and (S)-2-(hydroxymethyl) pyrrolidine as the starting materials. mp 267–268° C. (TFA salt); ESI-MS (M+H) calc'd for $C_{25}H_{27}N_6O_5S$: 523.1764, found: 523.1754.

Example CLXXXVI

Preparation of 3-(5-(2(R)-(methoxymethyl) pyrrolidinocarbonyl)-2-thienyl)-5-(morpholinocarbamoylamino)indeno[1,2-c]pyrazol-4-one Prepared in a similar fashion as described for example CXXXII using CXXXI and (R)-2-(methoxymethyl) pyrrolidine as the starting materials. mp 262° C. (TFA salt); ESI-MS (M+H) calc'd for $C_{26}H_{29}N_6O_4S$: 537.1920, found: 537.1936.

Example CLXXXVII

Preparation of 3-(5-(2(S)-(phenylaminomethyl) pyrrolidinocarbonyl)-2-thienyl)-5-(morpholinocarbamoylamino)indeno[1,2-c]pyrazol-4-one Prepared in a similar fashion as described for example CXXXII using CXXXI and (S)-2-(phenylaminomethyl)

Example CLXXXVIII

Preparation of 3-(5-(2(R)-(methoxymethyl) pyrrolidinoaminocarbonyl)-2-thienyl)-5-(morpholinocarbamoylamino)indeno[1,2-c]pyrazol-4-one Prepared in a similar fashion as described for example CXXXII using CXXXI and (R)-1-amino-2-(methoxymethyl)pyrrolidine as the starting materials. mp 266–267° C. (TFA salt); ESI-MS (M+H) calc'd for $C_{26}H_{30}N_7O_5S$: 552.2029, found: 552.2036.

Example CLXXXIX

Preparation of 3-(5-homopiperidinocarbonyl-2-thienyl)-5-(morpholinocarbamoylamino)indeno[1,2-c]pyrazol-4-one Prepared in a similar fashion as described for example CXXXII using CXXXI and homopiperidine as the starting materials. ESI-MS (M+H) calc'd for $C_{26}H_{29}N_6O_4S$: 521.1971, found: 521.1943.

Example CXC

Preparation of 3-(5-homopiperazinocarbonyl-2-thienyl)-5-(morpholinocarbamoylamino)indeno[1,2-c]pyrazol-4-one Prepared in a similar fashion as described for example CXXXII using CXXXI and homopiperazine as the starting materials. mp 209° C. (TFA salt); ESI-MS (M+H) calc'd for $C_{25}H_{28}N_7O_4S$: 522.1923, found: 522.1901.

Example CXCI

Preparation of 3-(5-(4-methylhomopiperazinocarbonyl)-2-thienyl)-5-(morpholinocarbamoylamino)indeno[1,2-c]pyrazol-4-one Prepared in a similar fashion as described for example CXXXII using CXXXI and 1-methylhomopiperazine as the starting materials. mp 207–208° C. (TFA salt); ESI-MS (M+H) calc'd for $C_{26}H_{30}N_7O_4S$: 536.2080, found: 536.2086.

Example CXCII

Preparation of 3-(5-(4-ethylhomopiperazinocarbonyl)-2-thienyl)-5-(morpholinocarbamoylamino)indeno[1,2-c]pyrazol-4-one Prepared in a similar fashion as described for example CXXXII using CXXXI and 1-ethylhomopiperazine as the starting materials. mp 192–193° C. (TFA salt); ESI-MS (M+H) calc'd for $C_{27}H_{32}N_7O_4S$: 550.2237, found: 550.2241.

Example CXCIII

Preparation of 3-(5-(4-(cyclopropylmethyl) homopiperazinocarbonyl)-2-thienyl)-5-(morpholinocarbamoylamino)indeno[1,2-c]pyrazol-4-one Prepared in a similar fashion as described for example CXXXII using CXXXI and 1-(cyclopropylmethyl) pyrrolidine as the starting materials. mp >300° C. (TFA salt); ESI-MS (M+H) calc'd for $C_{31}H_{32}N_7O_4S$: 598.2236, found: 598.2225.

Example CXCIV

Preparation of 3-(5-(4-(t-butoxycarbonyl) homopiperazinocarbonyl)-2-thienyl)-5-(morpholinocarbamoylamino)indeno[1,2-c]pyrazol-4-one Prepared in a similar fashion as described for example CXXXII using CXXXI and 1-t-butoxycarbonylhomopiperazine as the starting materials. mp 210–211° C. (TFA salt); ESI-MS (M+H) calc'd for $C_{30}H_{36}N_7O_6S$: 622.2488, found: 622.2450.

Example CXCV

Preparation of 3-(5-(4-acetylhomopiperazinocarbonyl)-2-thienyl)-5-(morpholinocarbamoylamino)indeno[1,2-c]pyrazol-4-one Prepared in a similar fashion as described for example CXXXII using CXXXI and 1-acetylhomopiperazine as the starting materials. mp 274–275° C. (TFA salt); ESI-MS (M+H) calc'd for $C_{27}H_{30}N_7O_5S$: 564.2029, found: 564.2056.

Example CXCVI

Preparation of 3-(5-((4-methylaminophenyl) aminocarbonyl)-2-thienyl)-5-(morpholinocarbamoylamino)indeno[1,2-c]pyrazol-4-one Prepared in a similar fashion as described for example CXXXII using CXXXI and 4-(methylamino)aniline as the starting materials. mp 230° C. (TFA salt); ESI-MS (M+H) calc'd for $C_{27}H_{26}N_7O_4S$: 544.1767, found: 544.1772.

Example CXCVII

Preparation of 3-(5-((4-acetamidophenyl) aminocarbonyl)-2-thienyl)-5-(morpholinocarbamoylamino)indeno[1,2-c]pyrazol-4-one Prepared in a similar fashion as described for example CXXXII using CXXXI and 4-(acetamido)aniline as the starting materials. mp 253–254° C. (TFA salt); ESI-MS (M+H) calc'd for $C_{30}H_{28}N_4O_6S$: 572.1730, found: 572.1723.

Example CXCVIII

Preparation of 3-(5-(4-(diethylamino) phenylaminocarbonyl)-2-thienyl)-5-(morpholinocarbamoylamino)indeno[1,2-c]pyrazol-4-one Prepared in a similar fashion as described for example CXXXII using CXXXI and 4-(diethylamino)aniline as the starting materials. mp 198–199° C. (TFA salt); ESI-MS (M+H) calc'd for $C_{30}H_{32}N_7O_4S$: 586.2236, found: 586.2224.

Example CXCIX

Preparation of 3-(5-((1-methyl-3-cyclopropylpyrazo-5-yl)aminocarbonyl)-2-thienyl)-5-(morpholinocarbamoylamino)indeno[1,2-c]pyrazol-4-one Prepared in a similar fashion as described for example CXXXII using CXXXI and 5-amino-3-cyclopropyl-1- methylpyrazole as the starting materials. mp 290° C. (TFA salt); ESI-MS (M+H) calc'd for $C_{27}H_{27}N_8O_4S$: 559.1876, found: 559.1849.

Example CC

Preparation of 3-(1-methyl-3-pyrrolyl)-5-(morpholinocarbamoylamino)indeno[1,2-c]pyrazol-4-one Prepared in a similar fashion as described for example LXXXVII and XLII using 4-aminomorpholine and the 1-methyl-3-pyrrolyl analog of 15 as the starting materials. mp 301° C.; ESI-MS (M+H) calc'd for $C_{20}H_{21}N_6O_3$: 393.1675, found: 393.1669.

Example CCI

Preparation of 3-(5-carboethoxy-2-thienyl)-5-(2 (R)-(methoxymethyl)pyrrolidinocarbamoylamino)indeno[1,2-c]pyrazol-4-one Prepared in a similar fashion as described for example LXXXVII and XLII using 1-amino-2(R)-(methoxymethyl)pyrrolidine and the 5-carboethoxy-2-thienyl analog of 15 as the starting materials. mp 221–222° C.; ESI-MS (M+H) calc'd for $C_{24}H_{26}N_5O_5S$: 496.1655, found: 496.1658.

Example CCII

Preparation of 3-(5-carboxyl-2-thienyl)-5-(2(R)-(methoxymethyl)pyrrolidinocarbamoylamino)indeno[1,2-c]pyrazol-4-one Prepared in a similar fashion as described for example CXXIII using CCI as the starting material. mp 258–259° C. (TFA salt); ESI-MS (M+H) calc'd for $C_{22}H_{22}N_5O_5S$: 468.1342, found: 468.1346.

Example CCIII

Preparation of 3-(5-(4-methylpiperazinocarbonyl)-2-thienyl)-5-(2(R)-(methoxymethyl)pyrrolidinocarbamoylamino)indeno[1,2-c]pyrazol-4-one Prepared in a similar fashion as described for example CXXXII using 1-methylpiperazine and CCII as the starting materials. mp 181–183° C. (TFA salt); ESI-MS (M+H) calc'd for $C_{27}H_{32}N_7O_4S$: 550.2236, found: 550.2251.

Example CCIV

Preparation of 3-(5-piperazinocarbonyl-2-thienyl)-5-(2(R)-(methoxymethyl)pyrrolidinocarbamoylamino)indeno[1,2-c]pyrazol-4-one Prepared in a similar fashion as described for example CXXXII using piperazine and CCII as the starting materials. mp >300° C. (TFA salt); ESI-MS (M+H) calc'd for $C_{26}H_{31}N_7O_4S$: 536.2080, found: 536.2091.

Example CCV

Preparation of 3-(5-(4-(t-butoxycarbonyl)piperazinocarbonyl)-2-thienyl)-5-(2(R)-(methoxymethyl)pyrrolidinocarbamoylamino)indeno[1,2-c]pyrazol-4-one Prepared in a similar fashion as described for example CXXXII using 1-t-butoxycarbonylpiperazine and CCII as the starting materials. mp >300° C. (TFA salt); ESI-MS (M+H) calc'd for $C_{31}H_{38}N_7O_6S$: 636.2604, found: 636.2633.

Example CCVI

Preparation of 3-(5-(4-methylhomopiperazinocarbonyl)-2-thienyl)-5-(2(R)-(methoxymethyl)pyrrolidinocarbamoylamino)indeno[1,2-c]pyrazol-4-one Prepared in a similar fashion as described for example CXXXII using 1-methylhomopiperazine and CCII as the starting materials. mp 176–177° C. (TFA salt); ESI-MS (M+H) calc'd for $C_{28}H_{34}N_7O_4S$: 564.2393, found: 564.2388.

Example CCVII

Preparation of 3-(5-homopiperazinocarbonyl-2-thienyl)-5-(2(R)-(methoxymethyl)pyrrolidinocarbamoylamino)indeno[1,2-c]pyrazol-4-one Prepared in a similar fashion as described for example CXXXII using homopiperazine and CCII as the starting materials. mp 185–186° C. (TFA salt); ESI-MS (M+H) calc'd for $C_{27}H_{32}N_7O_4S$: 550.2236, found: 550.2231.

Example CCVIII

Preparation of 3-(5-(4-(t-butoxycarbonyl)homopiperazinocarbonyl)-2-thienyl)-5-(2 (R)-(methoxymethyl)pyrrolidinocarbamoylamino)indeno[1,2-c]pyrazol-4-one Prepared in a similar fashion as described for example CXXXII using 1-t-butoxycarbonylhomopiperazine and CCII as the starting materials. mp >300° C. (TFA salt); ESI-MS (M+H) calc'd for $C_{32}H_{40}N_7O_6S$: 650.2761, found: 650.2753.

Example CCIX

Preparation of 3-(4-(trifluoromethyl)phenyl)-5-(acetamido)indeno[1,2-c]pyrazol-4-one Prepared in a similar fashion as described for example LXXXVI employing 1-(4-(trifluoromethyl)phenyl)-4,4,4-trifluoro-1,3-butanedione as the starting material. mp >300 ° C.; ESI -MS m/e calc'd for $C_{19}H_{11}N_3O_2$: 370.0804, found: 370.0809.

Example CCX

Preparation of 3-(4-(4-t-butoxycarbonylpiperazino)phenyl)-5-(morpholinocarbamoylamino)indeno[1,2-c]pyrazol-4-one

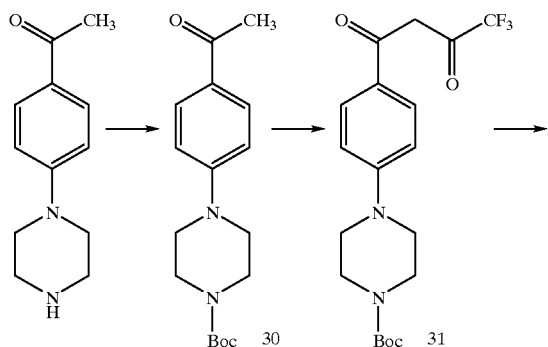

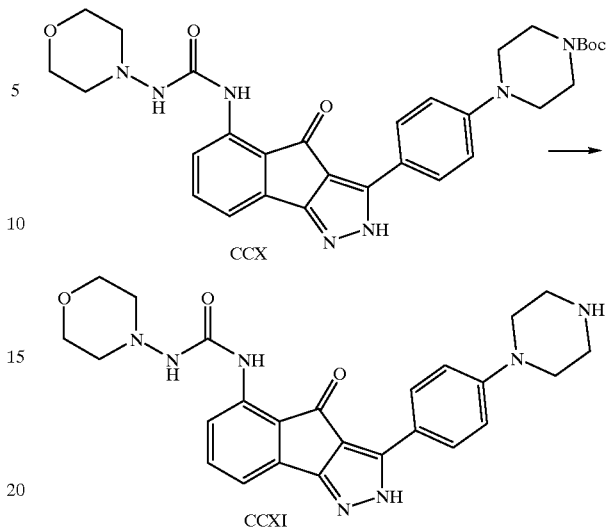

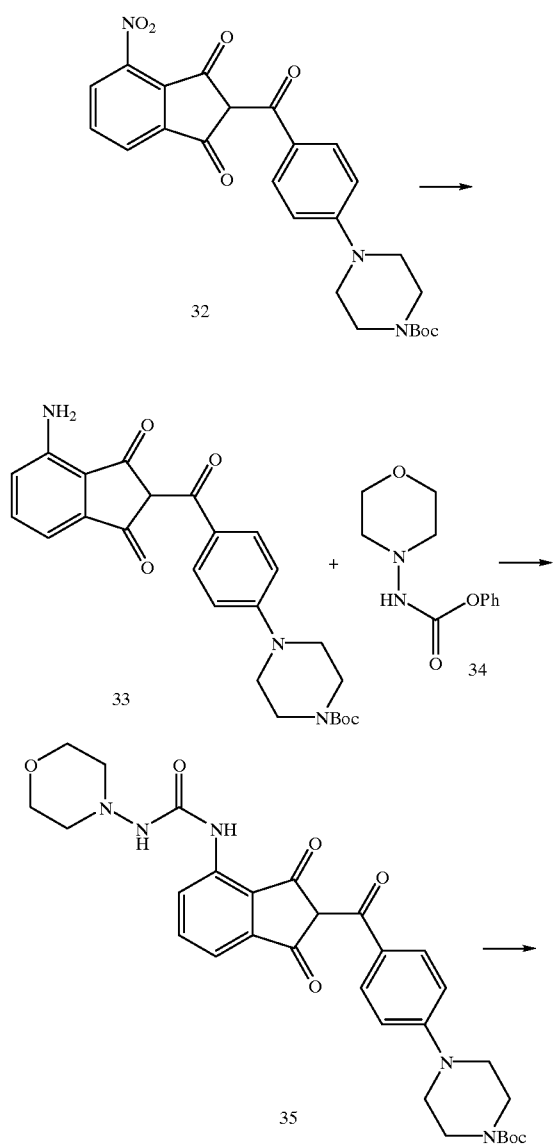

Step 1. Synthesis of 30

To a suspension of 139 g (680 mmol) of 4-piperazinoacetophenone in 700 mL of tetrahydrofuran at 25° C. was added slowly over 20 min. a solution of 157 g (720 mmol) of di-tert-butyl dicarbonate in 300 mL of tetrahydrofuran. The resulting mixture was refluxed for 15 h. After cooling the mixture was filtered, and the filtrate was concentrated under vacuum to provide an off-white solid. This crude product was recrystallized from diethyl ether/hexane to afford 192 g of the 30 as a white solid. NMR (CDCl$_3$) δ 7.89 (d, 2H, J=9 Hz), 6.87 (d, 2H, J=9 Hz), 3.59 (m, 4H), 3.33 (m, 4H), 2.53 (s, 3H), 1.49 (s, 9H).

Step 2. Synthesis of 31 from 30

To a solution of 192 g (630 mmol) of 30 and 90 mL (750 mmol) of ethyl trifluoroacetate in 1000 mL of tetrahydrofuran at 25° C. was added slowly over 15 min. 280 mL (750 mmol) of 21% sodium ethoxide in ethanol, and the resulting solution then was stirred at 25° C. for 16 h. The reaction mixture was diluted with 500 mL of water, and to this mixture was added 45 mL of acetic acid. The resulting precipitate was recovered by filtration. The solids were washed with diethyl ether/hexane and dried to furnish 236 g of 31 as an orange solid. NMR (CDCl$_3$) δ 7.87 (d, 2H, J=9 Hz), 6.87 (d, 2H, J=9 Hz), 6.45 (s, 1H), 3.60 (m, 4H), 3.41 (m, 4H), 1.48 (s, 9H).

Step 3. Synthesis of 32 from 31

A suspension of 117 g (610 mmol) of 3-nitrophthalic anhydride in 560 mL of acetic anhydride was heated until the mixture became homogeneous, and the solution then was allowed to cool to room temperature. To this solution was added 236 g (590 mmol) of 31. The resulting mixture was cooled to 0° C., and 165 mL (1200 mmol) of triethylamine was added slowly over 10 min. The mixture was allowed to warm to 25° C., was stirred at 25° C. for 1 h, and then was heated to 65° C. for 0.5 h. After cooling to room temperature, the reaction mixture was poured into a well-stirred solution of 1200 mL of 1.0 N hydrochloric acid and 2000 mL of ethanol. The resulting precipitate was recovered by filtration, washed with ethanol, and dried to provide 140 g of 32 as an orange solid. NMR (acetone-d$_6$) δ 8.34 (d, 2H, J=9 Hz), 8.05 (m, 3H), 7.07 (d, 2H, J=9 Hz), 3.59 (br s, 8H), 1.48 (s, 9H).

Step 4. Synthesis of 33 from 32

To a solution of 12.00 g (25 mmol) of 32 in 500 mL of ethanol and 50 mL of conc. ammonium hydroxide at 25° C. was added 500 mL of water, followed by 15.3 g (88 mmol) of sodium dithionite. The resulting mixture was stirred at 25° C. for 16 h. The reaction mixture was filtered, and the filtrate was reduced to ~½ the original volume under vacuum. This solution was adjusted to pH 3 employing hydrochloric acid and then extracted with ethyl acetate. The combined extracts were washed with water and brine, dried over anhyd. sodium sulfate, filtered, and concentrated. The resulting solids were recrystallized from ethanol/water to provide 8.40 g of 33 as a green solid. NMR (DMSO-$d_6$) δ 8.20 (d, 2H, J=9 Hz), 7.44 (t, 1H, J=8 Hz), 7.02 (d, 2H, J=9 Hz), 6.96 (d, 1H, J=8 Hz), 6.91 (d, 1H, J=8 Hz), 6.70 (br s, 2H), 3.46 (br s, 8H), 1.43 (s, 9H).

Step 5. Synthesis of 35 from 33 and 34.

A solution of 4.50 g (10 mmol) of 33, 4.45 g (20 mmol) of 34, 3.68 g (30 mmol) of 4-dimethylaminopyridine, and 80 mL of DMSO was stirred at 90° C. for 2.5 h. After cooling to room temperature the reaction mixture was poured into a well-stirred solution of 80 mL of ethanol and 30 mL of 1N hydrochloric acid. The resulting solution was diluted further by the slow addition of 120 mL of water. A precipitate formed. It was recovered by filtration, washed with 50% aqueous ethanol, and dried to provide 3.83 g of 35 as an orange solid. NMR (DMSO-$d_6$) δ 10.95 (br s, 1H), 8.60 (d, 1H, J=8.5 Hz), 8.38 (br s, 1H), 8.24 (d, 2H, J=9 Hz), 7.69 (t, 1H, J=8.5 Hz), 7.32 (d, 1H, J=8.5 Hz), 7.04 (d, 2H, J=9 Hz), 3.86 (m, 4H), 3.74 (m, 4H), 2.91 (m, 4H), 2.73 (m, 4H), 1.44 (s, 9H).

Step 6. Synthesis of CCX from 35.

A mixture of 3.82 g (6.6 mmol) of 35, 0.64 mL (13.2 mmol) of hydrazine monohydrate, 0.090 g (1.32 mmol) of hydrazine hydrochloride, and 130 mL of ethanol was refluxed for 18 h. While still at reflux the solution was diluted by the dropwise addition of 30 mL of water. The mixture then was allowed to cool to room temperature. The resulting precipitate was recovered by filtration, washed with 80% aqueous ethanol, and dried to afford 1.80 g of CCX as a yellow solid. mp 242° C.; ESI-MS m/e calc'd for $C_{30}H_{36}N_7O_5$: 574.2778, found: 574.2762.

Example CCXI

Preparation of 3-(4-piperazinophenyl)-5-(morpholinocarbamoylamino)indeno[1,2-c]pyrazol-4-one A solution of CCX (0.58 g, 1.0 mmol) in 20 mL of trifluoroacetic acid was stirred at 25° C. for 2 h. The reaction mixture was concentrated under vacuum, and the residue was recrystallized from ethanol to provide 0.53 g of the yellow product as its TFA-salt. mp 263° C.; ESI-MS m/e calc'd for $C_{25}H_{28}N_7O_3$: 474.2254, found: 474.2280.

Example CCXII

Preparation of 3-(4-piperazinophenyl)-5-(carbamoylamino)indeno[1,2-c]pyrazol-4-one Prepared in a similar fashion as described for examples CCX and CCXI employing 2-(4-(4-t-butoxycarbonyl-1-piperazinyl)benzoyl)-4-amino-1,3-indanedione obtained in example CCX and ammonia as the starting materials. mp 257° C. (TFA salt); ESI-MS m/e calc'd for $C_{21}H_{21}N_6O_2$: 389.1726, found: 389.1724.

Example CCXIII

Preparation of 3-(4-piperazinophenyl)-5-(aminocarbamoylamino)indeno[1,2-c]pyrazol-4-one Prepared in a similar fashion as described for examples CCX and CCXI employing 2-(4-(4-t-butoxycarbonylpiperazino)benzoyl)-4-amino-1,3-indanedione obtained in example CCX and hydrazine as the starting materials. mp 257° C. (TFA salt); ESI-MS m/e calc'd for $C_{21}H_{22}N_7O_2$: 404.1835, found: 404.1834.

Example CCXIV

Preparation of 3-(4-piperazinophenyl)-5-((N,N-dimethylamino)acetamido)indeno[1,2-c]pyrazol-4-one Prepared employing 2-(4-(4-t-butoxycarbonylpiperazino)benzoyl)-4-amino-1,3-indanedione obtained in example CCX as the starting material. Chloroacetylation and treatment with dimethylamine in a similar fashion as described for examples II and XXIII, followed by treatment with hydrazine and removal of the t-butoxycarbonyl group in a similar fashion as described for examples I and CCXI, afforded the example compound. mp 243° C. (TFA salt); ESI-MS m/e calc'd for $C_{24}H_{27}N_6O_2$: 431.2196, found: 431.2198.

Example CCXV

Preparation of 3-(4-piperazinophenyl)-5-(morpholinoacetamido)indeno[1,2-c]pyrazol-4-one Prepared employing 2-(4-(4-t-butoxycarbonylpiperazino)benzoyl)-4-amino-1,3-indanedione obtained in example CCX as the starting material. Chloroacetylation and treatment with morpholine in a similar fashion as described for examples II and XXIII, followed by treatment with hydrazine and removal of the t-butoxycarbonyl group in a similar fashion as described for examples I and CCXI, afforded the example compound. mp 259° C. (TFA salt); ESI-MS m/e calc'd for $C_{26}H_{29}N_6O_3$: 473.2301, found: 473.2302.

Example CCXVI

Preparation of 3-(4-piperazinophenyl)-5-((4-methylpiperazino)acetamido)indeno[1,2-c]pyrazol-4-one Prepared employing 2-(4-(4-t-butoxycarbonylpiperazino)benzoyl)-4-amino-1,3-indanedione obtained in example CCX as the starting material. Chloroacetylation and treatment with 1-methylpiperazine in a similar fashion as described for examples II and XXIII, followed by treatment with hydrazine and removal of the t-butoxycarbonyl group in a similar fashion as described for examples I and CCXI, afforded the example compound. ESI-MS m/e calc'd for $C_{27}H_{32}N_7O_2$: 486.2618, found: 486.2608.

Example CCXVII

Preparation of 3-(4-piperazinophenyl)-5-(4-(aminomethyl)piperidinoacetamido)indeno[1,2-c]pyrazol-4-one Prepared employing 2-(4-(4-t-butoxycarbonylpiperazino)benzoyl)-4-amino-1,3-indanedione obtained in example CCX as the starting material. Chloroacetylation and treatment with 4-(aminomethyl)piperidine in a similar fashion as described for examples II and XXIII, followed by treatment with hydrazine and removal of the t-butoxycarbonyl group in a similar fashion as described for examples I and CCXI, afforded the example compound. mp 239° C. (TFA salt); ESI-MS m/e calc'd for $C_{28}H_{34}N_7O_2$: 500.2774, found: 500.2772.

Example CCXVIII

Preparation of 3-(4-(4-methylpiperazino)phenyl)-5-(morpholinocarbamoylamino)indeno[1,2-c]pyrazol-4-one

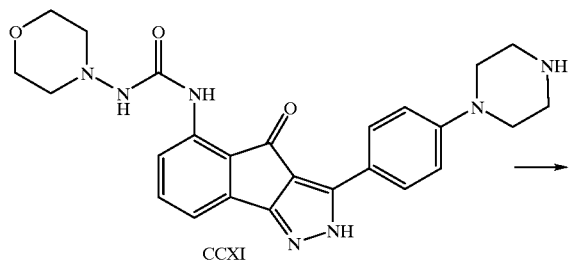

To a solution of CCXI (0.17 g, 0.29 mmol) in 10 mL of methanol and 2 mL of water at 25° C. was added sequentially 37% aqueous formaldehyde (0.45 g, 5.8 mmol), sodium cyanoborohydride (0.18 g, 2.9 mmol), and 4 drops of acetic acid. The resulting solution was stirred at 25° C. for 16 h. The mixture was diluted with water. It then was made acidic (~pH 1) with conc. hydrochloric acid and stirred for 10 min. The solution next was made basic (~pH 13) with 50% aqueous sodium hydroxide and finally adjusted to pH 10 with 1 N hydrochloric acid. The mixture was extracted with 4:1 chloroform/isopropanol. The combined extracts were washed with water and brine, dried over anhydrous sodium sulfate, and filtered. To the filtrate was added excess trifluoroacetic acid, and the solution was concentrated under vacuum. The residue was recrystallized from isopropanol to furnish 0.16 g (92%) of the yellow product as its TFA-salt. mp 245° C.; ESI-MS m/e calc'd for $C_{26}H_{30}N_7O_3$: 488.2410, found: 488.2420.

Example CCXIX

Preparation of 3-(4-(4-ethylpiperazino)phenyl)-5-(morpholinocarbamoylamino)indeno[1,2-c]pyrazol-4-one Prepared in a similar fashion as described for example CCXVIII employing CCXI and acetaldehyde as the starting materials. mp 245° C. (TFA salt); ESI-MS m/e calc'd for $C_{27}H_{32}N_7O_3$: 502.2567, found: 502.2555.

Example CCXX

Preparation of 3-(4-(4-isopropylpiperazino)phenyl)-5-(morpholinocarbamoylamino)indeno[1,2-c]pyrazol-4-one Prepared in a similar fashion as described for example CCXVIII employing CCXI and acetone as the starting materials. mp 253° C. (TFA salt); ESI-MS m/e calc'd for $C_{28}H_{34}N_7O_3$: 516.2723, found: 516.2726.

Example CCXXI

Preparation of 3-(4-piperazinophenyl)-5-((N,N-dimethylamino)carbamoylamino)indeno[1,2-c]pyrazol-4-one Prepared in a similar fashion as described for example CCXI employing 33 from example CCX and 1,1-dimethylhydrazine as the starting materials. mp 238° C. (TFA salt); ESI-MS m/e calc'd for $C_{23}H_{26}N_7O_2$: 432.2148, found: 432.2150.

Example CCXXII

Preparation of 3-(4-(4-methylpiperazino)phenyl)-5-((N,N-dimethylamino)carbamoylamino)indeno[1,2-c]pyrazol-4-one Prepared in a similar fashion as described for example CCXVIII employing CCXI as the starting material. mp 192° C. (TFA salt); ESI-MS m/e calc'd for $C_{24}H_{28}N_7O_2$: 446.2305, found: 446.2313.

Example CCXXIII

Preparation of 3-(4-piperazinophenyl)-5-((4-methylpiperazino)carbamoylamino)indeno[1,2-c]pyrazol-4-one Prepared in a similar fashion as described for example CCXI employing 33 from example CCX and 1-amino-4-methylpiperazine as the starting materials. mp 254° C. (TFA salt); ESI-MS m/e calc'd for $C_{26}H_{31}N_8O_2$: 487.2570, found: 487.2574.

Example CCXXIV

Preparation of 3-(4-(4-methylpiperazino)phenyl)-5-((4-methylpiperazino)carbamoylamino)indeno[1,2-c]pyrazol-4-one Prepared in a similar fashion as described for example CCXVIII employing CCXXIII as the starting material. mp 293° C. (TFA salt); ESI-MS m/e calc'd for $C_{27}H_{33}N_8O_2$: 501.2727, found: 501.2731.

Example CCXXV

Preparation of 3-(4-(4-ethylpiperazino)phenyl)-5-((4-methylpiperazino)carbamoylamino)indeno[1,2-c]pyrazol-4-one Prepared in a similar fashion as described for example CCXVIII employing CCXXIII and acetaldehyde as the starting materials. ESI-MS m/e calc'd for $C_{28}H_{35}N_8O_2$: 515.2883, found: 515.2894.

Example CCXXVI

Preparation of 3-(4-(4-isopropylpiperazino)phenyl)-5-((4-methylpiperazino)carbamoylamino)indeno[1,2-c]pyrazol-4-one Prepared in a similar fashion as described for example CCXVIII employing CCXXIII and acetone as the starting materials. mp 272° C. (TFA salt); ESI-MS m/e calc'd for $C_{27}H_{33}N_8O_2$: 529.3039, found: 529.3053.

Example CCXXVII

Preparation of 3-(4-piperazinophenyl)-5-((2,6-dimethylpiperidino)carbamoylamino)indeno[1,2-c]pyrazol-4-one Prepared in a similar fashion as described for example CCXI employing 33 from example CCX and 1-amino-2,6-dimethylpiperidine as the starting materials. mp 270° C. (TFA salt); ESI-MS m/e calc'd for $C_{28}H_{34}N_7O_2$: 500.2774, found: 500.2786.

Example CCXXVIII

Preparation of 3-(4-piperazinophenyl)-5-((4-(2-hydroxyethyl)piperazino)carbamoylamino)indeno[1,2-c]pyrazol-4-one Prepared in a similar fashion as described for example CCXI employing 33 from example CCX and 1-amino-4-(2-hydroxyethyl)piperazine as the starting materials. mp 279° C. (TFA salt); ESI-MS m/e calc'd for $C_{27}H_{33}N_8O_3$: 517.2676, found: 517.2865.

Example CCXXIX

Preparation of 3-(4-piperazinophenyl)-5-((2(R)-(methoxymethyl)pyrrolidino)carbamoylamino)indeno[1,2-c] pyrazol-4-one Prepared in a similar fashion as described for example CCXI employing 33 from example CCX and 1-amino-2(R)-(methoxymethyl)pyrrolidine as the starting materials. ESI-MS m/e calc'd for $C_{27}H_{32}N_7O_3$: 502.2567, found: 502.2574.

Example CCXXX

Preparation of 3-(4-piperazinophenyl)-5-((2(S)-(methoxymethyl)pyrrolidino)carbamoylamino)indeno[1,2-c]pyrazol-4-one Prepared in a similar fashion as described for example CCXI employing 33 from example CCX and 1-amino-2(S)-(methoxymethyl)pyrrolidine as the starting materials. ESI-MS m/e calc'd for $C_{27}H_{32}N_7O_3$: 502.2566, found: 502.2570.

Example CCXXXI

Preparation of 3-(4-piperazinophenyl)-5-((2(R)-(1-methoxy-1-methylethyl)pyrrolidino)carbamoylamino)indeno[1,2-c]pyrazol-4-one Prepared in a similar fashion as described for example CCXI employing 33 from example CCX and 1-amino-2(R)-(1-methoxy-1-methylethyl)pyrrolidine as the starting materials. mp 221° C. (TFA salt); ESI-MS m/e calc'd for $C_{29}H_{36}N_7O_3$: 530.2879, found: 530.2878.

Example CCXXXII

Preparation of 3-(4-piperazinophenyl)-5-((2(S)-(1-methoxy-1-methylethyl)pyrrolidino)carbamoylamino)indeno[1,2-c]pyrazol-4-one Prepared in a similar fashion as described for example CCXI employing 33 from example CCX and 1-amino-2(S)-(1-methoxy-1-methylethyl)pyrrolidine as the starting materials. mp 218° C. (TFA salt); ESI-MS m/e calc'd for $C_{29}H_{36}N_7O_3$: 530.2880, found: 530.2895.

Example CCXXXIII

Preparation of 3-(4-piperazinophenyl)-5-((2(R)-(hydroxymethyl)pyrrolidino)carbamoylamino)indeno[1,2-c]pyrazol-4-one Prepared in a similar fashion as described for example CCXI employing 33 from example CCX and 1-amino-2(R)-(hydroxymethyl)pyrrolidine as the starting materials. mp 193° C. (TFA salt); ESI-MS m/e calc'd for $C_{26}H_{30}N_7O_3$: 488.2411, found: 488.2380.

Example CCXXXIV

Preparation of 3-(4-piperazinophenyl)-5-((2(S)-(hydroxymethyl)pyrrolidino)carbamoylamino)indeno[1,2-c]pyrazol-4-one Prepared in a similar fashion as described for example CCXI employing 33 from example CCX and 1-amino-2(S)-(hydroxymethyl)pyrrolidine as the starting materials. mp 190° C. (TFA salt); ESI-MS m/e calc'd for $C_{26}H_{30}N_7O_3$: 488.2410, found: 488.2401.

Example CCXXXV

Preparation of 3-(4-piperazinophenyl)-5-((2(R)-(benzyloxymethyl)pyrrolidino)carbamoylamino)indeno[1,2-c]pyrazol-4-one Prepared in a similar fashion as described for example CCXI employing 33 from example CCX and 1-amino-2(R)-(benzyloxymethyl)pyrrolidine as the starting materials. mp 207° C. (TFA salt); ESI-MS m/e calc'd for $C_{33}H_{36}N_7O_3$: 578.2880, found: 578.2889.

Example CCXXXVI

Preparation of 3-(4-piperazinophenyl)-5-((2(S)-(benzyloxymethyl)pyrrolidino)carbamoylamino)indeno[1,2-c]pyrazol-4-one Prepared in a similar fashion as described for example CCXI employing 33 from example CCX and 1-amino-2(S)-(benzyloxymethyl)pyrrolidine as the starting materials. ESI-MS m/e calc'd for $C_{33}H_{36}N_7O_3$: 578.2879, found: 578.2897.

Example CCXXXVII

Preparation of 3-(4-(3-methylpiperazino)phenyl)-5-(morpholinocarbamoylamino)indeno[1,2-c]pyrazol-4-one Prepared in a similar fashion as described for example CCXI and CCX employing 4-(4-tert-butoxycarbonyl-3-methylpiperazino)acetophenone as the starting materials. mp 230° C. (TFA salt); ESI-MS m/e calc'd for $C_{26}H_{30}N_7O_3$: 488.2410, found: 488.2416.

Example CCXXXVIII

Preparation of 3-(4-(cis-3,5-dimethylpiperazino)phenyl)-5-(morpholinocarbamoylamino)indeno[1,2-c]pyrazol-4-one Prepared in a similar fashion as described for example CCXI and CCX employing 4-(cis-4-tert-butoxycarbonyl-3,5-dimethylpiperazino)acetophenone as the starting materials. mp 237° C. (TFA salt); ESI-MS m/e calc'd for $C_{27}H_{32}N_7O_3$: 502.2567, found: 502.2571.

Example CCXXXIX

Preparation of 3-(4-(cis-3,4,5-trimethylpiperazino)phenyl)-5-(morpholinocarbamoylamino)indeno[1,2-c]pyrazol-4-one Prepared in a similar fashion as described for example CCXVIII employing CCXXXVIII as the starting material. mp 240° C. (TFA salt); ESI-MS m/e calc'd for $C_{28}H_{34}N_7O_3$: 516.2723, found: 516.2734.

Example CCXL

Preparation of 3-(4-(4-isopropylpiperazino)-2-methylphenyl)-5-(morpholinocarbamoylamino)indeno[1,2-c]pyrazol-4-one Prepared in a similar fashion as described for example CCXVIII, CCXI, and CCX employing 4-(4-tertbutoxycarbonylpiperazino)-2-methylacetophenone as the starting materials. ESI-MS m/e calc'd for $C_{29}H_{36}N_7O_3$: 530.2879, found: 530.2893.

Example CCXLI

Preparation of 3-(4-homopiperazinophenyl)-5-(morpholinocarbamoylamino)indeno[1,2-c]pyrazol-4-one Prepared in a similar fashion as described for example CCXI and CCX employing 4-(4-tert-butoxycarbonylhomopiperazino)acetophenone as the starting materials. mp 253° C. (TFA salt); ESI-MS m/e calc'd for $C_{26}H_{30}N_7O_3$: 488.2410, found: 488.2406.

Example CCXLII

Preparation of 3-(4-(4-methylhomopiperazino)phenyl)-5-(morpholinocarbamoylamino)indeno[1,2-c]pyrazol-4-one Prepared in a similar fashion as described for example CCXVIII employing CCXLI as the starting material. ESI-MS m/e calc'd for $C_{27}H_{32}N_7O_3$: 502.2567, found: 502.2581.

Example CCXLIII

Preparation of 3-(4-(4-ethylhomopiperazino)phenyl)-5-(morpholinocarbamoylamino)indeno[1,2-c]pyrazol-4-one Prepared in a similar fashion as described for example CCXVIII employing CCXLI and acetaldehyde as the starting materials. mp 240° C. (TFA salt); ESI-MS m/e calc'd for $C_{28}H_{34}N_7O_3$: 516.2723, found: 516.2732.

Example CCXLIV

Preparation of 3-(4-(4-isopropylhomopiperazino)phenyl)-5-(morpholinocarbamoylamino)indeno[1,2-c]pyrazol-4-one Prepared in a similar fashion as described for example CCXVIII employing CCXLI and acetone as the starting materials. mp 245° C. (TFA salt); ESI-MS m/e calc'd for $C_{29}H_{36}N_7O_3$: 530.2880, found: 530.2876.

Example CCXLV

Preparation of 3-(4-homopiperazino-2-methylphenyl)-5-(morpholinocarbamoylamino)indeno[1,2-c]pyrazol-4-one Prepared in a similar fashion as described for example CCXI and CCX employing 4-(4-tert-butoxycarbonylhomopiperazino)-2-methylacetophenone as the starting materials. mp 209° C. (TFA salt); ESI-MS m/e calc'd for $C_{27}H_{32}N_7O_3$: 502.2566, found: 502.2580.

Example CCXLVI

Preparation of 3-(4-(4-ethylhomopiperazino)-2-methylphenyl)-5-(morpholinocarbamoylamino)indeno[1,2-c]pyrazol-4-one Prepared in a similar fashion as described for example CCXVIII employing CCXLV and acetaldehyde as the starting materials. mp 217° C. (TFA salt); ESI-MS m/e calc'd for $C_{29}H_{36}N_7O_3$: 530.2880, found: 530.2891.

Example CCXLVII

Preparation of 3-(4-(4-isopropylhomopiperazino)-2-methylphenyl)-5-(morpholinocarbamoylamino)indeno[1,2-c]pyrazol-4-one Prepared in a similar fashion as described for example CCXVIII employing CCXLV and acetone as the starting materials. mp 197° C. (TFA salt); ESI-MS m/e calc'd for $C_{30}H_{38}N_7O_3$: 544.3036, found: 544.3059.

Example CCXLVIII

Preparation of 3-(4-(4-(N,N-dimethylamino)piperidino)phenyl)-5-(morpholinocarbamoylamino)indeno[1,2-c]pyrazol-4-one

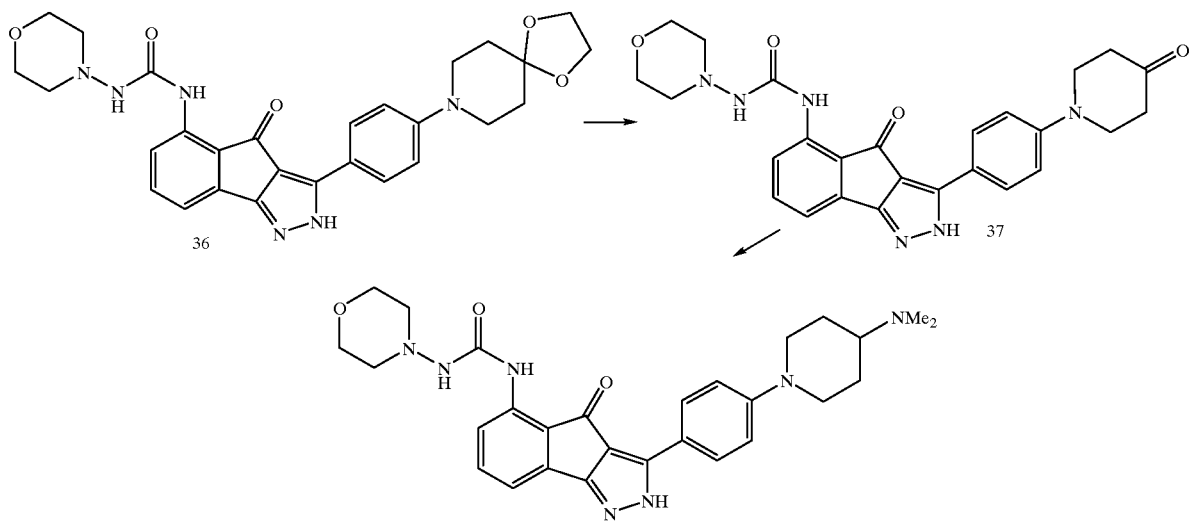

Step 1. Synthesis of 36.

Prepared in a similar fashion as described for example CCX employing 4-(4,4-ethylenedioxypiperidino) acetophenone as starting material.

Step 2. Synthesis of 37 from 36.

A mixture of 12.40 g (23.4 mmol) of 36, 500 mL of acetone, 125 mL of water, and 25 mL of trifluoroacetic acid was refluxed for 24 h. After cooling to room temperature the mixture was concentrated under vacuum. The residue was slurried in 95% aqueous ethanol, and the mixture was adjusted to pH 7 employing aqueous sodium hydroxide solution. The resulting mixture was filtered. The recovered solids were washed with 95% aqueous ethanol and dried to afford 10.68 g of 37 as a yellow solid. NMR (DMSO-$d_6$) δ 13.46 (br s, 1H), 10.96 (br s, 1H), 8.30 (d, 1H, J=9 Hz), 8.27 (s, 1H), 8.14 (d, 2H, J=9 Hz), 7.43 (t, 1H, J=9 Hz), 7.18 (d, 2H, J=9 Hz), 7.10 (d, 1H, J=9 Hz), 3.90-3.75 (m, 8H), 3.34 (s, 8H), 2.92 (m, 2H), 2.72 (m, 2H), 2.45 (t, 4H, J=6 Hz).

Step 3. Synthesis of CCXLVIII from 37.

To a mixture of 1.00 g (2 mmol) of 37, 200 mL of 2M dimethylamine in methanol, 200 mL of acetonitrile, and 1 mL of acetic acid at 25° C. was added 2.60 g (40 mmol) of sodium cyanoborohydride, and the reaction mixture was stirred at 25° C. for 20 h. The mixture was diluted with 200 mL of water and then acidified (pH<2) employing conc. hydrochloric acid. After 30 min. gas evolution had ceased, and the solution was made strongly basic (pH>12) employing conc. aqueous sodium hydroxide solution. The solution was stirred for 20 min. and then was adjusted to pH 10 by the addition of 1N hydrochloric acid. The resulting precipitate was recovered by filtration, washed with water, and dried. These solids were dissolved in 10 mL of trifluoroacetic acid, and the solution was diluted with 50 mL of anhydrous ethanol. A yellow precipitate formed, was recovered by filtration, and was dried under vacuum to provide 0.41 g of the product as its TFA-salt. mp 258° C.; ESI-MS m/e calc'd for $C_{28}H_{34}N_7O_3$: 516.2723, found: 516.2737.

Example CCXLIX

Preparation of 3-(4-(4-morpholinopiperidino) phenyl)-5-(morpholinocarbamoylamino)indeno[1,2-c]pyrazol-4-one Prepared in a similar fashion as described for example CCXLVIII employing 37, morpholine, and methanesulfonic acid as the starting materials. mp 249° C. (MSOH salt); ESI-MS m/e calc'd for $C_{30}H_{36}N_7O_4$: 558.2828, found: 558.2817.

Example CCL

Preparation of 3-(4-(4-piperidinopiperidino)phenyl)-5-(morpholinocarbamoylamino)indeno[1,2-c] pyrazol-4-one Prepared in a similar fashion as described for example CCXLVIII employing 37 and piperidine as the starting materials. mp 233° C. (TFA salt); ESI-MS m/e calc'd for $C_{31}H_{38}N_7O_3$: 556.3036, found: 556.3039.

Example CCLI

Preparation of 3-(4-(4-pyrrolidinopiperidino) phenyl)-5-(morpholinocarbamoylamino)indeno[1,2-c]pyrazol-4-one Prepared in a similar fashion as described for example CCXLVIII employing 37 and pyrrolidine as the starting materials. mp 247° C. (TFA salt); ESI-MS m/e calc'd for $C_{30}H_{36}N_7O_3$: 542.2879, found: 542.2860.

Example CCLII

Preparation of 3-(4-(4-(N,N-diethylamino) piperidino)phenyl)-5-(morpholinocarbamoylamino) indeno[1,2-c]pyrazol-4-one Prepared in a similar fashion as described for example CCXLVIII employing 37 and diethylamine as the starting materials. mp 251° C. (TFA salt); ESI-MS m/e calc'd for $C_{30}H_{38}N_7O_3$: 544.3036, found: 544.3035.

Example CCLIII

Preparation of 3-(4-(4-(1-iminoethyl)piperazino) phenyl)-5-(morpholinocarbamoylamino)indeno[1,2-c]pyrazol-4-one

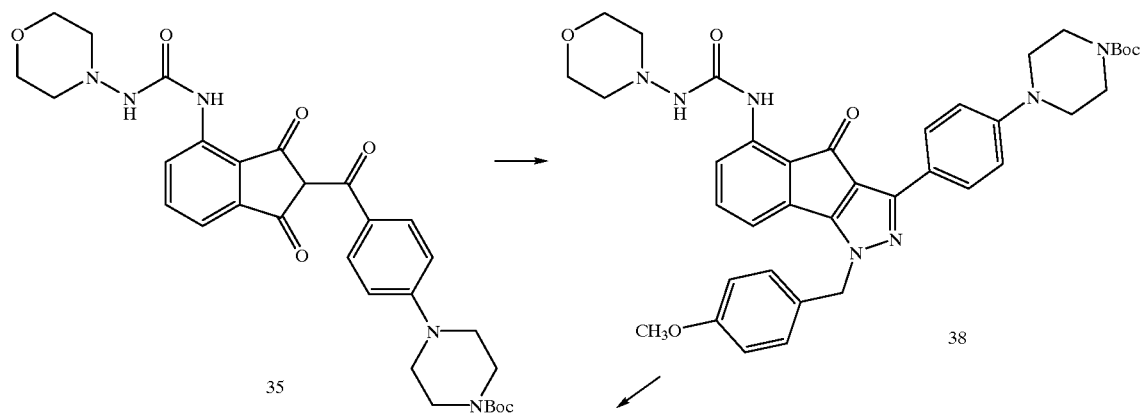

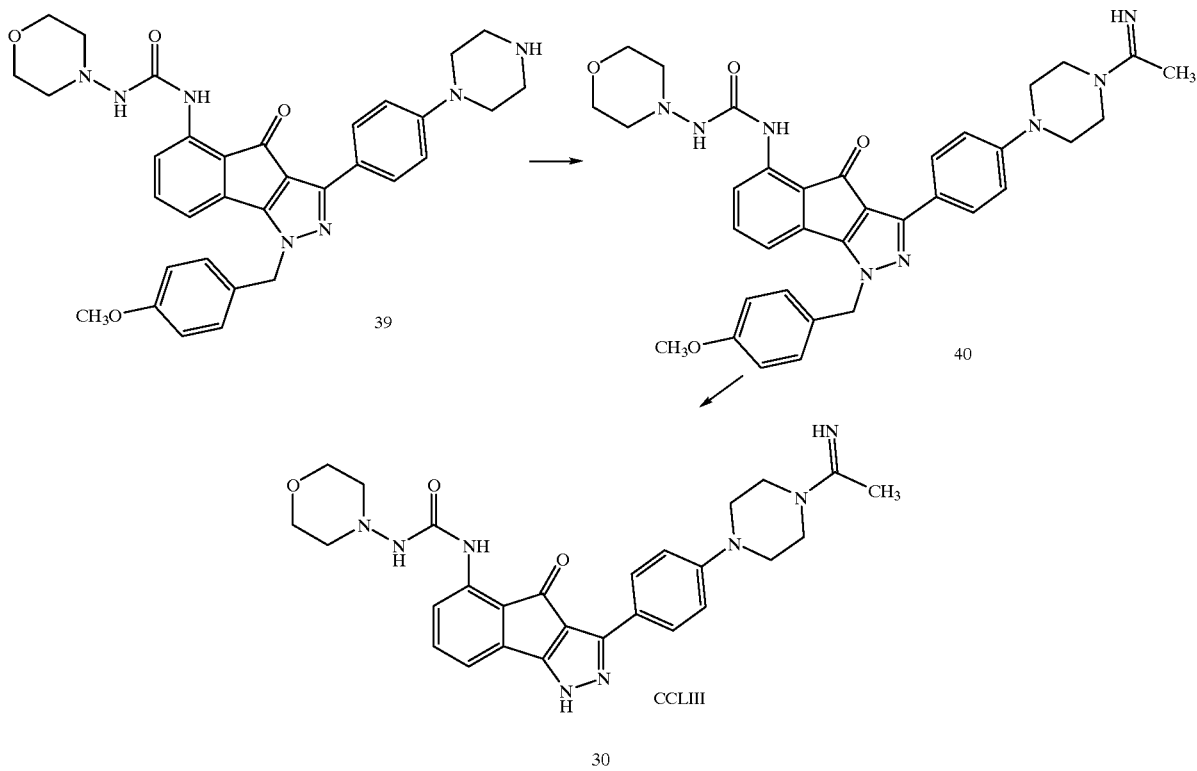

Step 1. Synthesis of 38 from 35.

A mixture of 4.43 g (7.7 mmol) of 35 (example CCX), 3.15 g (20.7 mnmol) of 4-methoxybenzylhydrazine, 0.29 g (1.50 mmol) of 4-methoxybenzylhydrazine hydrochloride, and 150 mL of ethanol was refluxed for 22 h. While the reaction mixture was maintained at reflux 30 mL of water was added dropwise, and the mixture then was allowed to cool to room temperature. The resulting precipitate was recovered by filtration, washed with 95% aqueous ethanol, and dried to furnish 1.40 g of 38. NMR (CDCl$_3$) δ 11.04 (s, 1H), 8.32 (d, 1H, J=9 Hz), 8.19 (d, 2H, J=9 Hz), 7.28 (d, 2H, J=9 Hz), 7.24 (t, 1H, J=9 Hz), 7.02 (d, 2H, J=9 Hz), 6.88 (d, 2H, J=9 Hz), 6.68 (d, 1H, J=9 Hz), 5.52 (s, 1H), 5.38 (s, 2H), 4.00 (m, 4H), 3.78 (s, 3H), 3.62 (m, 4H), 3.27 (m, 4H), 3.08 (m, 2H), 2.72 (m, 2H), 1.49 (s, 9H).

Step 2. Synthesis of 39 from 38.

A solution of 1.38 g of 38 in 20 mL of trifluoroacetic acid was stirred at 25° C. for 0.5 h. The excess trifluoroacetic acid was removed under vacuum, and the residue was recyrstallized from ethanol to afford 1.25 g of 39 as its TFA-salt. ESI-MS m/e=594 (M+H)$^+$.

Step 3. Synthesis of 40 from 39.

A solution of 0.18 g (0.25 mmol) of 39, 0.27 g (2.5 mmol) of methyl acetimidate hydrochloride, 0.31 g (2.5 mmol) of 4-dimethylaminopyridine, and 10 mL of methanol was refluxed for 48 h. To the hot solution was added 2 mL of water, and the miture was allowed to cool to room temperature. The resulting precipitate was washed with 95% aqueous ethanol and dried to provide 0.125 g of 40 as an orange solid.

Step 4. Synthesis of CCLIII from 40.

A solution of 0.122 g of 40 in 10 mL of trifluoroacetic acid was stirred at 25° C. for 120 h and then concentrated under vacuum. The residue was purified by reverse-phase preparative HPLC to afford 0.045 g of CCLIII as its TFA-salt. mp 240° C.; ESI-MS m/e calc'd for $C_{27}H_{31}N_8O_3$: 515.2519, found: 515.2529.

Example CCLIV

Preparation of 3-(4-(4-(2-pyridinyl)piperazino) phenyl)-5-(morpholinocarbamoylamino)indeno[1,2-c]pyrazol-4-one Prepared in a similar fashion as described for example CCLIII employing 39 and 2-bromopyridine as the starting materials. ESI-MS m/e calc'd for $C_{30}H_{31}N_8O_3$: 551.2519, found: 551.2514.

Example CCLV

Preparation of 3-(c-propyl)-5-(4-carbamoylpiperidinoacetamido)indeno[1,2-c]pyrazol-4-one Prepared in a similar fashion as described for example XXIII using isonipecotamide and the c-propyl analog of 14 as the starting materials. mp 178–180° C. (TFA salt); ESI-MS (M+H) calc'd for $C_{21}H_{24}N_5O_3$: 394.1879, found: 394.1876.

Example CCLVI

Preparation of 3-ethyl-5-(4-methylpiperazinocarbamoylamino)indeno[1,2-c]pyrazol-4-one Prepared in a similar fashion as described for example XLII using 1-amino-4-methylpiperazine and the ethyl analog of 15 as the starting materials. mp 244–246° C. (TFA salt); ESI-MS (M+H) calc'd for $C_{18}H_{23}N_6O_2$: 355.1882, found: 355.1858.

Example CCLVII

Preparation of 3-(c-propyl)-5-(4-methylpiperazinocarbamoylamino)indeno[1,2-c]pyrazol-4-one Prepared in a similar fashion as described for example XLII using 1-amino-4-methylpiperazine and the c-propyl analog of 15 as the starting materials. mp 215–217° C. (TFA salt); ESI-MS (M+H) calc'd for $C_{19}H_{23}N_6O_2$: 367.1882, found: 367.1862.

Example CCLVIII

Preparation of 3-(c-hexyl)-5-(4-methylpiperazinocarbamoylamino)indeno[1,2-c]pyrazol-4-one Prepared in a similar fashion as described for example XLII using 1-amino-4-methylpiperazine and the c-hexyl analog of 15 as the starting materials. mp 241–242° C. (TFA salt); ESI-MS (M+H) calc'd for $C_{22}H_{29}N_6O_2$: 409.2352, found: 409.2371.

Example CCLIX

Preparation of 3-ethyl-5-(morpholinocarbamoylamino)indeno[1,2-c]pyrazol-4-one

Prepared in a similar fashion as described for example XLII using 4-aminomorpholine and the ethyl analog of 15 as the starting materials. mp 253–254° C. (TFA salt); ESI-MS (M+H) calc'd for $C_{17}H_{20}N_5O_3$: 342.1566, found: 342.1555.

Example CCLX

Preparation of 3-(c-propyl)-5-(morpholinocarbamoylamino)indeno[1,2-c]pyrazol-4-one Prepared in a similar fashion as described for example XLII using 4-aminomorpholine and the c-propyl analog of 15 as the starting materials. ESI-MS (M+H) calc'd for $C_{18}H_{20}N_5O_3$: 354.1566, found: 354.1548.

Example CCLXI

Preparation of 3-(c-hexyl)-5-(morpholinocarbamoylamino)indeno[1,2-c]pyrazol-4-one Prepared in a similar fashion as described for example XLII using 4-aminomorpholine and the c-hexyl analog of 15 as the starting materials. mp >260° C. (TFA salt); ESI-MS (M+H) calc'd for $C_{21}H_{26}N_5O_3$: 396.2036, found: 396.2021.

Example CCLXII

Preparation of 3-(1-ethoxycarbonylpiperidin-4-yl)-5-(morpholinocarbamoylamino)indeno[1,2-c]pyrazol-4-one Prepared in a similar fashion as described for example CXXVI using ethylchloroformate and 29G as the starting materials. mp 206–207° C. (TFA salt); ESI-MS (M+H) calc'd for $C_{23}H_{29}N_6O_5$: 469.2199, found: 469.2170.

Example CCLXIII

Preparation of 3-(1-phenoxycarbonylpiperidin-4-yl)-5-(morpholinocarbamoylamino)indeno[1,2-c]pyrazol-4-one Prepared in a similar fashion as described for example CXXVI using phenylchloroformate and 29G as the starting materials. mp 250–252° C. (TFA salt); ESI-MS (M+H) calc'd for $C_{27}H_{29}N_6O_5$: 517.2199, found: 517.2182.

Example CCLXIV

Preparation of 3-(1-(imidazol-1-ylcarbonyl)piperidin-4-yl)-5-(morpholinocarbamoylamino)indeno[1,2-c]pyrazol-4-one

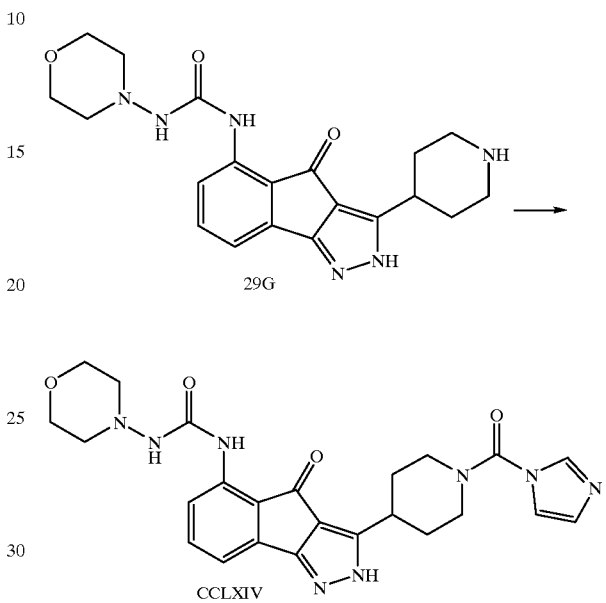

A solution of 29G (0.255 g, 0.5 mmol) in dimethylformamide (10 mL) was treated with carbonyldiimidazole (0.16 g, 1 mmol) and stirred at 50° C. for 2 h. The reaction mixture was cooled, poured into water (20 mL), and extracted with EtOAc (40 mL). The organic layer was separated, dried (MgSO$_4$), filtered, and concentrated at reduced pressure to give a yellow oil. Purification using reverse phase HPLC (CH$_3$CN/water) gave the product as a yellow solid (18.5 mg, 6%). mp 202–204° C. (TFA salt); ESI-MS (M+H) calc'd for $C_{24}H_{27}N_8O_4$: 491.2155, found: 491.2138.

Example CCLXV

Preparation of 3-(1-(2-thienylcarbonyl)piperidin-4-yl)-5-(morpholinocarbamoylamino)indeno[1,2-c]pyrazol-4-one Prepared in a similar fashion as described for example CXXXII using 29G and 2-thiophenecarboxylic acid as the starting materials. mp 218–220° C. (TFA salt); ESI-MS (M+H) calc'd for $C_{25}H_{27}N_6O_4S$: 507.1815, found: 507.1822.

Example CCLXVI

Preparation of 3-(1-carbamoylpiperidin-4-yl)-5-(morpholinocarbamoylamino)indeno[1,2-c]pyrazol-4-one

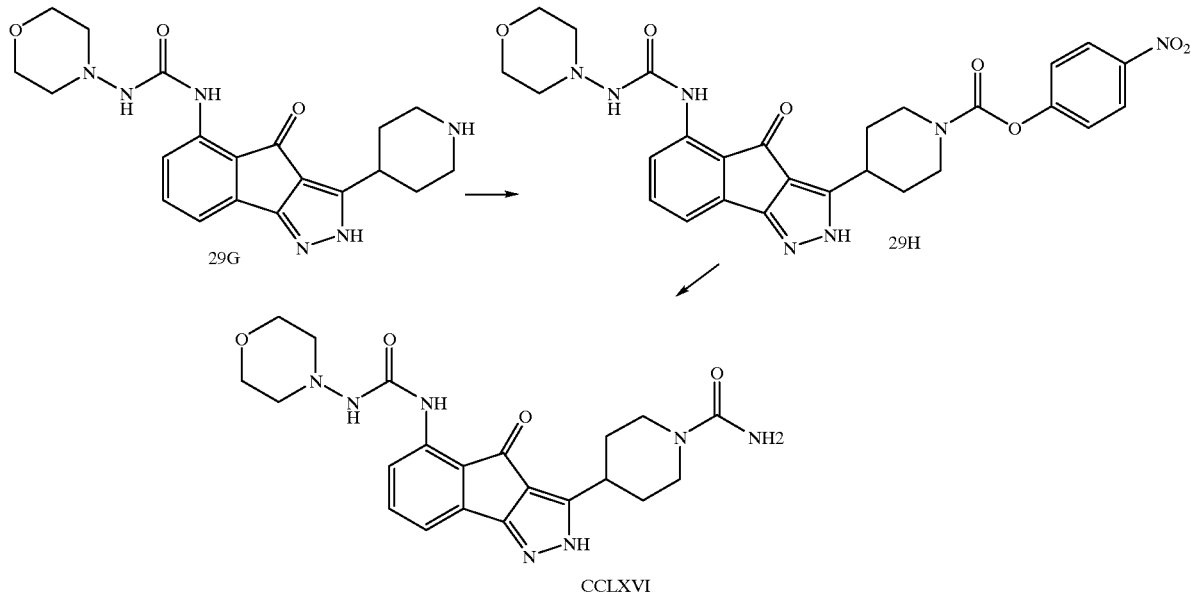

Step 1. Synthesis of 29H from 29G

Prepared in a similar fashion as described for example CXXVI using 29G and 4-nitrophenylchloroformate as the starting materials to give the product as a tan solid (1.22 g, 72%). mp 255–257° C.; ESI-MS (M+H) calc'd for $C_{27}H_{28}N_7O_7$: 562.2050, found: 562.2032.

Step 2. Synthesis of CCLXVI from 29H.

A suspension of 29H (0.20 g, 0.36 mmol) in dimethylsulfoxide (1 mL) was treated with conc. $NH_4OH$ (0.048 mL, 0.72 mmol) and heated to 90° C. for 6 h. The reaction mixture was cooled and the solvent removed at reduced pressure to give an yellow oil. Purification using reverse phase HPLC ($CH_3CN$/water) gave the product as a pale yellow solid (11.3 mg, 57%). mp 258–259° C. (TFA salt); ESI-MS (M+H) calc'd for $C_{21}H_{26}N_7O_4$: 440.2046, found: 440.2068.

Example CCLXVII

Preparation of 3-(1-(ethylcarbamoyl)piperidin-4-yl)-5-(morpholinocarbamoylamino)indeno[1,2-c]pyrazol-4-one Prepared in a similar fashion as described for example CCLXVI using 29H and ethylamine as the starting materials. mp 215–216° C. (TFA salt); ESI-MS (M–H) calc'd for $C_{23}H_{28}N_7O_4$: 466.2203, found: 466.2208.

Example CCLXVIII

Preparation of 3-(1-(2-(1-methylpyrrolidin-2-yl)ethylaminocarbamoyl)piperidin-4-yl)-5-(morpholinocarbamoylamino)indeno[1,2-c]pyrazol-4-one Prepared in a similar fashion as described for example CCLXVI using 29H and 2-(2-aminoethyl)-1-methylpyrrolidine as the starting materials. mp 91–93° C. (TFA salt); ESI-MS (M+H) calc'd for $C_{28}H_{39}N_8O_4$: 551.3094, found: 551.3095.

Example CCLXIX

Preparation of 3-(1-(4-(dimethylamino)piperidinocarbonyl)piperidin-4-yl)-5-(morpholinocarbamoylamino)indeno[1,2-c]pyrazol-4-one Prepared in a similar fashion as described for example CCLXVI using 29H and 4-(dimethylamino)piperidine as the starting materials. mp 172–174° C. (TFA salt); ESI-MS (M+H) calc'd for $C_{28}H_{39}N_8O_4$: 551.3109, found: 551.3109.

Example CCLXX

Preparation of 3-(1-(piperazinocarbonyl)piperidin-4-yl)-5-(morpholinocarbamoylamino)indeno[1,2-c]pyrazol-4-one Prepared in a similar fashion as described for example CXXVI, step 7, using CCLXXI as the starting material. mp 195–197° C. (TFA salt); ESI-MS (M+H) calc'd for $C_{25}H_{33}N_8O_4$: 509.2625, found: 509.2635.

Example CCLXXI

Preparation of 3-(1-(4-(t-butoxycarbonyl)piperazinocarbonyl)piperidin-4-yl)-5-(morpholinocarbamoylamino)indeno[1,2-c]pyrazol-4-one Prepared in a similar fashion as described for example CCLXVI using 29H and 1-(t-butoxycarbonyl)piperazine as the starting materials. mp 231–232° C. (TFA salt); ESI-MS (M+H) calc'd for $C_{30}H_{41}N_8O_6$: 609.3149, found: 609.3123.

Example CCLXXII

Preparation of 3-(1-(((1S,4S)-(+)-2,5-diazabicyclo[2.2.1]hept-2-yl)carbonyl)piperidin-4-yl)-5-(morpholinocarbamoylamino)indeno[1,2-c]pyrazol-4-one Prepared in a similar fashion as described for example CXXVI, step 7, using the 3-(1-((5-t-butoxycarbonyl-(1S, 4S)-(+)-2,5-diazabicyclo[2.2.1]hept-2-yl)carbonyl) piperidin-4-yl)-5-(morpholinocarbamoylamino)indeno[1,2-c]pyrazol-4-one as the starting material. mp 196–198° C. (TFA salt); ESI-MS (M+H) calc'd for $C_{26}H_{33}N_8O_4$: 521.2613, found: 521.2613.

Example CCLXXIII

Preparation of 3-(1-(((1S,4S)-(+)-5-methyl-2,5-diazabicyclo[2.2.1]hept-2-yl)carbonyl)piperidin-4-yl)-5-(morpholinocarbamoylamino)indeno[1,2-c]pyrazol-4-one Prepared in a similar fashion as described for example CCLXVI using 29H and (1S,4S)-(+)-2-methyl-2,5-diazabicyclo[2.2.1]heptane as the starting materials. mp 224–225° C. (TFA salt); ESI-MS (M+H) calc'd for $C_{27}H_5N_8O_4$: 535.2781, found: 535.2783.

Example CCLXXIV

Preparation of 3-(1-(3-aminopropylcarbonyl) piperidin-4-yl)-5-(morpholinocarbamoylamino) indeno[1,2-c]pyrazol-4-one Prepared in a similar fashion as described for example CXXVI, step 7, using CCLXXVI as the starting material. mp 172–174° C. (TFA salt); ESI-MS (M+H) calc'd for $C_{24}H_{32}N_7O_4$: 482.2516, found: 482.2497.

Example CCLXXV

Preparation of 3-(1-(3-(dimethylamino) propylcarbonyl)piperidin-4-yl)-5-(morpholinocarbamoylamino)indeno[1,2-c]pyrazol-4-one Prepared in a similar fashion as described for example CXXXII using 29G and 4-(dimethylamino)butyric acid as the starting materials. mp 145–147° C. (TFA salt); ESI-MS (M+H) calc'd for $C_{26}H_{35}N_7O_4$: 510.2829, found: 510.2830.

Example CCLXXVI

Preparation of 3-(1-(3-(t-butoxycarbonylamino) propylcarbonyl)piperidin-4-yl)-5-(morpholinocarbamoylamino)indeno[1,2-c]pyrazol-4-one Prepared in a similar fashion as described for example CXXXII using 29G and 5-(t-butoxycarbonylamino)butyric acid as the starting materials. mp 73–75° C.; ESI-MS (M+H) calc'd for $C_{29}H_{40}N_7O_6$: 582.3040, found: 582.3050.

Example CCLXXVII

Preparation of 3-(1-(4-aminobutylcarbonyl) piperidin-4-yl)-5-(morpholinocarbamoylamino) indeno[1,2-c]pyrazol-4-one Prepared in a similar fashion as described for example CXXVI, step 7, using CCLXXIX as the starting material. mp 103–105° C. (TFA salt); ESI-MS (M+H) calc'd for $C_{25}H_{34}N_7O_4$: 496.2672, found: 496.2648.

Example CCLXXVIII

Preparation of 3-(1-(4-(dimethylamino) butylcarbonyl)piperidin-4-yl)-5-(morpholinocarbamoylamino)indeno[1,2-c]pyrazol-4-one Prepared in a similar fashion as described for example CXXXII using 29G and 5-(dimethylamino)valeric acid as the starting materials. mp 68–70° C. (TFA salt); ESI-MS (M+H) calc'd for $C_{27}H_{38}N_7O_4$: 524.2985, found: 524.2978.

Example CCLXXIX

Preparation of 3-(1-(4-(t-butoxycarbonylamino) butylcarbonyl)piperidin-4-yl)-5-(morpholinocarbamoylamino)indeno[1,2-c]pyrazol-4-one Prepared in a similar fashion as described for example CXXXII using 29G and 5-(t-butoxycarbonylamino)valeric acid as the starting material. mp 98–99° C. (TFA salt); ESI-MS (M+H) calc'd for $C_{30}H_{42}N_7O_6$: 596.3197, found: 596.3182.

Example CCLXXX

Preparation of 3-(1-((1-methylpiperidin-4-yl) carbonyl)piperidin-4-yl)-5-(morpholinocarbamoylamino)indeno[1,2-c]pyrazol-4-one Prepared in a similar fashion as described for example CXXXII using 29G and 1-methylpiperidine-4-carboxylic acid as the starting materials. mp 148–150° C. (TFA salt); ESI-MS (M+H) calc'd for $C_{27}H_{36}N_7O_4$: 522.2829, found: 522.2840.

Example CCLXXXI

Preparation of 3-(1-((1-(t-butoxycarbonyl)piperidin-4-yl)carbonyl)piperidin-4-yl)-5-(morpholinocarbamoylamino)indeno[1,2-c]pyrazol-4-one Prepared in a similar fashion as described for example CXXXII using 29G and 1-(t-butoxycarbonyl)piperidine-4-carboxylic acid as the starting materials. mp 220–222° C.; ESI-MS (M+H) calc'd for $C_{31}H_{42}N_7O_6$: 608.3197, found: 608.3174.

Example CCLXXXII

Preparation of 3-(1-(cis-4-aminocyclohexylcarbonyl)piperidin-4-yl)-5-(morpholinocarbamoylamino)indeno[1,2-c]pyrazol-4-one Prepared in a similar fashion as described for example CXXVI, step 7, using CCLXXXV as the starting material. mp 212–214° C. (TFA salt); ESI-MS (M+H) calc'd for $C_{27}H_{36}N_7O_4$: 522.2829, found: 522.2818.

Example CCLXXXIII

Preparation of 3-(1-(4-aminocyclohexylcarbonyl) piperidin-4-yl)-5-(morpholinocarbamoylamino) indeno[1,2-c]pyrazol-4-one Prepared in a similar fashion as described for example CXXVI, step 7, using CCLXXXVI as the starting material. mp 202–204° C. (TFA salt); ESI-MS (M+H) calc'd for $C_{27}H_{36}N_7O_4$: 522.2829, found: 522.2857.

Example CCLXXXIV

Preparation of 3-(1-(cis-4-(dimethylamino) cyclohexylcarbonyl)piperidin-4-yl)-5-(morpholinocarbamoylamino)indeno[1,2-c]pyrazol-4-one Prepared in a similar fashion as described for example CXXXII using 29G and 4-(dimethylamino)cyclohexane carboxylic acid as the starting materials. mp 123–125° C. (TFA salt); ESI-MS (M+H) calc'd for $C_{29}H_{39}N_7O_4$: 550.3142, found: 550.3148.

Example CCLXXXV

Preparation of 3-(1-(4-(t-butoxycarbonylamino) cyclohexylcarbonyl)piperidin-4-yl)-5-(morpholinocarbamoylamino)indeno[1,2-c]pyrazol-4-one Prepared in a similar fashion as described for example CXXXII using 29G and 4-(t-butoxycarbonylamino) cyclohexane carboxylic acid as the starting materials. mp 210–212° C. (TFA salt); ESI-MS (M+H) calc'd for $C_{32}H_{44}N_7O_6$: 622.3353, found: 622.3340.

Example CCLXXXVI

Preparation of 3-(1-(trans-4-(t-butoxycarbonylamino)cyclohexylcarbonyl)piperidin-4-yl)-5-(morpholinocarbamoylamino)indeno[1,2-c] pyrazol-4-one Prepared in a similar fashion as described for example CXXXII using 29G and 4-(t-butoxycarbonylamino) cyclohexane carboxylic acid as the starting materials. mp 178–180° C.; ESI-MS (M+H) calc'd for $C_{32}H_{44}N_7O_6$: 622.3353, found: 622.3349.

Example CCLXXXVII

Preparation of 3-(1-(piperidin-3-ylcarbonyl) piperidin-4-yl)-5-(morpholinocarbamoylamino) indeno[1,2-c]pyrazol-4-one Prepared in a similar fashion as described for example CXXVI, step 7, using CCLXXXIX as the starting material. mp 169–170° C. (TFA salt); ESI-MS (M+H) calc'd for $C_{26}H_{34}N_7O_4$: 508.2672, found: 508.2669.

Example CCLXXXVIII

Preparation of 3-(1-(1-methylpiperidin-3-ylcarbonyl)piperidin-4-yl)-5-(morpholinocarbamoylamino)indeno[1,2-c]pyrazol-4-one Prepared in a similar fashion as described for example CXXXII using 29G and 1-methylpiperidine-3-carboxylic acid as the starting materials. mp 158–160° C. (TFA salt); ESI-MS (M+H) calc'd for $C_{27}H_{36}N_7O_4$: 522.2829, found: 522.2842.

Example CCLXXXIX

Preparation of 3-(1(1-(t-butoxycarbonyl)piperidin-3-ylcarbonyl)piperidin-4-yl)-5-(morpholinocarbamoylamino)indeno[1,2-c]pyrazol-4-one Prepared in a similar fashion as described for example CXXXII using 29G and 1-t-butoxycarbonylpiperidine-3-carboxylic acid as the starting materials. mp 196–198° C.; ESI-MS (M+H) calc'd for $C_{31}H_{41}N_7O_6$: 608.3197, found: 608.3198.

Example CCXC

Preparation of 3-(1-(3-aminocyclohexylcarbonyl) piperidin-4-yl)-5-(morpholinocarbamoylamino) indeno[1,2-c]pyrazol-4-one Prepared in a similar fashion as described for example CXXVI, step 7, using 3-(1-(3-t-butoxycarbonylamino) cyclohexylcarbonyl)piperidin-4-yl)-5-(morpholinocarbamoylamino)indeno[1,2-c]pyrazol-4-one as the starting material. mp 201–203° C. (TFA salt); ESI-MS (M+H) calc'd for $C_{27}H_{36}N_7O_4$: 522.2829, found: 522.2815.

Example CCXCI

Preparation of 3-(1-(3-(dimethylamino) cyclohexylcarbonyl)piperidin-4-yl)-5-(morpholinocarbamoylamino)indeno[1,2-c]pyrazol-4-one Prepared in a similar fashion as described for example CXXXII using 29G and 1-(dimethylamino)cyclohexane-3-carboxylic acid as the starting materials. mp 153–155° C. (TFA salt); ESI-MS (M+H) calc'd for $C_{29}H_{40}N_7O_4$: 550.3142, found: 550.3131.

Example CCXCII

Preparation of 3-(1-(trans-4-methoxycyclohexylcarbonyl)piperidin-4-yl)-5-(morpholinocarbamoylamino)indeno[1,2-c]pyrazol-4-one Prepared in a similar fashion as described for example CXXXII using 29G and 4-trans-methoxycyclohexane carboxylic acid as the starting materials. mp 246–248° C. (TFA salt); ESI-MS (M+H) calc'd for $C_{28}H_{37}N_6O_5$: 537.2825, found: 537.2841.

Example CCXCIII

Preparation of 3-(1-(cis-4-methoxycyclohexylcarbonyl)piperidin-4-yl)-5-(morpholinocarbamoylamino)indeno[1,2-c]pyrazol-4-one Prepared in a similar fashion as described for example CXXXII using 29G and 4-cis-methoxycyclohexane carboxylic acid as the starting materials. mp 178–180° C. (TFA salt); ESI-MS (M+H) calc'd for $C_{28}H_{37}N_6O_5$: 537.2825, found: 537.2828.

Example CCXCIV

Preparation of 3-(1-(4-aminobenzylcarbonyl) piperidin-4-yl)-5-(morpholinocarbamoylamino) indeno[1,2-c]pyrazol-4-one Prepared in a similar fashion as described for example CXXVI, step 7, using CCXCVI as the starting material. mp 177–179° C. (TFA salt); ESI-MS (M+H) calc'd for $C_{28}H_{32}N_7O_4$: 530.2516, found: 530.2519.

Example CCXCV

Preparation of 3-(1-(4-(dimethylamino) benzylcarbonyl)piperidin-4-yl)-5-(morpholinocarbamoylamino)indeno[1,2-c]pyrazol-4-one Prepared in a similar fashion as described for example CXXXII using 29G and 4-(dimethylamino)phenyl acetic acid as the starting materials. mp 107–109° C. (TFA salt); ESI-MS (M+H) calc'd for $C_{30}H_{36}N_7O_4$: 558.2829, found: 558.2834.

Example CCXCVI

Preparation of 3-(1-(4-(t-butoxycarbonylamino) benzylcarbonyl)piperidin-4-yl)-5-(morpholinocarbamoylamino)indeno[1,2-c]pyrazol-4-one Prepared in a similar fashion as described for example CXXXII using 29G and 4-(t-butoxycarbonylamino)phenyl acetic acid as the starting materials. mp 177–178° C.; ESI-MS (M+H) calc'd for $C_{33}H_{40}N_7O_6$: 630.3040, found: 630.3040.

Example CCXCVII

Preparation of 3-(1-(4-aminophenylcarbonyl) piperidin-4-yl)-5-(morpholinocarbamoylamino) indeno[1,2-c]pyrazol-4-one Prepared in a similar fashion as described for example CXXVI, step 7, using CCXCIX as the starting material. mp 198–200° C. (TFA salt); ESI-MS (M+H) calc'd for $C_{27}H_{30}N_7O_4$: 516.2359, found: 516.2376.

Example CCXCVIII

Preparation of 3-(1-(4-(dimethylamino) phenylcarbonyl)piperidin-4-yl)-5-(morpholinocarbamoylamino)indeno[1,2-c]pyrazol-4-one Prepared in a similar fashion as described for example CXXXIII using 29G and 4-(dimethylamino)benzoic acid as the starting materials. mp 189–191° C. (TFA salt); ESI-MS (M+H) calc'd for $C_{29}H_{34}N_7O_4$: 544.2672, found: 544.2647.

Example CCXCIX

Preparation of 3-(1-(4-(t-butoxycarbonylamino) phenylcarbonyl)piperidin-4-yl)-5-(morpholinocarbamoylamino)indeno[1,2-c]pyrazol-4-one Prepared in a similar fashion as described for example CXXXIII using 29G and 4-(t-butoxycarbonylamino)benzoic acid as the starting materials. mp 212–214° C.; ESI-MS (M+H) calc'd for $C_{32}H_{38}N_7O_6$: 616.2884, found: 616.2884.

Example CCC

Preparation of 3-(trans-4-carboxylcyclohexyl)-5-(morpholinocarbamoylamino)indeno[1,2-c]pyrazol-4-one Prepared in a similar fashion as described for example CXXIII using CCCI as the starting material. mp 264–266° C. (TFA salt); ESI-MS (M+H) calc'd for $C_{22}H_{26}N_5O_5$: 440.1934, found: 440.1905.

Example CCCI

Preparation of 3-(trans-4-(methoxycarbonyl) cyclohexyl)-5-(morpholinocarbamoylamino)indeno [1,2-c]pyrazol-4-one Prepared in a similar fashion as described for example XLII using 4-aminomorpholine and the trans-4-(methoxycarbonyl)cyclohexyl analog of 15 as the starting materials. mp 259–261° C. (TFA salt); ESI-MS (M+H) calc'd for $C_{23}H_{28}N_5O_5$: 454.2090, found: 454.2100.

Example CCCII

Preparation of 3-(trans-4-(3-(dimethylamino) pyrrolidinocarbonyl)cyclohexyl)-5-(morpholinocarbamoylamino)indeno[1,2-c]pyrazol-4-one Prepared in a similar fashion as described for example CXXXII using 3-(dimethylamino)pyrrolidine and acid CCC as the starting materials. mp 191–193° C. (TFA salt); ESI-MS (M+H) calc'd for $C_{28}H_{38}N_7O_4$: 536.2985, found: 536.2970.

Example CCCIII

Preparation of 3-(trans-4-(piperazinocarbonyl) cyclohexyl)-5-(morpholinocarbamoylamino)indeno [1,2-c]pyrazol-4-one Prepared in a similar fashion as described for exampleCXXVI, step 7, using 3-(trans-4-(4-(t-butoxycarbonyl)piperazinocarbonyl)cyclohexyl)-5-(morpholinocarbamoylamino)indeno[1,2-c]pyrazol-4-one as the starting material. mp 247–248° C. (TFA salt); ESI-MS (M+H) calc'd for $C_{26}H_{34}N_7O_4$: 508.2672, found: 508.2670.

Example CCCIV

Preparation of 3-(trans-4-(4-methylpiperazinocarbonyl)cyclohexyl)-5-(morpholinocarbamoylamino)indeno[1,2-c]pyrazol-4-one Prepared in a similar fashion as described for example CXXXII using 1-methylpiperazine and CCC as the starting materials. mp 228–230° C. (TFA salt); ESI-MS (M+H) calc'd for $C_{27}H_{36}N_7O_4$: 522.2829, found: 522.2844.

Example CCCV

Preparation of 3-(trans-4-(homopiperazinocarbonyl) cyclohexyl)-5-(morpholinocarbamoylamino)indeno [1,2-c]pyrazol-4-one Prepared in a similar fashion as described for example CXXVI, step 7, using 3-(trans-4-(4-(t-butoxycarbonyl) homopiperazinocarbonyl)cyclohexyl)-5-(morpholinocarbamoylamino)indeno[1,2-c]pyrazol-4-one as the starting material. mp >265° C. (TFA salt); ESI-MS (M+H) calc'd for $C_{27}H_{36}N_7O_4$: 522.2829, found: 522.2833.

Example CCCVI

Preparation of 3-(trans-4-(4-methylhomopiperazinocarbonyl)cyclohexyl)-5-(morpholinocarbamoylamino)indeno[1,2-c]pyrazol-4-one Prepared in a similar fashion as described for example CXXXIII using 1-methylhomopiperazine and CCC as the starting materials. mp 218–220° C. (TFA salt); ESI-MS (M+H) calc'd for $C_{28}H_{38}N_7O_4$: 536.2985, found: 536.2988.

Example CCCVII

Preparation of 3-(2,4-dimethylthiazol-5-yl)-5-(carbamoylamino)indeno[1,2-c]pyrazol-4-one HCl (484 mL, diluted with 1 L of water). The solid which precipitated was filtered and washed repeatedly with water (3×150 mL) to give a brown solid (24.4 g, 46%, 2 steps). ESI-MS (M–H) found for $C_{15}H_9N_2O_5S$: 329.

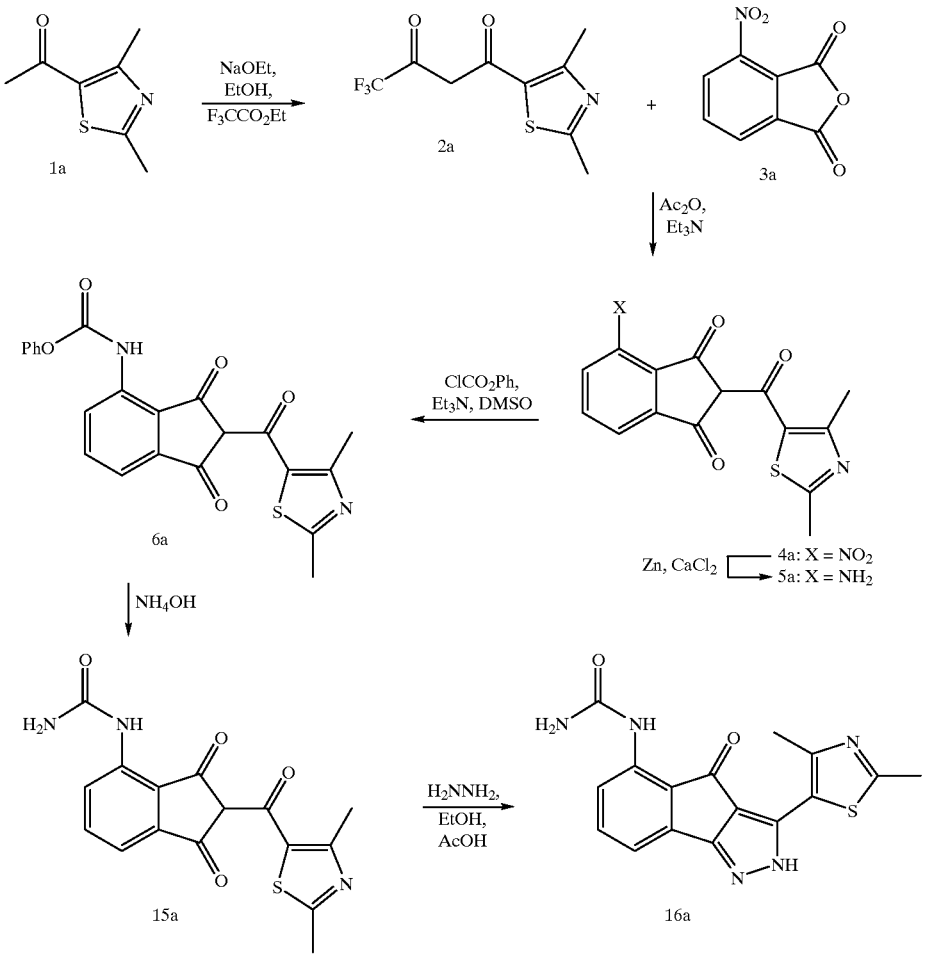

Step 1. Synthesis of Nitrotriketone 4a from 1a.

Ethyl trifluoroacetate (22.9 g, 161 mmol) and 2,4-dimethyl-5-acetylthiazole (25.0 g, 161 mmol) were added to a solution sodium ethoxide, freshly prepared from sodium (3.71 g, 161 mmol) and ethanol (500 mL), and stirred at 23° C. for 12 h. Half of the volume of organic solvent was concentrated in vacuo and the reaction mixture was diluted with 6 M HCl (400 mL) and extracted with ethyl acetate (2×300 mL). The combined organic extracts were washed with brine (2×300 mL), dried (MgSO$_4$), filtered, and concentrated in vacuo to give 1,3-diketone 2a as an orange oil which was used without purification.

3-Nitrophthalic anhydride (31.1 g, 161 mmol) was added to a solution of diketone 2a in acetic anhydride (91.2 mL, 968 mmol). The reaction mixture was cooled to 0° C. and triethylamine (67.3 mL, 484 mmol) was added dropwise over 1 h. The reaction mixture was warmed to 23° C. and stirred for 12 h, heated to 50° C. for 30 min, and then cooled to 23° C. The reaction mixture was slowly poured into 1 M Step 2. Synthesis of Aniline 5a from 4a.

A solution of nitrotriketone 4a (24.4 g, 73.9 mmol), zinc powder (160 g, 2.4 mol), and calcium chloride (5.3 g, 48 mmol) in 4:1 ethanol/water (370 mL) was heated to reflux for 1 h. The reaction mixture was filtered over celite and washed with methanol (3×150 mL) and ethyl acetate (3×150 mL). The filtrate was concentrated in vacuo to give a crude brown solid. Purification by flash column chromatography (silica, chloroform→2% methanol/chloroform→5% methanol/chloroform→7% methanol/chloroform) gave aniline 5a (13.0 g, 59%) as a brown solid. ESI-MS (M–H) found for $C_{15}H_{11}N_2O_3S$: 299.

Step 3. Synthesis of Carbamate 6a from 5a.

A solution of aniline 5a (840 mg, 2.8 mmol), phenyl chloroformate (0.42 mL, 3.4 mmol), and sodium carbonate (1.6 g) in acetone (14 mL) was heated to 50° C. for 4 h. The reaction mixture was cooled to 23° C. and diluted with water (20 mL) and ethyl acetate (20 mL). The organic layer was separated and washed with brine (20 mL), dried (MgSO4), filtered, and concentrated in vacuo to give a crude brown solid. Trituration with ether gave carbamate 6a (1.18 g, 99%) as a brown solid. ESI-MS (M–H) found for $C_{22}H_{15}N_2O_5S$: 419.

Step 4. Synthesis of Urea 15a from 6a.

A solution of carbamate 6a (1.18 g, 2.8 mmol) and ammonium hydroxide (0.47 mL, 3.4 mmol) in N,N-dimethylformamide (5 mL) was heated to 90° C. for 1 h. The solvent was concentrated in vacuo to give a crude residue. Purification using reverse phase HPLC (acetonitrile/water/trifluoroacetic acid) gave the product as a yellow solid (117 mg, 12%). ESI-MS (M–H) found for $C_{16}H_{12}N_3O_4S$: 342.

Step 5. Synthesis of Pyrazole 16a from 15a.

A solution of urea 15a (117 mg, 0.34 mmol), hydrazine (21 μL, 0.68 mmol), and p-toluenesulfonic acid (3.2 mg, 17 μmol) in ethanol (1.7 mL) was refluxed for 4 h. The reaction mixture was cooled to 23° C. and concentrated in vacuo to give a crude residue. Purification using reverse phase HPLC (acetonitrile/water/trifluoroacetic acid) gave the product as its TFA-salt (10 mg, 9%). ESI-MS (M+H) calc'd for $C_{16}H_{14}N_5O_2S$: 340.0868, found: 340.0895.

Example CCCVIII
Preparation of 3-(2,4-dimethylthiazol-5-yl)-5-(morpholinocarbamoylamino)indeno[1,2-c]pyrazol-4-one

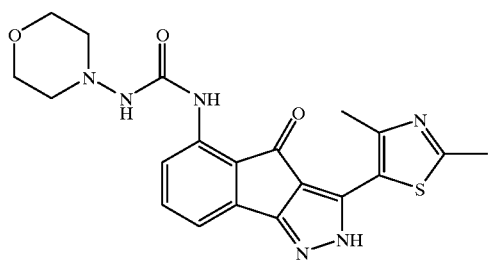

Prepared in a similar fashion as described for example CCCVII using 6a and morpholine as the starting materials. mp >300° C. (TFA salt); ESI-MS (M+H) calc'd for $C_{20}H_{21}N_6O_3S$: 425.1396, found: 425.1424.

Example CCCIX
Preparation of 3-(2,4-dimethylthiazol-5-yl)-5-((1-methyl-1-phenylamino)carbamoylamino)indeno[1,2-c]pyrazol-4-one

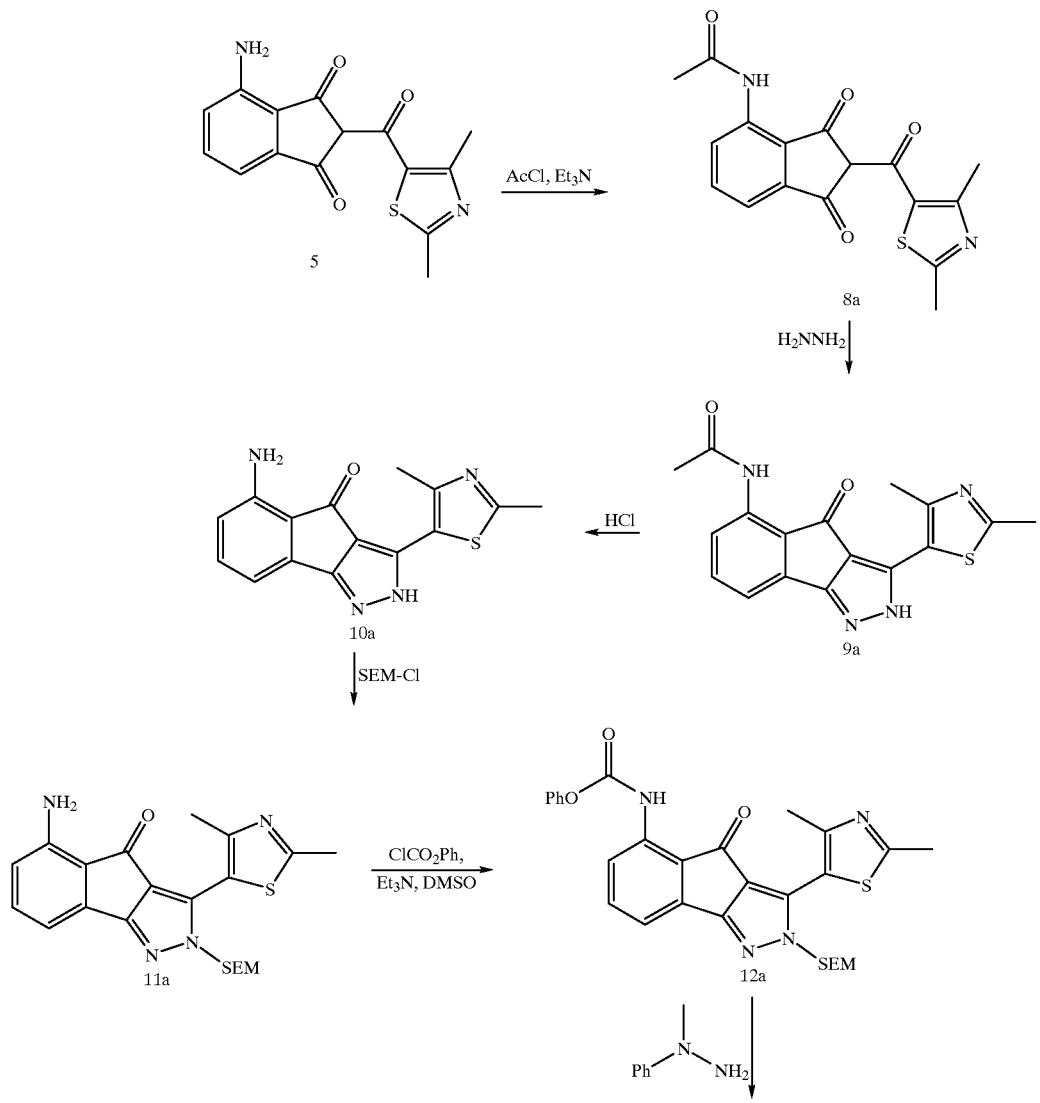

-continued

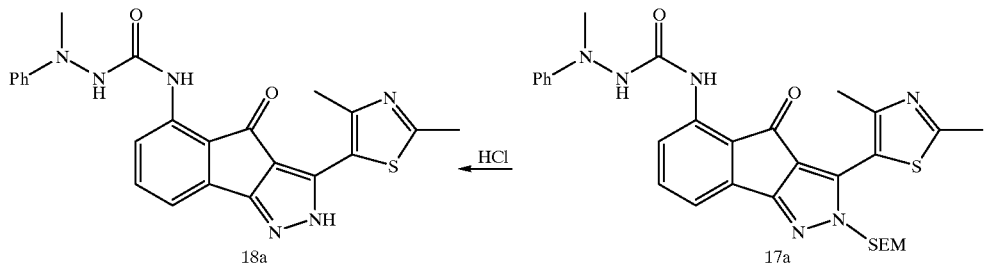

Step 1. Synthesis of Acetamide 8a from 5a.

A solution of aniline 5a (3.3 g, 10.8 mmol) in N,N-dimethylformamide (54 mL) was treated with acetyl chloride (0.81 mL, 11.4 mmol) and triethylamine (1.7 mL, 11.9 mmol) and refluxed for 4 h. The reaction mixture was cooled to 23° C. and diluted with ethyl acetate (100 mL) and water (100 mL). The aqueous layer was separated and washed with ethyl acetate (100 mL). The combined organic extracts were washed with brine (100 mL), dried (MgSO$_4$), filtered, and concentrated in vacuo to give a crude brown solid. The solid was dissolved in a small amount of methylene chloride (~10 mL) and treated with ether. The solid which precipatated was filtered and washed with ether (3×100 mL) to give a brown solid (1.6 g, 43%). ESI-MS (M−H) found for $C_{17}H_{13}N_2O_4S$: 341.

Step 2. Synthesis of pyrazole 9a from 8a.

A solution of triketone 8a (1.6 g, 4.7 mmol), hydrazine (0.71 mL, 9.4 mmol), and p-toluenesulfonic acid (44 mg, 0.23 mmol) in ethanol (23 mL) was refluxed for 4 h. The reaction mixture was cooled to 23° C. and the solid was filtered and washed with ethanol (20 mL) and ether (20 mL). Recrystalization of the precipatate from ethanol gave the product as a brown solid (400 mg, 25%). ESI-MS (M−H) found for $C_{17}H_{13}N_4O_2S$: 337.

Step 3. Synthesis of aniline 10a from 9a.

A solution of pyrazole 9a (400 mg, 1.2 mmol) and concentrated hydrochloric acid (2 mL) in methanol was refluxed for 3 h. The reaction mixture was cooled to 23° C. and concentrated in vacuo to give the product as a yellow solid (350 mg, 99%). ESI-MS (M−H) found for $C_{15}H_{11}N_4OS$: 295.

Step 4. Synthesis of aniline 11a from 10a.

A solution of aniline 10a (350 mg, 1.2 mmol) in dioxane (6 mL) was treated with triethylamine (0.69 mL, 5 mmol) and 2-(trimethylsilyl)ethoxymethyl chloride (0.52 mL, 3 mmol) and heated to reflux for 3 h. The reaction mixture was cooled to 23° C. and diluted with EtOAc (20 mL) and water (20 mL). The aqueous layer was separated and extracted with ethyl acetate (20 mL). The combined organic extracts were washed with brine (20 mL), dried (MgSO$_4$), filtered, and concentrated in vacuo to give a yellow solid. The yellow solid was treated with methylene chloride (50 mL) and methanol (50 mL) and filtered. The filtrate was concentrated in vacuo to give a crude brown residue. Purification by flash column chromatography (silica, 10% ethyl acetate/hexane→20% ethyl acetate/hexane≦40% ethyl acetate/hexane→80% ethyl acetate/hexane) gave aniline 11a (235 mg, 47%) as a brown solid. ESI-MS (M+H) found for $C_{21}H_{27}N_4O_2SSi$: 427.

Step 5. Synthesis of carbamate 12a from 11a.

Prepared in a similar fashion as described for example 1, step 3, using aniline 11a as the starting material. ESI-MS (M+H) found for $C_{28}H_{31}N_4O_4SSi$: 547.

Step 6. Synthesis of pyrazole 17a from 12a.

A solution of carbamate 12a (167 mg, 0.3 mmol) and 1-methyl-1-phenylhydrazine (72 µL, 0.6 mmol) in dimethyl sulfoxide (2 mL) was heated to 90° C. for 1 h. The solvent was concentrated in vacuo to give a crude residue which was diluted with 1:1 acetonitrile/water (3 mL). The solid which precipitated was filtered to give the product as a yellow solid (110 mg, 63%). ESI-MS (M+H) found for $C_{29}H_{35}N_6O_3SSi$: 574.

Step 7. Synthesis of pyrazole 18a from 17a.

A solution of 17a (110 mg, 0.2 mmol) in ethanol (10 mL) was treated with 4M hydrochloric acid in dioxane (10 mL) and heated to 70° C. for 1 h. The reaction mixture was cooled to 23° C. and the solid which precipitated was filtered to give the product as its HCl-salt (50 mg, 59%). mp=250° C.; ESI-MS (M+H) calc'd for $C_{23}H_{21}N_6O_2S$: 445.1447, found: 445.1432.

Example CCCX

Preparation of 3-(2,4-dimethylthiazol-5-yl)-5-((2,6-dimethylpiperidino)carbamoylamino)indeno[1,2-c]pyrazol-4-one

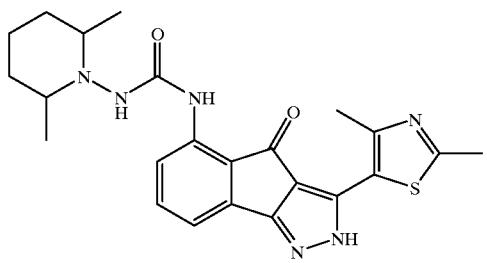

Prepared in a similar fashion as described for example 3 using 12a and 1-amino-2,6-dimethylpiperidine as the starting materials. ESI-MS (M+H) found for $C_{23}H_{37}N_6O_2S$: 451.

Example CCCXI

Preparation of 3-(2,4-dimethylthiazol-5-yl)-5-((4-methylpiperazino)carbamoylamino)indeno[1,2-c]pyrazol-4-one

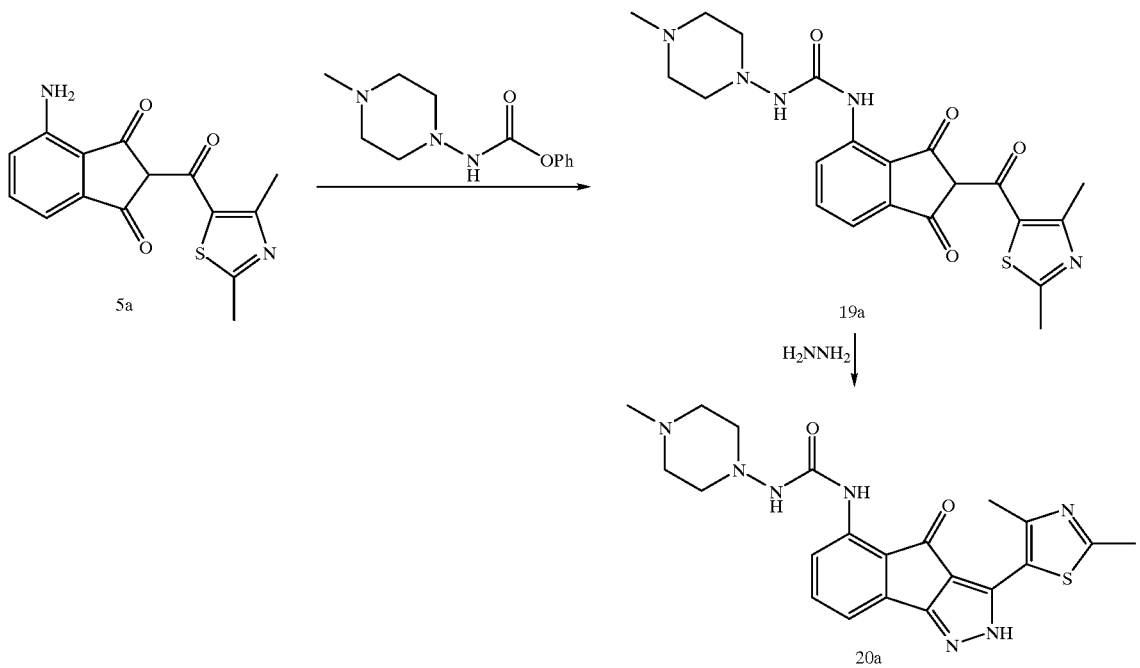

Step 1. Synthesis of semicarbazide 19a from aniline 5a.

A solution of aniline 5a (13.0 g, 43.3 mmol), N-(4-methylpiperazinyl)-O-(phenyl)carbamate (20.4 g, 86.7 mmol), and triethylamine (18.1 mL, 130 mmol) in dimethylsulfoxide (217 mL) was heated to 90° C. for 1 h. The reaction mixture was cooled to 23° C. and diluted with water (500 mL). The solid which precipitated was collected and washed with water (300 mL), ethanol (300 mL), and ether (300 mL) and dried to give a brown solid (15.6 g, 82%). ESI-MS (M+H) calc'd for $C_{21}H_{24}N_5O_4S$: 442.1549, found: 442.1531.

Step 2. Synthesis of pyrazole 20a from semicarbazide 19a.

A solution of semicarbazide 19a (15.6 g, 35.3 mmol), hydrazine (6.7 mL, 212 mmol), and acetic acid (4.0 mL, 71 mmol) was refluxed in ethanol (354 mL) for 84 h. The reaction mixture was cooled to 23° C., filtered, washed with ethanol (300 mL) and ether (300 mL), and dried to give a yellow solid which was dissolved in 10% acetic acid in water (20 mL). The solution was adjusted to pH=7 with 10% sodium hydroxide. The solid which precipitated was filtered and dried to give the free base (6.8 g, 29%) as a yellow solid. The free base was dissolved in 1M hydrochloric acid (31 mL) and the water was removed with a lyophilizer to give the product as a light brown powder (7.9 g, 99% from the free base). mp=278° C.; ESI-MS (M+H) calc'd for $C_{21}H_{24}N_7O_2S$: 438.1712, found: 438.1714.

The compounds in the following tables are produced by suitabl methods from among the methods of the above examples.

TABLE 1

| Example # | $R^1$ | $R^2$ | mass $(M + H)^+$ | mp (° C.) |
|---|---|---|---|---|
| I | Methyl | 4-MeOC$_6$H$_4$ | 334 | 268 |
| II | ClCH$_2$ | 4-MeOC$_6$H$_4$ | 382 | 274 |

TABLE 1-continued

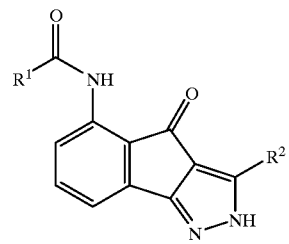

| Example # | $R^1$ | $R^2$ | mass $(M + H)^+$ | mp (° C.) |
|---|---|---|---|---|
| III | cyclopropyl | 4-MeOC$_6$H$_4$ | 360 | 289 |
| IV | isopropyl | 4-MeOC$_6$H$_4$ | 362 | 288 |
| V | ethyl | 4-MeOC$_6$H$_4$ | 348 | 287 |
| VI | cyclopentyl | 4-MeOC$_6$H$_4$ | 388 | 267 |
| VII | cyclobutyl | 4-MeOC$_6$H$_4$ | 374 | 297 |
| VIII | benzyl | 4-MeOC$_6$H$_4$ | 410 | 280 |
| IX | n-propyl | 4-MeOC$_6$H$_4$ | 362 | 282 |
| X | 4-ClC$_6$H$_4$CH$_2$ | 4-MeOC$_6$H$_4$ | 444 | 238 |
| XI | 3-MeOC$_6$H$_4$CH$_2$ | 4-MeOC$_6$H$_4$ | 440 | >300 |
| XII | 4-MeOC$_6$H$_4$CH$_2$ | 4-MeOC$_6$H$_4$ | 440 | 280 |
| XIII | 3,4-diMeOC$_6$H$_4$CH$_2$ | 4-MeOC$_6$H$_4$ | 470 | >300 |
| XIV | 2,5-diMeOC$_6$H$_4$CH$_2$ | 4-MeOC$_6$H$_4$ | 470 | 226 |
| XV | Methyl | 2-MeOC$_6$H$_4$ | 334 | 276 |
| XVI | Methyl | 3,4-diMeOC$_6$H$_4$ | 364 | >300 |
| XVII | 3,4-(OCH$_2$O)C$_6$H$_4$CH$_2$ | 4-MeOC$_6$H$_4$ | 454 | 297 |
| XVIII | 3-thiophenylCH$_2$ | 4-MeOC$_6$H$_4$ | 416 | 293 |
| XIX | 2-MeOC$_6$H$_4$CH$_2$ | 4-MeOC$_6$H$_4$ | 440 | 255 |
| XX | 3,4-diClOC$_6$H$_4$CH$_2$ | 4-MeOC$_6$H$_4$ | 479 | 299 |
| XXI | 2,4-diClOC$_6$H$_4$CH$_2$ | 4-MeOC$_6$H$_4$ | 479 | 286 |
| XXII | 2-ClC$_6$H$_4$CH$_2$ | 4-MeOC$_6$H$_4$ | 444 | 300 |
| XXIII | H$_2$NCH$_2$ | 4-MeOC$_6$H$_4$ | 349 | >300 |
| XXIV | HOCH$_2$CH$_2$NHCH$_2$ | 4-MeOC$_6$H$_4$ | 393 | 243 |
| XXV | Me$_2$NCH$_2$ | 4-MeOC$_6$H$_4$ | 377 | 279 |
| XXVI | PiperazinoCH$_2$ | 4-MeOC$_6$H$_4$ | 418 | 277 |
| XXVII | 4-Me-piperazinoCH$_2$ | 4-MeOC$_6$H$_4$ | 432 | >300 |
| XXVIII | 4-HOCH$_2$CH$_2$-pipierazino-CH$_2$ | 4-MeOC$_6$H$_4$ | 462 | >300 |
| XXIX | piperisinoCH$_2$ | 4-MeOC$_6$H$_4$ | 417 | 291 |
| XXX | 4-NH$_2$CH$_2$-piperidinoCH$_2$ | 4-MeOC$_6$H$_4$ | 446 | >300 |
| XXXI | CH$_3$CH$_2$NHCH$_2$ | 4-MeOC$_6$H$_4$ | 377 | 250 |
| XXXII | thiomorpholinoCH$_2$ | 4-MeOC$_6$H$_4$ | 435 | 298 |
| XXXIII | morpholinoCH$_2$ | 4-MeOC$_6$H$_4$ | 419 | 295 |
| XXXIV | pyrrolidinoCH$_2$ | 4-MeOC$_6$H$_4$ | 403 | 279 |
| XXXV | 4-pyridylCH$_2$NHCH$_2$ | 4-MeOC$_6$H$_4$ | 440 | >300 |
| XXXVI | 4-CH$_3$CONHC$_6$H$_4$CH$_2$ | 4-MeOC$_6$H$_4$ | 467 | 268 |
| XXXVII | 4-CH$_3$OCONHC$_6$H$_4$CH$_2$ | 4-MeOC$_6$H$_4$ | 483 | 257 |
| XXXVIII | 4-NH$_2$CH$_2$CONHC$_6$H$_4$CH$_2$ | 4-MeOC$_6$H$_4$ | 482 | 228 |
| XXXIX | 4-Me$_2$NCH$_2$CONHC$_6$H$_4$CH$_2$ | 4-MeOC$_6$H$_4$ | 510 | >300 |
| XL | 4-N$_3$C$_6$H$_4$CH$_2$ | 4-MeOC$_6$H$_4$ | 451 | >300 |
| XLI | 4-NH$_2$C$_6$H$_4$CH$_2$ | 4-MeOC$_6$H$_4$ | 425 | 283 |
| XLII | C$_6$H$_5$NH | 4-MeOC$_6$H$_4$ | 411 | >300 |
| XLIII | CH$_3$CH$_2$CH$_2$NH | 4-MeOC$_6$H$_4$ | 377 | 252 |
| XLIV | 4-NH$_2$C$_6$H$_4$CH$_2$NH | 4-MeOC$_6$H$_4$ | 440 | >300 |
| XLV | 4-pyridylCH$_2$NH | 4-MeOC$_6$H$_4$ | 426 | >300 |
| XLVI | Methyl | 4-HOC$_6$H$_4$ | 320 | >300 |
| XLVII | H | 4-MeOC$_6$H$_4$ | 320 | 280 |
| XLVIII | Methyl | 3-pyridyl | 305 | >300 |
| XLIX | Methyl | 4-pyridyl | 305 | >300 |
| L | H | 4-pyridyl | 291 | >300 |
| LI | Methyl | C$_6$H$_5$ | 305 | >300 |
| LII | Methyl | 4-MeSC$_6$H$_4$ | 351 | 283 |
| LIII | Methyl | 4-MeSO$_2$C$_6$H$_4$ | 383 | >300 |
| LVI | Methyl | 4-Me$_2$NC$_6$H$_4$ | 348 | >300 |
| LV | morpholinoCH$_2$ | 4-Me$_2$NC$_6$H$_4$ | 432 | >300 |
| LVI | Me$_2$NCH$_2$ | 4-Me$_2$NC$_6$H$_4$ | 390 | >300 |
| LVII | Methyl | 4-(piperidino)C$_6$H$_4$ | 388 | 291 |
| LVIII | Methyl | 4-(morpholino)C$_6$H$_4$ | 389 | >300 |
| LIX | Methyl | 4-CH$_3$CH$_2$OC$_6$H$_4$ | 349 | 288 |
| LX | Methyl | 4-CH$_3$CH$_2$CH$_2$CH$_2$C$_6$H$_4$ | 361 | 259 |
| LXI | Methyl | 4-CH$_3$CH$_2$C$_6$H$_4$ | 332 | 294 |
| LXII | Methyl | 4-CH$_3$CH$_2$CH$_2$C$_6$H$_4$ | 347 | 269 |
| LXIII | NH$_2$ | 4-MeOC$_6$H$_4$ | 335 | >300 |
| LXIV | Me$_2$NNH | 4-MeOC$_6$H$_4$ | 378 | >300 |

TABLE 1-continued

[Structure: R¹-C(=O)-NH- substituted indeno-pyrazolone core with R² substituent]

| Example # | R¹ | R² | mass (M + H)⁺ | mp (° C.) |
|---|---|---|---|---|
| LXV | MeNH | 4-MeOC₆H₄ | 349 | >300 |
| LXVI | morpholinoNH | 4-MeOC₆H₄ | 420 | >300 |
| LXVII | cis-1,2-diaminocyclohexanyl | 4-MeOC₆H₄ | 432 | >300 |
| LXVIII | 4-methylpiperazinoNH | 4-MeOC₆H₄ | 433 | >300 |
| LXVIX | 4-uridomethylpiperidino-CH₂ | 4-MeOC₆H₄ | 489 | >300 |
| LXX | 4-(2-pyridyl)piperazinol-CH₂ | 4-MeOC₆H₄ | 495 | >300 |
| LXXI | 4-(aminoethyl)piperazinoCH₂ | 4-MeOC₆H₄ | 461 | >300 |
| LXXII | 4-carbamoylpiperidinoCH₂ | 4-MeOC₆H₄ | 460 | >300 |
| LXXIII | 4-hydroxypiperidinoCH₂ | 4-MeOC₆H₄ | 433 | >300 |
| LXXIV | 4-hydroxymethylpiperidino-CH₂ | 4-MeOC₆H₄ | 447 | >300 |
| LXXV | 4-amidopiperazinoCH₂ | 4-MeOC₆H₄ | 493 | >300 |
| LXXVI | 4-dimethylaminopiperidino-CH₂ | 4-MeOC₆H₄ | 492 | >300 |
| LXXVII | 4-aminopiperidinoCH₂ | 4-MeOC₆H₄ | 464 | >300 |
| LXXVIII | 4-Me-piperazinoCH₂ | 4-Me₂NC₆H₄ | 445 | >300 |
| LXXIX | 4-NH₂CH₂-piperidinoCH₂ | 4-Me₂NC₆H₄ | 459 | NA |
| LXXX | 4-OH-piperidinoCH₂ | 4-Me₂NC₆H₄ | 446 | 267 |
| LXXXI | morpholinoCH₂ | 4-(morpholino)C₆H₄ | 474 | 258 |
| LXXXII | 4-Me-piperazinoCH₂ | 4-(morpholino)C₆H₄ | 487 | 258 |
| LXXXIII | 4-OH-pipieridinoCH₂ | 4-(morpholino)C₆H₄ | 488 | 245 |
| LXXXIV | 4-NH₂CH₂-piperidinoCH₂ | 4-(morpholino)C₆H₄ | 501 | 240 |
| LXXXV | 4-Me-piperazinoNH | 4-Me₂NC₆H₄ | 446 | >300 |
| LXXXVI | 4-Me-piperazinoNH(X = S) | 4-MeOC₆H₄ | 449 | >300 |
| LXXXVII | Methyl | c-propyl | 268 | 220 |
| LXXXVIII | NH₂ | 1-Me-3-pyridyl | 308 | >300 |
| LXXXIX | Methyl | 2-thienyl | 310 | 269 |
| XC | Methyl | 3-Me-2-thienyl | 324 | 275 |
| XCI | NH₂ | Ethyl | 257 | >250 |
| XCII | NH₂ | n-propyl | 271 | 187 |
| XCIII | NH₂ | i-propyl | 271 | >250 |
| XCIV | NH₂ | c-propyl | 267 (M − H)⁻ | 252 |
| XCV | NH₂ | c-hexyl | 311 | 178 |
| XCVI | NH₂ | 2-thienyl | 310 (M⁺) | 214 |
| XCVII | NH₂ | 3-Me-2-thienyl | 325 | 270 |
| XCVIII | NH₂ | 5-Me-2-thienyl | 325 | >280 |
| XCIX | NH₂ | 5-CO₂Et-2-thienyl | 383 | >280 |
| C | NH₂ | 3-thienyl | 311 | >280 |
| CI | NH₂ | 5-Cl-3-thienyl | 345 | >300 |
| CII | NH₂ | 2,5-diMe-3-thienyl | 339 | >280 |
| CIII | NH₂ | 2-furanyl | 295 | 278 |
| CIV | Me₂NNH | i-propyl | 314 | 231 |
| CV | Me₂NNH | c-propyl | 312 | NA |
| CVI | Me₂NNH | c-hexyl | 354 | 229 |
| CVII | Me₂NNH | 2-thienyl | 354 | 279 |
| CVIII | Me₂NNH | 5-MeO-2-thienyl | 384 | 280 |
| CIX | Me₂NNH | 5-Me-2-thienyl | 368 | >280 |
| CX | Me₂NNH | 5-CO₂Et-2-thienyl | 426 | 252 |
| CXI | Me₂NNH | 3-thienyl | 354 | 202 |
| CXII | NH₂ | 1-methyl-3-pyrrolyl | 308 | >300 |
| CXIII | Me₂NNH | 2,5-diMe-3-thienyl | 382 | 252 |
| CXIV | Me₂NNH | 2-furanyl | 338 | 202 |
| CXV | 4-NH₂CO-piperidinylCH₂ | i-propyl | 396 | 224 |
| CXVI | 4-NH₂CO-piperidinylCH₂ | c-hexyl | 436 | 228 |
| CXVII | 4-NH₂CH₂-piperidinolCH₂ | ethyl | 368 | 174 |

TABLE 1-continued

[Structure: R¹-C(=O)-NH- attached to an indeno-pyrazolone core with R² substituent]

| Example # | R¹ | R² | mass (M + H)⁺ | mp (° C.) |
|---|---|---|---|---|
| CXVIII | 4-NH$_2$CH$_2$-piperidinoCH$_2$ | i-propyl | 382 | 218 |
| CXVIX | 4-NH$_2$CH$_2$-piperidinoCH$_2$ | c-propyl | 380 | 138 |
| CXX | 4-NH$_2$CH$_2$-piperidinoCH$_2$ | c-hexyl | 422 | 196 |
| CXXI | 4-CH$_3$-piperazinoNH | i-propyl | 369 | 231 |
| CXXII | 4-CH$_3$-piperazinoNH | 5-CO$_2$Et-2-thienyl | 481 | 249 |
| CXXIII | 4-CH$_3$-piperazinoNH | 5-CO$_2$H-2-thienyl | 453 | 270 |
| CXXIV | 4-CH$_3$-piperazinoNH | 2,5-diMe-3-thienyl | 437 | 250 |
| CXXV | morpholinoNH | i-propyl | 354 (M − H)⁻ | 256 |
| CXXVI | morpholinoNH | 1-CO$_2$Me-4-piperidinyl | 455 | 216 |
| CXXVII | morpholinoNH | 5-Me-2-thienyl | 410 | 261 |
| CXXVIII | morpholinoNH | 5-Cl-3-thienyl | 430 | 259 |
| CXXIX | morpholinoNH | 2,5-diMe-3-thienyl | 424 | >280 |
| CXXX | morpholinoNH | 5-CO$_2$Et-2-thienyl | 468 | 258 |
| CXXXI | morpholinoNH | 5-CO$_2$H-2-thienyl | 440 | 273 |
| CXXXII | morpholinoNH | 5-CONHBn-2-thienyl | 529 | 275 |
| CXXXIII | morpholinoNH | 5-CO(4-Me-piperazino)-2-thienyl | 537 | 190 |
| CXXXIV | morpholinoNH | 5-CONHCH$_2$CH$_2$(1-Me-2-pyrrolidinyl)-2-thienyl | 550 | 235 |
| CXXXV | morpholinoNH | 5-CONHNMe$_2$-2-thienyl | 482 | 201 |
| CXXXVI | morpholinoNH | 5-CONHCH$_2$CH$_2$NMe$_2$-2-thienyl | 510 | 190 |
| CXXXVII | morpholinoNH | 5-CONHCH$_2$CH$_2$(pyrrolidino)-2-thienyl | 536 | 224 |
| CXXXVIII | morpholinoNH | 5-CONHCH$_2$CH$_2$(morpholino)-2-thienyl | 552 | 241 |
| CXXXIX | morpholinoNH | 5-CONH(morpholino)-2-thienyl | 524 | 271 |
| CXL | morpholinoNH | 5-CONHCH$_2$CH$_2$CH$_2$(1-pyrrolidonyl)-2-thienyl | 564 | 260 |
| CXLI | morpholinoNH | 5-CONHCH$_2$CH$_2$(3-pyridyl)-2-thienyl | 544 | 203 |
| CXLII | morpholinoNH | 5-CONHCH$_2$CH$_2$(1-imidazolyl)-2-thienyl | 547 | 263 |
| CXLIII | morpholinoNH | 5-CONHCH$_2$CH$_2$(2-pyridyl)-2-thienyl | 544 | >280 |
| CXLIV | morpholinoNH | 5-CONHCH$_2$(2-pyridyl)-2-thienyl | 530 | 239 |
| CXLV | morpholinoNH | 5-CONHCH$_2$CH$_2$(piperidino)-2-thienyl | 550 | 228 |
| CXLVI | morpholinoNH | 5-pyrrolidino-aminocarbonyl-2-thienyl | 508 | 213* |
| CXLVII | morpholinoNH | 5-piperidino-aminocarbonyl-2-thienyl | 522 | 189* |
| CXLVIII | morpholinoNH | 5-piperidino-carbonyl-2-thienyl | 507 | N/A |
| CXLIX | morpholinoNH | 5-piperazino-carbonyl-2-thienyl | 508 | 241* |
| CL | morpholinoNH | 5-(4-Me-piperazino)carbonyl-2-thienyl | 522 | 186* |
| CLI | morpholinoNH | 5-(4-Et-piperazino)carbonyl-2-thienyl | 536 | 186* |
| CLII | morpholinoNH | 5-((4-CH$_2$CH$_2$OH)-piperazino)carbonyl-2-thienyl | 552 | 186* |
| CLIII | morpholinoNH | 5-(4-cyclopropylmethyl-piperazino)carbonyl-2-thienyl | 562 | 211* |

TABLE 1-continued

| Example # | R¹ | R² | mass (M + H)⁺ | mp (° C.) |
|---|---|---|---|---|
| CLIV | morpholinoNH | 5-(4-t-CO₂t-Bu-piperazino)carbonyl-2-thienyl | 608 | 225* |
| CLV | morpholinoNH | 5-(4-(2-pyridyl)-piperazino)carbonyl-2-thienyl | 585 | 202* |
| CLVI | morpholinoNH | 5-(1S,4S)-2,5-diazobicyclo[2.2.1]hept-yl)carbonyl-2-thienyl | 520 | >300* |
| CLVII | morpholinoNH | 5-((1S,4S)-2-Me-2,5-dizaobicyclo[2.2.1]hept-yl)carbonyl-2-thienyl | 534 | 244* |
| CLVIII | morpholinoNH | 5-(4-NMe₂-piperidino)carbonyl-2-thienyl | 550 | 185* |
| CLIX | morpholinoNH | 5-(4-pyrrolidino-piperidino)carbonyl-2-thienyl | 576 | 228* |
| CLX | morpholinoNH | 5-(4-piperidino-piperidino)carbonyl-2-thienyl | 590 | N/A |
| CLXI | morpholinoNH | 5-(cyclohexyl-aminocarbonyl)-2-thienyl | 521 | 264* |
| CLXII | morpholinoNH | 5-(4-piperidyl-aminocarbonyl)-2-thienyl | 522 | 224* |
| CLXIII | morpholinoNH | 5-((1-CO₂t-Bu-4-piperidyl)amino-carbonyl)-2-thienyl | 620 | 229* |
| CLXIV | morpholinoNH | 5-(N-(1-Me-4-piperidyl)-N-methyl-aminocarbonyl)-2-thienyl | 550 | 230* |
| CLXV | morpholinoNH | 5-(3-NMe₂-piperidinocarbonyl)-2-thienyl | 550 | >300* |
| CLXVI | morpholinoNH | 5-(3-(p-toluenesulfonyl-amino)piperidino-carbonyl)-2-thienyl | 676 | 193* |
| CLXVII | morpholinoNH | 5-(3-OH-piperidino-carbonyl)-2-thienyl | 523 | N/A |
| CLXVIII | morpholinoNH | 5-((3-piperidyl)-aminocarbonyl)-2-thienyl | 522 | >300* |
| CLXIX | morpholinoNH | 5-((3-quinuclidyl)-aminocarbonyl)-2-thienyl | 548 | 245* |
| CLXX | morpholinoNH | 5-(3-(aminocyclohexyl)-aminocarbonyl)-2-thienyl | 536 | >300* |
| CLXXI | morpholinoNH | 5-(3-(t-butoxy-carbonylaminocyclo-hexyl)aminocarbonyl)-2-thienyl | 636 | >300* |
| CLXXII | morpholinoNH | 5-(2-(Me₂NCH₂)-piperidinocarbonyl)-2-thienyl | 564 | >300* |
| CLXXIII | morpholinoNH | 5-(2-Et₂NCH₂)-piperidinocarbonyl)-2-thienyl | 592 | 210* |
| CLXXIV | morpholinoNH | 5-pyrrolidino-carbonyl)-2-thienyl | 493 | >300* |

TABLE 1-continued

| Example # | R¹ | R² | mass (M + H)⁺ | mp (° C.) |
|---|---|---|---|---|
| CLXXV | morpholinoNH | 5-(3-NH₂-pyrrolidinocarbonyl)-2-thienyl | 508 | 201* |
| CLXXVI | morpholinoNH | 5-(3(S)-(NHMe)pyrrolidino-carbonyl)-2-thienyl | 522 | N/A |
| CLXXVII | morpholinoNH | 5-(3(S)-(NHCOCH₃)-pyrrolidinocarbonyl)-2-thienyl | 550 | 264* |
| CLXXVIII | morpholinoNH | 5-(3(S)-(N(Me)COCH₃)-pyrrolidinocarbonyl)-2-thienyl | 564 | >300* |
| CLXXIX | morpholinoNH | 5-(3(S)-(N(Me)CO₂t-Bu)pyrrolidino-carbonyl)-2-thienyl | 622 | >300* |
| CLXXX | morpholinoNH | 5-(3-NMe₂-pyrrolidinocarbonyl)-2-thienyl | 536 | 216* |
| CLXXXI | morpholinoNH | 5-(3(R)-(NMe₂)-pyrrolidinocarbonyl)-2-thienyl | 536 | 265* |
| CLXXXII | morpholinoNH | 5-(3(S)-(NMe₂)-pyrrolidinocarbonyl)-2-thienyl | 536 | 264* |
| CLXXXIII | morpholinoNH | 5-((1-Me-3-pyrrolidinyl)methylamino-carbonyl)-2-thienyl | 536 | 151* |
| CLXXXIV | morpholinoNH | 5-(2(R)-(pyrrolidinomethyl)pyrro-lidino-carbonyl)-2-thienyl | 576 | 166* |
| CLXXXV | morpholinoNH | 5-(2(S)-(CH₂OH)pyrrolidino-carbonyl)-2-thienyl | 523 | 267* |
| CLXXXVI | morpholinoNH | 5-(2(R)-(CH₃OCH₂)-pyrrolidinocarbonyl)-2-thienyl | 537 | 262* |
| CLXXXVII | morpholinoNH | 5-(2(S)-(phenylaminomethyl)-pyrrolidinocarbonyl)-2-thienyl | 598 | >300* |
| CLXXXVIII | morpholinoNH | 5-(2(R)-(CH₃OCH₂)-pyrrolidinoamino-carbonyl)-2-thienyl | 552 | 266* |
| CLXXXIX | morpholinoNH | 5-homopiperidino-carbonyl-2-thienyl | 521 | N/A |
| CXC | morpholinoNH | 5-homopiperazino-carbonyl-2-thienyl | 522 | 209* |
| CXCI | morpholinoNH | 5-(4-Me-homopiperazino-carbonyl)-2-thienyl | 536 | 207* |
| CXCII | morpholinoNH | 5-(4-Et-homopiperazino-carbonyl)-2-thienyl | 550 | 192* |
| CXCIII | morpholinoNH | 5-((4-(cyclohexylmethyl)-homopiperazino)-carbonyl)-2-thienyl | 576 | 194* |
| CXCIV | morpholinoNH | 5-(4-(CO₂t-Bu)-homopiperazino-carbonyl)-2-thienyl | 622 | 210* |
| CXCV | morpholinoNH | 5-(4-(COCH₃)-homopiperazino-carbonyl)-2-thienyl | 564 | 274* |

TABLE 1-continued

| Example # | R¹ | R² | mass (M + H)⁺ | mp (° C.) |
|---|---|---|---|---|
| CXCVI | morpholinoNH | 5-((4-methylamino-phenyl)aminocarbonyl)-2-thienyl | 544 | 230* |
| CXCVII | morpholinoNH | 5-((4-acetamidophenyl)-aminocarbonyl)-2-thienyl | 572 | 253* |
| CXCVIII | morpholinoNH | 5-(4-(NEt₂)-phenylaminocarbonyl)-2-thienyl | 586 | 198* |
| CXCIX | morpholinoNH | 5-(1-Me-3-cyclopropyl-5-pyrazolyl)amino-carbonyl-1-thienyl | 559 | 290* |
| CC | morpholinoNH | 1-Me-3-pyrrolyl | 393 | 301 |
| CCI | 2(R)-(CH₃OCH₂)-pyrrolidinoNH | 5-CO₂Et-2-thienyl | 496 | 221 |
| CCII | 2(R)-(CH₃OCH₂)-pyrrolidinoNH | 5-CO₂H-2-thienyl | 468 | 258* |
| CCIII | 2(R)-(CH₃OCH₂)-pyrrolidinoNH | 5-(4-Me-piperazino-carbonyl)-2-thienyl | 550 | 181* |
| CCIV | 2(R)-(CH₃OCH₂)-pyrroldinoNH | 5-piperazino-carbonyl-2-thienyl | 536 | >300* |
| CCV | 2(R)-(CH₃OCH₂)-pyrrolidinoNH | 5-(4-(CO₂t-Bu)-piperazinocarbonyl)-2-thienyl | 636 | >300* |
| CCVI | 2(R)-(CH₃OCH₂)-pyrrolidinoNH | 5-(4-Me-homopiperazino-carbonyl)-2-thienyl | 564 | 176* |
| CCVII | 2(R)-(CH₃OCH₂)-pyrrolidinoNH | 5-homopiperazino-carbonyl-2-thienyl | 550 | 185* |
| CCVIII | 2(R)-(CH₃OCH₂)-pyrrolidinoNH | 5-(4-(CO₂t-Bu)-homopiperazino-carbonyl)-2-thienyl | 650 | >300* |
| CCIX | Methyl | 4-CF₃C₆H₄ | 370 (M − H)⁻ | >300 |
| CCX | morpholinoNH | 4-(4-Boc-piperazino)C₆H₄ | 574 | 242 |
| CCXI | morpholinoNH | 4-(piperazino)C₆H₄ | 474 | 263* |
| CCXII | NH₂ | 4-(piperazino)C₆H₄ | 389 | 257* |
| CCXIII | NH₂NH | 4-(piperazino)C₆H₄ | 404 | 257* |
| CCXIV | Me₂NCH₂ | 4-(piperazino)C₆H₄ | 431 | 243* |
| CCXV | morpholinylCH₂ | 4-(piperazino)C₆H₄ | 473 | 259* |
| CCXVI | 4-Me-piperazinoCH₂ | 4-(piperazino)C₆H₄ | 486 | NA |
| CCXVII | 4-NH₂CH₂-piperidinoCH₂ | 4-(piperazino)C₆H₄ | 500 | 239* |
| CCXVIII | morpholinoNH | 4-(4-Me-piperazino)C₆H₄ | 488 | 245* |
| CCXIX | morpholinoNH | 4-(4-Et-piperazino)C₆H₄ | 502 | 245* |
| CCXX | morpholinoNH | 4-(4-i-Pr-piperazino)C₆H₄ | 516 | 253* |
| CCXXI | Me₂NNH | 4-(piperazino)C₆H₄ | 432 | 238* |
| CCXXII | Me₂NNH | 4-(4-Me-piperazino)C₆H₄ | 446 | 192* |
| CCXXIII | 4-CH₃-piperazinoNH | 4-(piperazino)C₆H₄ | 487 | 254* |
| CCXXIV | 4-CH₃-piperazinoNH | 4-(4-Me-piperazino)C₆H₄ | 501 | 293* |
| CCXXV | 4-CH₃-piperazinoNH | 4-(4-Et-piperazino)C₆H₄ | 515 | NA |
| CCXXVI | 4-CH₃-piperazinoNH | 4-(4-i-Pr-piperazino)C₆H₄ | 529 | 272* |
| CCXXVII | 2,6-diCH₃-piperidinoNH | 4-(piperazino)C₆H₄ | 500 | 270* |
| CCXXVIII | 4-HOCH₂CH₂-piperazino-NH | 4-(piperazino)C₆H₄ | 517 | 279* |
| CCXXIX | 2(R)-CH₃OCH₂-pyrrolidinoNH | 4-(piperazino)C₆H₄ | 502 | NA |
| CCXXX | 2(S)-CH₃OCH₂-pyrrolidinoNH | 4-(piperazino)C₆H₄ | 502 | NA |
| CCXXXI | 2(R)-CH₃OC(CH₃)₂-pyrrolidinoNH | 4-(piperazino)C₆H₄ | 530 | 221* |
| CCXXXII | 2(S)-CH₃OC(CH₃)₂-pyrrolidinoNH | 4-(piperazino)C₆H₄ | 530 | 218* |

TABLE 1-continued

| Example # | R¹ | R² | mass (M + H)⁺ | mp (° C.) |
|---|---|---|---|---|
| CCXXXIII | 2(R)-HOCH₂-pyrrolidinoNH | 4-(piperazino)C₆H₄ | 488 | 193* |
| CCXXXIV | 2(S)-HOCH₂-pyrrolidinoNH | 4-(piperazino)C₆H₄ | 488 | 190* |
| CCXXXV | 2(R)-PhOCH₂-pyrrolidinoNH | 4-(piperazino)C₆H₄ | 578 | 207* |
| CCXXXVI | 2(S)-PhOCH₂-pyrrolidinoNH | 4-(piperazino)C₆H₄ | 578 | NA |
| CCXXXVII | morpholinoNH | 4-(3-Me-piperazino)C₆H₄ | 488 | 230* |
| CCXXXVIII | morpholinoNH | 4-(cis-3,5-diMe-piperazino)C₆H₄ | 502 | 237* |
| CCXXX | morpholinoNH | 4-(cis-3,4,5-triMe-piperazino)C₆H₄ | 516 | 240* |
| CCXXXI | morpholinoNH | 4-(4-i-Pr-piperazino)-2-Me—C₆H₄ | 530 | NA |
| CCXLI | morpholinoNH | 4-(homopiperazino)-C₆H₄ | 488 | 253* |
| CCXLII | morpholinoNH | 4-(4-Me-homopiperazino)-C₆H₄ | 502 | NA |
| CCXLIII | morpholinoNH | 4-(4-Et-homopiperazino)-C₆H₄ | 516 | 240* |
| CCXLIV | morpholinoNH | 4-(4-i-Pr-homopiperazino)-C₆H₄ | 530 | 245* |
| CCXLV | morpholinoNH | 4-(homopiperazino)-2-Me—C₆H₄ | 502 | 209* |
| CCXLVI | morpholinoNH | 4-(4-Et-homopiperazino)-2-Me-C₆H₄ | 530 | 217* |
| CCXLVII | morpholinoNH | 4-(4-i-Pr-homopiperazino)-2-Me—C₆H₄ | 544 | 197* |
| CCXLVIII | morpholinoNH | 4-(4-Me₂N-piperidino)C₆H₄ | 516 | 258* |
| CCXLIX | morpholinoNH | 4-(4-morpholino-piperidino)C₆H₄ | 558 | 249# |
| CCL | morpholinoNH | 4-(4-piperidino-piperidino)C₆H₄ | 556 | 233* |
| CCLI | morpholinoNH | 4-(4-pyrrolidino-piperidino)C₆H₄ | 542 | 247* |
| CCLII | morpholinoNH | 4-(4-Et₂N-piperidino)C₆H₄ | 544 | 251* |
| CCLIII | morpholinoNH | 4-(4-C(=NH)CH₃-piperazino)C₆H₄ | 515 | 240* |
| CCLIV | morpholinoNH | 4-(4-(2-pyridinyl)-piperazino)C₆H₄ | 551 | NA |
| CCLV | 4-NH₂CO-piperidinoCH₂ | c-propyl | 394 | 178* |
| CCLVI | 4-CH₃-piperazinoNH | ethyl | 355 | 244* |
| CCVLVII | 4-CH₃-piperazinoNH | c-propyl | 367 | 215* |
| CCLVIII | 4-CH₃-piperazinoNH | c-hexyl | 409 | 241* |
| CCLIX | morpholinoNH | ethyl | 342 | 253* |
| CCLX | morpholinoNH | c-propyl | 354 | N/A |
| CCLXI | morpholinoNH | c-hexyl | 396 | >260* |
| CCLXII | morpholinoNH | 1-CO₂Et-piperidin-4-yl | 469 | 206* |
| CCLXIII | morpholinoNH | 1-CO₂Ph-piperidin-4-yl | 517 | 250* |
| CCLXIV | morpholinoNH | 1-Coimidazolyl-piperidin-4-yl | 491 | 202* |
| CCLXV | morpholinoNH | 1-(2-thienylcarbonyl)piperidin-4-yl | 507 | 218* |
| CCLXVI | morpholinoNH | 1-CONH₂-piperidin-4-yl | 440 | 258* |
| CCLXVII | morpholinoNH | 1-CONHEt-piperidin-4-yl | 466 | 215* |
| CCLXVIII | morpholinoNH | 1-(2-(1-Me-pyrrolidin-2-yl)ethylaminocarbamoyl)-piperidin-4-yl | 551 | 91* |

TABLE 1-continued

| Example # | R¹ | R² | mass (M + H)⁺ | mp (° C.) |
|---|---|---|---|---|
| CCLXIX | morpholinoNH | 1-(4-Nme₂-piperidinocarbonyl)-piperidin-4-yl | 551 | 172* |
| CCLXX | morpholinoNH | 1-(piperazinocarbonyl)-piperidin-4-yl | 509 | 195* |
| CCLXXI | morpholinoNH | 1-(4-(CO₂t-Bu)-piperiazinocarbonyl)-piperidin-4-yl | 609 | 231 |
| CCLXXII | morpholinoNH | 1-((1S,4S)-(+)-2,5-diazabicyclo[2.2.1]hept-yl)carbonyl)-piperidin-4-yl | 521 | 196* |
| CCLXXIII | morpholinoNH | 1-((1S,4S)-(+)-2-methyl-2,5-diazabicyclo[2.2.1]hep-tyl)carbonyl)-pipieridin-4-yl | 535 | 225* |
| CCLXXIV | morpholinoNH | 1-(CO(CH₂)₃NH₂)-piperidin-4-yl | 483 | 172* |
| CCLXXV | morpholinoNH | 1-(CO(CH₂)₃Nme₂)-piperidin-4-yl | 482 | 172* |
| CCLXXVI | morpholinoNH | 1-(CO(CH₂)₃NHCO₂t-Bu)-piperidin-4-yl | 582 | 73 |
| CCLXXVII | morpholinoNH | 1-(CO(CH₂)₄NH₂)-piperidin-4-yl | 496 | 103* |
| CCLXXVIII | morpholinoNH | 1-(CO(CH₂)₄Nme₂)-piperidin-4-yl | 524 | 68* |
| CCLXXIX | morpholinoNH | 1-(CO(CH₂)₄NHCO₂t-Bu)-piperidin-4-yl | 596 | 98* |
| CCLXXX | morpholinoNH | 1-(1-Me-piperidin-4-ylcarbonyl)piperidin-4-yl | 522 | 148* |
| CCLXXXI | morpholinoNH | 1-(1-CO₂t-Bu-piperidin-4-yl-carbonyl)piperidin-4-yl | 608 | 220 |
| CCLXXXII | morpholinoNH | 1-(cis-4-NH₂-cyclohexylcarbonyl)piper-idin-4-yl | 522 | 212* |
| CCLXXXIII | morpholinoNH | 1-(4-NH₂-cyclohexylcarbonyl)piper-idin-4-yl | 522 | 202* |
| CCLXXXIV | morpholinoNH | 1-(cis-4-Nme₂-cyclohexylcarbonyl)piper-idin-4-yl | 522 | 202* |
| CCLXXXV | morpholinoNH | 1-(4-NHCO₂t-Bu)-cyclohexylcarbonyl)piper-idin-4-yl | 622 | 210* |
| CCLXXXVI | morpholinoNH | 1-(trans-4-(NHCO₂t-Bu)cyclohexylcar-bonyl)piperidin-4-yl | 622 | 178 |
| CCLXXXVII | morpholinoNH | 1-(piperidin-3-ylcarbonyl)piperidin-4-yl | 508 | 169* |
| CCLXXXVIII | morpholinoNH | 1-(1-Me-piperidin-3-ylcarbonyl)piperidin-4-yl | 522 | 158* |

TABLE 1-continued

| Example # | R¹ | R² | mass (M + H)⁺ | mp (° C.) |
|---|---|---|---|---|
| CCLXXXIX | morpholinoNH | 1-(1-CO₂t-Bu-piperidin-3-ylcarbonyl)piperidin-4-yl | 608 | 196 |
| CCXC | morpholinoNH | 1-(3-NH₂-cyclohexylcarbonyl)piperidin-4-yl | 522 | 201* |
| CCXCI | morpholinoNH | 1-(3-Nme₂-cyclohexylcarbonyl)piperidin-4-yl | 550 | 153* |
| CCXCII | morpholinoNH | 1-(trans-4-Ome-cyclohexylcarbonyl)piperidin-4-yl | 537 | 246* |
| CCXCIII | morpholinoNH | 1-(cis-4-Ome-cyclohexylcarbonyl)pipredin-4-yl | 537 | 178* |
| CCXCIV | morpholinoNH | 1-(4-NH₂-benzylcarbonyl)piperidin-4-yl | 530 | 177* |
| CCXCV | morpholinoNH | 1-(4-Nme₂-benzylcarbonyl)piperidin-4-yl | 558 | 107* |
| CCXCVI | morpholinoNH | 1-(4-NHCO₂C(CH₃)₃-benzylcarbonyl)piperidin-4-yl | 630 | 177 |
| CCXCVII | morpholinoNH | 1-(4-NH₂-phenylcarbonyl)piperidin-4-yl | 516 | 198* |
| CCXCVIII | morpholinoNH | 1-(4-Nme₂-phenylcarbonyl)piperidin-4-yl | 544 | 189* |
| CCXCIX | morpholinoNH | 1-(4-(NHCO₂t-Bu)-phenylcarbonyl)piperidin-4-yl | 616 | 212 |
| CCC | morpholinoNH | trans-4-CO₂H-cyclohexyl | 440 | 264* |
| CCCI | morpholinoNH | trans-4-CO₂Me-cyclohexyl | 454 | 259* |
| CCCII | morpholinoNH | trans-4-(3-Nme₂-pyrrolidinocarbonyl)-cyclohexyl | 536 | 191* |
| CCCIII | morpholinoNH | trans-4-(piperazinocarbonyl)-cyclohexyl | 508 | 248* |
| CCCIV | morpholinoNH | trans-4-(4-Me-piperazinocarbonyl)-cyclohexyl | 522 | 228* |
| CCCV | morpholinoNH | trans-4-(homopiperazinocarbonyl)cyclohexyl | 522 | >265* |
| CCCVI | morpholinoNH | trans-4-(4-methylhomopiperazinocarbonyl)cyclohexyl | 536 | 220* |

TABLE 2

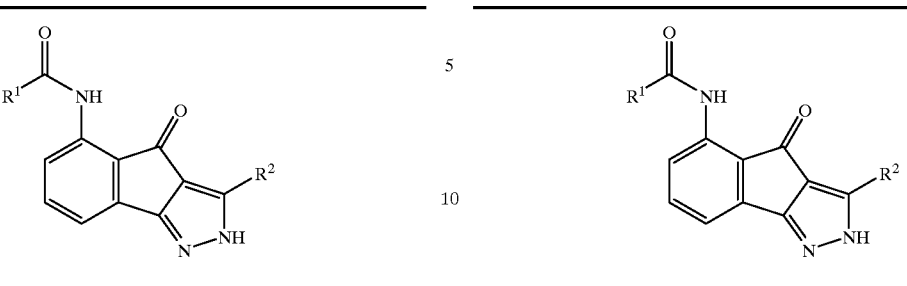

| Example Number | R¹ | R² |
|---|---|---|
| 100 | 2-pyridylmethyl | 4-MeOC₆H₄ |
| 101 | 2-pyridylmethyl | 3-MeOC₆H₄ |
| 102 | 2-pyridylmethyl | 4-NH₂C₆H₄ |
| 103 | 2-pyridylmethyl | 3-NH₂C₆H₄ |
| 104 | 2-pyridylmethyl | 2-NH₂C₆H₄ |
| 105 | 2-pyridylmethyl | 4-Me₂NC₆H₄ |
| 106 | 2-pyridylmethyl | 3-Me₂NC₆H₄ |
| 107 | 2-pyridylmethyl | 2-Me₂NC₆H₄ |
| 108 | 2-pyridylmethyl | 4-pyridyl |
| 109 | 2-pyridylmethyl | 3-pyridyl |
| 110 | 2-pyridylmethyl | 2-pyridyl |
| 111 | 2-pyridylmethyl | 2-thiazolyl |
| 112 | 2-pyridylmethyl | 2-pyrazolyl |
| 113 | 2-pyridylmethyl | 5-isoquinolyl |
| 114 | 2-pyridylmethyl | 3,4-methylenedioxyC₆H₃ |
| 115 | 2-pyridylmethyl | 3,4-ethylenedioxyC₆H₃ |
| 116 | 2-pyridylmethyl | 2-imidazolyl |
| 117 | 2-pyridylmethyl | 4-isoxazolyl |
| 119 | 2-pyridylmethyl | 4-HOC₆H₄ |
| 120 | 2-pyridylmethyl | 3-HOC₆H₄ |
| 121 | 2-pyridylmethyl | 3,4-diHOC₆H₄ |
| 122 | 2-pyridylmethyl | 4-NH₂CH₂C₆H₄ |
| 123 | 2-pyridylmethyl | 3-NH₂CH₂C₆H₄ |
| 124 | 3-pyridylmethyl | 4-MeOC₆H₄ |
| 125 | 3-pyridylmethyl | 3-MeOC₆H₄ |
| 126 | 3-pyridylmethyl | 4-NH₂C₆H₄ |
| 127 | 3-pyridylmethyl | 3-NH₂C₆H₄ |
| 128 | 3-pyridylmethyl | 2-NH₂C₆H₄ |
| 129 | 3-pyridylmethyl | 4-Me₂NC₆H₄ |
| 130 | 3-pyridylmethyl | 2-Me₂NC₆H₄ |
| 132 | 3-pyridylmethyl | 4-pyridyl |
| 133 | 3-pyridylmethyl | 2-pyridyl |
| 135 | 3-pyridylmethyl | 2-thiazolyl |
| 136 | 3-pyridylmethyl | 2-pyrazolyl |
| 137 | 3-pyridylmethyl | 5-isoquinolyl |
| 138 | 3-pyridylmethyl | 3,4-methylenedioxyC₆H₃ |
| 139 | 3-pyridylmethyl | 3,4-ethylenedioxyC₆H₃ |
| 140 | 3-pyridylmethyl | 2-imidazolyl |
| 141 | 3-pyridylmethyl | 2-oxazolyl |
| 142 | 3-pyridylmethyl | 4-isoxazolyl |
| 143 | 3-pyridylmethyl | 4-HOC₆H₄ |
| 144 | 3-pyridylmethyl | 3-HOC₆H₄ |
| 145 | 3-pyridylmethyl | 3,4-diHOC₆H₄ |
| 146 | 3-pyridylmethyl | 4-NH₂CH₂C₆H₄ |
| 147 | 3-pyridylmethyl | 3-NH₂CH₂C₆H₄ |
| 148 | 4-pyridylmethyl | 4-MeOC₆H₄ |
| 149 | 4-pyridylmethyl | 3-MeOC₆H₄ |
| 150 | 4-pyridylmethyl | 4-NH₂C₆H₄ |
| 151 | 4-pyridylmethyl | 3-NH₂C₆H₄ |
| 152 | 4-pyridylmethyl | 2-NH₂C₆H₄ |
| 153 | 4-pyridylmethyl | 4-Me₂NC₆H₄ |
| 154 | 4-pyridylmethyl | 3-Me₂NC₆H₄ |
| 155 | 4-pyridylmethyl | 2-Me₂NC₆H₄ |
| 156 | 4-pyridylmethyl | 4-pyridyl |
| 157 | 4-pyridylmethyl | 3-pyridyl |
| 158 | 4-pyridylmethyl | 2-pyridyl |
| 159 | 4-pyridylmethyl | 2-thiazolyl |
| 160 | 4-pyridylmethyl | 2-pyrazolyl |
| 161 | 4-pyridylmethyl | 5-isoquinolyl |
| 162 | 4-pyridylmethyl | 3,4-methylenedioxyC₆H₃ |
| 163 | 4-pyridylmethyl | 3,4-ethylenedioxyC₆H₃ |
| 164 | 4-pyridylmethyl | 2-imidazolyl |
| 165 | 4-pyridylmethyl | 2-oxazolyl |
| 166 | 4-pyridylmethyl | 4-isoxazolyl |
| 167 | 4-pyridylmethyl | 4-HOC₆H₄ |
| 168 | 4-pyridylmethyl | 3-HOC₆H₄ |
| 169 | 4-pyridylmethyl | 3,4-diHOC₆H₄ |
| 170 | 4-pyridylmethyl | 4-NH₂CH₂C₆H₄ |
| 171 | 4-pyridylmethyl | 3-NH₂CH₂C₆H₄ |
| 172 | 2-NH₂C₆H₄CH₂ | 4-MeOC₆H₄ |
| 173 | 2-NH₂C₆H₄CH₂ | 3-MeOC₆H₄ |
| 174 | 2-NH₂C₆H₄CH₂ | 4-NH₂C₆H₄ |
| 175 | 2-NH₂C₆H₄CH₂ | 3-NH₂C₆H₄ |
| 176 | 2-NH₂C₆H₄CH₂ | 2-NH₂C₆H₄ |
| 177 | 2-NH₂C₆H₄CH₂ | 4-Me₂NC₆H₄ |
| 178 | 2-NH₂C₆H₄CH₂ | 3-Me₂NC₆H₄ |
| 179 | 2-NH₂C₆H₄CH₂ | 2-Me₂NC₆H₄ |
| 180 | 2-NH₂C₆H₄CH₂ | 4-pyridyl |
| 181 | 2-NH₂C₆H₄CH₂ | 3-pyridyl |
| 182 | 2-NH₂C₆H₄CH₂ | 2-pyridyl |
| 183 | 2-NH₂C₆H₄CH₂ | 2-thiazolyl |
| 184 | 2-NH₂C₆H₄CH₂ | 2-pyrazolyl |
| 185 | 2-NH₂C₆H₄CH₂ | 5-isoquinolyl |
| 186 | 2-NH₂C₆H₄CH₂ | 3,4-methylenedioxyC₆H₃ |
| 187 | 2-NH₂C₆H₄CH₂ | 3,4-ethylenedioxyC₆H₃ |
| 188 | 2-NH₂C₆H₄CH₂ | 2-imidazolyl |
| 189 | 2-NH₂C₆H₄CH₂ | 2-oxazolyl |
| 190 | 2-NH₂C₆H₄CH₂ | 4-isoxazolyl |
| 191 | 2-NH₂C₆H₄CH₂ | 4-HOC₆H₄ |
| 192 | 2-NH₂C₆H₄CH₂ | 3-HOC₆H₄ |
| 193 | 2-NH₂C₆H₄CH₂ | 3,4-diHOC₆H₄ |
| 194 | 2-NH₂C₆H₄CH₂ | 4-NH₂CH₂C₆H₄ |
| 195 | 2-NH₂C₆H₄CH₂ | 3-NH₂CH₂C₆H₄ |
| 196 | 3-NH₂C₆H₄CH₂ | 3-MeOC₆H₄ |
| 197 | 3-NH₂C₆H₄CH₂ | 4-NH₂C₆H₄ |
| 198 | 3-NH₂C₆H₄CH₂ | 3-NH₂C₆H₄ |
| 199 | 3-NH₂C₆H₄CH₂ | 2-NH₂C₆H₄ |
| 200 | 3-NH₂C₆H₄CH₂ | 4-Me₂NC₆H₄ |
| 201 | 3-NH₂C₆H₄CH₂ | 3-Me₂NC₆H₄ |
| 202 | 3-NH₂C₆H₄CH₂ | 2-Me₂NC₆H₄ |
| 203 | 3-NH₂C₆H₄CH₂ | 4-pyridyl |
| 204 | 3-NH₂C₆H₄CH₂ | 3-pyridyl |
| 205 | 3-NH₂C₆H₄CH₂ | 2-pyridyl |
| 206 | 3-NH₂C₆H₄CH₂ | 2-thiazolyl |
| 207 | 3-NH₂C₆H₄CH₂ | 2-pyrazolyl |
| 208 | 3-NH₂C₆H₄CH₂ | 5-isoquinolyl |
| 209 | 3-NH₂C₆H₄CH₂ | 3,4-methylenedioxyC₆H₃ |
| 210 | 3-NH₂C₆H₄CH₂ | 3,4-ethylenedioxyC₆H₃ |
| 211 | 3-NH₂C₆H₄CH₂ | 2-imidazolyl |
| 212 | 3-NH₂C₆H₄CH₂ | 2-oxazolyl |
| 213 | 3-NH₂C₆H₄CH₂ | 4-isoxazolyl |
| 214 | 3-NH₂C₆H₄CH₂ | 4-HOC₆H₄ |
| 215 | 3-NH₂C₆H₄CH₂ | 3-HOC₆H₄ |
| 216 | 3-NH₂C₆H₄CH₂ | 3,4-diHOC₆H₄ |
| 217 | 3-NH₂C₆H₄CH₂ | 4-NH₂CH₂C₆H₄ |
| 218 | 3-NH₂C₆H₄CH₂ | 3-NH₂CH₂C₆H₄ |
| 219 | 4-NH₂C₆H₄CH₂ | 3-MeOC₆H₄ |
| 220 | 4-NH₂C₆H₄CH₂ | 4-NH₂C₆H₄ |
| 221 | 4-NH₂C₆H₄CH₂ | 3-NH₂C₆H₄ |
| 222 | 4-NH₂C₆H₄CH₂ | 2-NH₂C₆H₄ |
| 223 | 4-NH₂C₆H₄CH₂ | 4-Me₂NC₆H₄ |
| 224 | 4-NH₂C₆H₄CH₂ | 3-Me₂NC₆H₄ |
| 225 | 4-NH₂C₆H₄CH₂ | 2-Me₂NC₆H₄ |
| 226 | 4-NH₂C₆H₄CH₂ | 4-pyridyl |
| 227 | 4-NH₂C₆H₄CH₂ | 3-pyridyl |
| 228 | 4-NH₂C₆H₄CH₂ | 2-pyridyl |

TABLE 2-continued

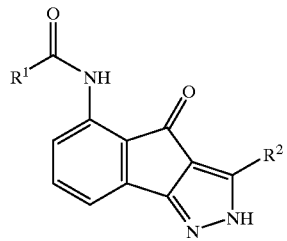

| Example Number | R¹ | R² |
|---|---|---|
| 229 | 4-NH$_2$C$_6$H$_4$CH$_2$ | 2-thiazolyl |
| 230 | 4-NH$_2$C$_6$H$_4$CH$_2$ | 2-pyrazolyl |
| 231 | 4-NH$_2$C$_6$H$_4$CH$_2$ | 5-isoquinolyl |
| 232 | 4-NH$_2$C$_6$H$_4$CH$_2$ | 3,4-methylenedioxyC$_6$H$_3$ |
| 233 | 4-NH$_2$C$_6$H$_4$CH$_2$ | 2-imidazolyl |
| 235 | 4-NH$_2$C$_6$H$_4$CH$_2$ | 2-oxazolyl |
| 236 | 4-NH$_2$C$_6$H$_4$CH$_2$ | 4-isoxazolyl |
| 237 | 4-NH$_2$C$_6$H$_4$CH$_2$ | 4-HOC$_6$H$_4$ |
| 238 | 4-NH$_2$C$_6$H$_4$CH$_2$ | 3-HOC$_6$H$_4$ |
| 239 | 4-NH$_2$C$_6$H$_4$CH$_2$ | 3,4-diHOC$_6$H$_4$ |
| 240 | 4-NH$_2$C$_6$H$_4$CH$_2$ | 4-NH$_2$CH$_2$C$_6$H$_4$ |
| 241 | 4-NH$_2$C$_6$H$_4$CH$_2$ | 3-NH$_2$CH$_2$C$_6$H$_4$ |
| 242 | 2-MeOC$_6$H$_4$CH$_2$ | 3-MeOC$_6$H$_4$ |
| 243 | 2-MeOC$_6$H$_4$CH$_2$ | 4-NH$_2$C$_6$H$_4$ |
| 244 | 2-MeOC$_6$H$_4$CH$_2$ | 3-NH$_2$C$_6$H$_4$ |
| 245 | 2-MeOC$_6$H$_4$CH$_2$ | 2-NH$_2$C$_6$H$_4$ |
| 246 | 2-MeOC$_6$H$_4$CH$_2$ | 4-Me$_2$NC$_6$H$_4$ |
| 247 | 2-MeOC$_6$H$_4$CH$_2$ | 3-Me$_2$NC$_6$H$_4$ |
| 248 | 2-MeOC$_6$H$_4$CH$_2$ | 2-Me$_2$NC$_6$H$_4$ |
| 249 | 2-MeOC$_6$H$_4$CH$_2$ | 4-pyridyl |
| 250 | 2-MeOC$_6$H$_4$CH$_2$ | 3-pyridyl |
| 251 | 2-MeOC$_6$H$_4$CH$_2$ | 2-pyridyl |
| 252 | 2-MeOC$_6$H$_4$CH$_2$ | 2-thiazolyl |
| 253 | 2-MeOC$_6$H$_4$CH$_2$ | 2-pyrazolyl |
| 254 | 2-MeOC$_6$H$_4$CH$_2$ | 5-isoquinolyl |
| 255 | 2-MeOC$_6$H$_4$CH$_2$ | 3,4-ethylenedioxyC$_6$H$_3$ |
| 257 | 2-MeOC$_6$H$_4$CH$_2$ | 2-imidazolyl |
| 258 | 2-MeOC$_6$H$_4$CH$_2$ | 2-oxazolyl |
| 259 | 2-MeOC$_6$H$_4$CH$_2$ | 4-isoxazolyl |
| 260 | 2-MeOC$_6$H$_4$CH$_2$ | 4-HOC$_6$H$_4$ |
| 261 | 2-MeOC$_6$H$_4$CH$_2$ | 3-HOC$_6$H$_4$ |
| 262 | 2-MeOC$_6$H$_4$CH$_2$ | 3,4-diHOC$_6$H$_4$ |
| 263 | 2-MeOC$_6$H$_4$CH$_2$ | 4-NH$_2$CH$_2$C$_6$H$_4$ |
| 264 | 2-MeOC$_6$H$_4$CH$_2$ | 3-NH$_2$CH$_2$C$_6$H$_4$ |
| 265 | 3-MeOC$_6$H$_4$CH$_2$ | 3-MeOC$_6$H$_4$ |
| 266 | 3-MeOC$_6$H$_4$CH$_2$ | 4-NH$_2$C$_6$H$_4$ |
| 267 | 3-MeOC$_6$H$_4$CH$_2$ | 3-NH$_2$C$_6$H$_4$ |
| 268 | 3-MeOC$_6$H$_4$CH$_2$ | 2-NH$_2$C$_6$H$_4$ |
| 269 | 3-MeOC$_6$H$_4$CH$_2$ | 4-Me$_2$NC$_6$H$_4$ |
| 270 | 3-MeOC$_6$H$_4$CH$_2$ | 3-Me$_2$NC$_6$H$_4$ |
| 271 | 3-MeOC$_6$H$_4$CH$_2$ | 2-Me$_2$NC$_6$H$_4$ |
| 272 | 3-MeOC$_6$H$_4$CH$_2$ | 4-pyridyl |
| 273 | 3-MeOC$_6$H$_4$CH$_2$ | 3-pyridyl |
| 274 | 3-MeOC$_6$H$_4$CH$_2$ | 2-pyridyl |
| 275 | 3-MeOC$_6$H$_4$CH$_2$ | 2-thiazolyl |
| 276 | 3-MeOC$_6$H$_4$CH$_2$ | 2-pyrazolyl |
| 277 | 3-MeOC$_6$H$_4$CH$_2$ | 5-isoquinolyl |
| 278 | 3-MeOC$_6$H$_4$CH$_2$ | 3,4-methylenedioxyC$_6$H$_3$ |
| 279 | 3-MeOC$_6$H$_4$CH$_2$ | 3,4-ethylenedioxyC$_6$H$_3$ |
| 280 | 3-MeOC$_6$H$_4$CH$_2$ | 2-imidazolyl |
| 281 | 3-MeOC$_6$H$_4$CH$_2$ | 2-oxazolyl |
| 282 | 3-MeOC$_6$H$_4$CH$_2$ | 4-isoxazolyl |
| 283 | 3-MeOC$_6$H$_4$CH$_2$ | 4-HOC$_6$H$_4$ |
| 284 | 3-MeOC$_6$H$_4$CH$_2$ | 3-HOC$_6$H$_4$ |
| 285 | 3-MeOC$_6$H$_4$CH$_2$ | 3,4-diHOC$_6$H$_4$ |
| 286 | 3-MeOC$_6$H$_4$CH$_2$ | 4-NH$_2$CH$_2$C$_6$H$_4$ |
| 287 | 3-MeOC$_6$H$_4$CH$_2$ | 3-NH$_2$CH$_2$C$_6$H$_4$ |
| 288 | 4-MeOC$_6$H$_4$CH$_2$ | 3-MeOC$_6$H$_4$ |
| 289 | 4-MeOC$_6$H$_4$CH$_2$ | 4-NH$_2$C$_6$H$_4$ |
| 290 | 4-MeOC$_6$H$_4$CH$_2$ | 3-NH$_2$C$_6$H$_4$ |
| 291 | 4-MeOC$_6$H$_4$CH$_2$ | 2-NH$_2$C$_6$H$_4$ |
| 292 | 4-MeOC$_6$H$_4$CH$_2$ | 4-Me$_2$NC$_6$H$_4$ |
| 293 | 4-MeOC$_6$H$_4$CH$_2$ | 3-Me$_2$NC$_6$H$_4$ |

TABLE 2-continued

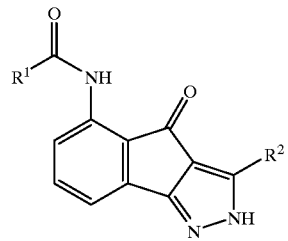

| Example Number | R¹ | R² |
|---|---|---|
| 294 | 4-MeOC$_6$H$_4$CH$_2$ | 2-Me$_2$NC$_6$H$_4$ |
| 295 | 4-MeOC$_6$H$_4$CH$_2$ | 4-pyridyl |
| 296 | 4-MeOC$_6$H$_4$CH$_2$ | 3-pyridyl |
| 297 | 4-MeOC$_6$H$_4$CH$_2$ | 2-pyridyl |
| 298 | 4-MeOC$_6$H$_4$CH$_2$ | 2-thiazolyl |
| 299 | 4-MeOC$_6$H$_4$CH$_2$ | 2-pyrazolyl |
| 300 | 4-MeOC$_6$H$_4$CH$_2$ | 5-isoquinolyl |
| 301 | 4-MeOC$_6$H$_4$CH$_2$ | 3,4-methylenedioxyC$_6$H$_3$ |
| 302 | 4-MeOC$_6$H$_4$CH$_2$ | 3,4-methylenedioxyC$_6$H$_3$ |
| 303 | 4-MeOC$_6$H$_4$CH$_2$ | 2-imidazolyl |
| 304 | 4-MeOC$_6$H$_4$CH$_2$ | 2-oxazolyl |
| 305 | 4-MeOC$_6$H$_4$CH$_2$ | 4-isoxazolyl |
| 306 | 4-MeOC$_6$H$_4$CH$_2$ | 4-HOC$_6$H$_4$ |
| 307 | 4-MeOC$_6$H$_4$CH$_2$ | 3-HOC$_6$H$_4$ |
| 308 | 4-MeOC$_6$H$_4$CH$_2$ | 3,4-diHOC$_6$H$_4$ |
| 309 | 4-MeOC$_6$H$_4$CH$_2$ | 4-NH$_2$CH$_2$C$_6$H$_4$ |
| 310 | 4-MeOC$_6$H$_4$CH$_2$ | 3-NH$_2$CH$_2$C$_6$H$_4$ |
| 311 | 2-HOC$_6$H$_4$CH$_2$ | 4-MeOC$_6$H$_4$ |
| 312 | 2-HOC$_6$H$_4$CH$_2$ | 3-MeOC$_6$H$_4$ |
| 313 | 2-HOC$_6$H$_4$CH$_2$ | 4-NH$_2$C$_6$H$_4$ |
| 314 | 2-HOC$_6$H$_4$CH$_2$ | 3-NH$_2$C$_6$H$_4$ |
| 315 | 2-HOC$_6$H$_4$CH$_2$ | 2-NH$_2$C$_6$H$_4$ |
| 316 | 2-HOC$_6$H$_4$CH$_2$ | 4-Me$_2$NC$_6$H$_4$ |
| 317 | 2-HOC$_6$H$_4$CH$_2$ | 3-Me$_2$NC$_6$H$_4$ |
| 318 | 2-HOC$_6$H$_4$CH$_2$ | 2-Me$_2$NC$_6$H$_4$ |
| 319 | 2-HOC$_6$H$_4$CH$_2$ | 4-pyridyl |
| 320 | 2-HOC$_6$H$_4$CH$_2$ | 3-pyridyl |
| 321 | 2-HOC$_6$H$_4$CH$_2$ | 2-pyridyl |
| 322 | 2-HOC$_6$H$_4$CH$_2$ | 2-thiazolyl |
| 323 | 2-HOC$_6$H$_4$CH$_2$ | 2-pyrazolyl |
| 324 | 2-HOC$_6$H$_4$CH$_2$ | 5-isoquinolyl |
| 325 | 2-HOC$_6$H$_4$CH$_2$ | 3,4-methylenedioxyC$_6$H$_3$ |
| 326 | 2-HOC$_6$H$_4$CH$_2$ | 3,4-methylenedioxyC$_6$H$_3$ |
| 327 | 2-HOC$_6$H$_4$CH$_2$ | 2-imidazolyl |
| 328 | 2-HOC$_6$H$_4$CH$_2$ | 2-oxazolyl |
| 329 | 2-HOC$_6$H$_4$CH$_2$ | 4-isoxazolyl |
| 330 | 2-HOC$_6$H$_4$CH$_2$ | 4-HOC$_6$H$_4$ |
| 331 | 2-HOC$_6$H$_4$CH$_2$ | 3-HOC$_6$H$_4$ |
| 332 | 2-HOC$_6$H$_4$CH$_2$ | 3,4-diHOC$_6$H$_4$ |
| 333 | 2-HOC$_6$H$_4$CH$_2$ | 4-NH$_2$CH$_2$C$_6$H$_4$ |
| 334 | 2-HOC$_6$H$_4$CH$_2$ | 3-NH$_2$CH$_2$C$_6$H$_4$ |
| 335 | 3-HOC$_6$H$_4$CH$_2$ | 4-MeOC$_6$H$_4$ |
| 336 | 3-HOC$_6$H$_4$CH$_2$ | 3-MeOC$_6$H$_4$ |
| 337 | 3-HOC$_6$H$_4$CH$_2$ | 4-NH$_2$C$_6$H$_4$ |
| 338 | 3-HOC$_6$H$_4$CH$_2$ | 3-NH$_2$C$_6$H$_4$ |
| 339 | 3-HOC$_6$H$_4$CH$_2$ | 2-NH$_2$C$_6$H$_4$ |
| 340 | 3-HOC$_6$H$_4$CH$_2$ | 4-Me$_2$NC$_6$H$_4$ |
| 341 | 3-HOC$_6$H$_4$CH$_2$ | 3-Me$_2$NC$_6$H$_4$ |
| 342 | 3-HOC$_6$H$_4$CH$_2$ | 2-Me$_2$NC$_6$H$_4$ |
| 343 | 3-HOC$_6$H$_4$CH$_2$ | 4-pyridyl |
| 344 | 3-HOC$_6$H$_4$CH$_2$ | 3-pyridyl |
| 345 | 3-HOC$_6$H$_4$CH$_2$ | 2-pyridyl |
| 346 | 3-HOC$_6$H$_4$CH$_2$ | 2-thiazolyl |
| 347 | 3-HOC$_6$H$_4$CH$_2$ | 2-pyrazolyl |
| 348 | 3-HOC$_6$H$_4$CH$_2$ | 5-isoquinolyl |
| 349 | 3-HOC$_6$H$_4$CH$_2$ | 3,4-methylenedioxyC$_6$H$_3$ |
| 350 | 3-HOC$_6$H$_4$CH$_2$ | 3,4-methylenedioxyC$_6$H$_3$ |
| 351 | 3-HOC$_6$H$_4$CH$_2$ | 2-imidazolyl |
| 352 | 3-HOC$_6$H$_4$CH$_2$ | 2-oxazolyl |
| 353 | 3-HOC$_6$H$_4$CH$_2$ | 4-isoxazolyl |
| 354 | 3-HOC$_6$H$_4$CH$_2$ | 4-HOC$_6$H$_4$ |
| 355 | 3-HOC$_6$H$_4$CH$_2$ | 3-HOC$_6$H$_4$ |
| 356 | 3-HOC$_6$H$_4$CH$_2$ | 3,4-diHOC$_6$H$_4$ |

TABLE 2-continued

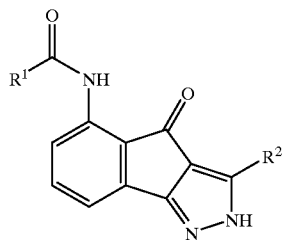

| Example Number | R¹ | R² |
|---|---|---|
| 357 | 3-HOC₆H₄CH₂ | 4-NH₂CH₂C₆H₄ |
| 358 | 3-HOC₆H₄CH₂ | 3-NH₂CH₂C₆H₄ |
| 359 | 4-HOC₆H₄CH₂ | 4-MeOC₆H₄ |
| 360 | 4-HOC₆H₄CH₂ | 3-MeOC₆H₄ |
| 361 | 4-HOC₆H₄CH₂ | 4-NH₂C₆H₄ |
| 362 | 4-HOC₆H₄CH₂ | 3-NH₂C₆H₄ |
| 363 | 4-HOC₆H₄CH₂ | 2-NH₂C₆H₄ |
| 364 | 4-HOC₆H₄CH₂ | 4-Me₂NC₆H₄ |
| 365 | 4-HOC₆H₄CH₂ | 3-Me₂NC₆H₄ |
| 366 | 4-HOC₆H₄CH₂ | 2-Me₂NC₆H₄ |
| 367 | 4-HOC₆H₄CH₂ | 4-pyridyl |
| 368 | 4-HOC₆H₄CH₂ | 3-pyridyl |
| 369 | 4-HOC₆H₄CH₂ | 2-pyridyl |
| 370 | 4-HOC₆H₄CH₂ | 2-thiazolyl |
| 371 | 4-HOC₆H₄CH₂ | 2-pyrazolyl |
| 372 | 4-HOC₆H₄CH₂ | 5-isoquinolyl |
| 373 | 4-HOC₆H₄CH₂ | 3,4-methylenedioxyC₆H₃ |
| 374 | 4-HOC₆H₄CH₂ | 3,4-ethylenedioxyC₆H₃ |
| 375 | 4-HOC₆H₄CH₂ | 2-imidazolyl |
| 376 | 4-HOC₆H₄CH₂ | 2-oxazolyl |
| 377 | 4-HOC₆H₄CH₂ | 4-isoxazolyl |
| 378 | 4-HOC₆H₄CH₂ | 4-HOC₆H₄ |
| 379 | 4-HOC₆H₄CH₂ | 3-HOC₆H₄ |
| 380 | 4-HOC₆H₄CH₂ | 3,4-diHOC₆H₄ |
| 381 | 4-HOC₆H₄CH₂ | 4-NH₂CH₂C₆H₄ |
| 382 | 4-HOC₆H₄CH₂ | 3-NH₂CH₂C₆H₄ |
| 383 | 4-ClC₆H₄CH₂ | 3-MeOC₆H₄ |
| 384 | 4-ClC₆H₄CH₂ | 4-NH₂C₆H₄ |
| 385 | 4-ClC₆H₄CH₂ | 3-NH₂C₆H₄ |
| 386 | 4-ClC₆H₄CH₂ | 2-NH₂C₆H₄ |
| 387 | 4-ClC₆H₄CH₂ | 4-Me₂NC₆H₄ |
| 388 | 4-ClC₆H₄CH₂ | 3-Me₂NC₆H₄ |
| 389 | 4-ClC₆H₄CH₂ | 2-Me₂NC₆H₄ |
| 390 | 4-ClC₆H₄CH₂ | 4-pyridyl |
| 391 | 4-ClC₆H₄CH₂ | 3-pyridyl |
| 392 | 4-ClC₆H₄CH₂ | 2-pyridyl |
| 393 | 4-ClC₆H₄CH₂ | 2-thiazolyl |
| 394 | 4-ClC₆H₄CH₂ | 2-pyrazolyl |
| 395 | 4-ClC₆H₄CH₂ | 5-isoquinolyl |
| 396 | 4-ClC₆H₄CH₂ | 3,4-methylenedioxyC₆H₃ |
| 397 | 4-ClC₆H₄CH₂ | 3,4-ethylenedioxyC₆H₃ |
| 398 | 4-ClC₆H₄CH₂ | 2-imidazolyl |
| 399 | 4-ClC₆H₄CH₂ | 2-oxazolyl |
| 400 | 4-ClC₆H₄CH₂ | 4-isoxazolyl |
| 401 | 4-ClC₆H₄CH₂ | 4-HOC₆H₄ |
| 402 | 4-ClC₆H₄CH₂ | 3-HOC₆H₄ |
| 403 | 4-ClC₆H₄CH₂ | 3,4-diHOC₆H₄ |
| 404 | 4-ClC₆H₄CH₂ | 4-NH₂CH₂C₆H₄ |
| 405 | 4-ClC₆H₄CH₂ | 3-NH₂CH₂C₆H₄ |
| 406 | 2-NH₂CH₂C₆H₄CH₂ | 4-MeOC₆H₄ |
| 407 | 2-NH₂CH₂C₆H₄CH₂ | 3-MeOC₆H₄ |
| 408 | 2-NH₂CH₂C₆H₄CH₂ | 4-NH₂C₆H₄ |
| 409 | 2-NH₂CH₂C₆H₄CH₂ | 3-NH₂C₆H₄ |
| 410 | 2-NH₂CH₂C₆H₄CH₂ | 2-NH₂C₆H₄ |
| 411 | 2-NH₂CH₂C₆H₄CH₂ | 4-Me₂NC₆H₄ |
| 412 | 2-NH₂CH₂C₆H₄CH₂ | 3-Me₂NC₆H₄ |
| 413 | 2-NH₂CH₂C₆H₄CH₂ | 2-Me₂NC₆H₄ |
| 414 | 2-NH₂CH₂C₆H₄CH₂ | 4-pyridyl |
| 415 | 2-NH₂CH₂C₆H₄CH₂ | 3-pyridyl |
| 416 | 2-NH₂CH₂C₆H₄CH₂ | 2-pyridyl |
| 417 | 2-NH₂CH₂C₆H₄CH₂ | 2-thiazolyl |
| 418 | 2-NH₂CH₂C₆H₄CH₂ | 2-pyrazolyl |
| 419 | 2-NH₂CH₂C₆H₄CH₂ | 5-isoquinolyl |

TABLE 2-continued

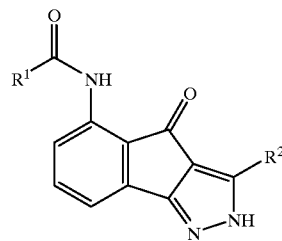

| Example Number | R¹ | R² |
|---|---|---|
| 420 | 2-NH₂CH₂C₆H₄CH₂ | 3,4-methylenedioxyC₆H₃ |
| 421 | 2-NH₂CH₂C₆H₄CH₂ | 3,4-ethylenedioxyC₆H₃ |
| 422 | 2-NH₂CH₂C₆H₄CH₂ | 2-imidazolyl |
| 423 | 2-NH₂CH₂C₆H₄CH₂ | 2-oxazolyl |
| 424 | 2-NH₂CH₂C₆H₄CH₂ | 4-isoxazolyl |
| 425 | 2-NH₂CH₂C₆H₄CH₂ | 4-HOC₆H₄ |
| 426 | 2-NH₂CH₂C₆H₄CH₂ | 3-HOC₆H₄ |
| 427 | 2-NH₂CH₂C₆H₄CH₂ | 3,4-diHOC₆H₄ |
| 428 | 2-NH₂CH₂C₆H₄CH₂ | 4-NH₂CH₂C₆H₄ |
| 429 | 2-NH₂CH₂C₆H₄CH₂ | 3-NH₂CH₂C₆H₄ |
| 430 | 3-NH₂CH₂C₆H₄CH₂ | 4-MeOC₆H₄ |
| 431 | 3-NH₂CH₂C₆H₄CH₂ | 3-MeOC₆H₄ |
| 432 | 3-NH₂CH₂C₆H₄CH₂ | 4-NH₂C₆H₄ |
| 433 | 3-NH₂CH₂C₆H₄CH₂ | 3-NH₂C₆H₄ |
| 434 | 3-NH₂CH₂C₆H₄CH₂ | 2-NH₂C₆H₄ |
| 435 | 3-NH₂CH₂C₆H₄CH₂ | 4-Me₂NC₆H₄ |
| 436 | 3-NH₂CH₂C₆H₄CH₂ | 3-Me₂NC₆H₄ |
| 437 | 3-NH₂CH₂C₆H₄CH₂ | 2-Me₂NC₆H₄ |
| 438 | 3-NH₂CH₂C₆H₄CH₂ | 4-pyridyl |
| 439 | 3-NH₂CH₂C₆H₄CH₂ | 3-pyridyl |
| 440 | 3-NH₂CH₂C₆H₄CH₂ | 2-pyridyl |
| 441 | 3-NH₂CH₂C₆H₄CH₂ | 2-thiazolyl |
| 442 | 3-NH₂CH₂C₆H₄CH₂ | 2-pyrazolyl |
| 443 | 3-NH₂CH₂C₆H₄CH₂ | 5-isoquinolyl |
| 444 | 3-NH₂CH₂C₆H₄CH₂ | 3,4-methylenedioxyC₆H₃ |
| 445 | 3-NH₂CH₂C₆H₄CH₂ | 3,4-ethylenedioxyC₆H₃ |
| 446 | 3-NH₂CH₂C₆H₄CH₂ | 2-imidazolyl |
| 447 | 3-NH₂CH₂C₆H₄CH₂ | 2-oxazolyl |
| 448 | 3-NH₂CH₂C₆H₄CH₂ | 4-isoxazolyl |
| 449 | 3-NH₂CH₂C₆H₄CH₂ | 4-HOC₆H₄ |
| 450 | 3-NH₂CH₂C₆H₄CH₂ | 3-HOC₆H₄ |
| 451 | 3-NH₂CH₂C₆H₄CH₂ | 3,4-diHOC₆H₄ |
| 452 | 3-NH₂CH₂C₆H₄CH₂ | 4-NH₂CH₂C₆H₄ |
| 453 | 3-NH₂CH₂C₆H₄CH₂ | 3-NH₂CH₂C₆H₄ |
| 454 | 4-NH₂CH₂C₆H₄CH₂ | 4-MeOC₆H₄ |
| 455 | 4-NH₂CH₂C₆H₄CH₂ | 3-MeOC₆H₄ |
| 456 | 4-NH₂CH₂C₆H₄CH₂ | 4-NH₂C₆H₄ |
| 457 | 4-NH₂CH₂C₆H₄CH₂ | 3-NH₂C₆H₄ |
| 458 | 4-NH₂CH₂C₆H₄CH₂ | 2-NH₂C₆H₄ |
| 459 | 4-NH₂CH₂C₆H₄CH₂ | 4-Me₂NC₆H₄ |
| 460 | 4-NH₂CH₂C₆H₄CH₂ | 3-Me₂NC₆H₄ |
| 461 | 4-NH₂CH₂C₆H₄CH₂ | 2-Me₂NC₆H₄ |
| 462 | 4-NH₂CH₂C₆H₄CH₂ | 4-pyridyl |
| 463 | 4-NH₂CH₂C₆H₄CH₂ | 3-pyridyl |
| 464 | 4-NH₂CH₂C₆H₄CH₂ | 2-pyridyl |
| 465 | 4-NH₂CH₂C₆H₄CH₂ | 2-thiazolyl |
| 466 | 4-NH₂CH₂C₆H₄CH₂ | 2-pyrazolyl |
| 467 | 4-NH₂CH₂C₆H₄CH₂ | 5-isoquinolyl |
| 468 | 4-NH₂CH₂C₆H₄CH₂ | 3,4-methylenedioxyC₆H₃ |
| 469 | 4-NH₂CH₂C₆H₄CH₂ | 3,4-ethylenedioxyC₆H₃ |
| 470 | 4-NH₂CH₂C₆H₄CH₂ | 2-imidazolyl |
| 471 | 4-NH₂CH₂C₆H₄CH₂ | 2-oxazolyl |
| 472 | 4-NH₂CH₂C₆H₄CH₂ | 4-isoxazolyl |
| 473 | 4-NH₂CH₂C₆H₄CH₂ | 4-HOC₆H₄ |
| 474 | 4-NH₂CH₂C₆H₄CH₂ | 3-HOC₆H₄ |
| 475 | 4-NH₂CH₂C₆H₄CH₂ | 3,4-diHOC₆H₄ |
| 476 | 4-NH₂CH₂C₆H₄CH₂ | 4-NH₂CH₂C₆H₄ |
| 477 | 4-NH₂CH₂C₆H₄CH₂ | 3-NH₂CH₂C₆H₄ |
| 478 | 2-Me₂NCH₂C₆H₄CH₂ | 4-MeOC₆H₄ |
| 479 | 2-Me₂NCH₂C₆H₄CH₂ | 3-MeOC₆H₄ |
| 480 | 2-Me₂NCH₂C₆H₄CH₂ | 4-NH₂C₆H₄ |
| 481 | 2-Me₂NCH₂C₆H₄CH₂ | 3-NH₂C₆H₄ |
| 482 | 2-Me₂NCH₂C₆H₄CH₂ | 2-NH₂C₆H₄ |

TABLE 2-continued

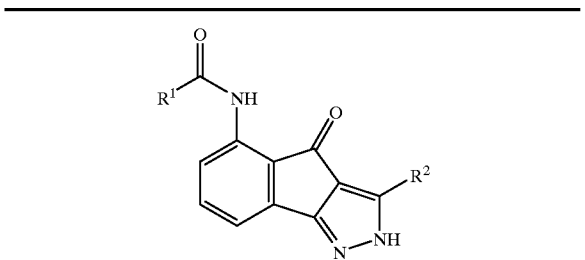

| Example Number | R¹ | R² |
|---|---|---|
| 483 | 2-Me$_2$NCH$_2$C$_6$H$_4$CH$_2$ | 4-Me$_2$NC$_6$H$_4$ |
| 484 | 2-Me$_2$NCH$_2$C$_6$H$_4$CH$_2$ | 3-Me$_2$NC$_6$H$_4$ |
| 485 | 2-Me$_2$NCH$_2$C$_6$H$_4$CH$_2$ | 2-Me$_2$NC$_6$H$_4$ |
| 486 | 2-Me$_2$NCH$_2$C$_6$H$_4$CH$_2$ | 4-pyridyl |
| 487 | 2-Me$_2$NCH$_2$C$_6$H$_4$CH$_2$ | 3-pyridyl |
| 488 | 2-Me$_2$NCH$_2$C$_6$H$_4$CH$_2$ | 2-pyridyl |
| 489 | 2-Me$_2$NCH$_2$C$_6$H$_4$CH$_2$ | 2-thiazolyl |
| 490 | 2-Me$_2$NCH$_2$C$_6$H$_4$CH$_2$ | 2-pyrazolyl |
| 491 | 2-Me$_2$NCH$_2$C$_6$H$_4$CH$_2$ | 5-isoquinolyl |
| 492 | 2-Me$_2$NCH$_2$C$_6$H$_4$CH$_2$ | 3,4-methylenedioxyC$_6$H$_3$ |
| 493 | 2-Me$_2$NCH$_2$C$_6$H$_4$CH$_2$ | 3,4-ethylenedioxyC$_6$H$_3$ |
| 494 | 2-Me$_2$NCH$_2$C$_6$H$_4$CH$_2$ | 2-imidazolyl |
| 495 | 2-Me$_2$NCH$_2$C$_6$H$_4$CH$_2$ | 2-oxazolyl |
| 496 | 2-Me$_2$NCH$_2$C$_6$H$_4$CH$_2$ | 4-isoxazolyl |
| 497 | 2-Me$_2$NCH$_2$C$_6$H$_4$CH$_2$ | 4-HOC$_6$H$_4$ |
| 498 | 2-Me$_2$NCH$_2$C$_6$H$_4$CH$_2$ | 3-HOC$_6$H$_4$ |
| 499 | 2-Me$_2$NCH$_2$C$_6$H$_4$CH$_2$ | 3,4-diHOC$_6$H$_4$ |
| 500 | 2-Me$_2$NCH$_2$C$_6$H$_4$CH$_2$ | 4-NH$_2$CH$_2$C$_6$H$_4$ |
| 501 | 2-Me$_2$NCH$_2$C$_6$H$_4$CH$_2$ | 3-NH$_2$CH$_2$C$_6$H$_4$ |
| 502 | 3-Me$_2$NCH$_2$C$_6$H$_4$CH$_2$ | 4-MeOC$_6$H$_4$ |
| 503 | 3-Me$_2$NCH$_2$C$_6$H$_4$CH$_2$ | 3-MeOC$_6$H$_4$ |
| 504 | 3-Me$_2$NCH$_2$C$_6$H$_4$CH$_2$ | 4-NH$_2$C$_6$H$_4$ |
| 505 | 3-Me$_2$NCH$_2$C$_6$H$_4$CH$_2$ | 3-NH$_2$C$_6$H$_4$ |
| 506 | 3-Me$_2$NCH$_2$C$_6$H$_4$CH$_2$ | 2-NH$_2$C$_6$H$_4$ |
| 507 | 3-Me$_2$NCH$_2$C$_6$H$_4$CH$_2$ | 4-Me$_2$NC$_6$H$_4$ |
| 508 | 3-Me$_2$NCH$_2$C$_6$H$_4$CH$_2$ | 3-Me$_2$NC$_6$H$_4$ |
| 509 | 3-Me$_2$NCH$_2$C$_6$H$_4$CH$_2$ | 2-Me$_2$NC$_6$H$_4$ |
| 510 | 3-Me$_2$NCH$_2$C$_6$H$_4$CH$_2$ | 4-pyridyl |
| 511 | 3-Me$_2$NCH$_2$C$_6$H$_4$CH$_2$ | 3-pyridyl |
| 512 | 3-Me$_2$NCH$_2$C$_6$H$_4$CH$_2$ | 2-pyridyl |
| 513 | 3-Me$_2$NCH$_2$C$_6$H$_4$CH$_2$ | 2-thiazolyl |
| 514 | 3-Me$_2$NCH$_2$C$_6$H$_4$CH$_2$ | 2-pyrazolyl |
| 515 | 3-Me$_2$NCH$_2$C$_6$H$_4$CH$_2$ | 5-isoquinolyl |
| 516 | 3-Me$_2$NCH$_2$C$_6$H$_4$CH$_2$ | 3,4-methylenedioxyC$_6$H$_3$ |
| 517 | 3-Me$_2$NCH$_2$C$_6$H$_4$CH$_2$ | 3,4-ethylenedioxyC$_6$H$_3$ |
| 518 | 3-Me$_2$NCH$_2$C$_6$H$_4$CH$_2$ | 2-imidazolyl |
| 519 | 3-Me$_2$NCH$_2$C$_6$H$_4$CH$_2$ | 2-oxazolyl |
| 520 | 3-Me$_2$NCH$_2$C$_6$H$_4$CH$_2$ | 4-isoxazolyl |
| 521 | 3-Me$_2$NCH$_2$C$_6$H$_4$CH$_2$ | 4-HOC$_6$H$_4$ |
| 522 | 3-Me$_2$NCH$_2$C$_6$H$_4$CH$_2$ | 3-HOC$_6$H$_4$ |
| 523 | 3-Me$_2$NCH$_2$C$_6$H$_4$CH$_2$ | 3,4-diHOC$_6$H$_4$ |
| 524 | 3-Me$_2$NCH$_2$C$_6$H$_4$CH$_2$ | 4-NH$_2$CH$_2$C$_6$H$_4$ |
| 525 | 3-Me$_2$NCH$_2$C$_6$H$_4$CH$_2$ | 3-NH$_2$CH$_2$C$_6$H$_4$ |
| 526 | 4-Me$_2$NCH$_2$C$_6$H$_4$CH$_2$ | 4-MeOC$_6$H$_4$ |
| 527 | 4-Me$_2$NCH$_2$C$_6$H$_4$CH$_2$ | 3-MeOC$_6$H$_4$ |
| 528 | 4-Me$_2$NCH$_2$C$_6$H$_4$CH$_2$ | 4-NH$_2$C$_6$H$_4$ |
| 529 | 4-Me$_2$NCH$_2$C$_6$H$_4$CH$_2$ | 3-NH$_2$C$_6$H$_4$ |
| 530 | 4-Me$_2$NCH$_2$C$_6$H$_4$CH$_2$ | 2-NH$_2$C$_6$H$_4$ |
| 531 | 4-Me$_2$NCH$_2$C$_6$H$_4$CH$_2$ | 4-Me$_2$NC$_6$H$_4$ |
| 532 | 4-Me$_2$NCH$_2$C$_6$H$_4$CH$_2$ | 3-Me$_2$NC$_6$H$_4$ |
| 533 | 4-Me$_2$NCH$_2$C$_6$H$_4$CH$_2$ | 2-Me$_2$NC$_6$H$_4$ |
| 534 | 4-Me$_2$NCH$_2$C$_6$H$_4$CH$_2$ | 4-pyridyl |
| 535 | 4-Me$_2$NCH$_2$C$_6$H$_4$CH$_2$ | 3-pyridyl |
| 536 | 4-Me$_2$NCH$_2$C$_6$H$_4$CH$_2$ | 2-pyridyl |
| 537 | 4-Me$_2$NCH$_2$C$_6$H$_4$CH$_2$ | 2-thiazolyl |
| 538 | 4-Me$_2$NCH$_2$C$_6$H$_4$CH$_2$ | 2-pyrazolyl |
| 539 | 4-Me$_2$NCH$_2$C$_6$H$_4$CH$_2$ | 5-isoquinolyl |
| 540 | 4-Me$_2$NCH$_2$C$_6$H$_4$CH$_2$ | 3,4-methylenedioxyC$_6$H$_3$ |
| 541 | 4-Me$_2$NCH$_2$C$_6$H$_4$CH$_2$ | 3,4-ethylenedioxyC$_6$H$_3$ |
| 542 | 4-Me$_2$NCH$_2$C$_6$H$_4$CH$_2$ | 2-imidazolyl |
| 543 | 4-Me$_2$NCH$_2$C$_6$H$_4$CH$_2$ | 2-oxazolyl |
| 545 | 4-Me$_2$NCH$_2$C$_6$H$_4$CH$_2$ | 4-isoxazolyl |
| 546 | 4-Me$_2$NCH$_2$C$_6$H$_4$CH$_2$ | 4-HOC$_6$H$_4$ |

TABLE 2-continued

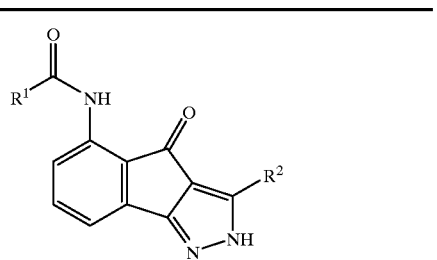

| Example Number | R¹ | R² |
|---|---|---|
| 547 | 4-Me$_2$NCH$_2$C$_6$H$_4$CH$_2$ | 3-HOC$_6$H$_4$ |
| 548 | 4-Me$_2$NCH$_2$C$_6$H$_4$CH$_2$ | 3,4-diHOC$_6$H$_4$ |
| 549 | 4-Me$_2$NCH$_2$C$_6$H$_4$CH$_2$ | 4-NH$_2$CH$_2$C$_6$H$_4$ |
| 550 | 4-Me$_2$NCH$_2$C$_6$H$_4$CH$_2$ | 3-NH$_2$CH$_2$C$_6$H$_4$ |
| 551 | H | 3-MeOC$_6$H$_4$ |
| 552 | H | 4-NH$_2$C$_6$H$_4$ |
| 553 | H | 3-NH$_2$C$_6$H$_4$ |
| 554 | H | 2-NH$_2$C$_6$H$_4$ |
| 555 | H | 4-Me$_2$NC$_6$H$_4$ |
| 556 | H | 3-Me$_2$NC$_6$H$_4$ |
| 557 | H | 2-Me$_2$NC$_6$H$_4$ |
| 558 | H | 3-pyridyl |
| 559 | H | 2-pyridyl |
| 560 | H | 2-thiazolyl |
| 561 | H | 2-pyrazolyl |
| 562 | H | 4-isoquinolyl |
| 563 | H | 3,4-methylenedioxyC$_6$H$_3$ |
| 564 | H | 3,4-ethylenedioxyC$_6$H$_3$ |
| 565 | H | 2-imidazolyl |
| 566 | H | 2-oxazolyl |
| 567 | H | 4-isoxazolyl |
| 568 | H | 4-HOC$_6$H$_4$ |
| 569 | H | 3-HOC$_6$H$_4$ |
| 570 | H | 3,4-diHOC$_6$H$_4$ |
| 571 | H | 4-NH$_2$CH$_2$C$_6$H$_4$ |
| 572 | H | 3-NH$_2$CH$_2$C$_6$H$_4$ |
| 573 | Me | 3-MeOC$_6$H$_4$ |
| 574 | Me | 4-NH$_2$C$_6$H$_4$ |
| 575 | Me | 3-NH$_2$C$_6$H$_4$ |
| 576 | Me | 2-NH$_2$C$_6$H$_4$ |
| 577 | Me | 4-Me$_2$NC$_6$H$_4$ |
| 578 | Me | 3-Me$_2$NC$_6$H$_4$ |
| 579 | Me | 2-Me$_2$NC$_6$H$_4$ |
| 580 | Me | 3-pyridyl |
| 581 | Me | 2-pyridyl |
| 582 | Me | 2-thiazolyl |
| 583 | Me | 2-pyrazolyl |
| 584 | Me | 5-isoquinolyl |
| 585 | Me | 3,4-ethylenedioxyC$_6$H$_3$ |
| 586 | Me | 2-imidazolyl |
| 587 | Me | 2-oxazolyl |
| 588 | Me | 4-isoxazolyl |
| 589 | Me | 3-HOC$_6$H$_4$ |
| 590 | Me | 3,4-diHOC$_6$H$_4$ |
| 591 | Me | 4-NH$_2$CH$_2$C$_6$H$_4$ |
| 592 | Me | 3-NH$_2$CH$_2$C$_6$H$_4$ |
| 593 | Et | 3-MeOC$_6$H$_4$ |
| 594 | Et | 4-NH$_2$C$_6$H$_4$ |
| 595 | Et | 3-NH$_2$C$_6$H$_4$ |
| 596 | Et | 2-NH$_2$C$_6$H$_4$ |
| 597 | Et | 4-Me$_2$NC$_6$H$_4$ |
| 598 | Et | 3-Me$_2$NC$_6$H$_4$ |
| 599 | Et | 2-Me$_2$NC$_6$H$_4$ |
| 600 | Et | 4-pyridyl |
| 601 | Et | 3-pyridyl |
| 601 | Et | 2-pyridyl |
| 603 | Et | 2-thiazolyl |
| 604 | Et | 2-pyrazolyl |
| 605 | Et | 5-isoquinolyl |
| 606 | Et | 3,4-methylenedioxyC$_6$H$_3$ |
| 607 | Et | 3,4-ethylenedioxyC$_6$H$_3$ |
| 608 | Et | 2-imidazolyl |
| 609 | Et | 2-oxazolyl |

TABLE 2-continued

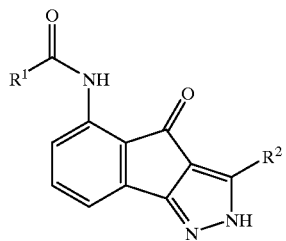

| Example Number | R¹ | R² |
|---|---|---|
| 610 | Et | 4-isoxazolyl |
| 611 | Et | 4-HOC$_6$H$_4$ |
| 612 | Et | 3-HOC$_6$H$_4$ |
| 613 | Et | 3,4-diHOC$_6$H$_4$ |
| 614 | Et | 4-NH$_2$CH$_2$C$_6$H$_4$ |
| 615 | Et | 3-NH$_2$CH$_2$C$_6$H$_4$ |
| 616 | Me$_2$NCH$_2$ | 3-MeOC$_6$H$_4$ |
| 617 | Me$_2$NCH$_2$ | 4-NH$_2$C$_6$H$_4$ |
| 618 | Me$_2$NCH$_2$ | 3-NH$_2$C$_6$H$_4$ |
| 619 | Me$_2$NCH$_2$ | 2-NH$_2$C$_6$H$_4$ |
| 620 | Me$_2$NCH$_2$ | 4-Me$_2$NC$_6$H$_4$ |
| 621 | Me$_2$NCH$_2$ | 3-Me$_2$NC$_6$H$_4$ |
| 622 | Me$_2$NCH$_2$ | 2-Me$_2$NC$_6$H$_4$ |
| 623 | Me$_2$NCH$_2$ | 4-pyridyl |
| 624 | Me$_2$NCH$_2$ | 3-pyridyl |
| 625 | Me$_2$NCH$_2$ | 2-pyridyl |
| 626 | Me$_2$NCH$_2$ | 2-thiazolyl |
| 627 | Me$_2$NCH$_2$ | 2-pyrazolyl |
| 628 | Me$_2$NCH$_2$ | 5-isoquinolyl |
| 629 | Me$_2$NCH$_2$ | 3,4-methylenedioxyC$_6$H$_3$ |
| 630 | Me$_2$NCH$_2$ | 3,4-ethylenedioxyC$_6$H$_3$ |
| 631 | Me$_2$NCH$_2$ | 2-imidazolyl |
| 632 | Me$_2$NCH$_2$ | 2-oxazolyl |
| 633 | Me$_2$NCH$_2$ | 4-isoxazolyl |
| 634 | Me$_2$NCH$_2$ | 4-HOC$_6$H$_4$ |
| 635 | Me$_2$NCH$_2$ | 3-HOC$_6$H$_4$ |
| 636 | Me$_2$NCH$_2$ | 3,4-diHOC$_6$H$_4$ |
| 637 | Me$_2$NCH$_2$ | 4-NH$_2$CH$_2$C$_6$H$_4$ |
| 638 | Me$_2$NCH$_2$ | 3-NH$_2$CH$_2$C$_6$H$_4$ |
| 639 | EtNHCH$_2$ | 3-MeOC$_6$H$_4$ |
| 640 | EtNHCH$_2$ | 4-NH$_2$C$_6$H$_4$ |
| 641 | EtNHCH$_2$ | 3-NH$_2$C$_6$H$_4$ |
| 642 | EtNHCH$_2$ | 2-NH$_2$C$_6$H$_4$ |
| 643 | EtNHCH$_2$ | 4-Me$_2$NC$_6$H$_4$ |
| 644 | EtNHCH$_2$ | 3-Me$_2$NC$_6$H$_4$ |
| 645 | EtNHCH$_2$ | 2-Me$_2$NC$_6$H$_4$ |
| 646 | EtNHCH$_2$ | 4-pyridyl |
| 647 | EtNHCH$_2$ | 3-pyridyl |
| 648 | EtNHCH$_2$ | 2-pyridyl |
| 649 | EtNHCH$_2$ | 2-thiazolyl |
| 650 | EtNHCH$_2$ | 2-pyrazolyl |
| 651 | EtNHCH$_2$ | 5-isoquinolyl |
| 652 | EtNHCH$_2$ | 3,4-methylenedioxyC$_6$H$_3$ |
| 653 | EtNHCH$_2$ | 3,4-ethylenedioxyC$_6$H$_3$ |
| 654 | EtNHCH$_2$ | 2-imidazolyl |
| 655 | EtNHCH$_2$ | 2-oxazolyl |
| 656 | EtNHCH$_2$ | 4-isoxazolyl |
| 657 | EtNHCH$_2$ | 4-HOC$_6$H$_4$ |
| 658 | EtNHCH$_2$ | 3-HOC$_6$H$_4$ |
| 659 | EtNHCH$_2$ | 3,4-diHOC$_6$H$_4$ |
| 660 | EtNHCH$_2$ | 4-NH$_2$CH$_2$C$_6$H$_4$ |
| 661 | EtNHCH$_2$ | 3-NH$_2$CH$_2$C$_6$H$_4$ |
| 662 | HOCH$_2$CH$_2$NHCH$_2$ | 3-MeOC$_6$H$_4$ |
| 663 | HOCH$_2$CH$_2$NHCH$_2$ | 4-NH$_2$C$_6$H$_4$ |
| 664 | HOCH$_2$CH$_2$NHCH$_2$ | 3-NH$_2$C$_6$H$_4$ |
| 665 | HOCH$_2$CH$_2$NHCH$_2$ | 2-NH$_2$C$_6$H$_4$ |
| 666 | HOCH$_2$CH$_2$NHCH$_2$ | 4-Me$_2$NC$_6$H$_4$ |
| 667 | HOCH$_2$CH$_2$NHCH$_2$ | 3-Me$_2$NC$_6$H$_4$ |
| 668 | HOCH$_2$CH$_2$NHCH$_2$ | 2-Me$_2$NC$_6$H$_4$ |
| 669 | HOCH$_2$CH$_2$NHCH$_2$ | 4-pyridyl |
| 670 | HOCH$_2$CH$_2$NHCH$_2$ | 3-pyridyl |
| 671 | HOCH$_2$CH$_2$NHCH$_2$ | 2-pyridyl |
| 672 | HOCH$_2$CH$_2$NHCH$_2$ | 2-thiazolyl |

TABLE 2-continued

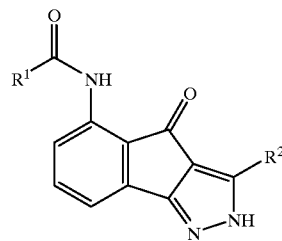

| Example Number | R¹ | R² |
|---|---|---|
| 673 | HOCH$_2$CH$_2$NHCH$_2$ | 2-pyrazolyl |
| 674 | HOCH$_2$CH$_2$NHCH$_2$ | 5-isoquinolyl |
| 675 | HOCH$_2$CH$_2$NHCH$_2$ | 3,4-methylenedioxyC$_6$H$_3$ |
| 676 | HOCH$_2$CH$_2$NHCH$_2$ | 3,4-ethylenedioxyC$_6$H$_3$ |
| 677 | HOCH$_2$CH$_2$NHCH$_2$ | 2-imidazolyl |
| 678 | HOCH$_2$CH$_2$NHCH$_2$ | 2-oxazolyl |
| 679 | HOCH$_2$CH$_2$NHCH$_2$ | 4-isoxazolyl |
| 680 | HOCH$_2$CH$_2$NHCH$_2$ | 4-HOC$_6$H$_4$ |
| 681 | HOCH$_2$CH$_2$NHCH$_2$ | 3-HOC$_6$H$_4$ |
| 682 | HOCH$_2$CH$_2$NHCH$_2$ | 3,4-diHOC$_6$H$_4$ |
| 683 | HOCH$_2$CH$_2$NHCH$_2$ | 4-NH$_2$CH$_2$C$_6$H$_4$ |
| 684 | HOCH$_2$CH$_2$NHCH$_2$ | 3-NH$_2$CH$_2$C$_6$H$_4$ |
| 685 | H$_2$NCH$_2$CH$_2$NHCH$_2$ | 4-MeOC$_6$H$_4$ |
| 686 | H$_2$NCH$_2$CH$_2$NHCH$_2$ | 3-MeOC$_6$H$_4$ |
| 687 | H$_2$NCH$_2$CH$_2$NHCH$_2$ | 4-NH$_2$C$_6$H$_4$ |
| 688 | H$_2$NCH$_2$CH$_2$NHCH$_2$ | 3-NH$_2$C$_6$H$_4$ |
| 689 | H$_2$NCH$_2$CH$_2$NHCH$_2$ | 2-NH$_2$C$_6$H$_4$ |
| 690 | H$_2$NCH$_2$CH$_2$NHCH$_2$ | 4-Me$_2$NC$_6$H$_4$ |
| 691 | H$_2$NCH$_2$CH$_2$NHCH$_2$ | 3-Me$_2$NC$_6$H$_4$ |
| 692 | H$_2$NCH$_2$CH$_2$NHCH$_2$ | 2-Me$_2$NC$_6$H$_4$ |
| 693 | H$_2$NCH$_2$CH$_2$NHCH$_2$ | 4-pyridyl |
| 694 | H$_2$NCH$_2$CH$_2$NHCH$_2$ | 3-pyridyl |
| 695 | H$_2$NCH$_2$CH$_2$NHCH$_2$ | 2-pyridyl |
| 696 | H$_2$NCH$_2$CH$_2$NHCH$_2$ | 2-thiazolyl |
| 697 | H$_2$NCH$_2$CH$_2$NHCH$_2$ | 2-pyrazolyl |
| 698 | H$_2$NCH$_2$CH$_2$NHCH$_2$ | 5-isoquinolyl |
| 699 | H$_2$NCH$_2$CH$_2$NHCH$_2$ | 3,4-methylenedioxyC$_6$H$_3$ |
| 700 | H$_2$NCH$_2$CH$_2$NHCH$_2$ | 3,4-ethylenedioxyC$_6$H$_3$ |
| 701 | H$_2$NCH$_2$CH$_2$NHCH$_2$ | 2-imidazolyl |
| 702 | H$_2$NCH$_2$CH$_2$NHCH$_2$ | 2-oxazolyl |
| 703 | H$_2$NCH$_2$CH$_2$NHCH$_2$ | 4-isoxazolyl |
| 704 | H$_2$NCH$_2$CH$_2$NHCH$_2$ | 4-HOC$_6$H$_4$ |
| 705 | H$_2$NCH$_2$CH$_2$NHCH$_2$ | 3-HOC$_6$H$_4$ |
| 706 | H$_2$NCH$_2$CH$_2$NHCH$_2$ | 3,4-diHOC$_6$H$_4$ |
| 707 | H$_2$NCH$_2$CH$_2$NHCH$_2$ | 4-NH$_2$CH$_2$C$_6$H$_4$ |
| 708 | H$_2$NCH$_2$CH$_2$NHCH$_2$ | 3-NH$_2$CH$_2$C$_6$H$_4$ |
| 709 | Me$_2$NCH$_2$CH$_2$NHCH$_2$ | 4-MeOC$_6$H$_4$ |
| 710 | Me$_2$NCH$_2$CH$_2$NHCH$_2$ | 3-MeOC$_6$H$_4$ |
| 711 | Me$_2$NCH$_2$CH$_2$NHCH$_2$ | 4-NH$_2$C$_6$H$_4$ |
| 712 | Me$_2$NCH$_2$CH$_2$NHCH$_2$ | 3-NH$_2$C$_6$H$_4$ |
| 713 | Me$_2$NCH$_2$CH$_2$NHCH$_2$ | 2-NH$_2$C$_6$H$_4$ |
| 714 | Me$_2$NCH$_2$CH$_2$NHCH$_2$ | 4-Me$_2$NC$_6$H$_4$ |
| 715 | Me$_2$NCH$_2$CH$_2$NHCH$_2$ | 3-Me$_2$NC$_6$H$_4$ |
| 716 | Me$_2$NCH$_2$CH$_2$NHCH$_2$ | 2-Me$_2$NC$_6$H$_4$ |
| 717 | Me$_2$NCH$_2$CH$_2$NHCH$_2$ | 4-pyridyl |
| 718 | Me$_2$NCH$_2$CH$_2$NHCH$_2$ | 3-pyridyl |
| 719 | Me$_2$NCH$_2$CH$_2$NHCH$_2$ | 2-pyridyl |
| 720 | Me$_2$NCH$_2$CH$_2$NHCH$_2$ | 2-thiazolyl |
| 721 | Me$_2$NCH$_2$CH$_2$NHCH$_2$ | 2-pyrazolyl |
| 722 | Me$_2$NCH$_2$CH$_2$NHCH$_2$ | 5-isoquinolyl |
| 723 | Me$_2$NCH$_2$CH$_2$NHCH$_2$ | 3,4-methylenedioxyC$_6$H$_3$ |
| 724 | Me$_2$NCH$_2$CH$_2$NHCH$_2$ | 3,4-ethylenedioxyC$_6$H$_3$ |
| 725 | Me$_2$NCH$_2$CH$_2$NHCH$_2$ | 2-imidazolyl |
| 726 | Me$_2$NCH$_2$CH$_2$NHCH$_2$ | 2-oxazolyl |
| 727 | Me$_2$NCH$_2$CH$_2$NHCH$_2$ | 4-isoxazolyl |
| 728 | Me$_2$NCH$_2$CH$_2$NHCH$_2$ | 4-HOC$_6$H$_4$ |
| 729 | Me$_2$NCH$_2$CH$_2$NHCH$_2$ | 3-HOC$_6$H$_4$ |
| 730 | Me$_2$NCH$_2$CH$_2$NHCH$_2$ | 3,4-diHOC$_6$H$_4$ |
| 731 | Me$_2$NCH$_2$CH$_2$NHCH$_2$ | 4-NH$_2$CH$_2$C$_6$H$_4$ |
| 732 | Me$_2$NCH$_2$CH$_2$NHCH$_2$ | 3-NH$_2$CH$_2$C$_6$H$_4$ |
| 733 | 1-morpholinylmethyl | 3-MeOC$_6$H$_4$ |
| 734 | 1-morpholinylmethyl | 4-NH$_2$C$_6$H$_4$ |
| 735 | 1-morpholinylmethyl | 3-NH$_2$C$_6$H$_4$ |

TABLE 2-continued

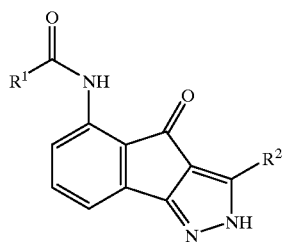

| Example Number | R¹ | R² |
|---|---|---|
| 736 | 1-morpholinylmethyl | 2-NH₂C₆H₄ |
| 737 | 1-morpholinylmethyl | 4-Me₂NC₆H₄ |
| 738 | 1-morpholinylmethyl | 3-Me₂NC₆H₄ |
| 739 | 1-morpholinylmethyl | 2-Me₂NC₆H₄ |
| 740 | 1-morpholinylmethyl | 4-pyridyl |
| 741 | 1-morpholinylmethyl | 3-pyridyl |
| 742 | 1-morpholinylmethyl | 2-pyridyl |
| 743 | 1-morpholinylmethyl | 2-thiazolyl |
| 744 | 1-morpholinylmethyl | 2-pyrazolyl |
| 745 | 1-morpholinylmethyl | 5-isoquinolyl |
| 746 | 1-morpholinylmethyl | 3,4-methylenedioxyC₆H₃ |
| 747 | 1-morpholinylmethyl | 3,4-ethylenedioxyC₆H₃ |
| 748 | 1-morpholinylmethyl | 2-imidazolyl |
| 749 | 1-morpholinylmethyl | 2-oxazolyl |
| 750 | 1-morpholinylmethyl | 4-isoxazolyl |
| 751 | 1-morpholinylmethyl | 4-HOC₆H₄ |
| 752 | 1-morpholinylmethyl | 3-HOC₆H₄ |
| 753 | 1-morpholinylmethyl | 3,4-diHOC₆H₄ |
| 754 | 1-morpholinylmethyl | 4-NH₂CH₂C₆H₄ |
| 755 | 1-morpholinylmethyl | 3-NH₂CH₂C₆H₄ |
| 756 | 1-thiomorpholinylmethyl | 3-MeOC₆H₄ |
| 757 | 1-thiomorpholinylmethyl | 4-NH₂C₆H₄ |
| 758 | 1-thiomorpholinylmethyl | 3-NH₂C₆H₄ |
| 759 | 1-thiomorpholinylmethyl | 2-NH₂C₆H₄ |
| 760 | 1-thiomorpholinylmethyl | 4-Me₂NC₆H₄ |
| 761 | 1-thiomorpholinylmethyl | 3-Me₂NC₆H₄ |
| 762 | 1-thiomorpholinylmethyl | 2-Me₂NC₆H₄ |
| 763 | 1-thiomorpholinylmethyl | 4-pyridyl |
| 764 | 1-thiomorpholinylmethyl | 3-pyridyl |
| 765 | 1-thiomorpholinylmethyl | 2-pyridyl |
| 766 | 1-thiomorpholinylmethyl | 2-thiazolyl |
| 767 | 1-thiomorpholinylmethyl | 2-pyrazolyl |
| 768 | 1-thiomorpholinylmethyl | 5-isoquinolyl |
| 769 | 1-thiomorpholinylmethyl | 3,4-methylenedioxyC₆H₃ |
| 771 | 1-thiomorpholinylmethyl | 2-imidazolyl |
| 772 | 1-thiomorpholinylmethyl | 2-oxazolyl |
| 773 | 1-thiomorpholinylmethyl | 4-isoxazolyl |
| 774 | 1-thiomorpholinylmethyl | 4-HOC₆H₄ |
| 775 | 1-thiomorpholinylmethyl | 3-HOC₆H₄ |
| 776 | 1-thiomorpholinylmethyl | 3,4-diHOC₆H₄ |
| 777 | 1-thiomorpholinylmethyl | 4-NH₂CH₂C₆H₄ |
| 778 | 1-thiomorpholinylmethyl | 3-NH₂CH₂C₆H₄ |
| 779 | 1-piperazinylmethyl | 3-MeOC₆H₄ |
| 780 | 1-piperazinylmethyl | 4-NH₂C₆H₄ |
| 781 | 1-piperazinylmethyl | 3-NH₂C₆H₄ |
| 782 | 1-piperazinylmethyl | 2-NH₂C₆H₄ |
| 783 | 1-piperazinylmethyl | 4-Me₂NC₆H₄ |
| 784 | 1-piperazinylmethyl | 3-Me₂NC₆H₄ |
| 785 | 1-piperazinylmethyl | 2-Me₂NC₆H₄ |
| 786 | 1-piperazinylmethyl | 4-pyridyl |
| 787 | 1-piperazinylmethyl | 3-pyridyl |
| 788 | 1-piperazinylmethyl | 2-pyridyl |
| 789 | 1-piperazinylmethyl | 2-thiazolyl |
| 790 | 1-piperazinylmethyl | 2-pyrazolyl |
| 791 | 1-piperazinylmethyl | 5-isoquinolyl |
| 792 | 1-piperazinylmethyl | 3,4-methylenedioxyC₆H₃ |
| 793 | 1-piperazinylmethyl | 3,4-ethylenedioxyC₆H₃ |
| 794 | 1-piperazinylmethyl | 2-imidazolyl |
| 795 | 1-piperazinylmethyl | 2-oxazolyl |
| 796 | 1-piperazinylmethyl | 4-isoxazolyl |
| 797 | 1-piperazinylmethyl | 4-HOC₆H₄ |
| 798 | 1-piperazinylmethyl | 3-HOC₆H₄ |
| 799 | 1-piperazinylmethyl | 3,4-diHOC₆H₄ |

TABLE 2-continued

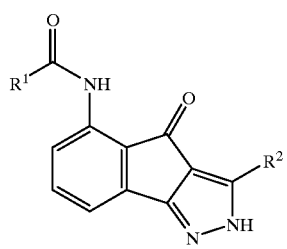

| Example Number | R¹ | R² |
|---|---|---|
| 800 | 1-piperazinylmethyl | 4-NH₂CH₂C₆H₄ |
| 801 | 1-piperazinylmethyl | 3-NH₂CH₂C₆H₄ |

TABLE 3

| Example Number | R¹ | R² |
|---|---|---|
| 802 | 2-pyridylmethyl | 4-MeOC₆H₄ |
| 803 | 2-pyridylmethyl | 3-MeOC₆H₄ |
| 804 | 2-pyridylmethyl | 4-NH₂C₆H₄ |
| 805 | 2-pyridylmethyl | 3-NH₂C₆H₄ |
| 806 | 2-pyridylmethyl | 2-NH₂C₆H₄ |
| 807 | 2-pyridylmethyl | 4-Me₂NC₆H₄ |
| 808 | 2-pyridylmethyl | 3-Me₂NC₆H₄ |
| 809 | 2-pyridylmethyl | 2-Me₂NC₆H₄ |
| 810 | 2-pyridylmethyl | 4-pyridyl |
| 811 | 2-pyridylmethyl | 3-pyridyl |
| 812 | 2-pyridylmethyl | 2-pyridyl |
| 813 | 2-pyridylmethyl | 2-thiazolyl |
| 814 | 2-pyridylmethyl | 2-pyrazolyl |
| 815 | 2-pyridylmethyl | 5-isoquinolyl |
| 816 | 2-pyridylmethyl | 3,4-methylenedioxyC₆H₃ |
| 817 | 2-pyridylmethyl | 3,4-ethylenedioxyC₆H₃ |
| 818 | 2-pyridylmethyl | 2-imidazolyl |
| 819 | 2-pyridylmethyl | 2-oxazolyl |
| 820 | 2-pyridylmethyl | 4-isoxazolyl |
| 821 | 2-pyridylmethyl | 4-HOC₆H₄ |
| 822 | 2-pyridylmethyl | 3-HOC₆H₄ |
| 823 | 2-pyridylmethyl | 3,4-diHOC₆H₄ |
| 824 | 2-pyridylmethyl | 4-NH₂CH₂C₆H₄ |
| 825 | 2-pyridylmethyl | 3-NH₂CH₂C₆H₄ |
| 826 | 3-pyridylmethyl | 4-MeOC₆H₄ |
| 827 | 3-pyridylmethyl | 3-MeOC₆H₄ |
| 828 | 3-pyridylmethyl | 4-NH₂C₆H₄ |
| 829 | 3-pyridylmethyl | 3-NH₂C₆H₄ |
| 830 | 3-pyridylmethyl | 2-NH₂C₆H₄ |
| 831 | 3-pyridylmethyl | 4-Me₂NC₆H₄ |
| 832 | 3-pyridylmethyl | 3-Me₂NC₆H₄ |
| 833 | 3-pyridylmethyl | 2-Me₂NC₆H₄ |
| 834 | 3-pyridylmethyl | 4-pyridyl |
| 835 | 3-pyridylmethyl | 3-pyridyl |
| 836 | 3-pyridylmethyl | 2-pyridyl |
| 837 | 3-pyridylmethyl | 2-thiazolyl |
| 838 | 3-pyridylmethyl | 2-pyrazolyl |
| 839 | 3-pyridylmethyl | 5-isoquinolyl |
| 840 | 3-pyridylmethyl | 3,4-methylenedioxyC₆H₃ |
| 841 | 3-pyridylmethyl | 3,4-ethylenedioxyC₆H₃ |

TABLE 3-continued

[Structure: R¹-NH-C(=O)-NH- attached to indeno-pyrazolone core with R² substituent]

| Example Number | R¹ | R² |
|---|---|---|
| 842 | 3-pyridylmethyl | 2-imidazolyl |
| 843 | 3-pyridylmethyl | 2-oxazolyl |
| 844 | 3-pyridylmethyl | 4-isoxazolyl |
| 845 | 3-pyridylmethyl | 4-HOC$_6$H$_4$ |
| 846 | 3-pyridylmethyl | 3-HOC$_6$H$_4$ |
| 847 | 3-pyridylmethyl | 3,4-diHOC$_6$H$_4$ |
| 848 | 3-pyridylmethyl | 4-NH$_2$CH$_2$C$_6$H$_4$ |
| 849 | 3-pyridylmethyl | 3-NH$_2$CH$_2$C$_6$H$_4$ |
| 850 | 4-pyridylmethyl | 4-MeOC$_6$H$_4$ |
| 851 | 4-pyridylmethyl | 3-MeOC$_6$H$_4$ |
| 852 | 4-pyridylmethyl | 4-NH$_2$C$_6$H$_4$ |
| 853 | 4-pyridylmethyl | 3-NH$_2$C$_6$H$_4$ |
| 854 | 4-pyridylmethyl | 2-NH$_2$C$_6$H$_4$ |
| 855 | 4-pyridylmethyl | 4-Me$_2$NC$_6$H$_4$ |
| 856 | 4-pyridylmethyl | 3-Me$_2$NC$_6$H$_4$ |
| 857 | 4-pyridylmethyl | 2-Me$_2$NC$_6$H$_4$ |
| 858 | 4-pyridylmethyl | 4-pyridyl |
| 859 | 4-pyridylmethyl | 3-pyridyl |
| 860 | 4-pyridylmethyl | 2-pyridyl |
| 861 | 4-pyridylmethyl | 2-thiazolyl |
| 862 | 4-pyridylmethyl | 2-pyrazolyl |
| 863 | 4-pyridylmethyl | 5-isoquinolyl |
| 864 | 4-pyridylmethyl | 3,4-methylenedioxyC$_6$H$_3$ |
| 865 | 4-pyridylmethyl | 3,4-ethylenedioxyC$_6$H$_3$ |
| 866 | 4-pyridylmethyl | 2-imidazolyl |
| 867 | 4-pyridylmethyl | 2-oxazolyl |
| 868 | 4-pyridylmethyl | 4-isoxazolyl |
| 869 | 4-pyridylmethyl | 4-HOC$_6$H$_4$ |
| 870 | 4-pyridylmethyl | 3-HOC$_6$H$_4$ |
| 871 | 4-pyridylmethyl | 3,4-diHOC$_6$H$_4$ |
| 872 | 4-pyridylmethyl | 4-NH$_2$CH$_2$C$_6$H$_4$ |
| 873 | 4-pyridylmethyl | 3-NH$_2$CH$_2$C$_6$H$_4$ |
| 874 | 2-NH$_2$C$_6$H$_4$ | 4-MeOC$_6$H$_4$ |
| 875 | 2-NH$_2$C$_6$H$_4$ | 3-MeOC$_6$H$_4$ |
| 876 | 2-NH$_2$C$_6$H$_4$ | 4-NH$_2$C$_6$H$_4$ |
| 877 | 2-NH$_2$C$_6$H$_4$ | 3-NH$_2$C$_6$H$_4$ |
| 878 | 2-NH$_2$C$_6$H$_4$ | 2-NH$_2$C$_6$H$_4$ |
| 879 | 2-NH$_2$C$_6$H$_4$ | 4-Me$_2$NC$_6$H$_4$ |
| 880 | 2-NH$_2$C$_6$H$_4$ | 3-Me$_2$NC$_6$H$_4$ |
| 881 | 2-NH$_2$C$_6$H$_4$ | 2-Me$_2$NC$_6$H$_4$ |
| 882 | 2-NH$_2$C$_6$H$_4$ | 4-pyridyl |
| 883 | 2-NH$_2$C$_6$H$_4$ | 3-pyridyl |
| 884 | 2-NH$_2$C$_6$H$_4$ | 2-pyridyl |
| 885 | 2-NH$_2$C$_6$H$_4$ | 2-thiazolyl |
| 886 | 2-NH$_2$C$_6$H$_4$ | 2-pyrazolyl |
| 887 | 2-NH$_2$C$_6$H$_4$ | 5-isoquinolyl |
| 888 | 2-NH$_2$C$_6$H$_4$ | 3,4-methylenedioxyC$_6$H$_3$ |
| 889 | 2-NH$_2$C$_6$H$_4$ | 3,4-ethylenedioxyC$_6$H$_3$ |
| 890 | 2-NH$_2$C$_6$H$_4$ | 2-imidazolyl |
| 891 | 2-NH$_2$C$_6$H$_4$ | 2-oxazolyl |
| 892 | 2-NH$_2$C$_6$H$_4$ | 4-isoxazolyl |
| 893 | 2-NH$_2$C$_6$H$_4$ | 4-HOC$_6$H$_4$ |
| 894 | 2-NH$_2$C$_6$H$_4$ | 3-HOC$_6$H$_4$ |
| 895 | 2-NH$_2$C$_6$H$_4$ | 3,4-diHOC$_6$H$_4$ |
| 896 | 2-NH$_2$C$_6$H$_4$ | 4-NH$_2$CH$_2$C$_6$H$_4$ |
| 897 | 2-NH$_2$C$_6$H$_4$ | 3-NH$_2$CH$_2$C$_6$H$_4$ |
| 898 | 3-NH$_2$C$_6$H$_4$ | 4-MeOC$_6$H$_4$ |
| 899 | 3-NH$_2$C$_6$H$_4$ | 3-MeOC$_6$H$_4$ |
| 900 | 3-NH$_2$C$_6$H$_4$ | 4-NH$_2$C$_6$H$_4$ |
| 901 | 3-NH$_2$C$_6$H$_4$ | 3-NH$_2$C$_6$H$_4$ |
| 902 | 3-NH$_2$C$_6$H$_4$ | 2-NH$_2$C$_6$H$_4$ |
| 903 | 3-NH$_2$C$_6$H$_4$ | 4-Me$_2$NC$_6$H$_4$ |
| 904 | 3-NH$_2$C$_6$H$_4$ | 3-Me$_2$NC$_6$H$_4$ |
| 905 | 3-NH$_2$C$_6$H$_4$ | 2-Me$_2$NC$_6$H$_4$ |
| 906 | 3-NH$_2$C$_6$H$_4$ | 4-pyridyl |
| 907 | 3-NH$_2$C$_6$H$_4$ | 3-pyridyl |
| 908 | 3-NH$_2$C$_6$H$_4$ | 2-pyridyl |
| 909 | 3-NH$_2$C$_6$H$_4$ | 2-thiazolyl |
| 910 | 3-NH$_2$C$_6$H$_4$ | 2-pyrazolyl |
| 911 | 3-NH$_2$C$_6$H$_4$ | 5-isoquinolyl |
| 912 | 3-NH$_2$C$_6$H$_4$ | 3,4-methylenedioxyC$_6$H$_3$ |
| 913 | 3-NH$_2$C$_6$H$_4$ | 3,4-ethylenedioxyC$_6$H$_3$ |
| 914 | 3-NH$_2$C$_6$H$_4$ | 2-imidazolyl |
| 915 | 3-NH$_2$C$_6$H$_4$ | 2-oxazolyl |
| 916 | 3-NH$_2$C$_6$H$_4$ | 4-isoxazolyl |
| 917 | 3-NH$_2$C$_6$H$_4$ | 4-HOC$_6$H$_4$ |
| 918 | 3-NH$_2$C$_6$H$_4$ | 3-HOC$_6$H$_4$ |
| 919 | 3-NH$_2$C$_6$H$_4$ | 3,4-diHOC$_6$H$_4$ |
| 920 | 3-NH$_2$C$_6$H$_4$ | 4-NH$_2$CH$_2$C$_6$H$_4$ |
| 921 | 3-NH$_2$C$_6$H$_4$ | 3-NH$_2$CH$_2$C$_6$H$_4$ |
| 922 | 4-NH$_2$C$_6$H$_4$ | 4-MeOC$_6$H$_4$ |
| 923 | 4-NH$_2$C$_6$H$_4$ | 3-MeOC$_6$H$_4$ |
| 924 | 4-NH$_2$C$_6$H$_4$ | 4-NH$_2$C$_6$H$_4$ |
| 925 | 4-NH$_2$C$_6$H$_4$ | 3-NH$_2$C$_6$H$_4$ |
| 926 | 4-NH$_2$C$_6$H$_4$ | 2-NH$_2$C$_6$H$_4$ |
| 927 | 4-NH$_2$C$_6$H$_4$ | 4-Me$_2$NC$_6$H$_4$ |
| 928 | 4-NH$_2$C$_6$H$_4$ | 3-Me$_2$NC$_6$H$_4$ |
| 930 | 4-NH$_2$C$_6$H$_4$ | 2-Me$_2$NC$_6$H$_4$ |
| 931 | 4-NH$_2$C$_6$H$_4$ | 4-pyridyl |
| 932 | 4-NH$_2$C$_6$H$_4$ | 3-pyridyl |
| 933 | 4-NH$_2$C$_6$H$_4$ | 2-pyridyl |
| 934 | 4-NH$_2$C$_6$H$_4$ | 2-thiazolyl |
| 935 | 4-NH$_2$C$_6$H$_4$ | 2-pyrazolyl |
| 936 | 4-NH$_2$C$_6$H$_4$ | 5-isoquinolyl |
| 937 | 4-NH$_2$C$_6$H$_4$ | 3,4-methylenedioxyC$_6$H$_3$ |
| 938 | 4-NH$_2$C$_6$H$_4$ | 3,4-ethylenedioxyC$_6$H$_3$ |
| 939 | 4-NH$_2$C$_6$H$_4$ | 2-imidazolyl |
| 940 | 4-NH$_2$C$_6$H$_4$ | 2-oxazolyl |
| 941 | 4-NH$_2$C$_6$H$_4$ | 4-isoxazolyl |
| 942 | 4-NH$_2$C$_6$H$_4$ | 4-HOC$_6$H$_4$ |
| 943 | 4-NH$_2$C$_6$H$_4$ | 3-HOC$_6$H$_4$ |
| 944 | 4-NH$_2$C$_6$H$_4$ | 3,4-diHOC$_6$H$_4$ |
| 945 | 4-NH$_2$C$_6$H$_4$ | 4-NH$_2$CH$_2$C$_6$H$_4$ |
| 946 | 4-NH$_2$C$_6$H$_4$ | 3-NH$_2$CH$_2$C$_6$H$_4$ |
| 947 | 2-MeOC$_6$H$_4$ | 4-MeOC$_6$H$_4$ |
| 948 | 2-MeOC$_6$H$_4$ | 3-MeOC$_6$H$_4$ |
| 949 | 2-MeOC$_6$H$_4$ | 4-NH$_2$C$_6$H$_4$ |
| 950 | 2-MeOC$_6$H$_4$ | 3-NH$_2$C$_6$H$_4$ |
| 951 | 2-MeOC$_6$H$_4$ | 2-NH$_2$C$_6$H$_4$ |
| 952 | 2-MeOC$_6$H$_4$ | 4-Me$_2$NC$_6$H$_4$ |
| 953 | 2-MeOC$_6$H$_4$ | 3-Me$_2$NC$_6$H$_4$ |
| 954 | 2-MeOC$_6$H$_4$ | 2-Me$_2$NC$_6$H$_4$ |
| 955 | 2-MeOC$_6$H$_4$ | 4-pyridyl |
| 956 | 2-MeOC$_6$H$_4$ | 3-pyridyl |
| 957 | 2-MeOC$_6$H$_4$ | 2-pyridyl |
| 958 | 2-MeOC$_6$H$_4$ | 2-thiazolyl |
| 959 | 2-MeOC$_6$H$_4$ | 2-pyrazolyl |
| 960 | 2-MeOC$_6$H$_4$ | 5-isoquinolyl |
| 961 | 2-MeOC$_6$H$_4$ | 3,4-methylenedioxyC$_6$H$_3$ |
| 962 | 2-MeOC$_6$H$_4$ | 3,4-ethylenedioxyC$_6$H$_3$ |
| 963 | 2-MeOC$_6$H$_4$ | 2-imidazolyl |
| 964 | 2-MeOC$_6$H$_4$ | 2-oxazolyl |
| 965 | 2-MeOC$_6$H$_4$ | 4-isoxazolyl |
| 966 | 2-MeOC$_6$H$_4$ | 4-HOC$_6$H$_4$ |
| 967 | 2-MeOC$_6$H$_4$ | 3-HOC$_6$H$_4$ |
| 968 | 2-MeOC$_6$H$_4$ | 3,4-diHOC$_6$H$_4$ |

TABLE 3-continued

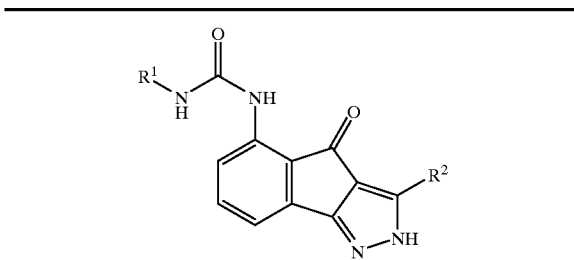

| Example Number | R¹ | R² |
|---|---|---|
| 969 | 2-MeOC$_6$H$_4$ | 4-NH$_2$CH$_2$C$_6$H$_4$ |
| 970 | 2-MeOC$_6$H$_4$ | 3-NH$_2$CH$_2$C$_6$H$_4$ |
| 971 | 3-MeOC$_6$H$_4$ | 4-MeOC$_6$H$_4$ |
| 972 | 3-MeOC$_6$H$_4$ | 3-MeOC$_6$H$_4$ |
| 973 | 3-MeOC$_6$H$_4$ | 4-NH$_2$C$_6$H$_4$ |
| 974 | 3-MeOC$_6$H$_4$ | 3-NH$_2$C$_6$H$_4$ |
| 975 | 3-MeOC$_6$H$_4$ | 2-NH$_2$C$_6$H$_4$ |
| 976 | 3-MeOC$_6$H$_4$ | 4-Me$_2$NC$_6$H$_4$ |
| 977 | 3-MeOC$_6$H$_4$ | 3-Me$_2$NC$_6$H$_4$ |
| 978 | 3-MeOC$_6$H$_4$ | 2-Me$_2$NC$_6$H$_4$ |
| 979 | 3-MeOC$_6$H$_4$ | 4-pyridyl |
| 980 | 3-MeOC$_6$H$_4$ | 3-pyridyl |
| 981 | 3-MeOC$_6$H$_4$ | 2-pyridyl |
| 982 | 3-MeOC$_6$H$_4$ | 2-thiazolyl |
| 983 | 3-MeOC$_6$H$_4$ | 2-pyrazolyl |
| 984 | 3-MeOC$_6$H$_4$ | 5-isoquinolyl |
| 985 | 3-MeOC$_6$H$_4$ | 3,4-methylenedioxyC$_6$H$_3$ |
| 986 | 3-MeOC$_6$H$_4$ | 3,4-ethylenedioxyC$_6$H$_3$ |
| 987 | 3-MeOC$_6$H$_4$ | 2-imidazolyl |
| 988 | 3-MeOC$_6$H$_4$ | 2-oxazolyl |
| 989 | 3-MeOC$_6$H$_4$ | 4-isoxazolyl |
| 990 | 3-MeOC$_6$H$_4$ | 4-HOC$_6$H$_4$ |
| 991 | 3-MeOC$_6$H$_4$ | 3-HOC$_6$H$_4$ |
| 992 | 3-MeOC$_6$H$_4$ | 3,4-diHOC$_6$H$_4$ |
| 993 | 3-MeOC$_6$H$_4$ | 4-NH$_2$CH$_2$C$_6$H$_4$ |
| 994 | 3-MeOC$_6$H$_4$ | 3-NH$_2$CH$_2$C$_6$H$_4$ |
| 995 | 4-MeOC$_6$H$_4$ | 4-MeOC$_6$H$_4$ |
| 996 | 4-MeOC$_6$H$_4$ | 3-MeOC$_6$H$_4$ |
| 997 | 4-MeOC$_6$H$_4$ | 4-NH$_2$C$_6$H$_4$ |
| 998 | 4-MeOC$_6$H$_4$ | 3-NH$_2$C$_6$H$_4$ |
| 999 | 4-MeOC$_6$H$_4$ | 2-NH$_2$C$_6$H$_4$ |
| 1000 | 4-MeOC$_6$H$_4$ | 4-Me$_2$NC$_6$H$_4$ |
| 1001 | 4-MeOC$_6$H$_4$ | 3-Me$_2$NC$_6$H$_4$ |
| 1002 | 4-MeOC$_6$H$_4$ | 2-Me$_2$NC$_6$H$_4$ |
| 1003 | 4-MeOC$_6$H$_4$ | 4-pyridyl |
| 1004 | 4-MeOC$_6$H$_4$ | 3-pyridyl |
| 1005 | 4-MeOC$_6$H$_4$ | 2-pyridyl |
| 1006 | 4-MeOC$_6$H$_4$ | 2-thiazolyl |
| 1007 | 4-MeOC$_6$H$_4$ | 2-pyrazolyl |
| 1008 | 4-MeOC$_6$H$_4$ | 5-isoquinolyl |
| 1009 | 4-MeOC$_6$H$_4$ | 3,4-methylenedioxyC$_6$H$_3$ |
| 1010 | 4-MeOC$_6$H$_4$ | 3,4-ethylenedioxyC$_6$H$_3$ |
| 1011 | 4-MeOC$_6$H$_4$ | 2-imidazolyl |
| 1012 | 4-MeOC$_6$H$_4$ | 2-oxazolyl |
| 1013 | 4-MeOC$_6$H$_4$ | 4-isoxazolyl |
| 1014 | 4-MeOC$_6$H$_4$ | 4-HOC$_6$H$_4$ |
| 1015 | 4-MeOC$_6$H$_4$ | 3-HOC$_6$H$_4$ |
| 1016 | 4-MeOC$_6$H$_4$ | 3,4-diHOC$_6$H$_4$ |
| 1017 | 4-MeOC$_6$H$_4$ | 4-NH$_2$CH$_2$C$_6$H$_4$ |
| 1018 | 4-MeOC$_6$H$_4$ | 3-NH$_2$CH$_2$C$_6$H$_4$ |
| 1019 | 2-HOC$_6$H$_4$ | 4-MeOC$_6$H$_4$ |
| 1020 | 2-HOC$_6$H$_4$ | 3-MeOC$_6$H$_4$ |
| 1021 | 2-HOC$_6$H$_4$ | 4-NH$_2$C$_6$H$_4$ |
| 1022 | 2-HOC$_6$H$_4$ | 3-NH$_2$C$_6$H$_4$ |
| 1023 | 2-HOC$_6$H$_4$ | 2-NH$_2$C$_6$H$_4$ |
| 1024 | 2-HOC$_6$H$_4$ | 4-Me$_2$NC$_6$H$_4$ |
| 1025 | 2-HOC$_6$H$_4$ | 3-Me$_2$NC$_6$H$_4$ |
| 1026 | 2-HOC$_6$H$_4$ | 2-Me$_2$NC$_6$H$_4$ |
| 1027 | 2-HOC$_6$H$_4$ | 4-pyridyl |
| 1028 | 2-HOC$_6$H$_4$ | 3-pyridyl |
| 1029 | 2-HOC$_6$H$_4$ | 2-pyridyl |
| 1030 | 2-HOC$_6$H$_4$ | 2-thiazolyl |
| 1031 | 2-HOC$_6$H$_4$ | 2-pyrazolyl |

TABLE 3-continued

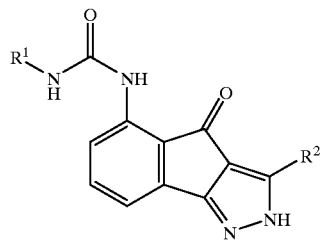

| Example Number | R¹ | R² |
|---|---|---|
| 1032 | 2-HOC$_6$H$_4$ | 5-isoquinolyl |
| 1033 | 2-HOC$_6$H$_4$ | 3,4-methylenedioxyC$_6$H$_3$ |
| 1034 | 2-HOC$_6$H$_4$ | 3,4-ethylenedioxyC$_6$H$_3$ |
| 1035 | 2-HOC$_6$H$_4$ | 2-imidazolyl |
| 1036 | 2-HOC$_6$H$_4$ | 2-oxazolyl |
| 1037 | 2-HOC$_6$H$_4$ | 4-isoxazolyl |
| 1038 | 2-HOC$_6$H$_4$ | 4-HOC$_6$H$_4$ |
| 1039 | 2-HOC$_6$H$_4$ | 3-HOC$_6$H$_4$ |
| 1040 | 2-HOC$_6$H$_4$ | 3,4-diHOC$_6$H$_4$ |
| 1041 | 2-HOC$_6$H$_4$ | 4-NH$_2$CH$_2$C$_6$H$_4$ |
| 1042 | 2-HOC$_6$H$_4$ | 3-NH$_2$CH$_2$C$_6$H$_4$ |
| 1043 | 3-HOC$_6$H$_4$ | 4-MeOC$_6$H$_4$ |
| 1044 | 3-HOC$_6$H$_4$ | 3-MeOC$_6$H$_4$ |
| 1045 | 3-HOC$_6$H$_4$ | 4-NH$_2$C$_6$H$_4$ |
| 1046 | 3-HOC$_6$H$_4$ | 3-NH$_2$C$_6$H$_4$ |
| 1047 | 3-HOC$_6$H$_4$ | 2-NH$_2$C$_6$H$_4$ |
| 1048 | 3-HOC$_6$H$_4$ | 4-Me$_2$NC$_6$H$_4$ |
| 1049 | 3-HOC$_6$H$_4$ | 3-Me$_2$NC$_6$H$_4$ |
| 1050 | 3-HOC$_6$H$_4$ | 2-Me$_2$NC$_6$H$_4$ |
| 1051 | 3-HOC$_6$H$_4$ | 4-pyridyl |
| 1052 | 3-HOC$_6$H$_4$ | 3-pyridyl |
| 1053 | 3-HOC$_6$H$_4$ | 2-pyridyl |
| 1054 | 3-HOC$_6$H$_4$ | 2-thiazolyl |
| 1055 | 3-HOC$_6$H$_4$ | 2-pyrazolyl |
| 1056 | 3-HOC$_6$H$_4$ | 5-isoquinolyl |
| 1057 | 3-HOC$_6$H$_4$ | 3,4-methylenedioxyC$_6$H$_3$ |
| 1058 | 3-HOC$_6$H$_4$ | 3,4-ethylenedioxyC$_6$H$_3$ |
| 1059 | 3-HOC$_6$H$_4$ | 2-imidazolyl |
| 1060 | 3-HOC$_6$H$_4$ | 2-oxazolyl |
| 1061 | 3-HOC$_6$H$_4$ | 4-isoxazolyl |
| 1062 | 3-HOC$_6$H$_4$ | 4-HOC$_6$H$_4$ |
| 1063 | 3-HOC$_6$H$_4$ | 3-HOC$_6$H$_4$ |
| 1064 | 3-HOC$_6$H$_4$ | 3,4-diHOC$_6$H$_4$ |
| 1065 | 3-HOC$_6$H$_4$ | 4-NH$_2$CH$_2$C$_6$H$_4$ |
| 1066 | 3-HOC$_6$H$_4$ | 3-NH$_2$CH$_2$C$_6$H$_4$ |
| 1067 | 4-HOC$_6$H$_4$ | 4-MeOC$_6$H$_4$ |
| 1068 | 4-HOC$_6$H$_4$ | 3-MeOC$_6$H$_4$ |
| 1069 | 4-HOC$_6$H$_4$ | 4-NH$_2$C$_6$H$_4$ |
| 1070 | 4-HOC$_6$H$_4$ | 3-NH$_2$C$_6$H$_4$ |
| 1071 | 4-HOC$_6$H$_4$ | 2-NH$_2$C$_6$H$_4$ |
| 1072 | 4-HOC$_6$H$_4$ | 4-Me$_2$NC$_6$H$_4$ |
| 1073 | 4-HOC$_6$H$_4$ | 3-Me$_2$NC$_6$H$_4$ |
| 1074 | 4-HOC$_6$H$_4$ | 2-Me$_2$NC$_6$H$_4$ |
| 1075 | 4-HOC$_6$H$_4$ | 4-pyridyl |
| 1076 | 4-HOC$_6$H$_4$ | 3-pyridyl |
| 1077 | 4-HOC$_6$H$_4$ | 2-pyridyl |
| 1078 | 4-HOC$_6$H$_4$ | 2-thiazolyl |
| 1079 | 4-HOC$_6$H$_4$ | 2-pyrazolyl |
| 1080 | 4-HOC$_6$H$_4$ | 5-isoquinolyl |
| 1081 | 4-HOC$_6$H$_4$ | 3,4-methylenedioxyC$_6$H$_3$ |
| 1082 | 4-HOC$_6$H$_4$ | 3,4-ethylenedioxyC$_6$H$_3$ |
| 1083 | 4-HOC$_6$H$_4$ | 2-imidazolyl |
| 1084 | 4-HOC$_6$H$_4$ | 2-oxazolyl |
| 1085 | 4-HOC$_6$H$_4$ | 4-isoxazolyl |
| 1086 | 4-HOC$_6$H$_4$ | 4-HOC$_6$H$_4$ |
| 1087 | 4-HOC$_6$H$_4$ | 3-HOC$_6$H$_4$ |
| 1088 | 4-HOC$_6$H$_4$ | 3,4-diHOC$_6$H$_4$ |
| 1089 | 4-HOC$_6$H$_4$ | 4-NH$_2$CH$_2$C$_6$H$_4$ |
| 1090 | 4-HOC$_6$H$_4$ | 3-NH$_2$CH$_2$C$_6$H$_4$ |
| 1091 | 4-ClC$_6$H$_4$ | 4-MeOC$_6$H$_4$ |
| 1092 | 4-ClC$_6$H$_4$ | 3-MeOC$_6$H$_4$ |
| 1093 | 4-ClC$_6$H$_4$ | 4-NH$_2$C$_6$H$_4$ |
| 1094 | 4-ClC$_6$H$_4$ | 3-NH$_2$C$_6$H$_4$ |

TABLE 3-continued

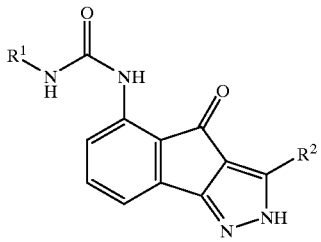

| Example Number | R¹ | R² |
|---|---|---|
| 1095 | 4-ClC₆H₄ | 2-NH₂C₆H₄ |
| 1096 | 4-ClC₆H₄ | 4-Me₂NC₆H₄ |
| 1097 | 4-ClC₆H₄ | 3-Me₂NC₆H₄ |
| 1098 | 4-ClC₆H₄ | 2-Me₂NC₆H₄ |
| 1099 | 4-ClC₆H₄ | 4-pyridyl |
| 1100 | 4-ClC₆H₄ | 3-pyridyl |
| 1101 | 4-ClC₆H₄ | 2-pyridyl |
| 1102 | 4-ClC₆H₄ | 2-thiazolyl |
| 1103 | 4-ClC₆H₄ | 2-pyrazolyl |
| 1104 | 4-ClC₆H₄ | 5-isoquinolyl |
| 1105 | 4-ClC₆H₄ | 3,4-methylenedioxyC₆H₃ |
| 1106 | 4-ClC₆H₄ | 3,4-ethylenedioxyC₆H₃ |
| 1107 | 4-ClC₆H₄ | 2-imidazolyl |
| 1108 | 4-ClC₆H₄ | 2-oxazolyl |
| 1109 | 4-ClC₆H₄ | 4-isoxazolyl |
| 1110 | 4-ClC₆H₄ | 4-HOC₆H₄ |
| 1111 | 4-ClC₆H₄ | 3-HOC₆H₄ |
| 1112 | 4-ClC₆H₄ | 3,4-diHOC₆H₄ |
| 1113 | 4-ClC₆H₄ | 4-NH₂CH₂C₆H₄ |
| 1114 | 4-ClC₆H₄ | 3-NH₂CH₂C₆H₄ |
| 1115 | 2-NH₂CH₂C₆H₄ | 4-MeOC₆H₄ |
| 1116 | 2-NH₂CH₂C₆H₄ | 3-MeOC₆H₄ |
| 1117 | 2-NH₂CH₂C₆H₄ | 4-NH₂C₆H₄ |
| 1118 | 2-NH₂CH₂C₆H₄ | 3-NH₂C₆H₄ |
| 1119 | 2-NH₂CH₂C₆H₄ | 2-NH₂C₆H₄ |
| 1120 | 2-NH₂CH₂C₆H₄ | 4-Me₂NC₆H₄ |
| 1121 | 2-NH₂CH₂C₆H₄ | 3-Me₂NC₆H₄ |
| 1122 | 2-NH₂CH₂C₆H₄ | 2-Me₂NC₆H₄ |
| 1123 | 2-NH₂CH₂C₆H₄ | 4-pyridyl |
| 1124 | 2-NH₂CH₂C₆H₄ | 3-pyridyl |
| 1125 | 2-NH₂CH₂C₆H₄ | 2-pyridyl |
| 1126 | 2-NH₂CH₂C₆H₄ | 2-thiazolyl |
| 1127 | 2-NH₂CH₂C₆H₄ | 2-pyrazolyl |
| 1128 | 2-NH₂CH₂C₆H₄ | 5-isoquinolyl |
| 1129 | 2-NH₂CH₂C₆H₄ | 3,4-methylenedioxyC₆H₃ |
| 1130 | 2-NH₂CH₂C₆H₄ | 3,4-ethylenedioxyC₆H₃ |
| 1131 | 2-NH₂CH₂C₆H₄ | 2-imidazolyl |
| 1132 | 2-NH₂CH₂C₆H₄ | 2-oxazolyl |
| 1133 | 2-NH₂CH₂C₆H₄ | 4-isoxazolyl |
| 1134 | 2-NH₂CH₂C₆H₄ | 4-HOC₆H₄ |
| 1135 | 2-NH₂CH₂C₆H₄ | 3-HOC₆H₄ |
| 1136 | 2-NH₂CH₂C₆H₄ | 3,4-diHOC₆H₄ |
| 1137 | 2-NH₂CH₂C₆H₄ | 4-NH₂CH₂C₆H₄ |
| 1138 | 2-NH₂CH₂C₆H₄ | 3-NH₂CH₂C₆H₄ |
| 1139 | 3-NH₂CH₂C₆H₄ | 4-MeOC₆H₄ |
| 1140 | 3-NH₂CH₂C₆H₄ | 3-MeOC₆H₄ |
| 1141 | 3-NH₂CH₂C₆H₄ | 4-NH₂C₆H₄ |
| 1142 | 3-NH₂CH₂C₆H₄ | 3-NH₂C₆H₄ |
| 1143 | 3-NH₂CH₂C₆H₄ | 2-NH₂C₆H₄ |
| 1144 | 3-NH₂CH₂C₆H₄ | 4-Me₂NC₆H₄ |
| 1145 | 3-NH₂CH₂C₆H₄ | 3-Me₂NC₆H₄ |
| 1146 | 3-NH₂CH₂C₆H₄ | 2-Me₂NC₆H₄ |
| 1147 | 3-NH₂CH₂C₆H₄ | 4-pyridyl |
| 1148 | 3-NH₂CH₂C₆H₄ | 3-pyridyl |
| 1149 | 3-NH₂CH₂C₆H₄ | 2-pyridyl |
| 1150 | 3-NH₂CH₂C₆H₄ | 2-thiazolyl |
| 1151 | 3-NH₂CH₂C₆H₄ | 2-pyrazolyl |
| 1152 | 3-NH₂CH₂C₆H₄ | 5-isoquinolyl |
| 1153 | 3-NH₂CH₂C₆H₄ | 3,4-methylenedioxyC₆H₃ |
| 1154 | 3-NH₂CH₂C₆H₄ | 3,4-ethylenedioxyC₆H₃ |
| 1155 | 3-NH₂CH₂C₆H₄ | 2-imidazolyl |
| 1156 | 3-NH₂CH₂C₆H₄ | 2-oxazolyl |
| 1157 | 3-NH₂CH₂C₆H₄ | 4-isoxazolyl |

TABLE 3-continued

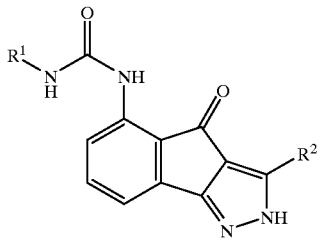

| Example Number | R¹ | R² |
|---|---|---|
| 1158 | 3-NH₂CH₂C₆H₄ | 4-HOC₆H₄ |
| 1159 | 3-NH₂CH₂C₆H₄ | 4-HOC₆H₄ |
| 1160 | 3-NH₂CH₂C₆H₄ | 3,4-diHOC₆H₄ |
| 1161 | 3-NH₂CH₂C₆H₄ | 4-NH₂CH₂C₆H₄ |
| 1162 | 3-NH₂CH₂C₆H₄ | 3-NH₂CH₂C₆H₄ |
| 1163 | 4-NH₂CH₂C₆H₄ | 4-MeOC₆H₄ |
| 1164 | 4-NH₂CH₂C₆H₄ | 3-MeOC₆H₄ |
| 1165 | 4-NH₂CH₂C₆H₄ | 4-NH₂C₆H₄ |
| 1166 | 4-NH₂CH₂C₆H₄ | 3-NH₂C₆H₄ |
| 1167 | 4-NH₂CH₂C₆H₄ | 2-NH₂C₆H₄ |
| 1168 | 4-NH₂CH₂C₆H₄ | 4-Me₂NC₆H₄ |
| 1169 | 4-NH₂CH₂C₆H₄ | 3-Me₂NC₆H₄ |
| 1170 | 4-NH₂CH₂C₆H₄ | 2-Me₂NC₆H₄ |
| 1171 | 4-NH₂CH₂C₆H₄ | 4-pyridyl |
| 1172 | 4-NH₂CH₂C₆H₄ | 3-pyridyl |
| 1173 | 4-NH₂CH₂C₆H₄ | 2-pyridyl |
| 1174 | 4-NH₂CH₂C₆H₄ | 2-thiazolyl |
| 1175 | 4-NH₂CH₂C₆H₄ | 2-pyrazolyl |
| 1176 | 4-NH₂CH₂C₆H₄ | 5-isoquinolyl |
| 1177 | 4-NH₂CH₂C₆H₄ | 3,4-methylenedioxyC₆H₃ |
| 1178 | 4-NH₂CH₂C₆H₄ | 3,4-ethylenedioxyC₆H₃ |
| 1179 | 4-NH₂CH₂C₆H₄ | 2-imidazolyl |
| 1180 | 4-NH₂CH₂C₆H₄ | 2-oxazolyl |
| 1181 | 4-NH₂CH₂C₆H₄ | 4-isoxazolyl |
| 1182 | 4-NH₂CH₂C₆H₄ | 4-HOC₆H₄ |
| 1183 | 4-NH₂CH₂C₆H₄ | 3-HOC₆H₄ |
| 1184 | 4-NH₂CH₂C₆H₄ | 3,4-diHOC₆H₄ |
| 1185 | 4-NH₂CH₂C₆H₄ | 4-NH₂CH₂C₆H₄ |
| 1186 | 4-NH₂CH₂C₆H₄ | 3-NH₂CH₂C₆H₄ |
| 1187 | 2-Me₂NCH₂C₆H₄ | 4-MeOC₆H₄ |
| 1188 | 2-Me₂NCH₂C₆H₄ | 3-MeOC₆H₄ |
| 1189 | 2-Me₂NCH₂C₆H₄ | 4-NH₂C₆H₄ |
| 1190 | 2-Me₂NCH₂C₆H₄ | 3-NH₂C₆H₄ |
| 1191 | 2-Me₂NCH₂C₆H₄ | 2-NH₂C₆H₄ |
| 1192 | 2-Me₂NCH₂C₆H₄ | 4-Me₂NC₆H₄ |
| 1193 | 2-Me₂NCH₂C₆H₄ | 3-Me₂NC₆H₄ |
| 1194 | 2-Me₂NCH₂C₆H₄ | 2-Me₂NC₆H₄ |
| 1195 | 2-Me₂NCH₂C₆H₄ | 4-pyridyl |
| 1196 | 2-Me₂NCH₂C₆H₄ | 3-pyridyl |
| 1197 | 2-Me₂NCH₂C₆H₄ | 2-pyridyl |
| 1198 | 2-Me₂NCH₂C₆H₄ | 2-thiazolyl |
| 1199 | 2-Me₂NCH₂C₆H₄ | 2-pyrazolyl |
| 1200 | 2-Me₂NCH₂C₆H₄ | 5-isoquinolyl |
| 1201 | 2-Me₂NCH₂C₆H₄ | 3,4-methylenedioxyC₆H₃ |
| 1202 | 2-Me₂NCH₂C₆H₄ | 3,4-ethylenedioxyC₆H₃ |
| 1203 | 2-Me₂NCH₂C₆H₄ | 2-imidazolyl |
| 1204 | 2-Me₂NCH₂C₆H₄ | 2-oxazolyl |
| 1205 | 2-Me₂NCH₂C₆H₄ | 4-isoxazolyl |
| 1206 | 2-Me₂NCH₂C₆H₄ | 4-HOC₆H₄ |
| 1207 | 2-Me₂NCH₂C₆H₄ | 3-HOC₆H₄ |
| 1208 | 2-Me₂NCH₂C₆H₄ | 3,4-diHOC₆H₄ |
| 1209 | 2-Me₂NCH₂C₆H₄ | 4-NH₂CH₂C₆H₄ |
| 1210 | 2-Me₂NCH₂C₆H₄ | 3-NH₂CH₂C₆H₄ |
| 1211 | 3-Me₂NCH₂C₆H₄ | 4-MeOC₆H₄ |
| 1212 | 3-Me₂NCH₂C₆H₄ | 3-MeOC₆H₄ |
| 1213 | 3-Me₂NCH₂C₆H₄ | 4-NH₂C₆H₄ |
| 1214 | 3-Me₂NCH₂C₆H₄ | 3-NH₂C₆H₄ |
| 1215 | 3-Me₂NCH₂C₆H₄ | 2-NH₂C₆H₄ |
| 1216 | 3-Me₂NCH₂C₆H₄ | 4-Me₂NC₆H₄ |
| 1217 | 3-Me₂NCH₂C₆H₄ | 3-Me₂NC₆H₄ |
| 1218 | 3-Me₂NCH₂C₆H₄ | 2-Me₂NC₆H₄ |
| 1219 | 3-Me₂NCH₂C₆H₄ | 4-pyridyl |
| 1220 | 3-Me₂NCH₂C₆H₄ | 3-pyridyl |

TABLE 3-continued

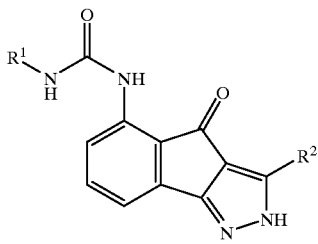

TABLE 3-continued

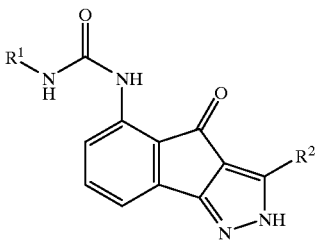

| Example Number | R¹ | R² |
|---|---|---|
| 1221 | 3-Me₂NCH₂C₆H₄ | 2-pyridyl |
| 1222 | 3-Me₂NCH₂C₆H₄ | 2-thiazolyl |
| 1223 | 3-Me₂NCH₂C₆H₄ | 2-oyrazolyl |
| 1224 | 3-Me₂NCH₂C₆H₄ | 5-isoquinolyl |
| 1225 | 3-Me₂NCH₂C₆H₄ | 3,4-methylenedioxyC₆H₃ |
| 1226 | 3-Me₂NCH₂C₆H₄ | 3,4-ethylenedioxyC₆H₃ |
| 1227 | 3-Me₂NCH₂C₆H₄ | 2-imidazolyl |
| 1228 | 3-Me₂NCH₂C₆H₄ | 2-oxazolyl |
| 1229 | 3-Me₂NCH₂C₆H₄ | 4-isoxazolyl |
| 1230 | 3-Me₂NCH₂C₆H₄ | 4-HOC₆H₄ |
| 1231 | 3-Me₂NCH₂C₆H₄ | 3-HOC₆H₄ |
| 1232 | 3-Me₂NCH₂C₆H₄ | 3,4-diHOC₆H₄ |
| 1233 | 3-Me₂NCH₂C₆H₄ | 4-NH₂CH₂C₆H₄ |
| 1234 | 3-Me₂NCH₂C₆H₄ | 3-NH₂CH₂C₆H₄ |
| 1235 | 4-Me₂NCH₂C₆H₄ | 4-MeOC₆H₄ |
| 1236 | 4-Me₂NCH₂C₆H₄ | 3-MeOC₆H₄ |
| 1237 | 4-Me₂NCH₂C₆H₄ | 4-NH₂C₆H₄ |
| 1238 | 4-Me₂NCH₂C₆H₄ | 3-0NH₂C₆H₄ |
| 1239 | 4-Me₂NCH₂C₆H₄ | 2-NH₂C₆H₄ |
| 1240 | 4-Me₂NCH₂C₆H₄ | 4-Me₂C₆H₄ |
| 1241 | 4-Me₂NCH₂C₆H₄ | 3-Me₂NC₆H₄ |
| 1242 | 4-Me₂NCH₂C₆H₄ | 2-Me₂NC₆H₄ |
| 1243 | 4-Me₂NCH₂C₆H₄ | 4-pyridyl |
| 1244 | 4-Me₂NCH₂C₆H₄ | 3-pyridyl |
| 1245 | 4-Me₂NCH₂C₆H₄ | 2-pyridyl |
| 1246 | 4-Me₂NCH₂C₆H₄ | 2-thiazolyl |
| 1247 | 4-Me₂NCH₂C₆H₄ | 2-pyrazolyl |
| 1248 | 4-Me₂NCH₂C₆H₄ | 5-isoquinolyl |
| 1249 | 4-Me₂NCH₂C₆H₄ | 3,4-methylenedioxyC₆H₃ |
| 1250 | 4-Me₂NCH₂C₆H₄ | 3,4-ethylenedioxyC₆H₃ |
| 1251 | 4-Me₂NCH₂C₆H₄ | 2-imidazolyl |
| 1252 | 4-Me₂NCH₂C₆H₄ | 2-oxazolyl |
| 1253 | 4-Me₂NCH₂C₆H₄ | 4-isoxazolyl |
| 1254 | 4-Me₂NCH₂C₆H₄ | 4-HOC₆H₄ |
| 1255 | 4-Me₂NCH₂C₆H₄ | 3-HOC₆H₄ |
| 1256 | 4-Me₂NCH₂C₆H₄ | 3,4-diHOC₆H₄ |
| 1257 | 4-Me₂NCH₂C₆H₄ | 4-NH₂CH₂C₆H₄ |
| 1258 | 4-Me₂NCH₂C₆H₄ | 3-NH₂CH₂C₆H₄ |
| 1259 | H | 4-MeOC₆H₄ |
| 1260 | H | 3-MeOC₆H₄ |
| 1261 | H | 4-NH₂C₆H₄ |
| 1262 | H | 3-NH₂C₆H₄ |
| 1263 | H | 2-NH₂C₆H₄ |
| 1264 | H | 4-Me₂NC₆H₄ |
| 1265 | H | 3-Me₂NC₆H₄ |
| 1266 | H | 2-Me₂NC₆H₄ |
| 1267 | H | 4-pyridyl |
| 1268 | H | 3-pyridyl |
| 1269 | H | 2-pyridyl |
| 1270 | H | 2-thiazolyl |
| 1271 | H | 2-pyrazolyl |
| 1272 | H | 5-isoquinolyl |
| 1273 | H | 3,4-methylenedioxyC₆H₃ |
| 1274 | H | 3,4-ethylenedioxyC₆H₃ |
| 1275 | H | 2-imidazolyl |
| 1276 | H | 2-oxazolyl |
| 1277 | H | 4-isoxazolyl |
| 1278 | H | 4-HOC₆H₄ |
| 1279 | H | 3-HOC₆H₄ |
| 1280 | H | 3,4-diHOC₆H₄ |
| 1281 | H | 4-NH₂CH₂C₆H₄ |
| 1282 | H | 3-NH₂CH₂C₆H₄ |
| 1283 | Me | 4-MeOC₆H₄ |
| 1284 | Me | 3-MeOC₆H₄ |
| 1285 | Me | 4-NH₂C₆H₄ |
| 1286 | Me | 3-NH₂C₆H₄ |
| 1287 | Me | 2-NH₂C₆H₄ |
| 1288 | Me | 4-Me₂C₆H₄ |
| 1289 | Me | 3-Me₂NC₆H₄ |
| 1290 | Me | 2-Me₂NC₆H₄ |
| 1291 | Me | 4-pyridyl |
| 1292 | Me | 3-pyridyl |
| 1293 | Me | 2-pyridyl |
| 1294 | Me | 2-thiazolyl |
| 1295 | Me | 2-pyrazolyl |
| 1296 | Me | 5-isoquinolyl |
| 1297 | Me | 3,4-methylenedioxyC₆H₃ |
| 1298 | Me | 3,4-ethylenedioxyC₆H₃ |
| 1299 | Me | 2-imidazolyl |
| 1300 | Me | 2-oxazolyl |
| 1301 | Me | 4-isoxazolyl |
| 1302 | Me | 4-HOC₆H₄ |
| 1303 | Me | 3-HOC₆H₄ |
| 1304 | Me | 3,4-diHOC₆H₄ |
| 1305 | Me | 4-NH₂CH₂C₆H₄ |
| 1306 | Me | 3-NH₂CH₂C₆H₄ |
| 1307 | Et | 3-MeOC₆H₄ |
| 1309 | Et | 4-NH₂C₆H₄ |
| 1310 | Et | 2-NH₂C₆H₄ |
| 1311 | Et | 4-Me₂NC₆H₄ |
| 1313 | Et | 3-Me₂NC₆H₄ |
| 1314 | Et | 2-Me₂NC₆H₄ |
| 1315 | Et | 4-pyridyl |
| 1316 | Et | 3-pyridyl |
| 1317 | Et | 2-pyridyl |
| 1318 | Et | 2-thiazolyl |
| 1319 | Et | 2-pyrazolyl |
| 1320 | Et | 5-isoquinolyl |
| 1321 | Et | 3,4-methylenedioxC₆H₃ |
| 1322 | Et | 3,4-ethylenedioxyC₆H₃ |
| 1323 | Et | 2-imidazolyl |
| 1324 | Et | 2-oxazolyl |
| 1325 | Et | 4-isoxazolyl |
| 1326 | Et | 4-HOC₆H₄ |
| 1327 | Et | 3-HOC₆H₄ |
| 1328 | Et | 3,4-diHOC₆H₄ |
| 1329 | Et | 4-NH₂CH₂C₆H₄ |
| 1330 | Et | 3-NH₂CH₂C₆H₄ |
| 1331 | 2-NH₂C₆H₄CH₂ | 4-MeOC₆H₄ |
| 1332 | 2-NH₂C₆H₄CH₂ | 3-MeOC₆H₄ |
| 1333 | 2-NH₂C₆H₄CH₂ | 4-NH₂C₆H₄ |
| 1334 | 2-NH₂C₆H₄CH₂ | 3-NH₂C₆H₄ |
| 1335 | 2-NH₂C₆H₄CH₂ | 2-NH₂C₆H₄ |
| 1336 | 2-NH₂C₆H₄CH₂ | 4-Me₂NC₆H₄ |
| 1337 | 2-NH₂C₆H₄CH₂ | 3-Me₂NC₆H₄ |
| 1338 | 2-NH₂C₆H₄CH₂ | 2-Me₂NC₆H₄ |
| 1339 | 2-NH₂C₆H₄CH₂ | 4-pyridyl |
| 1340 | 2-NH₂C₆H₄CH₂ | 3-pyridyl |
| 1341 | 2-NH₂C₆H₄CH₂ | 2-pyridyl |
| 1342 | 2-NH₂C₆H₄CH₂ | 2-thiazolyl |
| 1343 | 2-NH₂C₆H₄CH₂ | 2-pyrazolyl |
| 1344 | 2-NH₂C₆H₄CH₂ | 5-isoquinolyl |
| 1345 | 2-NH₂C₆H₄CH₂ | 3,4-methylenedioxyC₆H₃ |
| 1346 | 2-NH₂C₆H₄CH₂ | 3,4-ethylenedioxyC₆H₃ |
| 1347 | 2-NH₂C₆H₄CH₂ | 2-imidazolyl |
| 1348 | 2-NH₂C₆H₄CH₂ | 2-oxazolyl |

TABLE 3-continued

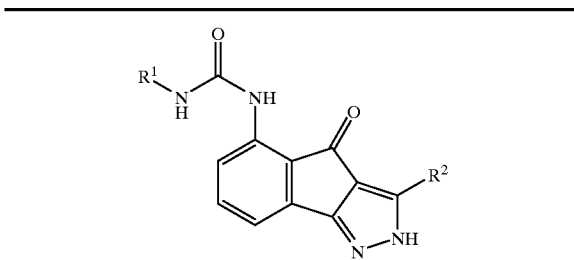

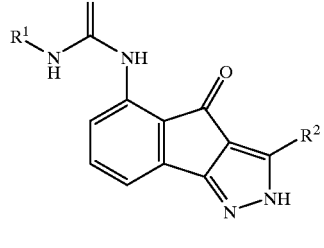

| Example Number | R¹ | R² |
|---|---|---|
| 1349 | 2-NH$_2$C$_6$H$_4$CH$_2$ | 4-isoxazolyl |
| 1350 | 2-NH$_2$C$_6$H$_4$CH$_2$ | 4-HOC$_6$H$_4$ |
| 1351 | 2-NH$_2$C$_6$H$_4$CH$_2$ | 3-HOC$_6$H$_4$ |
| 1352 | 2-NH$_2$C$_6$H$_4$CH$_2$ | 3,4-diHOC$_6$H$_4$ |
| 1353 | 2-NH$_2$C$_6$H$_4$CH$_2$ | 4-NH$_2$CH$_2$C$_6$H$_4$ |
| 1354 | 2-NH$_2$C$_6$H$_4$CH$_2$ | 3-NH$_2$CH$_2$C$_6$H$_4$ |
| 1355 | 3-NH$_2$C$_6$H$_4$CH$_2$ | 4-MeOC$_6$H$_4$ |
| 1356 | 3-NH$_2$C$_6$H$_4$CH$_2$ | 3-MeOC$_6$H$_4$ |
| 1357 | 3-NH$_2$C$_6$H$_4$CH$_2$ | 4-NH$_2$C$_6$H$_4$ |
| 1358 | 3-NH$_2$C$_6$H$_4$CH$_2$ | 3-NH$_2$C$_6$H$_4$ |
| 1359 | 3-NH$_2$C$_6$H$_4$CH$_2$ | 2-NH$_2$C$_6$H$_4$ |
| 1360 | 3-NH$_2$C$_6$H$_4$CH$_2$ | 4-Me$_2$NC$_6$H$_4$ |
| 1361 | 3-NH$_2$C$_6$H$_4$CH$_2$ | 3-MNe$_2$NC$_6$H$_4$ |
| 1362 | 3-NH$_2$C$_6$H$_4$CH$_2$ | 2-Me$_2$NC$_6$H$_4$ |
| 1363 | 3-NH$_2$C$_6$H$_4$CH$_2$ | 4-pyridyl |
| 1364 | 3-NH$_2$C$_6$H$_4$CH$_2$ | 3-pyridyl |
| 1365 | 3-NH$_2$C$_6$H$_4$CH$_2$ | 2-pyridyl |
| 1366 | 3-NH$_2$C$_6$H$_4$CH$_2$ | 2-thiazolyl |
| 1367 | 3-NH$_2$C$_6$H$_4$CH$_2$ | 2-pyrazolyl |
| 1367 | 3-NH$_2$C$_6$H$_4$CH$_2$ | 5-isoquinolyl |
| 1369 | 3-NH$_2$C$_6$H$_4$CH$_2$ | 3,4-methylenedioxyC$_6$H$_3$ |
| 1370 | 3-NH$_2$C$_6$H$_4$CH$_2$ | 3,4-ethylenedioxyC$_6$H$_3$ |
| 1371 | 3-NH$_2$C$_6$H$_4$CH$_2$ | 2-imidazolyl |
| 1372 | 3-NH$_2$C$_6$H$_4$CH$_2$ | 2-oxazolyl |
| 1373 | 3-NH$_2$C$_6$H$_4$CH$_2$ | 4-isoxazolyl |
| 1374 | 3-NH$_2$C$_6$H$_4$CH$_2$ | 4-HOC$_6$H$_4$ |
| 1375 | 3-NH$_2$C$_6$H$_4$CH$_2$ | 3-HOC$_6$H$_4$ |
| 1376 | 3-NH$_2$C$_6$H$_4$CH$_2$ | 3,4-diHOC$_6$H$_4$ |
| 1377 | 3-NH$_2$C$_6$H$_4$CH$_2$ | 4-NH$_2$CH$_2$C$_6$H$_4$ |
| 1378 | 3-NH$_2$C$_6$H$_4$CH$_2$ | 3-NH$_2$CH$_2$C$_6$H$_4$ |
| 1379 | 4-NH$_2$C$_6$H$_4$CH$_2$ | 4-MeOC$_6$H$_4$ |
| 1380 | 4-NH$_2$C$_6$H$_4$CH$_2$ | 3-MeOC$_6$H$_4$ |
| 1381 | 4-NH$_2$C$_6$H$_4$CH$_2$ | 4-NH$_2$C$_6$H$_4$ |
| 1382 | 4-NH$_2$C$_6$H$_4$CH$_2$ | 3-NH$_2$C$_6$H$_4$ |
| 1383 | 4-NH$_2$C$_6$H$_4$CH$_2$ | 2-NH$_2$C$_6$H$_4$ |
| 1384 | 4-NH$_2$C$_6$H$_4$CH$_2$ | 4-Me$_2$NC$_6$H$_4$ |
| 1385 | 4-NH$_2$C$_6$H$_4$CH$_2$ | 3-Me$_2$NC$_6$H$_4$ |
| 1386 | 4-NH$_2$C$_6$H$_4$CH$_2$ | 2-Me$_2$NC$_6$H$_4$ |
| 1387 | 4-NH$_2$C$_6$H$_4$CH$_2$ | 4-pyridyl |
| 1388 | 4-NH$_2$C$_6$H$_4$CH$_2$ | 3-pyridyl |
| 1389 | 4-NH$_2$C$_6$H$_4$CH$_2$ | 2-pyridyl |
| 1390 | 4-NH$_2$C$_6$H$_4$CH$_2$ | 2-thiazolyl |
| 1391 | 4-NH$_2$C$_6$H$_4$CH$_2$ | 2-pyrazolyl |
| 1392 | 4-NH$_2$C$_6$H$_4$CH$_2$ | 5-isoquinolyl |
| 1393 | 4-NH$_2$C$_6$H$_4$CH$_2$ | 3,4-methylenedioxyC$_6$H$_3$ |
| 1394 | 4-NH$_2$C$_6$H$_4$CH$_2$ | 3,4-ethylenedioxyC$_6$H$_3$ |
| 1395 | 4-NH$_2$C$_6$H$_4$CH$_2$ | 2-imidazolyl |
| 1396 | 4-NH$_2$C$_6$H$_4$CH$_2$ | 2-oxazolyl |
| 1397 | 4-NH$_2$C$_6$H$_4$CH$_2$ | 4-isoxazolyl |
| 1398 | 4-NH$_2$C$_6$H$_4$CH$_2$ | 4-HOC$_6$H$_4$ |
| 1399 | 4-NH$_2$C$_6$H$_4$CH$_2$ | 3-HOC$_6$H$_4$ |
| 1400 | 4-NH$_2$C$_6$H$_4$CH$_2$ | 3,4-diHOC$_6$H$_4$ |
| 1401 | 4-NH$_2$C$_6$H$_4$CH$_2$ | 4-NH$_2$CH$_2$C$_6$H$_4$ |
| 1402 | 4-NH$_2$C$_6$H$_4$CH$_2$ | 3-NH$_2$CH$_2$C$_6$H$_4$ |
| 1403 | 2-MeOC$_6$H$_4$CH$_2$ | 3-MeOC$_6$H$_4$ |
| 1405 | 2-MeOC$_6$H$_4$CH$_2$ | 4-NH$_2$C$_6$H$_4$ |
| 1406 | 2-MeOC$_6$H$_4$CH$_2$ | 3-NH$_2$C$_6$H$_4$ |
| 1407 | 2-MeOC$_6$H$_4$CH$_2$ | 2-NH$_2$C$_6$H$_4$ |
| 1408 | 2-MeOC$_6$H$_4$CH$_2$ | 4-Me$_2$NC$_6$H$_4$ |
| 1409 | 2-MeOC$_6$H$_4$CH$_2$ | 3-Me$_2$NC$_6$H$_4$ |
| 1410 | 2-MeOC$_6$H$_4$CH$_2$ | 2-Me$_2$NC$_6$H$_4$ |
| 1411 | 2-MeOC$_6$H$_4$CH$_2$ | 4-pyridyl |
| 1412 | 2-MeOC$_6$H$_4$CH$_2$ | 3-pyridyl |
| 1413 | 2-MeOC$_6$H$_4$CH$_2$ | 2-pyridyl |
| 1414 | 2-MeOC$_6$H$_4$CH$_2$ | 2-thiazolyl |
| 1415 | 2-MeOC$_6$H$_4$CH$_2$ | 2-pyrazolyl |
| 1416 | 2-MeOC$_6$H$_4$CH$_2$ | 5-isoquinolyl |
| 1417 | 2-MeOC$_6$H$_4$CH$_2$ | 3,4-methylenedioxyC$_6$H$_3$ |
| 1418 | 2-MeOC$_6$H$_4$CH$_2$ | 3,4-ethylenedioxyC$_6$H$_3$ |
| 1419 | 2-MeOC$_6$H$_4$CH$_2$ | 2-imidazolyl |
| 1420 | 2-MeOC$_6$H$_4$CH$_2$ | 2-oxazolyl |
| 1421 | 2-MeOC$_6$H$_4$CH$_2$ | 4-isoxazolyl |
| 1422 | 2-MeOC$_6$H$_4$CH$_2$ | 4-HOC$_6$H$_4$ |
| 1423 | 2-MeOC$_6$H$_4$CH$_2$ | 3-HOC$_6$H$_4$ |
| 1424 | 2-MeOC$_6$H$_4$CH$_2$ | 3,4-diHOC$_6$H$_4$ |
| 1425 | 2-MeOC$_6$H$_4$CH$_2$ | 4-NH$_2$CH$_2$C$_6$H$_4$ |
| 1426 | 2-MeOC$_6$H$_4$CH$_2$ | 3-NH$_2$CH$_2$C$_6$H$_4$ |
| 1427 | 3-MeOC$_6$H$_4$CH$_2$ | 4-MeOC$_6$H$_4$ |
| 1428 | 3-MeOC$_6$H$_4$CH$_2$ | 3-MeOC$_6$H$_4$ |
| 1429 | 3-MeOC$_6$H$_4$CH$_2$ | 4-NH$_2$C$_6$H$_4$ |
| 1430 | 3-MeOC$_6$H$_4$CH$_2$ | 3-NH$_2$C$_6$H$_4$ |
| 1431 | 3-MeOC$_6$H$_4$CH$_2$ | 2-NH$_2$C$_6$H$_4$ |
| 1432 | 3-MeOC$_6$H$_4$CH$_2$ | 4-Me$_2$NC$_6$H$_4$ |
| 1433 | 3-MeOC$_6$H$_4$CH$_2$ | 3-Me$_2$NC$_6$H$_4$ |
| 1434 | 3-MeOC$_6$H$_4$CH$_2$ | 2-Me$_2$NC$_6$H$_4$ |
| 1435 | 3-MeOC$_6$H$_4$CH$_2$ | 4-pyridyl |
| 1436 | 3-MeOC$_6$H$_4$CH$_2$ | 3-pyridyl |
| 1437 | 3-MeOC$_6$H$_4$CH$_2$ | 2-pyridyl |
| 1438 | 3-MeOC$_6$H$_4$CH$_2$ | 2-thiazolyl |
| 1439 | 3-MeOC$_6$H$_4$CH$_2$ | 2-pyrazolyl |
| 1440 | 3-MeOC$_6$H$_4$CH$_2$ | 5-isoquinolyl |
| 1441 | 3-MeOC$_6$H$_4$CH$_2$ | 3,4-methylenedioxyC$_6$H$_3$ |
| 1442 | 3-MeOC$_6$H$_4$CH$_2$ | 3,4-ethylenedioxyC$_6$H$_3$ |
| 1443 | 3-MeOC$_6$H$_4$CH$_2$ | 2-imidazolyl |
| 1444 | 3-MeOC$_6$H$_4$CH$_2$ | 2-oxazolyl |
| 1445 | 3-MeOC$_6$H$_4$CH$_2$ | 4-isoxazolyl |
| 1446 | 3-MeOC$_6$H$_4$CH$_2$ | 4-HOC$_6$H$_4$ |
| 1447 | 3-MeOC$_6$H$_4$CH$_2$ | 3-HOC$_6$H$_4$ |
| 1448 | 3-MeOC$_6$H$_4$CH$_2$ | 3,4-diHOC$_6$H$_4$ |
| 1449 | 3-MeOC$_6$H$_4$CH$_2$ | 4-NH$_2$CH$_2$C$_6$H$_4$ |
| 1450 | 3-MeOC$_6$H$_4$CH$_2$ | 3-NH$_2$CH$_2$C$_6$H$_4$ |
| 1451 | 4-MeOC$_6$H$_4$CH$_2$ | 4-MeOC$_6$H$_4$ |
| 1452 | 4-MeOC$_6$H$_4$CH$_2$ | 3-MeOC$_6$H$_4$ |
| 1453 | 4-MeOC$_6$H$_4$CH$_2$ | 4-NH$_2$C$_6$H$_4$ |
| 1454 | 4-MeOC$_6$H$_4$CH$_2$ | 3-NH$_2$C$_6$H$_4$ |
| 1455 | 4-MeOC$_6$H$_4$CH$_2$ | 2-NH$_2$C$_6$H$_4$ |
| 1456 | 4-MeOC$_6$H$_4$CH$_2$ | 4-Me$_2$NC$_6$H$_4$ |
| 1457 | 4-MeOC$_6$H$_4$CH$_2$ | 3-Me$_2$NC$_6$H$_4$ |
| 1458 | 4-MeOC$_6$H$_4$CH$_2$ | 2-Me$_2$NC$_6$H$_4$ |
| 1459 | 4-MeOC$_6$H$_4$CH$_2$ | 4-pyridyl |
| 1460 | 4-MeOC$_6$H$_4$CH$_2$ | 3-pyridyl |
| 1461 | 4-MeOC$_6$H$_4$CH$_2$ | 2-pyridyl |
| 1462 | 4-MeOC$_6$H$_4$CH$_2$ | 2-thiazolyl |
| 1463 | 4-MeOC$_6$H$_4$CH$_2$ | 2-pyrazolyl |
| 1464 | 4-MeOC$_6$H$_4$CH$_2$ | 5-isoquinolyl |
| 1465 | 4-MeOC$_6$H$_4$CH$_2$ | 3,4-methylenedioxyC$_6$H$_3$ |
| 1466 | 4-MeOC$_6$H$_4$CH$_2$ | 3,4-ethylenedioxyC$_6$H$_3$ |
| 1467 | 4-MeOC$_6$H$_4$CH$_2$ | 2-imidazolyl |
| 1468 | 4-MeOC$_6$H$_4$CH$_2$ | 2-oxazolyl |
| 1469 | 4-MeOC$_6$H$_4$CH$_2$ | 4-isoxazolyl |
| 1470 | 4-MeOC$_6$H$_4$CH$_2$ | 4-HOC$_6$H$_4$ |
| 1471 | 4-MeOC$_6$H$_4$CH$_2$ | 3-HOC$_6$H$_4$ |
| 1472 | 4-MeOC$_6$H$_4$CH$_2$ | 3,4-diHOC$_6$H$_4$ |
| 1473 | 4-MeOC$_6$H$_4$CH$_2$ | 4-NH$_2$CH$_2$C$_6$H$_4$ |
| 1474 | 4-MeOC$_6$H$_4$CH$_2$ | 3-NH$_2$CH$_2$C$_6$H$_4$ |
| 1475 | 2-HOC$_6$H$_4$CH$_2$ | 4-MeOC$_6$H$_4$ |

TABLE 3-continued

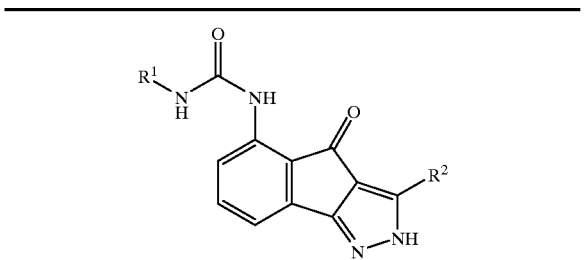

| Example Number | R¹ | R² |
|---|---|---|
| 1476 | 2-HOC₆H₄CH₂ | 3-MeOC₆H₄ |
| 1477 | 2-HOC₆H₄CH₂ | 4-NH₂C₆H₄ |
| 1478 | 2-HOC₆H₄CH₂ | 3-NH₂C₆H₄ |
| 1479 | 2-HOC₆H₄CH₂ | 2-NH₂C₆H₄ |
| 1480 | 2-HOC₆H₄CH₂ | 4-Me₂NC₆H₄ |
| 1481 | 2-HOC₆H₄CH₂ | 3-Me₂NC₆H₄ |
| 1482 | 2-HOC₆H₄CH₂ | 2-Me₂NC₆H₄ |
| 1483 | 2-HOC₆H₄CH₂ | 4-pyridyl |
| 1484 | 2-HOC₆H₄CH₂ | 3-pyridyl |
| 1485 | 2-HOC₆H₄CH₂ | 2-pyridyl |
| 1486 | 2-HOC₆H₄CH₂ | 2-thiazolyl |
| 1487 | 2-HOC₆H₄CH₂ | 2-pyrazolyl |
| 1488 | 2-HOC₆H₄CH₂ | 5-isoquinolyl |
| 1489 | 2-HOC₆H₄CH₂ | 3,4-methylenedioxyC₆H₃ |
| 1490 | 2-HOC₆H₄CH₂ | 3,4-ethylenedioxyC₆H₃ |
| 1491 | 2-HOC₆H₄CH₂ | 2-imidazolyl |
| 1492 | 2-HOC₆H₄CH₂ | 2-oxazolyl |
| 1493 | 2-HOC₆H₄CH₂ | 4-isoxazolyl |
| 1494 | 2-HOC₆H₄CH₂ | 4-HOC₆H₄ |
| 1495 | 2-HOC₆H₄CH₂ | 3-HOC₆H₄ |
| 1496 | 2-HOC₆H₄CH₂ | 3,4-diHOC₆H₄ |
| 1497 | 2-HOC₆H₄CH₂ | 4-NH₂CH₂C₆H₄ |
| 1498 | 2-HOC₆H₄CH₂ | 3-NH₂CH₂C₆H₄ |
| 1499 | 3-HOC₆H₄CH₂ | 4-MeOC₆H₄ |
| 1500 | 3-HOC₆H₄CH₂ | 3-MeOC₆H₄ |
| 1501 | 3-HOC₆H₄CH₂ | 4-NH₂C₆H₄ |
| 1502 | 3-HOC₆H₄CH₂ | 3-NH₂C₆H₄ |
| 1503 | 3-HOC₆H₄CH₂ | 2-NH₂C₆H₄ |
| 1504 | 3-HOC₆H₄CH₂ | 4-Me₂NC₆H₄ |
| 1505 | 3-HOC₆H₄CH₂ | 3-Me₂NC₆H₄ |
| 1506 | 3-HOC₆H₄CH₂ | 2-Me₂NC₆H₄ |
| 1507 | 3-HOC₆H₄CH₂ | 4-pyridyl |
| 1508 | 3-HOC₆H₄CH₂ | 3-pyridyl |
| 1509 | 3-HOC₆H₄CH₂ | 2-pyridyl |
| 1510 | 3-HOC₆H₄CH₂ | 2-thiazolyl |
| 1511 | 3-HOC₆H₄CH₂ | 2-pyrazolyl |
| 1512 | 3-HOC₆H₄CH₂ | 5-isoquinolyl |
| 1513 | 3-HOC₆H₄CH₂ | 3,4-methylenedioxyC₆H₃ |
| 1514 | 3-HOC₆H₄CH₂ | 3,4-ethylenedioxyC₆H₃ |
| 1514 | 3-HOC₆H₄CH₂ | 2-imidazolyl |
| 1515 | 3-HOC₆H₄CH₂ | 2-oxazolyl |
| 1517 | 3-HOC₆H₄CH₂ | 4-isoxazolyl |
| 1518 | 3-HOC₆H₄CH₂ | 4-HOC₆H₄ |
| 1519 | 3-HOC₆H₄CH₂ | 3-HOC₆H₄ |
| 1520 | 3-HOC₆H₄CH₂ | 3,4-diHOC₆H₄ |
| 1521 | 3-HOC₆H₄CH₂ | 4-NH₂CH₂C₆H₄ |
| 1522 | 3-HOC₆H₄CH₂ | 3-NH₂CH₂C₆H₄ |
| 1523 | 4-HOC₆H₄CH₂ | 4-MeOC₆H₄ |
| 1524 | 4-HOC₆H₄CH₂ | 3-MeOC₆H₄ |
| 1525 | 4-HOC₆H₄CH₂ | 4-NH₂C₆H₄ |
| 1526 | 4-HOC₆H₄CH₂ | 3-NH₂C₆H₄ |
| 1527 | 4-HOC₆H₄CH₂ | 2-NH₂C₆H₄ |
| 1528 | 4-HOC₆H₄CH₂ | 4-Me₂NC₆H₄ |
| 1529 | 4-HOC₆H₄CH₂ | 3-Me₂NC₆H₄ |
| 1530 | 4-HOC₆H₄CH₂ | 2-Me₂NC₆H₄ |
| 1531 | 4-HOC₆H₄CH₂ | 4-pyridyl |
| 1532 | 4-HOC₆H₄CH₂ | 3-pyridyl |
| 1533 | 4-HOC₆H₄CH₂ | 2-pyridyl |
| 1534 | 4-HOC₆H₄CH₂ | 2-thiazolyl |
| 1535 | 4-HOC₆H₄CH₂ | 2-pyrazolyl |
| 1536 | 4-HOC₆H₄CH₂ | 5-isoquinolyl |
| 1537 | 4-HOC₆H₄CH₂ | 3,4-methylenedioxyC₆H₃ |
| 1538 | 4-HOC₆H₄CH₂ | 3,4-ethylenedioxyC₆H₃ |

TABLE 3-continued

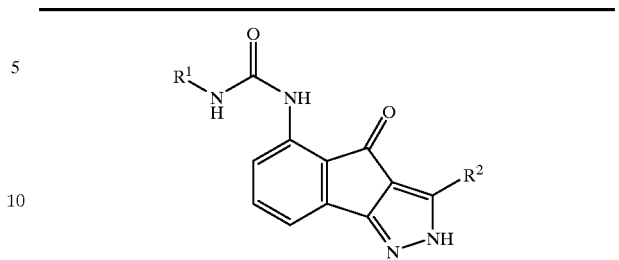

| Example Number | R¹ | R² |
|---|---|---|
| 1539 | 4-HOC₆H₄CH₂ | 2-imidazolyl |
| 1540 | 4-HOC₆H₄CH₂ | 2-oxazolyl |
| 1541 | 4-HOC₆H₄CH₂ | 4-isoxazolyl |
| 1542 | 4-HOC₆H₄CH₂ | 4-HOC₆H₄ |
| 1543 | 4-HOC₆H₄CH₂ | 3-HOC₆H₄ |
| 1544 | 4-HOC₆H₄CH₂ | 3,4-diHOC₆H₄ |
| 1545 | 4-HOC₆H₄CH₂ | 4-NH₂CH₂C₆H₄ |
| 1546 | 4-HOC₆H₄CH₂ | 3-NH₂CH₂C₆H₄ |
| 1547 | 4-ClC₆H₄CH₂ | 4-MeOC₆H₄ |
| 1548 | 4-ClC₆H₄CH₂ | 3-MeOC₆H₄ |
| 1549 | 4-ClC₆H₄CH₂ | 4-NH₂C₆H₄ |
| 1550 | 4-ClC₆H₄CH₂ | 3-NH₂C₆H₄ |
| 1551 | 4-ClC₆H₄CH₂ | 2-NH₂C₆H₄ |
| 1552 | 4-ClC₆H₄CH₂ | 4-Me₂NC₆H₄ |
| 1553 | 4-ClC₆H₄CH₂ | 3-Me₂NC₆H₄ |
| 1554 | 4-ClC₆H₄CH₂ | 2-Me₂NC₆H₄ |
| 1555 | 4-ClC₆H₄CH₂ | 4-pyridyl |
| 1556 | 4-ClC₆H₄CH₂ | 3-pyridyl |
| 1557 | 4-ClC₆H₄CH₂ | 2-pyridyl |
| 1558 | 4-ClC₆H₄CH₂ | 2-thiazolyl |
| 1559 | 4-ClC₆H₄CH₂ | 2-pyrazolyl |
| 1560 | 4-ClC₆H₄CH₂ | 5-isoquinolyl |
| 1561 | 4-ClC₆H₄CH₂ | 3,4-methylenedioxyC₆H₃ |
| 1562 | 4-ClC₆H₄CH₂ | 3,4-ethylenedioxyC₆H₃ |
| 1563 | 4-ClC₆H₄CH₂ | 2-imidazolyl |
| 1564 | 4-ClC₆H₄CH₂ | 2-oxazolyl |
| 1565 | 4-ClC₆H₄CH₂ | 4-isoxazolyl |
| 1566 | 4-ClC₆H₄CH₂ | 4-HOC₆H₄ |
| 1567 | 4-ClC₆H₄CH₂ | 3-HOC₆H₄ |
| 1568 | 4-ClC₆H₄CH₂ | 3,4-diHOC₆H₄ |
| 1569 | 4-ClC₆H₄CH₂ | 4-NH₂CH₂C₆H₄ |
| 1570 | 4-ClC₆H₄CH₂ | 3-NH₂CH₂C₆H₄ |
| 1571 | 2-NH₂CH₂C₆H₄CH₂ | 3-MeOC₆H₄ |
| 1573 | 2-NH₂CH₂C₆H₄CH₂ | 4-NH₂C₆H₄ |
| 1574 | 2-NH₂CH₂C₆H₄CH₂ | 3-NH₂C₆H₄ |
| 1575 | 2-NH₂CH₂C₆H₄CH₂ | 2-NH₂C₆H₄ |
| 1576 | 2-NH₂CH₂C₆H₄CH₂ | 4-Me₂NC₆H₄ |
| 1577 | 2-NH₂CH₂C₆H₄CH₂ | 3-Me₂NC₆H₄ |
| 1578 | 2-NH₂CH₂C₆H₄CH₂ | 2-Me₂NC₆H₄ |
| 1579 | 2-NH₂CH₂C₆H₄CH₂ | 4-pyridyl |
| 1580 | 2-NH₂CH₂C₆H₄CH₂ | 3-pyridyl |
| 1581 | 2-NH₂CH₂C₆H₄CH₂ | 2-pyridyl |
| 1582 | 2-NH₂CH₂C₆H₄CH₂ | 2-thiazolyl |
| 1583 | 2-NH₂CH₂C₆H₄CH₂ | 2-pyrazolyl |
| 1584 | 2-NH₂CH₂C₆H₄CH₂ | 5-isoquinolyl |
| 1585 | 2-NH₂CH₂C₆H₄CH₂ | 3,4-methylenedioxyC₆H₃ |
| 1586 | 2-NH₂CH₂C₆H₄CH₂ | 3,4-ethylenedioxyC₆H₃ |
| 1587 | 2-NH₂CH₂C₆H₄CH₂ | 2-imidazolyl |
| 1588 | 2-NH₂CH₂C₆H₄CH₂ | 2-oxazolyl |
| 1589 | 2-NH₂CH₂C₆H₄CH₂ | 4-isoxazolyl |
| 1590 | 2-NH₂CH₂C₆H₄CH₂ | 4-HOC₆H₄ |
| 1591 | 2-NH₂CH₂C₆H₄CH₂ | 3-HOC₆H₄ |
| 1592 | 2-NH₂CH₂C₆H₄CH₂ | 3,4-diHOC₆H₄ |
| 1593 | 2-NH₂CH₂C₆H₄CH₂ | 4-NH₂CH₂C₆H₄ |
| 1594 | 2-NH₂CH₂C₆H₄CH₂ | 3-NH₂CH₂C₆H₄ |
| 1595 | 3-NH₂CH₂C₆H₄CH₂ | 4-MeOC₆H₄ |
| 1596 | 3-NH₂CH₂C₆H₄CH₂ | 3-MeOC₆H₄ |
| 1597 | 3-NH₂CH₂C₆H₄CH₂ | 4-NH₂C₆H₄ |
| 1598 | 3-NH₂CH₂C₆H₄CH₂ | 3-NH₂C₆H₄ |
| 1599 | 3-NH₂CH₂C₆H₄CH₂ | 2-NH₂C₆H₄ |
| 1600 | 3-NH₂CH₂C₆H₄CH₂ | 4-Me₂NC₆H₄ |
| 1601 | 3-NH₂CH₂C₆H₄CH₂ | 3-Me₂NC₆H₄ |
| 1602 | 3-NH₂CH₂C₆H₄CH₂ | 2-Me₂NC₆H₄ |

TABLE 3-continued

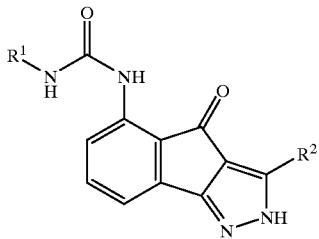

| Example Number | R¹ | R² |
|---|---|---|
| 1603 | 3-NH$_2$CH$_2$C$_6$H$_4$CH$_2$ | 4-pyridyl |
| 1604 | 3-NH$_2$CH$_2$C$_6$H$_4$CH$_2$ | 3-pyridyl |
| 1605 | 3-NH$_2$CH$_2$C$_6$H$_4$CH$_2$ | 2-pyridyl |
| 1606 | 3-NH$_2$CH$_2$C$_6$H$_4$CH$_2$ | 2-thiazolyl |
| 1607 | 3-NH$_2$CH$_2$C$_6$H$_4$CH$_2$ | 2-pyrazolyl |
| 1608 | 3-NH$_2$CH$_2$C$_6$H$_4$CH$_2$ | 5-isoquinolyl |
| 1609 | 3-NH$_2$CH$_2$C$_6$H$_4$CH$_2$ | 3,4-methylenedioxyC$_6$H$_3$ |
| 1610 | 3-NH$_2$CH$_2$C$_6$H$_4$CH$_2$ | 3,4-ethylenedioxyC$_6$H$_3$ |
| 1611 | 3-NH$_2$CH$_2$C$_6$H$_4$CH$_2$ | 2-imidazolyl |
| 1612 | 3-NH$_2$CH$_2$C$_6$H$_4$CH$_2$ | 2-oxazolyl |
| 1613 | 3-NH$_2$CH$_2$C$_6$H$_4$CH$_2$ | 4-isoxazolyl |
| 1614 | 3-NH$_2$CH$_2$C$_6$H$_4$CH$_2$ | 4-HOC$_6$H$_4$ |
| 1615 | 3-NH$_2$CH$_2$C$_6$H$_4$CH$_2$ | 3-HOC$_6$H$_4$ |
| 1616 | 3-NH$_2$CH$_2$C$_6$H$_4$CH$_2$ | 3,4-diHOC$_6$H$_4$ |
| 1617 | 3-NH$_2$CH$_2$C$_6$H$_4$CH$_2$ | 4-NH$_2$CH$_2$C$_6$H$_4$ |
| 1618 | 3-NH$_2$CH$_2$C$_6$H$_4$CH$_2$ | 3-NH$_2$CH$_2$C$_6$H$_4$ |
| 1619 | 4-NH$_2$CH$_2$C$_6$H$_4$CH$_2$ | 4-MeOC$_6$H$_4$ |
| 1620 | 4-NH$_2$CH$_2$C$_6$H$_4$CH$_2$ | 3-MeOC$_6$H$_4$ |
| 1621 | 4-NH$_2$CH$_2$C$_6$H$_4$CH$_2$ | 4-NH$_2$C$_6$H$_4$ |
| 1622 | 4-NH$_2$CH$_2$C$_6$H$_4$CH$_2$ | 3-NH$_2$C$_6$H$_4$ |
| 1623 | 4-NH$_2$CH$_2$C$_6$H$_4$CH$_2$ | 2-NH$_2$C$_6$H$_4$ |
| 1624 | 4-NH$_2$CH$_2$C$_6$H$_4$CH$_2$ | 4-Me$_2$NC$_6$H$_4$ |
| 1625 | 4-NH$_2$CH$_2$C$_6$H$_4$CH$_2$ | 3-Me$_2$NC$_6$H$_4$ |
| 1626 | 4-NH$_2$CH$_2$C$_6$H$_4$CH$_2$ | 2-Me$_2$NC$_6$H$_4$ |
| 1627 | 4-NH$_2$CH$_2$C$_6$H$_4$CH$_2$ | 4-pyridyl |
| 1628 | 4-NH$_2$CH$_2$C$_6$H$_4$CH$_2$ | 3-pyridyl |
| 1629 | 4-NH$_2$CH$_2$C$_6$H$_4$CH$_2$ | 2-pyridyl |
| 1630 | 4-NH$_2$CH$_2$C$_6$H$_4$CH$_2$ | 2-thiazolyl |
| 1631 | 4-NH$_2$CH$_2$C$_6$H$_4$CH$_2$ | 2-pyrazolyl |
| 1632 | 4-NH$_2$CH$_2$C$_6$H$_4$CH$_2$ | 5-isoquinolyl |
| 1633 | 4-NH$_2$CH$_2$C$_6$H$_4$CH$_2$ | 3,4-methylenedioxyC$_6$H$_3$ |
| 1634 | 4-NH$_2$CH$_2$C$_6$H$_4$CH$_2$ | 3,4-ethylenedioxyC$_6$H$_3$ |
| 1635 | 4-NH$_2$CH$_2$C$_6$H$_4$CH$_2$ | 2-imidazolyl |
| 1636 | 4-NH$_2$CH$_2$C$_6$H$_4$CH$_2$ | 2-oxazolyl |
| 1637 | 4-NH$_2$CH$_2$C$_6$H$_4$CH$_2$ | 4-isoxazolyl |
| 1638 | 4-NH$_2$CH$_2$C$_6$H$_4$CH$_2$ | 4-HOC$_6$H$_4$ |
| 1639 | 4-NH$_2$CH$_2$C$_6$H$_4$CH$_2$ | 3-HOC$_6$H$_4$ |
| 1640 | 4-NH$_2$CH$_2$C$_6$H$_4$CH$_2$ | 3,4-diHOC$_6$H$_4$ |
| 1641 | 4-NH$_2$CH$_2$C$_6$H$_4$CH$_2$ | 4-NH$_2$CH$_2$C$_6$H$_4$ |
| 1642 | 4-NH$_2$CH$_2$C$_6$H$_4$CH$_2$ | 3-NH$_2$CH$_2$C$_6$H$_4$ |
| 1643 | 2-Me$_2$NCH$_2$C$_6$H$_4$CH$_2$ | 4-MeOC$_6$H$_4$ |
| 1644 | 2-Me$_2$NCH$_2$C$_6$H$_4$CH$_2$ | 3-MeOC$_6$H$_4$ |
| 1645 | 2-Me$_2$NCH$_2$C$_6$H$_4$CH$_2$ | 4-NH$_2$C$_6$H$_4$ |
| 1646 | 2-Me$_2$NCH$_2$C$_6$H$_4$CH$_2$ | 3-NH$_2$C$_6$H$_4$ |
| 1647 | 2-Me$_2$NCH$_2$C$_6$H$_4$CH$_2$ | 2-NH$_2$C$_6$H$_4$ |
| 1648 | 2-Me$_2$NCH$_2$C$_6$H$_4$CH$_2$ | 4-Me$_2$NC$_6$H$_4$ |
| 1649 | 2-Me$_2$NCH$_2$C$_6$H$_4$CH$_2$ | 3-Me$_2$NC$_6$H$_4$ |
| 1650 | 2-Me$_2$NCH$_2$C$_6$H$_4$CH$_2$ | 2-Me$_2$NC$_6$H$_4$ |
| 1651 | 2-Me$_2$NCH$_2$C$_6$H$_4$CH$_2$ | 4-pyridyl |
| 1652 | 2-Me$_2$NCH$_2$C$_6$H$_4$CH$_2$ | 3-pyridyl |
| 1653 | 2-Me$_2$NCH$_2$C$_6$H$_4$CH$_2$ | 2-pyridyl |
| 1654 | 2-Me$_2$NCH$_2$C$_6$H$_4$CH$_2$ | 2-thiazolyl |
| 1655 | 2-Me$_2$NCH$_2$C$_6$H$_4$CH$_2$ | 2-pyrazolyl |
| 1656 | 2-Me$_2$NCH$_2$C$_6$H$_4$CH$_2$ | 5-isoquinolyl |
| 1657 | 2-Me$_2$NCH$_2$C$_6$H$_4$CH$_2$ | 3,4-methylenedioxyC$_6$H$_3$ |
| 1658 | 2-Me$_2$NCH$_2$C$_6$H$_4$CH$_2$ | 3,4-ethylenedioxyC$_6$H$_3$ |
| 1659 | 2-Me$_2$NCH$_2$C$_6$H$_4$CH$_2$ | 2-imidazolyl |
| 1660 | 2-Me$_2$NCH$_2$C$_6$H$_4$CH$_2$ | 2-oxazolyl |
| 1661 | 2-Me$_2$NCH$_2$C$_6$H$_4$CH$_2$ | 4-isoxazolyl |
| 1662 | 2-Me$_2$NCH$_2$C$_6$H$_4$CH$_2$ | 4-HOC$_6$H$_4$ |
| 1663 | 2-Me$_2$NCH$_2$C$_6$H$_4$CH$_2$ | 3-HOC$_6$H$_4$ |

TABLE 3-continued

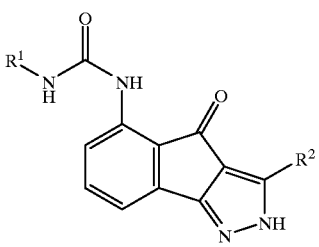

| Example Number | R¹ | R² |
|---|---|---|
| 1664 | 2-Me$_2$NCH$_2$C$_6$H$_4$CH$_2$ | 3,4-diHOC$_6$H$_4$ |
| 1665 | 2-Me$_2$NCH$_2$C$_6$H$_4$CH$_2$ | 4-NH$_2$CH$_2$C$_6$H$_4$ |
| 1666 | 2-Me$_2$NCH$_2$C$_6$H$_4$CH$_2$ | 3-NH$_2$CH$_2$C$_6$H$_4$ |
| 1667 | 3-Me$_2$NCH$_2$C$_6$H$_4$CH$_2$ | 4-MeOC$_6$H$_4$ |
| 1668 | 3-Me$_2$NCH$_2$C$_6$H$_4$CH$_2$ | 3-MeOC$_6$H$_4$ |
| 1669 | 3-Me$_2$NCH$_2$C$_6$H$_4$CH$_2$ | 4-NH$_2$C$_6$H$_4$ |
| 1670 | 3-Me$_2$NCH$_2$C$_6$H$_4$CH$_2$ | 3-NH$_2$C$_6$H$_4$ |
| 1671 | 3-Me$_2$NCH$_2$C$_6$H$_4$CH$_2$ | 2-NH$_2$C$_6$H$_4$ |
| 1672 | 3-Me$_2$NCH$_2$C$_6$H$_4$CH$_2$ | 4-Me$_2$NC$_6$H$_4$ |
| 1673 | 3-Me$_2$NCH$_2$C$_6$H$_4$CH$_2$ | 3-Me$_2$NC$_6$H$_4$ |
| 1674 | 3-Me$_2$NCH$_2$C$_6$H$_4$CH$_2$ | 2-Me$_2$NC$_6$H$_4$ |
| 1675 | 3-Me$_2$NCH$_2$C$_6$H$_4$CH$_2$ | 4-pyridyl |
| 1676 | 3-Me$_2$NCH$_2$C$_6$H$_4$CH$_2$ | 3-pyridyl |
| 1677 | 3-Me$_2$NCH$_2$C$_6$H$_4$CH$_2$ | 2-pyridyl |
| 1678 | 3-Me$_2$NCH$_2$C$_6$H$_4$CH$_2$ | 2-thiazolyl |
| 1679 | 3-Me$_2$NCH$_2$C$_6$H$_4$CH$_2$ | 2-pyrazolyl |
| 1680 | 3-Me$_2$NCH$_2$C$_6$H$_4$CH$_2$ | 5-isoquinolyl |
| 1681 | 3-Me$_2$NCH$_2$C$_6$H$_4$CH$_2$ | 3,4-methylenedioxyC$_6$H$_3$ |
| 1682 | 3-Me$_2$NCH$_2$C$_6$H$_4$CH$_2$ | 3,4-ethylenedioxyC$_6$H$_3$ |
| 1683 | 3-Me$_2$NCH$_2$C$_6$H$_4$CH$_2$ | 2-imidazolyl |
| 1684 | 3-Me$_2$NCH$_2$C$_6$H$_4$CH$_2$ | 2-oxazolyl |
| 1685 | 3-Me$_2$NCH$_2$C$_6$H$_4$CH$_2$ | 4-isoxazolyl |
| 1686 | 3-Me$_2$NCH$_2$C$_6$H$_4$CH$_2$ | 4-HOC$_6$H$_4$ |
| 1687 | 3-Me$_2$NCH$_2$C$_6$H$_4$CH$_2$ | 3-HOC$_6$H$_4$ |
| 1688 | 3-Me$_2$NCH$_2$C$_6$H$_4$CH$_2$ | 3,4-diHOC$_6$H$_4$ |
| 1689 | 3-Me$_2$NCH$_2$C$_6$H$_4$CH$_2$ | 4-NH$_2$CH$_2$C$_6$H$_4$ |
| 1690 | 3-Me$_2$NCH$_2$C$_6$H$_4$CH$_2$ | 3-NH$_2$CH$_2$C$_6$H$_4$ |
| 1691 | 4-Me$_2$NCH$_2$C$_6$H$_4$CH$_2$ | 4-MeOC$_6$H$_4$ |
| 1692 | 4-Me$_2$NCH$_2$C$_6$H$_4$CH$_2$ | 3-MeOC$_6$H$_4$ |
| 1693 | 4-Me$_2$NCH$_2$C$_6$H$_4$CH$_2$ | 4-NH$_2$C$_6$H$_4$ |
| 1694 | 4-Me$_2$NCH$_2$C$_6$H$_4$CH$_2$ | 3-NH$_2$C$_6$H$_4$ |
| 1695 | 4-Me$_2$NCH$_2$C$_6$H$_4$CH$_2$ | 2-NH$_2$C$_6$H$_4$ |
| 1696 | 4-Me$_2$NCH$_2$C$_6$H$_4$CH$_2$ | 4-Me$_2$NC$_6$H$_4$ |
| 1697 | 4-Me$_2$NCH$_2$C$_6$H$_4$CH$_2$ | 3-Me$_2$NC$_6$H$_4$ |
| 1698 | 4-Me$_2$NCH$_2$C$_6$H$_4$CH$_2$ | 2-Me$_2$NC$_6$H$_4$ |
| 1699 | 4-Me$_2$NCH$_2$C$_6$H$_4$CH$_2$ | 4-pyridyl |
| 1700 | 4-Me$_2$NCH$_2$C$_6$H$_4$CH$_2$ | 3-pyridyl |
| 1701 | 4-Me$_2$NCH$_2$C$_6$H$_4$CH$_2$ | 2-pyridyl |
| 1702 | 4-Me$_2$NCH$_2$C$_6$H$_4$CH$_2$ | 2-thiazolyl |
| 1703 | 4-Me$_2$NCH$_2$C$_6$H$_4$CH$_2$ | 2-pyrazolyl |
| 1704 | 4-Me$_2$NCH$_2$C$_6$H$_4$CH$_2$ | 5-isoquinolyl |
| 1705 | 4-Me$_2$NCH$_2$C$_6$H$_4$CH$_2$ | 3,4-methylenedioxyC$_6$H$_3$ |
| 1706 | 4-Me$_2$NCH$_2$C$_6$H$_4$CH$_2$ | 3,4-ethylenedioxyC$_6$H$_3$ |
| 1707 | 4-Me$_2$NCH$_2$C$_6$H$_4$CH$_2$ | 2-imidazolyl |
| 1708 | 4-Me$_2$NCH$_2$C$_6$H$_4$CH$_2$ | 2-oxazolyl |
| 1709 | 4-Me$_2$NCH$_2$C$_6$H$_4$CH$_2$ | 4-isoxazolyl |
| 1710 | 4-Me$_2$NCH$_2$C$_6$H$_4$CH$_2$ | 4-HOC$_6$H$_4$ |
| 1711 | 4-Me$_2$NCH$_2$C$_6$H$_4$CH$_2$ | 3-HOC$_6$H$_4$ |
| 1712 | 4-Me$_2$NCH$_2$C$_6$H$_4$CH$_2$ | 3,4-diHOC$_6$H$_4$ |
| 1713 | 4-Me$_2$NCH$_2$C$_6$H$_4$CH$_2$ | 4-NH$_2$CH$_2$C$_6$H$_4$ |
| 1714 | 4-Me$_2$NCH$_2$C$_6$H$_4$CH$_2$ | 3-NH$_2$CH$_2$C$_6$H$_4$ |

TABLE 4

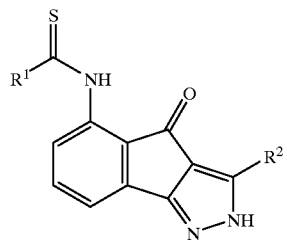

| Example Number | R¹ | R² |
|---|---|---|
| 1714 | 4-Me$_2$NCH$_2$C$_6$H$_4$CH$_2$ | 3-NH$_2$CH$_2$C$_6$H$_4$ |
| 1715 | Methyl | 4-MeOC$_6$H$_4$ |
| 1716 | ClCH$_2$ | 4-MeOC$_6$H$_4$ |
| 1717 | cyclopropyl | 4-MeOC$_6$H$_4$ |
| 1718 | isopropyl | 4-MeOC$_6$H$_4$ |
| 1719 | ethyl | 4-MeOC$_6$H$_4$ |
| 1720 | cyclopentyl | 4-MeOC$_6$H$_4$ |
| 1721 | cyclobutyl | 4-MeOC$_6$H$_4$ |
| 1722 | benzyl | 4-MeOC$_6$H$_4$ |
| 1723 | n-propyl | 4-MeOC$_6$H$_4$ |
| 1724 | 4-ClC$_6$H$_4$CH$_2$ | 4-MeOC$_6$H$_4$ |
| 1725 | 3-MeOC$_6$H$_4$CH$_2$ | 4-MeOC$_6$H$_4$ |
| 1726 | 4-MeOC$_6$H$_4$CH$_2$ | 4-MeOC$_6$H$_4$ |
| 1727 | 3,4-diMeOC$_6$H$_4$CH$_2$ | 4-MeOC$_6$H$_4$ |
| 1728 | 2,5-diMeOC$_6$H$_4$CH$_2$ | 4-MeOC$_6$H$_4$ |
| 1729 | Methyl | 2-MeOC$_6$H$_4$ |
| 1730 | Methyl | 3,4-diMeOC$_6$H$_4$ |
| 1731 | 3,4-(OCH$_2$O)C$_6$H$_4$CH$_2$ | 4-MeOC$_6$H$_4$ |
| 1732 | 3-thiophenylCH$_2$ | 4-MeOC$_6$H$_4$ |
| 1733 | 2-MeOC$_6$H$_4$CH$_2$ | 4-MeOC$_6$H$_4$ |
| 1734 | 3,4-diClOC$_6$H$_4$CH$_2$ | 4-MeOC$_6$H$_4$ |
| 1735 | 2,4-diClOC$_6$H$_4$CH$_2$ | 4-MeOC$_6$H$_4$ |
| 1736 | 2-ClC$_6$H$_4$CH$_2$ | 4-MeOC$_6$H$_4$ |
| 1737 | H$_2$NCH$_2$ | 4-MeOC$_6$H$_4$ |
| 1738 | HOCH$_2$NHCH$_2$CH$_2$ | 4-MeOC$_6$H$_4$ |
| 1739 | Me$_2$NCH$_2$ | 4-MeOC$_6$H$_4$ |
| 1740 | piperazinoCH$_2$ | 4-MeOC$_6$H$_4$ |
| 1741 | 4-Me-piperazinoCH$_2$ | 4-MeOC$_6$H$_4$ |
| 1742 | 4-HOCH$_2$CH$_2$-piperazinoCH$_2$ | 4-MeOC$_6$H$_4$ |
| 1743 | piperidinoCH$_2$ | 4-MeOC$_6$H$_4$ |
| 1744 | 4-NH$_2$CH$_2$-piperidinoCH$_2$ | 4-MeOC$_6$H$_4$ |
| 1745 | CH$_3$CH$_2$NHCH$_2$ | 4-MeOC$_6$H$_4$ |
| 1746 | thiomorpholinoCH$_2$ | 4-MeOC$_6$H$_4$ |
| 1747 | morpholinoCH$_2$ | 4-MeOC$_6$H$_4$ |
| 1748 | pyyrolidinoCH$_2$ | 4-MeOC$_6$H$_4$ |
| 1749 | 4-pyridylCH$_2$NHCH$_2$ | 4-MeOC$_6$H$_4$ |
| 1750 | 4-CH$_3$CONHC$_6$H$_4$CH$_2$ | 4-MeOC$_6$H$_4$ |
| 1751 | 4-CH$_3$OCONHC$_6$H$_4$CH$_2$ | 4-MeOC$_6$H$_4$ |
| 1752 | 4-NH$_2$CH$_2$CONHC$_6$H$_4$CH$_2$ | 4-MeOC$_6$H$_4$ |
| 1753 | 4-Me$_2$NCH$_2$CONHC$_6$H$_4$CH$_2$ | 4-MeOC$_6$H$_4$ |
| 1754 | 4-N$_3$C$_6$H$_4$CH$_2$ | 4-MeOC$_6$H$_4$ |
| 1755 | 4-NH$_2$C$_6$H$_4$CH$_2$ | 4-MeOC$_6$H$_4$ |
| 1756 | C$_6$H$_5$NH | 4-MeOC$_6$H$_4$ |
| 1757 | CH$_3$CH$_2$CH$_2$NH | 4-MeOC$_6$H$_4$ |
| 1758 | 4-NH$_2$C$_6$H$_4$CH$_2$NH | 4-MeOC$_6$H$_4$ |
| 1759 | 4-pyridyCH$_2$NH | 4-MeOC$_6$H$_4$ |
| 1760 | Methyl | 4-HOC$_6$H$_4$ |
| 1761 | H | 4-MeOC$_6$H$_4$ |
| 1762 | Methyl | 3-pyridyl |
| 1763 | Methyl | 4-pyridyl |
| 1764 | H | 4-pyridyl |
| 1765 | Methyl | C$_6$H$_5$ |
| 1766 | Methyl | 4-MeSC$_6$H$_4$ |
| 1767 | Methyl | 4-MeSO$_2$C$_6$H$_4$ |
| 1768 | Methyl | 4-Me$_2$NC$_6$H$_4$ |
| 1769 | morpholinoCH$_2$ | 4-Me$_2$NC$_6$H$_4$ |
| 1770 | Me$_2$NCH$_2$ | 4-Me$_2$NC$_6$H$_4$ |
| 1771 | Me$_2$NCH$_2$ | 4-(piperdinyl)C$_6$H$_4$ |
| 1772 | Me$_2$NCH$_2$ | 4-(morpholinyl)C$_6$H$_4$ |
| 1773 | Me$_2$NCH$_2$ | 4-CH$_3$CH$_2$OC$_6$H$_4$ |

TABLE 4-continued

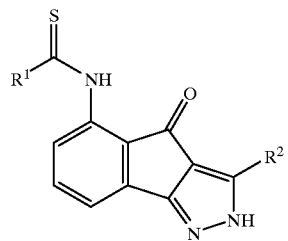

| Example Number | R¹ | R² |
|---|---|---|
| 1774 | Me$_2$NCH$_2$ | 4-CH$_3$CH$_2$CH$_2$CH$_2$C$_6$H$_4$ |
| 1775 | Me$_2$NCH$_2$ | 4-CH$_3$CH$_2$C$_6$H$_4$ |
| 1776 | Me$_2$NCH$_2$ | 4-CH$_3$CH$_2$CH$_2$C$_6$H$_4$ |

The compounds useful according to the invention optionally are supplied as salts. Those salts which are pharmaceutically acceptable are of particular interest since they are useful in administering the foregoing compounds for medical purposes. Salts which are not pharmaceutically acceptable are useful in manufacturing processes, for isolation and purification purposes, and in some instances, for use in separating stereoisomeric forms of the compounds of this invention. The latter is particularly true of amine salts prepared from optically active amines.

Where the compound useful according to the invention contains a carboxy group, or a sufficiently acidic bioisostere, base addition salts may be formed and are simply a more convenient form for use; and in practice, use of the salt form inherently amounts to use of the free acid form.

Also, where the compound useful according to the invention contains a basic group, or a sufficiently basic bioisostere, acid addition salts may be formed and are simply a more convenient form for use; and in practice, use of the salt form inherently amounts to use of the free base form.

The foregoing compounds useful according to the invention may also be mixed another therapeutic compound to form pharmaceutical compositions (with or without diluent or carrier) which, when administered, provide simultaneous administration of a combination of active ingredients resulting in the combination therapy of the invention.

While it is possible for the compounds useful according to the invention to be administered alone it is preferably to present them as pharmaceutical compositions. The pharmaceutical compositions, both for veterinary and for human use, useful according to the present invention comprise at lease one compound of the invention, as above defined, together with one or more acceptable carriers therefor and optionally other therapeutic ingredients.

In certain preferred embodiments, active ingredients necessary in combination therapy may be combined in a single pharmaceutical composition for simultaneous administration.

The choice of vehicle and the content of active substance in the vehicle are generally determined in accordance with the solubility and chemical properties of the active compound, the particular mode of administration and the provisions to be observed in pharmaceutical practice. For example, excipients such as lactose, sodium citrate, calcium carbonate, dicalcium phosphate and disintegrating agents such as starch, alginic acids and certain complex silicates combined with lubricants such as magnesium stearate, sodium lauryl sulphate and talc may be used for preparing tablets. To prepare a capsule, it is advantageous to use lactose and high molecular weight polyethylene glycols. When aqueous suspensions are used they can contain emulsifying agents or agents which facilitate suspension. Diluents such as sucrose, ethanol, polyethylene glycol, propylene glycol, glycerol and chloroform or mixtures thereof may also be used.

The oily phase of the emulsions of this invention may be constituted from known ingredients in a known manner. While the oily phase may comprise merely an emulsifier (otherwise known as an emulgent), it desirably comprises a mixture of at least one emulsifier with a fat or an oil or with both a fat and an oil. Preferably, a hydrophilic emulsifier is included together with a lipophilic emulsifier which acts as a stabilizer. It is also preferred to include both an oil and a fat. Together, the emulsifier(s) with or without stabilizer(s) make up the emulsifying wax, and the way together with the oil and fat make up the emulsifying ointment base which forms the oily dispersed phase of a cream formulation. Emulgents and emulsion stabilizers suitable for use in the formulation of the present invention include Tween® 60, Span® 80, cetostearyl alcohol, benzyl alcohol, myristyl alcohol, glyceryl mono-stearate and sodium lauryl sulfate.

If desired, the aqueous phase of the cream base may include, for example, a least 30% w/w of a polyhydric alcohol, i.e. an alcohol having two or more hydroxyl groups such as propylene glycol, butane 1,3-diol, mannitol, sorbitol, glycerol and polyethylene glycol (including PEG 400) and mixtures thereof. The topical formulations may desirably include a compound which enhances absorption or penetration of the active ingredient through the skin or other affected areas. Examples of such dermal penetration enhancers include dimethyl sulphoxide and related analogue.

The choice of suitable oils or fats for the formulation is based on achieving the desired cosmetic properties. Thus the cream should preferably be a non-greasy, non-staining and washable product with suitable consistency to avoid leakage from tubes or other containers. Straight or branched chain, mono- or dibasic alkyl esters such as di-isopropyl myristate, decyl oleate, isopropyl palmitate, butyl stearate, 2-ethylhexyl palmitate or a blend of branched chain esters known as Crodamol CAP may be used, the last three being preferred esters. These may be used alone or in combination depending on the properties required. Alternatively, high melting point lipids such as white soft paraffin and/or liquid paraffin or other mineral oils can be used. Solid compositions of may also be employed as fillers in soft and hard-filled gelatin capsules using such excipients as lactose or milk sugar as well as high molecular weight polyethylene glycols, and the like.

The pharmaceutical compositions can be administered in a suitable formulation to humans and animals by topical or systemic administration, including oral, inhalational, rectal, nasal, buccal, sublingual, vaginal, parenteral (including subcutaneous, intramuscular, intravenous, intradermal, intrathecal and epidural), intracisternal and intraperitoneal. It will be appreciated that the preferred route may vary with for example the condition of the recipient.

The formulations can be prepared in unit dosage form by any of the methods well known in the art of pharmacy. Such methods include the step of bringing into association the active ingredient with the carrier which constitutes one or more accessory ingredients. In general the formulations are prepared by uniformly and intimately bringing into association the active ingredient with liquid carriers or finely divided solid carriers or both, and then, if necessary, shaping the product.

A tablet may be made by compression or moulding, optionally with one or more accessory ingredients. Compressed tables may be prepared by compressing in a suitable machine the active ingredient in a free-flowing form such as a powder or granules, optionally mixed with a binder, lubricant, inert diluent, preservative, surface active or dispersing agent. Moulded tablets may be made by moulding in a suitable machine a mixture of the powdered compounds moistened with an inert liquid diluent. The tablets may optionally be coated or scored and may be formulated so as to provide slow or controlled release of the active ingredient therein.

Solid compositions for rectal administration include suppositories formulated in accordance with known methods and containing at least one compound of the invention.

If desired, and for more effective distribution, the compounds can be microencapsulated in, or attached to, a slow release or targeted delivery systems such as a biocompatible, biodegradable polymer matrices (e.g. poly(d,l-lactide co-glycolide)), liposomes, and microspheres and subcutaneously or intramuscularly injected by a technique called subcutaneous or intramuscular depot to provide continuous slow release of the compoundis) for a period of 2 weeks or longer. The compounds may be sterilized, for example, by filtration through a bacteria retaining filter, or by incorporating sterilizing agents in the form of sterile solid compositions which can be dissolved in sterile water, or some other sterile injectable medium immediately before use.

Actual dosage levels of active ingredient in the compositions of the invention may be varied so as to obtain an amount of active ingredient that is effective to obtain a desired therapeutic response for a particular composition and method of administration. The selected dosage level therefore depends upon the desired therapeutic effect, on the route of administration, on the desired duration of treatment and other factors.

Total daily dose of the compounds useful according to this invention administered to a host in single or divided doses may be in amounts, for example, of from about 0.001 to about 100 mg/kg body weight daily and preferably 0.01 to 10 mg/kg/day. Dosage unit compositions may contain such amounts of such submultiples thereof as may be used to make up the daily dose. It will be understood, however, that the specific dose level for any particular patient will depend upon a variety of factors including the body weight, general health, sex, diet, time and route of administration, rates of absorption and excretion, combination with other drugs and the severity of the particular disease being treated.

The amount of each component administered is determined by the attending clinicians taking into consideration the etiology and severity of the disease, the patient's condition and age, the potency of each component and other factors.

The formulations may be presented in unit-dose or multi-dose containers, for example sealed ampoules and vials with elastomeric stoppers, and may be stored in a freeze-dried (lyophilized) condition requiring only the addition of the sterile liquid carrier, for example water for injections, immediately prior to use. Extemporaneous injection solutions and suspensions may be prepared from sterile powders, granules and tablets of the kind previously described.

Administration of a compound of the present invention in combination with additional therapeutic agents, may afford an efficacy advantage over the compounds and agents alone, and may do so while permitting the use of lower doses of each. A lower dosage minimizes the potential of side effects, thereby providing an increased margin of safety. The combination of a compound of the present invention with such additional therapeutic agents is preferably a synergistic combination. Synergy, as described for example by Chou and Talalay, Adv. Enzyme Regul. 22:27–55 (1984), occurs when the therapeutic effect of the compound and agent when administered in combination is greater than the additive effect of the either the compound or agent when administered alone. In general, a synergistic effect is most clearly demonstrated at levels that are (therapeutically) sub-optimal for either the compound of the present invention or a known anti-proliferative agent alone, but which are highly efficacious in combination. Synergy can be in terms of improved inhibitory response without substantial increases in toxicity over individual treatments alone, or some other beneficial effect of the combination compared with the individual components.

The compounds of the invention, their methods or preparation and their biological activity will appear more clearly from the examination of the following examples which are presented as an illustration only and are not to be considered as limiting the invention in its scope.

Procedures for evaluating the biological activity of compounds or compositions according to the invention are carried out as described herein or by the application or adaptation of known procedures, by which is meant procedures used heretofore or as described in the literature.

Utility

Inhibition of Kinase/Cyclin Complex Enzymatic Activity

Several of the compounds disclosed in this invention were assayed for their inhibitory activity against cdk4/D1 and cdk2/E kinase complexes. Briefly, the in vitro assays employ cell lysates from insect cells expressing either of the kinases and subsequently their corresponding regulatory units. The cdk2/cyclinE is purified from insect cells expressing His-tagged cdk2 and cyclin E. The cdk/cyclin lysate is combined in a microtitre-type plate along with a kinase compatible buffer, $^{32}$P-labeled ATP at a concentration of 50 mM, a GST-Rb fusion protein and the test compound at varying concentrations. The kinase reaction is allowed to proceeded with the radiolabled ATP, then effectively stopped by the addition of a large excess of EDTA and unlabeled ATP. The GST-Rb labeled protein is sequestered on a GSH-Sepharose bead suspension, washed, resuspended in scintillant, and the $^{32}$P activity detected in a scintillation counter. The compound concentration which inhibits 50% of the kinase activity was calculated for each compound. A compound was considered active if its $IC_{50}$ was found to be less than 1 μM.

Inhibition of HCT 116 Cancer Cell Proliferation

To test the cellular activity of several compounds disclosed in this invention, we examined the effect of these compounds on cultured HCT116 cells and determined their effect on cell-cycle progression by the calorimetric cytotoxicity test using sulforhodamine B (Skehan et al. J. Natl. Cancer Inst. 82:1107–12, 1990). Briefly, HCT116 cells are cultured in the presence of test compounds at increasing concentrations. At selected time points, groups of cells are fixed with trichloroacetic acid and stained with sulforhodamine B (SRB). Unbound dye was removed by washing and protein-bound dye was extracted for determination of optical density. A compound was considered active if its $IC_{50}$ was found to be less than 10 μM.

What is claimed is:
1. A compound according to formula (I):

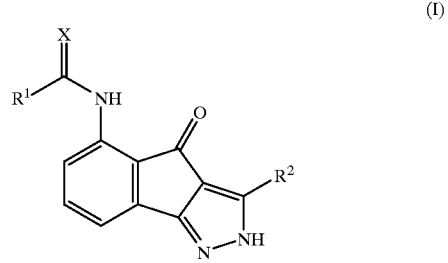

or stereoisomers, pharmaceutically acceptable salts, and prodrugs thereof, wherein:

X is selected from the groups: O, S, and NR;

R is selected from the groups: H, $C_{1-4}$ alkyl, and $NR^5R^{5a}$;

$R^1$ is selected from the groups: H, $C_{1-10}$ alkyl substituted with 0–3 $R^c$, $C_{2-10}$ alkenyl substituted with 0–3 $R^c$, $C_{2-10}$ alkynyl substituted with 0–3 $R^c$, —$NHR^4$, $C_{3-10}$ membered carbocycle substituted with 0–5 $R^a$, and 3–10 membered heterocycle containing from 1–4 heteroatoms selected from O, N, and S and substituted with 0–5 $R^b$;

$R^a$ is independently selected from the groups: $R^5$ $R^{5a}N(CR^6R^{6a})m$, $R^5O(CR^6R^{6a})m$, halo, —CN, $N_3$, $NO_2$, $C_{1-4}$ alkyl, $C_{1-4}$ haloalkyl, $NR^3R^{3a}$, =O, $OR^3$, $SR^3$, $COR^3$, $CO_2R^3$, $CONR^3R^{3a}$, $NHC(O)NR^3R^{3a}$, $NHC(S)NR^3R^{3a}$, $NR^3C(O)OR^3$, $NR^3C(O)R^3$, $SO_2NR^3R^{3a}$, $SO_2R^{3b}$, and 5–10 membered heterocycle containing from 1–4 heteroatoms selected from O, N, and S;

alternatively, when two $R^a$'s are present on adjacent carbon atoms they combine to form —$OCH_2O$— or —$OCH_2CH_2O$—;

$R^b$ is independently selected from the groups: halo, —CN, $NO_2$, $C_{1-4}$ alkyl, $C_{1-4}$ haloalkyl, $NR^3R^{3a}$, $NR^3C(O)OR^3$, $NR^3C(O)R^3$, $OR^3$, $COR^3$, $CO_2R^3$, $CONR^3R^{3a}$, $CON(R^6)((CH_2)_mR^7)$, $CO(CH_2)_mR^7$, $NHC(O)NR^3R^{3a}$, $NHC(S)NR^3R^{3a}$, $SO_2NR^3R^{3a}$, and $SO_2R^{3b}$;

$R^c$ is independently selected from the groups: halo, —CN, $NO_2$, $C_{1-4}$ alkyl, $C_{1-4}$ haloalkyl, $NR^3R^{3a}$, $NR^5NR^5R^{5a}$, $NR^3C(O)OR^3$, $NR^3C(O)R^3$, =O, $OR^3$, $COR^3$, $CO_2R^3$, $CONR^3R^{3a}$, $NHC(O)NR^3R^{3a}$, $NHC(S)NR^3R^{3a}$, $SO_2N^3R^{3a}$, $SO_2R^{3b}$, $C_{3-10}$ membered carbocycle substituted with 0–5 $R^a$, and 5–10 membered heterocycle containing from 1–4 heteroatoms selected from O, N, and S, substituted with 0–3 $R^3$;

$R^2$ is selected from the groups: H, $C^{1-10}$ alkyl substituted with 0–3 $R^c$, $C_{2-10}$ alkenyl substituted with 0–3 $R^c$, $C_{2-10}$ alkynyl substituted with 0–3 $R^c$, —$(CF_2)_mCF^3$, $C_{3-10}$ membered carbocycle substituted with 0–5 $R^a$, and 3–10 membered heterocycle containing from 1–4 heteroatoms selected from O, N, and S and substituted with 0–5 $R^b$;

$R^3$ is independently selected from the groups: H, halo, —CN, $NO_2$, $C_{1-4}$ haloalkyl, $R^5R^{5a}N(CR^6R^{6a})m$, $NR^5NR^5R^{5a}$, $NR^5C(O)OR^5$, $NR^5C(O)R^5$, =O, $R^5O(CR^6R^{6a})m$, $COR^5$, $CO_2R^5$, $CONR^5R^{5a}$, $NHC(O)NR^5R^{5a}$, $NHC(S)NR^5R^{5a}$, $SO_2NR^5R^{5a}$, $SO_2R^{5b}$, $C_{1-4}$ alkyl, phenyl, and benzyl;

$R^{3a}$ is independently selected from the groups: H, $C_{1-4}$ alkyl, phenyl, and benzyl;

alternatively, $R^3$ and $R^{3a}$, together with the atoms to which they are attached, form a heterocycle having 4–8 atoms in the ring and containing an additional 0–1 N, S, or O atom and substituted with 0–3 $R^{3c}$;

$R^{3b}$ is independently selected from the groups: H, $C_{1-4}$ alkyl, phenyl, and benzyl;

$R^{3c}$ is independently selected from the groups: halo, —CN $N_3$, $NO_2$, $C_{1-4}$ alkyl, $C_{3-8}$ cycloalkyl, $C_{4-10}$ cycloalkylalkyl, $C_{1-4}$ haloalkyl, $NR^3R^{3b}$, $R^5R^{5a}N(CR^6R^{6a})m$, =O, $OR^3$, $R^5O(CR^6R^{6a})m$, $COR^3$, $CO_2R^3$, $CONR^3R^{3b}$, $NHC(O)NR^3R^{3b}$, $NHC(S)NR^3R^{3b}$, $NR^3C(O)OR^3$, $NR^3C(O)R^3$, $C(=NR^5)R^{5a}$, $C(=NR^5)NR^{5a}R^{5b}$, $SO_2NR^3R^{3b}$, $SO_2R^{3b}$, and 5–10 membered heterocycle containing from 1–4 heteroatoms selected from O, N, and S;

$R^4$ is independently selected from the groups: H, —CN, $C_{1-4}$ alkyl, $C_{1-4}$ haloalkyl, $NR^3R^{3a}$, $NR^3C(O)OR^3$, $NR^3C(O)R^3$, $OR^3$, $COR^3$, $CO_2R^3$, $CONR^3R^{3a}$, NHC(O)$NR^3R^{3a}$, $NHC(S)NR^3R^{3a}$, $SO_2NR^3R^{3a}$, $SO_2R^{3b}$, $C_{3-10}$ membered carbocycle substituted with 0–5 $R^a$, and 5–10 membered heterocycle containing from 1–4 heteroatoms selected from O, N, and S, substituted with 0–3 $R^3$;

$R^5$ is independently selected from the groups: H, $C_{1-4}$ alkyl, phenyl and benzyl;

$R^{5a}$ is independently selected from the groups: H, $C_{1-4}$ alkyl, phenyl and benzyl;

alternatively, $R^5$ and $R^{5a}$, together with the atoms to which they are attached, form a heterocycle having 4–8 atoms in the ring and containing an additional 0–1 N, S, or O atom;

$R^{5b}$ is independently selected from the groups: H, $C_{1-4}$ alkyl, phenyl and benzyl;

$R^6$ is idependently selected from the groups: H, $C_{1-4}$ alkyl;

$R^{6a}$ is independently selected from the groups: H, $C_{1-4}$ alkyl;

$R^7$ is independently selected from the groups: $NR^3R^{3a}$, $C_{3-10}$ membered carbocycle substituted with 0–3 $R^3$, and 5–10 membered heterocycle containing from 1–4 heteroatoms selected from O, N, and S, substituted with 0–3 $R^3$; and m is independently selected from 0, 1, 2, 3, and 4;

provided that: when $R^2$ is a $C_{1-4}$ unsubstituted, branched alkyl then $R^1$ is not $CH_3$; or when $R^1$ is $NHR^4$ and $R^4$ is $NR^3R^{3a}$ then $R^3$ and $R^{3a}$ can not both be phenyl.

2. A compound according to claim 1, wherein

X is O or S;

$R^1$ is H, $C_{1-10}$ alkyl substituted with 0–3 $R^c$, —$NHR^4$, $C_{3-10}$ membered carbocycle substituted with 0–5 $R^a$, or 3–10 membered heterocycle containing from 1–4 heteroatoms selected from O, N, and S and substituted with 0–5;

$R^c$ is independently selected from the groups: halo, $C_{3-10}$ membered carbocycle substituted with 0–5 $R^a$, 5–10 membered heterocycle containing from 1–4 heteroatoms selected from O, N, and S, substituted with 0–3 $R^3$, $NR^3R^{3a}$;

$R^3$ is H, $C_{1-4}$ alkyl, phenyl, benzyl, or together with the atoms to which they are attached, form a heterocycle having 4–8 atoms in the ring and containing an additional 0–1 N, S, or O atom and substituted with 0–3 $R^{3c}$;

R4 is H, $C_{1-4}$ alkyl, $NR^3R^{3a}$, $C_{3-10}$ membered carbocycle substituted with 0–5 $R^a$, and 5–10 membered heterocycle containing from 1–4 heteroatoms selected from O, N, and S, substituted with 0–3 $R^3$;

$R^2$ is selected from the groups: $C_{3-10}$ membered carbocycle substituted with 0–5 $R^a$, and 3–10 membered heterocycle containing from 1–4 heteroatoms selected from O, N, and S and substituted with 0–5 $R^b$, and $C_{1-10}$ alkyl substituted with 0–3 $R^c$.

3. A compound according to claim 1, wherein

X is O or S;

$R^1$ is $C_{1-4}$ alkyl substituted with 0–3 $R^c$, wherein $R^c$ is independently selected from the group consisting of: $C_{3-6}$ membered carbocycle substituted with 0–5 $R^a$, 5–6 membered heterocycle substituted with 0–3 $R^3$, $NR^3R^{3a}$, and $OR^3$; $C_{3-6}$ membered carbocycle substituted with 0–5 $R^a$, wherein $R^a$ is independently selected from the group consisting of: $R^5R^{5a}N(CR^6R^{6a})m—$, $R^5O(CR^6R^{6a})m—$, $OR^3$, halo, $C_{1-4}$ alkyl, —$NR^3C(O)R^3$, $COR^3$, $CO_2R^3$, $N_3$, $NR^3C(O)OR^3$, $NR^3R^{3a}$, $CONR^3R^{3a}$, and 5–6 membered heterocycle; or when two $R^a$'s are present on adjacent carbon atoms they combine to form —$OCH_2O$— or —$OCH_2CH_2O$—; or 5–6 membered heterocycle and substituted with 0–5 $R^b$, wherein $R^b$ is independently selected from the group: $OR^3$, halo, $COR^3$, $C_{1-4}$ alkyl, $CO_2R^3$, $NR^3C(O)R^3$, $NR^3C(O)OR^3$, $NR^3R^{3a}$, and $CONR^3R^{3a}$;

$R^2$ is $C_{3-6}$ membered carbocycle substituted with 0–5 $R^a$, wherein $R^a$ is independently selected from the groups: $R^5R^{5a}N(CR^6R^{6a})m$, $R^5O(CR^6R^{6a})m$, $OR^3$, halo, $C_{1-4}$ alkyl, $NR^3C(O)R^3$, $COR^3$, $CO_2R^3$, $N_3$, $NR^3C(O)OR^3$, $NR^3R^{3a}$, $CONR^3R^{3a}$, and 5–6 membered heterocycle, or when two $R^a$'s are present on adjacent carbon atoms they combine to form —$OCH_2O$— or —$OCH_2CH_2O$—; 3–6 membered heterocycle containing from 1–4 heteroatoms selected from O, N, and S and substituted with 0–5 $R^b$, wherein $R^b$ is independently selected from the group: $OR^3$, halo, $COR^3$, $C_{1-4}$ alkyl, $CO_2R^3$, $NR^3C(O)R^3$, $NR^3C(O)OR^3$, $NR^3R^{3a}$, and $CONR^3R^{3a}$; or $C_{1-10}$ alkyl substituted with 0–3 $R^c$, wherein $R^c$ is independently selected from the groups: $C_{3-6}$ membered carbocycle substituted with 0–5 $R^a$, 5–6 membered heterocycle substituted with 0–3 $R^3$, $NR^3R^{3a}$, and $OR^3$.

4. A compound according to claim 1, wherein

X is O or S;

$R^1$ is selected from the groups: H, —$NHR^4$, $C_{1-4}$ alkyl substituted with 0–3 $R^c$, $C_{3-6}$ membered carbocycle substituted with 0–5 $R^a$, and 5–6 membered heterocycle and substituted with 0–5 $R^b$;

$R^2$ is selected from the group: $C_{3-6}$ membered carbocycle substituted with 0–5 $R^a$, 3–10 membered heterocycle containing from 1–4 heteroatoms selected from O, N, and S and substituted with 0–5 $R^b$, and $C_{1-10}$ alkyl substituted with 0–3 $R^c$, $C_{2-10}$ alkenyl substituted with 0–3 $R^c$;

$R^4$ is independently selected from the groups: H, $C_{1-4}$ alkyl, $NR^3R^{3a}$, 3–6 membered carbocycle substituted with 0–5 $R^a$, and 5–6 membered heterocycle substituted with 0–3 $R^3$;

$R^3$ is independently selected from the group: H, halo, $COR^5$, $CO_2R^5$, $R^5R^{5a}N(CR^6R^{6a})m$, $R^5O(CR^6R^{6a})m$, $CONR^5R^{5a}$, $NR^5C(O)OR^5$, $NR^5C(O)R^5$, $C_{1-4}$ alkyl, phenyl, and benzyl;

$R^{3a}$ is independently selected from the group: H, $C_{1-4}$ alkyl, phenyl, and benzyl; or $R^3$ and $R^{3a}$, together with the atoms to which they are attached, form a 5–6 membered heterocycle containing an additional 0–1 N, S, or O atom and substituted with 0–3 $R^{3c}$;

$R^c$ is independently selected from the groups: $C_{3-6}$ membered carbocycle substituted with 0–5 $R^a$, 5–6 membered heterocycle substituted with 0–3 $R^3$, $NR^3R^{3a}$, and $OR^3$;

$R^a$ is independently selected from the groups: $R^5$ $R^{5a}N$ $(CR^6R^{6a})m$, $R^5O(CR^6R^{6a})m$, $OR^3$, halo, $C_{1-4}$ alkyl, $NR^3C(O)R^3$, $COR^3$, $CO_2R^3$, $N_3$, $NR^3C(O)OR^3$, $NR^3R^{3a}$, $CONR^3R^{3a}$, 5–6 membered heterocycle; or when two $R^a$'s are present on adjacent carbon atoms they combine to form —$OCH_2O$— or —$OCH_2CH_2O$—;

$R^b$ is independently selected from the group: $OR^3$, halo, $COR^3$, $C_{1-4}$ alkyl, $CO_2R^3$, $NR^3C(O)R^3$, $NR^3C(O)OR^3$, $NR^3R^{3a}$, $CONR^3R^{3a}$;

$R^{3c}$ is independently selected from the groups: $OR^3$, halo, $COR^3$, $R^5R^{5a}N(CR^6R^{6a})m$—, $R^5O)(CR^6R^{6a})m$—, $CO_2R^3$, $N_3$, $NR^3R^{3b}$, $C_{1-4}$ alkyl, $NR^3C(O)R^3$, $NR^3C(O)OR^3$, $N_3$, $NR^3R^{3b}$, $CONR^3R^{3b}$, and 5–6 membered heterocycle; and m is independently selected from the group consisting of 1 2, 3 and 4.

5. A compound according to claim 1, wherein
$R^1$ is selected from the group: —$NHR^4$ and $C_{1-2}$ alkyl substituted with 1 $R^c$.

6. A compound according to claim 1 wherein
X is O or S; and
$R^1$ is selected from the group: H, $C_{1-4}$ alkyl substituted with 0–3 $R^c$, $C_{2-4}$ alkenyl substituted with 0–3 $R^c$, $C_{2-4}$ alkynyl substituted with 0–3 $R^C$, —$NHR^4$, $C_{3-6}$ carbocycle substituted with 0–5 $R^a$, and 3–6 membered heterocycle containing from 1–4 heteroatoms selected from O, N, and S and substituted with 0–5 $R^b$.

7. A compound according to claim 1 wherein
X is O or S; and
$R^1$ is selected from the group: H, $C_{1-4}$ alkyl substituted with 0–3 $R^c$, $C_{2-4}$ alkenyl substituted with 0–3 $R^c$, $C_{2-4}$ alkynyl substituted with 0–3 $R^c$, —$NHR^4$, $C_{3-6}$ carbocycle substituted with 0–5 $R^a$, and 3–6 membered heterocycle containing from 1–4 heteroatoms selected from O, N, and S and substituted with 0–5 $R^b$;

$R^a$ is independently at each occurrence selected from the group: —$CH_2N(CH_3)_2$, —$CH_2NH_2$, —SH, —$SCH_3$, —$NR_3C(O)R_3$, —$N_3$, halo, $C_{1-4}$ alkyl, $NR^3R^{3a}$, and $OR^3$; alternatively, when two $R^a$'s are present on adjacent carbon atoms they combine to form —$OCH_2O$— or —$OCH_2CH_2O$—;

$R^b$ is independently at each occurrence selected from the group: halo, $C_{1-4}$ alkyl, $NR^3R^{3a}$, $OR^3$, $COR^3$, and $CO_2R^3$;

$R^c$ is independently at each occurrence selected from the group: halo, $C_{1-4}$ alkyl, $NR^3R^{3a}$, $C_{3-6}$ carbocycle substituted with 0–5 $R^a$, and 5–7 membered heterocycle containing from 1–4 heteroatoms selected from O, N, and S, substituted with 0–3 $R^3$;

$R^{3a}$ is H or $C_{1-4}$ alkyl; and $R^3$ is selected from the group: H, —$CH_2CH_2OH$, —C(O)$CH_2NH_2$, —C(O)$CH_2N(CH3)2$, —$NR^5R^{5a}$, —$C_{1-4}$alkyl-$NR^5R^{5a}$, $C_{1-4}$ alkyl, phenyl, and benzyl.

8. A compound according to claim 1 wherein
X is O or S;
$R^1$ is selected from the group: H, $C_{1-4}$ alkyl substituted with 0–3 $R^c$, —$NHR^4$, $C_{3-6}$ carbocycle substituted with 0–5 $R^a$, and 3–6 membered heterocycle containing from 1–4 heteroatoms selected from O, N, and S and substituted with 0–5 $R^b$;

$R^a$ is independently at each occurrence selected from the group: —$CH_2N(CH_3)_2$, —$CH_2NH_2$, —SH, —$SCH_3$, halo, $C_{1-4}$ alkyl, $NR^3R^{3a}$, and $OR^3$; alternatively, when two $R^a$'s are present on adjacent carbon atoms they combine to form —$OCH_2O$— or —$OCH_2CH_2O$—;

$R^b$ is independently at each occurrence selected from the group: halo, $C_{1-4}$ alkyl, $NR^3R^{3a}$, $OR^3$, $COR^3$, and $CO_2R^3$;

$R^c$ is independently at each occurrence selected from the group: —OH, chloro, $C_{1-4}$ alkyl, —NH2, —NHCH3, —NHCH2CH3, —NHCH2CH2CH3, —NHCH2CH2OH, —N(CH3)2, phenyl substituted with 0–5 $R^a$, and 5–7 membered heterocycle containing from 1–4 heteroatoms selected from O, N, and S, substituted with 0–3 $R^3$.

9. A compound according to claim 1 wherein
$R^1$ is selected from the group: H, $C_{1-10}$ alkyl substituted with 0–3 $R^c$, $C_{2-10}$ alkenyl substituted with 0–3 $R^c$, $C_{2-10}$ alkynyl substituted with 0–3 $R^c$;

$R^2$ is selected from the group: H, —$(CF_2)_mCF_3$, $C_{3-10}$ carbocycle substituted with 0–5 $R^a$, and 3–10 membered heterocycle containing from 1–4 heteroatoms selected from O, N, and S and substituted with 0–5 $R^b$; and $R^c$ is independently at each occurrence selected from the group: phenyl substituted with 0–5 $R^a$, and thiophenyl or pyridyl, which is substituted with 0–3 $R^3$.

10. A compound according to claim 1 wherein
$R^1$ is selected from the group: H, $C_{1-10}$ alkyl substituted with 0–3 $R^c$, $C_{2-10}$ alkenyl substituted with 0–3 $R^c$, $C_{2-10}$ alkynyl substituted with 0–3 $R^c$;

$R^2$ is selected from the group: H, —$(CF_2)_mCF_3$, $C_{3-10}$ carbocycle substituted with 0–5 $R^a$, and 3–10 membered heterocycle containing from 1–4 heteroatoms selected from O, N, and S and substituted with 0–5 $R^b$; and $R^c$ is independently at each occurrence selected from the group: thiophenyl, piperazinyl, piperidinyl, thiomorpholinyl, morpholinyl, pyrrolidinyl, and pyridyl, which is substituted with 0–3 substituents indepently selected from the group consiting of CH3, CH2CH2OH, CH2CH2NH2, —C(=O)NH2, —OCH3, CH2NH2, NHCH2CH3,OH, NH2, halo, —CH2N(CH3)2, —OCH2CH2O—,—OCH2O—, —N(CH3)2, uridomethyl, and pyridyl.

11. A compound according to claim 1 wherein
$R^1$ is selected from the group: H, $C_{1-10}$ alkyl substituted with 0–3 $R^c$, $C_{2-10}$ alkenyl substituted with 0–3 $R^c$, $C_{2-10}$ alkynyl substituted with 0–3 $R^c$;

$R^2$ is selected from the group: H, —$(CF_2)_mCF_3$, $C_{3-10}$ carbocycle substituted with 0–5 $R^a$, and 3–10 membered heterocycle containing from 1–4 heteroatoms selected from O, N, and S and substituted with 0–5 $R^b$; and $R^c$ is phenyl substituted with 0–5 substituents indepently selected from the group consiting of CH3, CH2CH2OH, CH2CH2NH2, —C(=O)NH2, —OCH3, CH2NH2, NHCH2CH3, OH, NH2, halo, —CH2N(CH3)2, —OCH2CH2O—, —OCH2O—, —N(CH3)2, uridomethyl, and pyridyl.

12. A compound according to claim 1 wherein
X is O or S;
$R^1$ is —$NHR^4$ or methylene substituted with 0–3 $R^c$;
$R^c$ is $NR^3R^{3a}$;
$R^4$ is selected from the group consisting of H, C1–4 alkyl, and $NR^3R^{3a}$; and $R^3$ and $R^{3a}$, are independently hydrogen or C1–4alkyl, or $R^3$ and $R^{3a}$, together with the nitrogen atom to which they are attached, form a 4–8 membered heterocycle containing an additional 0–1 N, S, or O atom and substituted with 0–3 $R^{3c}$.

13. A compound according to claim 1 wherein

X is O or S;

$R^1$ is —NHR$^4$ or methylene substituted with 0–3 $R^c$;

$R^c$ is NR$^3$R$^{3a}$;

$R^4$ is selected from the group consisting of H, C1–4 alkyl, and NR$^3$R$^{3a}$; and $R^3$ and $R^{3a}$, are independently hydrogen or C1–4alkyl, or $R^3$ and $R^{3a}$, together with the nitrogen atom to which they are attached, form a 4–8 membered heterocycle containing an additional 0–1 N, S, or O atom and substituted with with 0–3 substituents independently selected from the group consisting of methyl, —CH$_2$OCH$_3$, —C(CH$_3$)$_2$OCH$_3$, —CH$_2$CH$_2$OH, —CH$_2$OH, —CH$_2$OCH$_2$Phenyl, —CH$_2$CH$_2$NH$_2$, —CH$_2$NH$_2$, —C(=NH)CH$_3$, and NH2.

14. A compound according to claim 1 wherein

X is O or S; and $R^1$ is selected from the group: methylene substituted with a substituent selected from the group consisting of: halo, NR$^3$R$_{3a}$, C$_{3-6}$ carbocycle substituted with 0–5 R$^a$, and 5–7 membered heterocycle containing from 1–4 heteroatoms selected from O, N, and S, substituted with 0–3 R$^3$.

15. A compound according to claim 1 wherein

X is O or S;

$R^1$ is selected from the group: methylene substituted with NR$^3$R$^{3a}$; and $R^3$ and $R^{3a}$, together with the nitrogen atom to which they are attached, form pyrrolyl, pyrrolinyl, pyrrolidinyl, imidazolyl, imidazolinyl, imidazolidinyl, pyrazolyl, pyrazolinyl, pyrazolidinyl, thiomorpholinyl, pymorpholinyl, piperidinyl, piperazinyl, or piperadinyl, which is substituted with 0–3 R$^{3c}$.

16. A compound according to claim 1 wherein $R^1$ is —NHR$^4$;

$R^4$ is NR3R3a; and $R^3$ and $R^{3a}$, together with the nitrogen atom to which they are attached, form pyrrolyl, pyrrolinyl, pyrrolidinyl, imidazolyl, imidazolinyl, imidazolidinyl, pyrazolyl, pyrazolinyl, pyrazolidinyl, thiomorpholinyl, pymorpholinyl, piperidinyl, piperazinyl, or piperadinyl, which is substituted with 0–3 R$^{3c}$.

17. A compound according to claim 1 wherein $R^1$ is —NHR$^4$;

$R^4$ is NR3R3a; and $R^3$ and R$^3$a, together with the nitrogen atom to which they are attached, form pyrrolyl, pyrrolinyl, pyrrolidinyl, imidazolyl, imidazolinyl, imidazolidinyl, pyrazolyl, pyrazolinyl, pyrazolidinyl, thiomorpholinyl, pymorpholinyl, piperidinyl, piperazinyl, or piperadinyl, which is substituted with 0–3 substituents independently selected from the group consisting of methyl, —CH$_2$OCH$_3$, —C(CH$_3$)$_2$OCH$_3$, —CH$_2$CH$_2$OH, —CH$_2$OH, —CH$_2$OCH$_2$Phenyl, —CH$_2$CH$_2$NH$_2$, —CH$_2$NH$_2$, —C(=NH)CH$_3$, and NH2.

18. A compound according to claim 1, wherein $R^2$ is selected from the group: 5- to 7- membered monocyclic saturated, or partially saturated, heterocyclic ring substituted with 0–5 $R^b$.

19. A compound according to claim 1, wherein $R^2$ is selected from the group: 5- to 7- membered monocyclic aromatice heterocyclic ring substituted with 0–5 $R^b$.

20. A compound according to claim 1, wherein $R^2$ is selected from the group: C$_{1-10}$ alkyl substituted with 0–3 R$^c$, C$_{3-10}$ carbocycle substituted with 0–5 R$^a$, and 3–10 membered heterocycle containing from 1–4 heteroatoms selected from O, N, and S and substituted with 0–5 R$^b$.

21. A compound according to claim 1, wherein $R^2$ is selected from the group: C$_{1-6}$ alkyl substituted with 0–3 R$^c$, C$_{3-6}$ carbocycle substituted with 0–5 R$^a$, and 3–7 membered heterocycle containing from 1–4 heteroatoms selected from O, N, and S and substituted with 0–5 R$^b$.

22. A compound according to claim 1, wherein $R^2$ is selected from the group: C$_{1-6}$ alkyl substituted with C$_{3-10}$ carbocycle substituted with 0–5 R$^a$, and C$_{1-6}$ alkyl substituted with 5–10 membered heterocycle containing from 1–4 heteroatoms selected from O, N, and S.

23. A compound according to claim 1, wherein $R^2$ is selected from the group: phenyl substituted with 0–5 R$^a$, and cyclopropyl or cyclohexyl substituted with 0–2 R$^a$; and R$^a$ is independently at each occurrence selected from the group: —CH$_2$N(CH$_3$)$_2$, —CH$_2$NH$_2$, —SR$^3$ halo, —CN , N$_3$, NO$_2$, C$_{1-4}$ alkyl, C$_{1-4}$ haloalkyl, NR$^3$R$^{3a}$, =O, OR$^3$, COR$^3$, CO$_2$R$^3$, CONR$^3$R$^{3a}$, NHC(O)NR$^3$R$^{3a}$, NHC(S)NR$^3$R$^{3a}$, NR$^3$C(O)OR$^3$, NR$^3$C(O)R$^3$, SO$_2$NR$^3$R$^{3a}$, SO$_2$R$^{3b}$, and 5–10 membered heterocycle containing from 1–4 heteroatoms selected from O, N, and S.

24. A compound according to claim 1, wherein $R^2$ is selected from the group: phenyl substituted with 0–5 R$^a$, and cyclopropyl or cyclohexyl substituted with 0–2 R$^a$; and R$^a$ is independently at each occurrence selected from the group: C$_{1-4}$ alkyl, COR$^3$, CO$_2$R$^3$, and CONR$^3$R$^{3a}$;

R$^{3a}$ is H or C$_{1-4}$ alkyl.

25. A compound according to claim 1, wherein $R^2$ is selected from the group: phenyl substituted with 0–5 R$^a$, and cyclopropyl or cyclohexyl substituted with 0–2 R$^a$;

R$^a$ is independently at each occurrence selected from the group: C$_{1-4}$ alkyl, COR$^3$, CO$_2$R$^3$, and CONR$^3$R$^{3a}$;

R$^{3a}$ is H or C$_{1-4}$ alkyl;

R$^3$ is C$_{1-4}$alkyl, C$_{1-4}$alkyl-NR5R5a; and

R$^5$ and R$^{5a}$, together with the atoms to which they are attached, form a heterocycle having 4–8 atoms in the ring and containing an additional 0–1 N, S, or O atom.

26. A compound according to claim 1, wherein $R^2$ is selected from the group: phenyl substituted with 0–5 R$^a$, and cyclopropyl or cyclohexyl substituted with 0–2 R$^a$;

R$^a$ is independently at each occurrence selected from the group: C$_{1-4}$ alkyl, COR$^3$, CO$_2$R$^3$, and CONR$^3$R$^{3a}$; and R$^{3a}$ is H or C$_{1-4}$ alkyl.

27. A compound according to claim 1, wherein $R^2$ is phenyl substituted with NR$^3$R$^{3a}$, wherein R$^3$ and R$^{3a}$, together with the nitrogen atom to which they are attached, form a 4–8 membered heterocycle containing an additional 0–1 N, S, or O atom and substituted with 0–3 R$^{3c}$.

28. A compound according to claim 25, wherein
$R^2$ is phenyl substituted with $NR^3R^{3a}$; and
$R^3$ and $R^{3a}$, together with the nitrogen atom to which they are attached, form a pyrrolinyl, pyrrolidinyl, imidazolinyl, pyrazolidinyl, pyrazolinyl, piperidinyl, morpholinyl, thiomorpholinyl, homopiperazinyl or piperazinyl group, substituted with 0–3 $R^{3c}$.

29. A compound according to claim 25, wherein
$R^2$ is phenyl substituted with $NR^3R^{3a}$, wherein $R^3$ and $R^{3a}$, together with the nitrogen atom to which they are attached, form a piperidinyl, homopiperazinyl or piperazinyl group, substituted with 0–3 $R^{3c}$.

30. A compound according to claim 25, wherein
$R^2$ is phenyl substituted with $NR^3R^{3a}$; and
$R^3$ and $R^{3a}$, together with the nitrogen atom to which they are attached, form a piperidinyl, homopiperazinyl or piperazinyl group, substituted with 0–3 substituents independently selected from the group consisting of: —C(=NH)CH$_3$, pyrrolinyl, pyrrolidinyl, imidazolinyl, pyrazolidinyl, pyrazolinyl, piperidinyl, morpholinyl, thiomorpholinyl, homopiperazinyl or piperazinyl group, pyridyl, $C_{1-4}$ alkyl, —$NR^3R^{3b}$.

31. A compound according to claim 1 which is selected from Table 1.

32. A compound according to claim 1 which is selected from Table 2.

33. A compound according to claim 1 which is selected from Table 3.

34. A compound according to claim 1 which is selected from Table 4.

35. A compound according to claim 1, wherein the compound is selected from:
3-(4-methoxyphenyl)-5-(acetamido)indeno[1,2-c]pyrazol-4-one;
3-phenyl-5-(acetamido)indeno[1,2-c]pyrazol-4-one;
3-(4-methylthiophenyl)-5-(acetamido)indeno[1,2-c]pyrazol-4-one;
3-(4-methanesulfonylphenyl)-5-(acetamido)indeno[1,2-c]pyrazol-4-one;
3-(4-(N,N-dimethylamino)phenyl)-5-(acetamido)indeno[1,2-c]pyrazol-4-one;
3-(3-pyridyl)-5-(acetamido)indeno[1,2-c]pyrazol-4-one;
3-(4-methoxyphenyl)-5-(formamido)indeno[1,2-c]pyrazol-4-one;
3-(4-hydroxyphenyl)-5-(acetamido)indeno[1,2-c]pyrazol-4-one;
3-(4-piperidinophenyl)-5-(acetamido)indeno[1,2-c]pyrazol-4-one;
3-(4-morpholinophenyl)-5-(acetamido)indeno[1,2-c]pyrazol-4-one;
3-(4-ethoxyphenyl)-5-(acetamido)indeno[1,2-c]pyrazol-4-one;
3-(4-butylphenyl)-5-(acetamido)indeno[1,2-c]pyrazol-4-one;
3-(4-ethylphenyl)-5-(acetamido)indeno[1,2-c]pyrazol-4-one;
3-(4-n-propylphenyl)-5-(acetamido)indeno[1,2-c]pyrazol-4-one;
3-(4-methoxyphenyl)-5-((4-aminophenyl)acetamido)indeno[1,2-c]pyrazol-4-one;
3-(4-pyridyl)-5-(formamido)indeno[1,2-c]pyrazol-4-one;
3-(4-pyridyl)-5-(acetamido)indeno[1,2-c]pyrazol-4-one;
3-(4-methoxyphenyl)-5-((4-aminophenyl)acetamido)indeno[1,2-c]pyrazol-4-one;
3-(4-methoxyphenyl)-5-((4-azidophenyl)acetamido)indeno[1,2-c]pyrazol-4-one;
3-(4-methoxyphenyl)-5-((4-(methoxycarbonylamino)phenyl) acetamido)indeno[1,2-c]pyrazol-4-one;
3-(4-methoxyphenyl)-5-((4-(aminomethylcarbonylamino)phenyl) acetamido)indeno[1,2-c]pyrazol-4-one;
3-(4-methoxyphenyl)-5-((4-((N,N-dimethylamino)methylcarbonyl amino)phenyl)acetamido)indeno[1,2-c]pyrazol-4-one;
3-(4-methoxyphenyl)-5-((4-acetamidophenyl)acetamido)indeno[1,2-c]pyrazol-4-one;
3-(4-methoxyphenyl)-5-(pyrrolidinoacetamido)indeno[1,2-c]pyrazol-4-one;
3-(4-methoxyphenyl)-5-(morpholinoacetamido)indeno[1,2-c]pyrazol-4-one;
3-(4-methoxyphenyl)-5-(thiomorpholinoacetamido)indeno[1,2-c]pyrazol-4-one;
3-(4-methoxyphenyl)-5-(ethylaminoacetamido)indeno[1,2-c]pyrazol-4-one;
3-(4-methoxyphenyl)-5-(piperidinoacetamido)indeno[1,2-c]pyrazol-4-one;
3-(4-methoxyphenyl)-5-(4-(aminomethyl)piperidinoacetamido) indeno[1,2-c]pyrazol-4-one;
3-(4-methoxyphenyl)-5-(piperazinoacetamido)indeno[1,2-c]pyrazol-4-one;
3-(4-methoxyphenyl)-5-(4-methylpiperazinoacetamido) indeno[1,2-c]pyrazol-4-one;
3-(4-methoxyphenyl)-5-(4-(2-hydroxyethyl)piperazinoacetamido)indeno[1,2-c]pyrazol-4-one;
3-(4-methoxyphenyl)-5-(N,N-dimethylaminoacetamido) indeno[1,2-c]pyrazol-4-one;
3-(4-methoxyphenyl)-5-((2-hydroxyethyl)aminoacetamido) indeno[1,2-c]pyrazol-4-one;
3-(4-methoxyphenyl)-5-(aminoacetamido)indeno[1,2-c]pyrazol-4-one;
3-(4-methoxyphenyl)-5-((2-chlorophenyl)acetamido)indeno [1,2-c]pyrazol-4-one;
3-(4-methoxyphenyl)-5-((2,4-dichlorophenyl)acetamido) indeno[1,2-c]pyrazol-4-one;
3-(4-methoxyphenyl)-5-((3',4-dichlorophenyl)acetamido) indeno[1,2-c]pyrazol-4-one;
3-(4-methoxyphenyl)-5-((2-methoxyphenyl)acetamido) indeno[1,2-c]pyrazol-4-one;
3-(4-dimethoxyphenyl)-5-(3-thienylacetamido)indeno[1,2-c]pyrazol-4-one;
3-(4-methoxyphenyl)-5-((3,4-methylenedioxyphenyl) acetamido)indeno[1,2-c]pyrazol-4-one;
3-(3,4-dimethoxyphenyl)-5-(acetamido)indeno[1,2-c]pyrazol-4-one;
3-(2-methoxyphenyl)-5-(acetamido)indeno[1,2-c]pyrazol-4-one;
3-(4-methoxyphenyl)-5-((2,5-dimethoxyphenyl)acetamido) indeno[1,2-c]pyrazol-4-one;
3-(4-methoxyphenyl)-5-((3,4-dimethoxyphenyl)acetamido) indeno[1,2-c]pyrazol-4-one;
3-(4-methoxyphenyl)-5-((4-methoxyphenyl)acetamido) indeno[1,2-c]pyrazol-4-one;
3-(4-methoxyphenyl)-5-((3-methoxyphenyl)acetamido) indeno[1,2-c]pyrazol-4-one;
3-(4-methoxyphenyl)-5-((4-chlorophenyl)acetamido)indeno [1,2-c]pyrazol-4-one;
3-(4-methoxyphenyl)-5-((butylcarbamoyl)amino)indeno[1,2-c]pyrazol-4-one;
3-(4-methoxyphenyl)-5-((4-aminobenzylcarbamoyl)amino) indeno [1,2-c]pyrazol-4-one;
3-(4-methoxyphenyl)-5-((4-pyridylcarbamoyl) amino) indeno[1,2-c]pyrazol-4-one;
3-(4-methoxyphenyl)-5-((phenylcarbamoyl)amino)indeno [1,2-c]pyrazol-4-one;

3-(4-methoxyphenyl)-5-(cyclobutanecarboxamido)indeno[1,2-c]pyrazol-4-one;
3-(4-methoxyphenyl)-5-(cyclopentanecarboxamido)indeno[1,2-c]pyrazol-4-one;
3-(4-methoxyphenyl)-5-(butanamido)indeno[1,2-c]pyrazol-4-one;
3-(4-methoxyphenyl)-5-(propanamido)indeno[1,2-c]pyrazol-4-one;
3-(4-methoxyphenyl)-5-(phenylacetamido)indeno[1,2-c]pyrazol-4-one;
3-(4-methoxyphenyl)-5-(2-methylpropanamido)indeno[1,2-c]pyrazol-4-one;
3-(4-methoxyphenyl)-5-(cyclopropanecarboxamido)indeno[1,2-c]pyrazol-4-one;
3-(4-methoxyphenyl)-5-(chloroacetamido)indeno[1,2-c]pyrazol-4-one;
3-(4-methoxyphenyl)-5-(4-(aminomethyl)piperidinoacetamido)-indeno[1,2-c]pyrazol-4-one;
3-(4-(N,N-dimethylamino)phenyl)-5-(morpholinoacetamido)indeno[1,2-c]pyrazol-4-one;
3-(4-(N,N-dimethylamino)phenyl)-5-(N,N-dimethylaminoacetamido)indeno[1,2-c]pyrazol-4-one;
3-(4-(trifluoromethyl)phenyl)-5-(acetamido)indeno[1,2-c]pyrazol-4-one;
3-(4-(N,N-dimethylamino)phenyl)-5-(4-methylpiperazinoacetamido)indeno[1,2-c]pyrazol-4-one;
3-(4-(N,N-dimethylamino)phenyl)-5-(4-(aminomethyl)-piperidinoacetamido)indeno[1,2-c]pyrazol-4-one;
3-(4-(N,N-dimethylamino)phenyl)-5-(4-hydroxy-piperidinoacetamido)indeno[1,2-c]pyrazol-4-one;
3-(4-morpholinophenyl)-5-(morpholinoacetamido)indeno[1,2-c]pyrazol-4-one;
3-(4-morpholinophenyl)-5-(4-methylpiperazinoacetamido)indeno[1,2-c]pyrazol-4-one;
3-(4-morpholinophenyl)-5-(4-hydroxy-piperidinoacetamido)indeno[1,2-c]pyrazol-4-one;
3-(4-morpholinophenyl)-5-(4-(aminomethyl)-piperidinoacetamido)indeno[1,2-c]pyrazol-4-one;
3-(4-piperazinophenyl)-5-(morpholinoacetamido)indeno[1,2-c]pyrazol-4-one;
3-(4-piperazinophenyl)-5-((N,N-dimethylamino)acetamido)indeno[1,2-c]pyrazol-4-one;
3-(4-piperazinophenyl)-5-(4-methylpiperazinoacetamido)indeno[1,2-c]pyrazol-4-one;
3-(4-piperazinophenyl)-5-(4-(aminomethyl)-piperidinoacetamido)indeno[1,2-c]pyrazol-4-one;
3-(4-piperazinophenyl)-5-(carbamoylamino)indeno[1,2-c]pyrazol-4-one;
3-(4-piperazinophenyl)-5-(aminocarbamoylamino)indeno[1,2-c]pyrazol-4-one;
3-(4-piperazinophenyl)-5-(morpholinocarbamoylamino)-indeno[1,2-c]pyrazol-4-one;
3-(4-(4-methylpiperazino)phenyl)-5-(morpholinocarbamoylamino)indeno[1,2-c]pyrazol-4-one;
3-(4-(4-ethylpiperazino)phenyl)-5-(morpholinocarbamoylamino)indeno[1,2-c]pyrazol-4-one;
3-(4-(4-isopropylpiperazino)phenyl)-5-(morpholinocarbamoylamino)indeno[1,2-c]pyrazol-4-one;
3-(4-(4-t-butoxycarbonylpiperazino)phenyl)-5-(morpholinocarbamoylamino)indeno[1,2-c]pyrazol-4-one;
3-(4-(N,N-dimethylamino)phenyl)-5-((4-methylpiperazino)-carbamoylamino)indeno[1,2-c]pyrazol-4-one;
3-(c-propyl)-5-(acetamido)indeno[1,2-c]pyrazol-4-one;
3-(2-thienyl)-5-(acetamido)indeno[1,2-c]pyrazol-4-one;
3-(3-methyl-2-thienyl)-5-(acetamido)indeno[1,2-c]pyrazol-4-one;
3-(ethyl)-5-(carbamoylamino)indeno[1,2-c]pyrazol-4-one;
3-(n-propyl)-5-(carbamoylamino)aminoindeno[1,2-c]pyrazol-4-one;
3-(i-propyl)-5-(carbamoylamino)indeno[1,2-c]pyrazol-4-one;
3-(c-propyl)-5-(carbamoylamino)indeno[1,2-c]pyrazol-4-one;
3-(c-hexyl)-5-(carbamoylamino)indeno[1,2-c]pyrazol-4-one;
3-(2-thienyl)-5-(carbamoylamino)indeno[1,2-c]pyrazol-4-one;
3-(3-methyl-2-thienyl)-5-(carbamoylamino)indeno[1,2-c]pyrazol-4-one;
3-(5-methyl-2-thienyl)-5-(carbamoylamino)indeno[1,2-c]pyrazol-4-one;
3-(5-carboethoxy-2-thienyl)-5-(carbamoylamino)indeno[1,2-c]pyrazol-4-one;
3-(3-thienyl)-5-(carbamoylamino)indeno[1,2-c]pyrazol-4-one;
3-(1-methyl-3-pyrrolyl)-5-(carbamoylamino)indeno[1,2-c]pyrazol-4-one;
3-(2,5-dimethyl-3-thienyl)-5-(carbamoylamino)indeno[1,2-c]pyrazol-4-one;
3-(2-furanyl)-5-(carbamoylamino)indeno[1,2-c]pyrazol-4-one;
3-(i-propyl)-5-((N,N-dimethylaminocarbamoyl)amino)indeno[1,2-c]pyrazol-4-one;
3-(c-propyl)-5-((N,N-dimethylaminocarbamoyl)amino)indeno[1,2-c]pyrazol-4-one;
3-(c-hexyl)-5-((N,N-dimethylaminocarbamoyl)amino)indeno[1,2-c]pyrazol-4-one;
3-(2-thienyl)-5-((N,N-dimethylaminocarbamoyl)amino)indeno[1,2-c]pyrazol-4-one;
3-(5-methoxy-2-thienyl)-5-((N,N-dimethylaminocarbamoyl)amino)indeno[1,2-c]pyrazol-4-one;
3-(5-methyl-2-thienyl)-5-((N,N-dimethylaminocarbamoyl)amino)indeno[1,2-c]pyrazol-4-one;
3-(5-carboethoxy-2-thienyl)-5-((N,N-dimethylaminocarbamoyl)amino)indeno[1,2-c]pyrazol-4-one;
3-(3-thienyl)-5-((N,N-dimethylaminocarbamoyl)amino)indeno[1,2-c]pyrazol-4-one;
3-(5-chloro-3-thienyl)-5-((N,N-dimethylaminocarbamoyl)amino)indeno[1,2-c]pyrazol-4-one;
3-(2,5-dimethyl-3-thienyl)-5-((N,N-dimethylaminocarbamoyl)amino)indeno[1,2-c]pyrazol-4-one;
3-(2-furanyl)-5-((N,N-dimethylaminocarbamoyl)amino)indeno[1,2-c]pyrazol-4-one;
3-(i-propyl)-5-((4-carbamoylpiperidino)acetamido)indeno[1,2-c]pyrazol-4-one;
3-(c-hexyl)-5-((4-carbamoylpiperidino)acetamido)indeno[1,2-c]pyrazol-4-one;
3-(ethyl)-5-(4-(aminomethyl)piperidinoacetamido)indeno[1,2-c]pyrazol-4-one;
3-(i-propyl)-5-(4-(aminomethyl)piperidinoacetamido)indeno[1,2-c]pyrazol-4-one;
3-(c-propyl)-5-(4-(aminomethyl)piperidinoacetamido)indeno[1,2-c]pyrazol-4-one;
3-(c-hexyl)-5-(4-(aminomethyl)piperidinoacetamido)indeno[1,2-c]pyrazol-4-one;
3-(i-propyl)-5-((4-methylpiperazino)carbamoylamino)indeno[1,2-c]pyrazol-4-one;

3-(5-carboethoxy-2-thienyl)-5-((4-methylpiperazino)carbamoylamino)indeno[1,2-c]pyrazol-4-one;
3-(5-carboxyl-2-thienyl)-5-((4-methylpiperazino)carbamoylamino)indeno[1,2-c]pyrazol-4-one;
3-(2,5-dimethyl-3-thienyl)-5-((4-methylpiperazino)carbamoylamino)indeno[1,2-c]pyrazol-4-one;
3-(i-propyl)-5-(morpholinocarbamoylamino)indeno[1,2-c]pyrazol-4-one;
3-(1-methoxycarbonyl-4-piperidinyl)-5-(morpholinocarbamoylamino)indeno[1,2-c]pyrazol-4-one;
3-(5-methyl-2-thienyl)-5-(morpholinocarbamoylamino)indeno[1,2-c]pyrazol-4-one;
3-(5-chloro-3-thienyl)-5-(morpholinocarbamoylamino)indeno[1,2-c]pyrazol-4-one;
3-(2,5-dimethyl-3-thienyl)-5-(morpholinocarbamoylamino)indeno[1,2-c]pyrazol-4-one;
3-(5-carboethoxy-2-thienyl)-5-(morpholinylcarbamoylamino)indeno[1,2-c]pyrazol-4-one;
3-(5-carboxyl-2-thienyl)-5-(morpholinylcarbamoylamino)indeno[1,2-c]pyrazol-4-one;
3-(5-(benzylaminocarbonyl)-2-thienyl)-5-(morpholinocarbamoylamino)indeno[1,2-c]pyrazol-4-one;
3-(5-((4-methylpiperazino)carbonyl)-2-thienyl)-5-(morpholinocarbamoylamino)indeno[1,2-c]pyrazol-4-one;
3-(5-((2-(1-methyl-2-pyrrolidinyl)ethyl)aminocarbonyl)-2-thienyl)-5-(morpholinocarbamoylamino)indeno[1,2-c]pyrazol-4-one;
3-(5-((N,N-dimethylamino)aminocarbonyl)-2-thienyl-5-(morpholinocarbamoylamino)indeno[1,2-c]pyrazol-4-one;
3-(5-((2-(N,N-dimethylamino)ethyl)aminocarbonyl)-2-thienyl-5-(morpholinocarbamoylamino)indeno[1,2-c]pyrazol-4-one;
3-(5-(2-pyrrolidinoethyl)aminocarbonyl)-2-thienyl-5-(morpholinocarbamoylamino)indeno [1,2-c]pyrazol-4-one;
3-(5-(2-morpholinoethyl)aminocarbonyl)-2-thienyl)-5-(morpholinocarbamoylamino)indeno[1,2-c]pyrazol-4-one;
3-(5-(morpholinocarbonyl)-2-thienyl)-5-(morpholinocarbamoylamino)indeno[1,2-c]pyrazol-4-one;
3-(5-((3-(2-pyrrolidon-1-yl)propyl)aminocarbonyl)-2-thienyl-5-(morpholinocarbamoylamino)indeno[1,2-c]pyrazol-4-one;
3-(5-((2-(3-pyridyl)ethyl)aminocarbonyl)-2-thienyl)-5-(morpholinocarbamoylamino)indeno[1,2-c]pyrazol-4-one;
3-(5-((3-(1-imidazolyl)propyl)aminocarbonyl)-2-thienyl)-5-(morpholinocarbamoylamino)indeno[1,2-c]pyrazol-4-one;
3-(5-((2-(2-pyridyl)ethyl)aminocarbonyl)-2-thienyl)-5-(morpholinocarbamoylamino)indeno[1,2-c]pyrazol-4-one;
3-(5-((2-pyridyl)methyl)aminocarbonyl)-2-thienyl)-5-(morpholinocarbamoylamino)indeno[1,2-c]pyrazol-4-one;
3-(5-((2-piperidinoethyl)aminocarbonyl)-2-thienyl)-5-(morpholinocarbamoylamino)indeno[1,2-c]pyrazol-4-one;
3-(4-piperazinophenyl)-5-((N,N-dimethylamino)carbamoylamino)indeno[1,2-c]pyrazol-4-one;
3-(4-(4-methylpiperazino)phenyl)-5-((N,N-dimethylamino)carbamoylamino)indeno[1,2-c]pyrazol-4-one;
3-(4-piperazinophenyl)-5-((4-methylpiperazino)carbamoylamino)-indeno[1,2-c]pyrazol-4-one;
3-(4-(4-methylpiperazino)phenyl)-5-((4-methylpiperazino)carbamoylamino)indeno[1,2-c]pyrazol-4-one;
3-(4-(4-ethylpiperazino)phenyl)-5-((4-methylpiperazino)carbamoylamino)indeno[1,2-c]pyrazol-4-one;
3-(4-(4-isopropylpiperazino)phenyl)-5-((4-methylpiperazino)carbamoylamino)indeno[1,2-c]pyrazol-4-one;
3-(4-piperazinopheny)-5-((2,6-dimethylpiperidino)carbamoylamino)indeno[1,2-c]pyrazol-4-one;
3-(4-piperazinophenyl)-5-((4-(2-hydroxyethyl)piperazino)carbamoylamino)indeno[1,2-c]pyrazol-4-one;
3-(4-piperazinophenyl)-5-((2(R)-(methoxymethyl)pyrrolidino)carbamoylamino)indeno[1,2-c]pyrazol-4-one;
3-(4-piperazinophenyl)-5-((2(S)-(methoxymethyl)pyrrolidino)carbamoylamino)indeno[1,2-c]pyrazol-4-one;
3-(4-piperazinophenyl)-5-((2(R)-(1-methoxy-1-methylethyl)pyrrolidino)carbamoylamino)indeno[1,2-c]pyrazol-4-one;
3-(4-piperazinophenyl)-5-((2(S)-(1-methoxy-1-methylethyl)pyrrolidino)carbamoylamino)indeno[1,2-c]pyrazol-4-one;
3-(4-piperazinophenyl)-5-((2(R)-(hydroxymethyl)pyrrolidino)carbamoylamino)indeno[1,2-c]pyrazol-4-one;
3-(4-piperazinophenyl)-5-((2(S)-(hydroxymethyl)pyrrolidino)carbamoylamino)indeno[1,2-c]pyrazol-4-one;
3-(4-piperazinophenyl)-5-((2(R)-(benzyloxymethyl)pyrrolidino)carbamoylamino)indeno[1,2-c]pyrazol-4-one;
3-(4-piperazinophenyl)-5-((2(S)-(benzyloxymethyl)pyrrolidino)carbamoylamino)indeno[1,2-c]pyrazol-4-one;
3-(4-(3-methylpiperazino)phenyl)-5-(morpholinocarbamoylamino)indeno[1,2-c]pyrazol-4-one;
3-(4-(cis-3,5-dimethylpiperazino)phenyl)-5-(morpholinocarbamoylamino)indeno[1,2-c]pyrazol-4-one;
3-(4-(cis-3,4,5-trimethylpiperazino)phenyl)-5-(morpholinocarbamoylamino)indeno[1,2-c]pyrazol-4-one;
3-(4-(4-isopropylpiperazino)-2-methylphenyl)-5-(morpholinocarbamoylamino)indeno[1,2-c]pyrazol-4-one;
3-(4-homopiperazinophenyl)-5-(morpholinocarbamoylamino)indeno[1,2-c]pyrazol-4-one;
3-(4-(4-methylhomopiperazino)phenyl)-5-(morpholinocarbamoylamino)indeno[1,2-c]pyrazol-4-one;
3-(4-(4-ethylhomopiperazino)phenyl)-5-(morpholinocarbamoylamino)indeno[1,2-c]pyrazol-4-one;
3-(4-(4-isopropylhomopiperazino)phenyl)-5-(morpholinocarbamoylamino)indeno[1,2-c]pyrazol-4-one;
3-(4-homopiperazino-2-methylphenyl)-5-(morpholinocarbamoylamino)indeno[1,2-c]pyrazol-4-one;
3-(4-(4-ethylhomopiperazino)-2-methylphenyl)-5-(morpholinocarbamoylamino)indeno[1,2-c]pyrazol-4-one;

3-(4-(4-isopropylhomopiperazino)-2-methylphenyl)-5-(morpholinocarbamoylamino)indeno[1,2-c]pyrazol-4-one;

3-(4-(4-(N,N-dimethylamino)piperidino)phenyl)-5-(morpholinocarbamoylamino)indeno[1,2-c]pyrazol-4-one;

3-(4-(4-(N,N-diethylamino)piperidino)phenyl)-5-(morpholinocarbamoylamino)indeno[1,2-c]pyrazol-4-one;

3-(4-(4-piperidinopiperidino)phenyl)-5-(morpholinocarbamoylamino)indeno[1,2-c]pyrazol-4-one;

3-(4-(4-pyrrolidinopiperidino)phenyl)-5-(morpholinocarbamoylamino)indeno[1,2-c]pyrazol-4-one;

3-(4-(4-(N,N-diethylamino)piperidino)phenyl)-5-(morpholinocarbamoylamino)indeno[1,2-c]pyrazol-4-one;

3-(4-methoxyphenyl)-5-((4-methylpiperazino)-thionocarbamoylamino)indeno[1,2-c]pyrazol-4-one;

3-(1-methyl-3-pyrrolyl)-5-(carbamoylamino)indeno[1,2-c]pyrazol-4-one;

3-(5-pyrrolidinoaminocarbonyl-2-thienyl)-5-(morpholinocarbamoylamino)indeno[1,2-c]pyrazol-4-one;

3-(5-piperidinoaminocarbonyl-2-thienyl)-5-(morpholinocarbamoylamino)indeno[1,2-c]pyrazol-4-one;

3-(5-piperidinocarbonyl-2-thienyl)-5-(morpholinocarbamoylamino)indeno[1,2-c]pyrazol-4-one;

3-(5-piperazinocarbonyl-2-thienyl)-5-(morpholinocarbamoylamino)indeno[1,2-c]pyrazol-4-one;

3-(5-(4-methylpiperazinocarbonyl)-2-thienyl)-5-(morpholinocarbamoylamino)indeno[1,2-c]pyrazol-4-one;

3-(5-(4-ethylpiperazinocarbonyl)-2-thienyl)-5-(morpholinocarbamoylamino)indeno[1,2-c]pyrazol-4-one;

3-(5-(4-(2-hydroxyethyl)piperazinocarbonyl)-2-thienyl)-5-(morpholinocarbamoylamino)indeno[1,2-c]pyrazol-4-one;

3-(5-(4-(cyclopropylmethyl)piperazinocarbonyl)-2-thienyl)-5-(morpholinocarbamoylamino)indeno[1,2-c]pyrazol-4-one;

3-(5-(4-(t-butoxycarbonyl)piperazinocarbonyl)-2-thienyl)-5-(morpholinocarbamoylamino)indeno[1,2-c]pyrazol-4-one;

3-(5-(4-(2-pyridyl)piperazinocarbonyl)-2-thienyl)-5-(morpholinocarbamoylamino)indeno[1,2-c]pyrazol-4-one;

3-(5-(((1S,4S)-(+)-2,5-diazabicyclo[2.2.1]heptyl)carbonyl)-2-thienyl)-5-(morpholinocarbamoylamino)indeno[1,2-c]pyrazol-4-one;

3-(5-(((1S,4S)-(+)-2-methyl-2,5-diazabicyclo[2.2.1]heptyl)carbonyl)-2-thienyl)-5-(morpholinocarbamoylamino)indeno[1,2-c]pyrazol-4-one;

3-(5-(4-(N,N-dimethylamino)piperidinocarbonyl)-2-thienyl)-5-(morpholinocarbamoylamino)indeno[1,2-c]pyrazol-4-one;

3-(5-(4-pyrrolidinopiperidinocarbonyl)-2-thienyl)-5-(morpholinocarbamoylamino)indeno[1,2-c]pyrazol-4-one;

3-(5-(4-piperidinopiperidinocarbonyl)-2-thienyl)-5-(morpholinocarbamoylamino)indeno[1,2-c]pyrazol-4-one;

3-(5-cyclohexylaminocarbonyl-2-thienyl)-5-(morpholinocarbamoylamino)indeno[1,2-c]pyrazol-4-one;

3-(5-(4-piperidylaminocarbonyl)-2-thienyl)-5-(morpholinocarbamoylamino)indeno[1,2-c]pyrazol-4-one;

3-(5-((1-(t-butoxycarboxyl)piperidin-4-yl)aminocarbonyl)-2-thienyl)-5-(morpholinocarbamoylamino)indeno[1,2-c]pyrazol-4-one;

3-(5-(4-(1-methylpiperidin-4-yl)methylaminocarbonyl)-2-thienyl)-5-(morpholinocarbamoylamino)indeno[1,2-c]pyrazol-4-one;

3-(5-(3-(N,N-dimethylamino)piperidinocarbonyl)-2-thienyl)-5-(morpholinocarbamoylamino)indeno[1,2-c]pyrazol-4-one;

3-(5-(3-p-toluenesulfonylamino)piperidinocarbonyl-2-thienyl)-5-(morpholinocarbamoylamino)indeno[1,2-c]pyrazol-4-one;

3-(5-(3-hydroxypiperidinocarbonyl)-2-thienyl)-5-(morpholinocarbamoylamino)indeno[1,2-c]pyrazol-4-one;

3-(5-((3-piperidyl)aminocarbonyl)-2-thienyl)-5-(morpholinocarbamoylamino)indeno[1,2-c]pyrazol-4-one;

3-(5-((3-quinuclidyl)aminocarbonyl)-2-thienyl)-5-(morpholinocarbamoylamino)indeno[1,2-c]pyrazol-4-one;

3-(5-((3-aminocyclohexyl)aminocarbonyl)-2-thienyl)-5-(morpholinocarbamoylamino)indeno[1,2-c]pyrazol-4-one;

3-(5-((3-(t-butoxycarbonylamino)cyclohexyl)aminocarbonyl)-2-thienyl)-5-(morpholinocarbamoylamino)indeno[1,2-c]pyrazol-4-one;

3-(5-(2-(N,N-dimethylaminomethyl)piperidinocarbonyl)-2-thienyl)-5-(morpholinocarbamoylamino)indeno[1,2-c]pyrazol-4-one;

3-(5-(2-(N,N-diethylaminomethyl)piperidinocarbonyl)-2-thienyl)-5-(morpholinocarbamoylamino)indeno[1,2-c]pyrazol-4-one;

3-(5-pyrrolidinocarbonyl-2-thienyl)-5-(morpholinocarbamnoylamino) indeno[1,2-c]pyrazol-4-one;

3-(5-(3-aminopyrrolidinocarbonyl)-2-thienyl)-5-(morpholinocarbamnoylamino)indeno[1,2-c]pyrazol-4-one;

3-(5(3(S)-N-methylamino)pyrrolidinocarbonyl-2-thienyl)-5-(morpholinocarbamoylamino)indeno[1,2-c]pyrazol-4-one;

3-(5-(3(S)-acetamidopyrrolidinocarbonyl)-2-thienyl)-5-(morpholinocarbamoylamino)indeno[1,2-c]pyrazol-4-one;

3-(5-(3(S)-(N-methylacetamido)pyrrolidinocarbonyl)-2-thienyl)-5-(morpholinocarbamoylamino)indeno[1,2-c]pyrazol-4-one;

3-(5(3(S)-(N-methyl-t-butoxycarbonylamino)pyrrolidinocarbonyl)-2-thienyl)-5-(morpholinocarbamoylamino)indeno[1,2-c]pyrazol-4-one;

3-(5-(3-(N,N-dimethylamino)pyrrolidinocarbonyl)-2-thienyl)-5-(morpholinocarbamoylamino)indeno[1,2-c]pyrazol-4-one;

3-(5-(3(R)-(N,N-dimethylamino)pyrrolidinocarbonyl)-2-thienyl)-5-(morpholinocarbamoylamino)indeno[1,2-c]pyrazol-4-one;

3-(5-(3(S)-(N,N-dimethylamino)pyrrolidinocarbonyl)-2-thienyl)-5-(morpholinocarbamoylamino)indeno[1,2-c]pyrazol-4-one;

3-(5-((1-methylpyrrolidin-3-yl)methylaminocarbonyl)-2-thienyl)-5-(morpholinocarbamoylamino)indeno[1,2-c]pyrazol-4-one;

3-(5-(2(R)-(pyrrolidinomethyl)pyrrolidinocarbonyl)-2-thienyl)-5-(morpholinocarbamoylamino)indeno[1,2-c]pyrazol-4-one;

3-(5-(2(S)-(hydroxymethyl)pyrrolidinocarbonyl)-2-thienyl)-5-(morpholinocarbamoylamino)indeno[1,2-c]pyrazol-4-one;

3-(5-(2(R)-(methoxymethyl)pyrrolidinocarbonyl)-2-thienyl)-5-(morpholinocarbamoylamino)indeno[1,2-c]pyrazol-4-one;

3-(5-(2(S)-(phenylaminomethyl)pyrrolidinocarbonyl)-2-thienyl)-5-(morpholinocarbamoylamino)indeno[1,2-c]pyrazol-4-one;

3-(5-(2(R)-(methoxymethyl)pyrrolidinoaminocarbonyl)-2-thienyl)-5-(morpholinocarbamoylamino)indeno[1,2-c]pyrazol-4-one;

3-(5-homopiperidinocarbonyl-2-thienyl)-5-(morpholinocarbamoylamino)indeno[1,2-c]pyrazol-4-one;

3-(5-homopiperazinocarbonyl-2-thienyl)-5-(morpholinocarbamoylamino)indeno[1,2-c]pyrazol-4-one;

3-(5-(4-methylhomopiperazinocarbonyl)-2-thienyl)-5-(morpholinocarbamoylamino)indeno[1,2-c]pyrazol-4-one;

3-(5-(4-ethylhomopiperazinocarbonyl)-2-thienyl)-5-(morpholinocarbamoylamino)indeno[1,2-c]pyrazol-4-one;

3-(5-(4-(cyclopropylmethyl)homopiperazinocarbonyl)-2-thienyl)-5-(morpholinocarbamoylamino)indeno[1,2-c]pyrazol-4-one;

3-(5-(4-(t-butoxycarbonyl)homopiperazinocarbonyl)-2-thienyl)-5-(morpholinocarbamoylamino)indeno[1,2-c]pyrazol-4-one;

3-(5-(4-acetylhomopiperazinocarbonyl)-2-thienyl)-5-(morpholinocarbamoylamino)indeno[1,2-c]pyrazol-4-one;

3-(5-((4-methylaminophenyl)aminocarbonyl)-2-thienyl)-5-(morpholinocarbamoylamino)indeno[1,2-c]pyrazol-4-one;

3-(5-((4-acetamidophenyl)aminocarbonyl)-2-thienyl)-5-(morpholinocarbamoylamino)indeno[1,2-c]pyrazol-4-one;

3-(5-(4-(diethylamino)phenylaminocarbonyl)-2-thienyl)-5-(morpholinocarbamoylamino)indeno[1,2-c]pyrazol-4-one;

3-(5-((1-methyl-3-cyclopropylpyrazo-5-yl)aminocarbonyl)-2-thienyl)-5-(morpholinocarbamoylamino)indeno[1,2-c]pyrazol-4-one;

3-(1-methyl-3-pyrrolyl)-5-(morpholinocarbamoylamino) indeno[1,2-c]pyrazol-4-one;

3-(5-carboethoxy-2-thienyl)-5-(2(R)-(methoxymethyl) pyrrolidinocarbamoylamino)indeno[1,2-c]pyrazol-4-one;

3-(5-carboxyl-2-thienyl)-5-(2(R)-(methoxymethyl) pyrrolidinocarbamoylamino)indeno[1,2-c]pyrazol-4-one;

3-(5-(4-methylpiperazinocarbonyl)-2-thienyl)-5-(2(R)-(methoxymethyl)pyrrolidinocarbamoylamino)indeno[1,2-c]pyrazol-4-one;

3-(5-piperazinocarbonyl-2-thienyl)-5-(2(R)-(methoxymethyl)pyrrolidinocarbamoylamino)indeno[1,2-c]pyrazol-4-one;

3-(5-(4-(t-butoxycarbonyl)piperazinocarbonyl)-2-thienyl)-5-(2(R)-(methoxymethyl)pyrrolidinocarbamoylamino) indeno[1,2-c]pyrazol-4-one;

3-(5-(4-methylhomopiperazinocarbonyl)-2-thienyl)-5-(2(R)-(methoxymethyl)pyrrolidinocarbamoylamino)indeno[1,2-c]pyrazol-4-one;

3-(5-homopiperazinocarbonyl-2-thienyl)-5-(2(R)-(methoxymethyl)pyrrolidinocarbamoylamino)indeno[1,2-c]pyrazol-4-one;

3-(5-(4-(t-butoxycarbonyl)homopiperazinocarbonyl)-2-thienyl)-5-(2(R)-(methoxymethyl)pyrrolidinocarbamoylamino)indeno[1,2-c]pyrazol-4-one;

3-(c-propyl)-5-(4-carbamoylpiperidinoacetamido)indeno[1,2-c]pyrazol-4-one;

3-ethyl-5-(4-methylpiperazinocarbamoylamino)indeno[1,2-c]pyrazol-4-one;

3-(c-propyl)-5-(4-methylpiperazinocarbamoylamino)indeno[1,2-c]pyrazol-4-one;

3-(c-hexyl)-5-(4-methylpiperazinocarbamoylamino)indeno[1,2-c]pyrazol-4-one;

3-ethyl-5-(morpholinocarbamoylamino)indeno[1,2-c]pyrazol-4-one;

3-(c-propyl)-5-(morpholinocarbamoylamino)indeno[1,2-c]pyrazol-4-one;

3-(c-hexyl)-5-(morpholinocarbamoylamino)indeno[1,2-c]pyrazol-4-one;

3-(1-ethoxycarbonylpiperidin-4-yl)-5-(morpholinocarbamoylamino)indeno[1,2-c]pyrazol-4-one;

3-(1-phenoxycarbonylpiperidin-4-yl)-5-(morpholinocarbamoylamino)indeno[1,2-c]pyrazol-4-one;

3-(1-(imidazol-1-ylcarbonyl)piperidin-4-yl)-5-(morpholinocarbamoylamino)indeno[1,2-c]pyrazol-4-one;

3-(1-(2-thienylcarbonyl)piperidin-4-yl)-5-(morpholinocarbamoylamino)indeno[1,2-c]pyrazol-4-one;

3-(1-carbamoylpiperidin-4-yl)-5-(morpholinocarbamoylamino)indeno[1,2-c]pyrazol-4-one;

3-(1-(ethylcarbamoyl)piperidin-4-yl)-5-(morpholinocarbamoylamino)indeno[1,2-c]pyrazol-4-one;

3-(1-(2-(1-methylpyrrolidin-2-yl) ethylaminocarbamoyl) piperidin-4-yl)-5-(morpholinocarbamoylamino)indeno[1,2-c]pyrazol-4-one;

3-(1-(4-(dimethylamino)piperidinocarbonyl)piperidin-4-yl)-5-(morpholinocarbamoylamino)indeno[1,2-c]pyrazol-4-one;

3-(1-(piperazinocarbonyl)piperidin-4-yl)-5-(morpholinocarbamoylamino)indeno[1,2-c]pyrazol-4-one;

3-(1-(4-(-butoxycarbonyl)piperazinoarbonyl)piperidin-4-yl)-5-(morpholinocarbamoylamino)indeno[1,2-c]pyrazol-4-one;

3-(1-(((1S,4S)-(+)-2,5-diazabicyclo[2.2.1]hept-2-yl) carbonyl)piperidin-4-yl)-5-(morpholinocarbamoylamino) indeno[1,2-c]pyrazol-4-one;

3-(1-(((1S,4S)-(+)-5-methyl-2,5-diazabicyclo[2.2.1]hept-2-yl)carbonyl)piperidin-4-yl)-5-(morpholinocarbamoylamnino)indeno[1,2-c]pyrazol-4-one;

3-(1-(3-aminopropylcarbonyl)piperidin-4-yl)-5-(morpholinocarbamoylamino)indeno[1,2-c]pyrazol-4-one;

3-(1-(3-(dimethylamino)propylcarbonyl)piperidin-4-yl)-5-(morpholinocarbamoylamino)indeno[1,2-c]pyrazol-4-one;

3-(1-(3-(t-butoxycarbonylamino)propylcarbonyl)piperidin-4-yl)-5-(morpholinocarbamoylainino)indeno[1,2-c]pyrazol-4-one;

3-(1-(4-aminobutylcarbonyl)piperidin-4-yl)-5-(morpholinocarbamoylamino)indeno[1,2-c]pyrazol-4-one;

3-(1-(4-(dimethylamino)butylcarbonyl)piperidin-4-yl)-5-(morpholinocarbamoylamnino)indeno[1,2-c]pyrazol-4-one;

3-(1-(4-(t-butoxycarbonylamino)butylcarbonyl)piperidin-4-yl)-5-(morpholinocarbamnoylamino)indeno[1,2-c]pyrazol-4-one;

3-(1-((1-methylpiperidin-4-yl)carbonyl)piperidin-4-yl)-5-(morpholinocarbamroylamino)indeno[1,2-c]pyrazol-4-one;

3-(1-((1-(t-butoxycarbonyl)piperidin-4-yl) carbonyl)piperidin-4-yl)-5-(morpholinocarbamoylamino)indeno[1,2-c]pyrazol-4-one;

3-(1-(cis-4-aminocyclohexylcarbonyl)piperidin-4-yl)-5-(morpholinocarbamoylamino)indeno[1,2-c]pyrazol-4-one;

3-(1-(4-aminocyclohexylcarbonyl)piperidin-4-yl)-5-(morpholinocarbamoylamino)indeno[1,2-c]pyrazol-4-one;

3(1-(cis-4-(dimethylamino)cyclohexylcarbonyl)piperidin-4-yl)-5-(morpholinocarbamoylamino)indeno[1,2-c]pyrazol-4-one;

3-(1-(4-(t-butoxycarbonylamino)cyclohexylcarbonyl)piperidin-4-yl)-5-(morpholinocarbamoylamino)indeno[1,2-c]pyrazol-4-one;

3-(1-(trans-4-(t-butoxycarbonylamino)cyclohexylcarbonyl)piperidin-4-yl)-5-(morpholinocarbamoylamino)indeno[1,2-c]pyrazol-4-one;

3-(1-(piperidin-3-ylcarbonyl)piperidin-4-yl)-5-(morpholinocarbamoylamino)indeno[1,2-c]pyrazol-4-one;

3-(1-(1-methylpiperidin-3-ylcarbonyl)piperidin-4-yl)-5-(morpholinocarbamoylamino)indeno[1,2-c]pyrazol-4-one;

3-(1-(1-(t-butoxycarbonyl)piperidin-3-ylcarbonyl)piperidin-4-yl)-5-(morpholinocarbamoylamino)indeno[1,2-c]pyrazol-4-one;

3-(1-(3-aminocyclohexylcarbonyl)piperidin-4-yl)-5-(morpholinocarbamoylamino)indeno[1,2-c]pyrazol-4-one;

3-(1-(3-(dimethylamino)cyclohexylcarbonyl)piperidin-4-yl)-5-(morpholinocarbamoylamino)indeno[1,2-c]pyrazol-4-one;

3-(1-(trans-4-methoxycyclohexylcarbonyl)piperidin-4-yl)-5-(morpholinocarbamoylamino)indeno[1,2-c]pyrazol-4-one;

3-(1-(cis-4-methoxycyclohexylcarbonyl)piperidin-4-yl)-5-(morpholinocarbamoylamino)indeno[1,2-c]pyrazol-4-one;

3-(1-(4-aminobenzylcarbonyl)piperidin-4-yl)-5-(morpholinocarbamoylamino)indeno[1,2-c]pyrazol-4-one;

3-(1-(4-(dimethylamino)benzylcarbonyl)piperidin-4-yl)-5-(morpholinocarbamoylamino)indeno[1,2-c]pyrazol-4-one;

3-(1-(4-(t-butoxycarbonylamino)benzylcarbonyl)piperidin-4-yl)-5-(morpholinocarbamoylamino)indeno[1,2-c]pyrazol-4-one;

3-(1-(4-aminophenylcarbonyl)piperidin-4-yl)-5-(morpholinocarbamoylamino)indeno[1,2-c]pyrazol-4-one;

3-(1-(4-(dimethylamino)phenylcarbonyl)piperidin-4-yl)-5-(morpholinocarbamoylamino)indeno[1,2-c]pyrazol-4-one;

3-(1-(4-(t-butoxycarbonylamino)phenylcarbonyl)piperidin-4-yl)-5-(morpholinocarbamoylamino)indeno[1,2-c]pyrazol-4-one;

3-(trans-4-carboxylcyclohexyl)-5-(morpholinocarbamoylamino)indeno[1,2-c]pyrazol-4-one;

3-(trans-4-(methoxycarbonyl)cyclohexyl)-5-(morpholinocarbamoylamino)indeno[1,2-c]pyrazol-4-one;

3-(trans-4-(3-(dimethylamino)pyrrolidinocarbonyl)cyclohexyl)-5-(morpholinocarbamoylamino)indeno[1,2-c]pyrazol-4-one;

3-(trans-4-(piperazinocarbonyl)cyclohexyl)-5-(morpholinocarbamoylamino)indeno[1,2-c]pyrazol-4-one;

3-(trans-4-(4-methylpiperazinocarbonyl)cyclohexyl)-5-(morpholinocarbamoylamino)indeno[1,2-c]pyrazol-4-one;

3-(trans-4-(homopiperazinocarbonyl)cyclohexyl)-5-(morpholinocarbamoylamino)indeno[1,2-c]pyrazol-4-one;

3-(trans-4-(4-methylhomopiperazinocarbonyl)cyclohexyl)-5-(morpholinocarbamoylamino)indeno[1,2-c]pyrazol-4-one;

or pharmaceutically acceptable salt form thereof.

36. A compound according to claim 1, wherein the compound is selected from:

3-(4-piperazinophenyl)-5-(morpholinocarbamoylamino)indeno[1,2-c]pyrazol-4-one;

3-(4-(4-methylpiperazino)phenyl)-5-(morpholinocarbamoylamino)indeno[1,2-c]pyrazol-4-one;

3-(4-(4-ethylpiperazino)phenyl)-5-(morpholinocarbamoylamino)indeno[1,2-c]pyrazol-4-one;

3-(4-(4-isopropylpiperazino)phenyl)-5-(morpholinocarbamoylamino)indeno[1,2-c]pyrazol-4-one;

3-(4-piperazinophenyl)-5-((N,N-dimethylamino)carbamoylamino)indeno[1,2-c]pyrazol-4-one;

3-(4-(4-methylpiperazino)phenyl)-5-((N,N-dimethylamino)-carbamoylamino)indeno[1,2-c]pyrazol-4-one;

3-(4-piperazinophenyl)-5-((4-methylpiperazino)carbamoylamino)indeno[1,2-c]pyrazol-4-one;

3-(4-(4-methylpiperazino)phenyl)-5-((4-methylpiperazino)carbamoylamino)indeno[1,2-c]pyrazol-4-one;

3-(4-(4-ethylpiperazino)phenyl)-5-((4-methylpiperazino)carbamoylamino)indeno[1,2-c]pyrazol-4-one;

3-(4-(4-isopropylpiperazino)phenyl)-5-((4-methylpiperazino)carbamoylamino)indeno[1,2-c]pyrazol-4-one;

3-(4-piperazinophenyl)-5-((2(R)-(methoxymethyl)pyrrolidino)carbamoylamino)indeno[1,2-c]pyrazol-4-one;

3-(4-piperazinophenyl)-5-((2(R)-(1-methoxy-1-methylethyl)pyrrolidino)carbamoylamino)indeno[1,2-c]pyrazol-4-one;

3-(4-homopiperazinophenyl)-5-(morpholinocarbamoylamino)-indeno[1,2-c]pyrazol-4-one;

3-(4-(4-methylhomopiperazino)phenyl)-5-(morpholinocarbamoylamino)indeno[1,2-c]pyrazol-4-one;

3-(4-(4-ethylhomopiperazino)phenyl)-5-(morpholinocarbamoylamino)indeno[1,2-c]pyrazol-4-one;

3-(4-(4-isopropylhomopiperazino)phenyl)-5-(morpholinocarbamoylamino)indeno[1,2-c]pyrazol-4-one;

3-(4-(4-(N,N-dimethylamino)piperidino)phenyl)-5-(morpholinocarbamoylamino)indeno[1,2-c]pyrazol-4-one;

3-(4-(4-(N,N-diethylamino)piperidino)phenyl)-5-(morpholinocarbamoylamino)indeno[1,2-c]pyrazol-4-one;

3-(4-(4-piperidinopiperidino)phenyl)-5-(morpholinocarbamoylamino)indeno[1,2-c]pyrazol-4-one;

3-(4-(4-pyrrolidinopiperidino)phenyl)-5-(morpholinocarbamoylamino)indeno[1,2-c]pyrazol-4-one;

or pharmaceutically acceptable salt form thereof.

37. A pharmaceutical composition, comprising a pharmaceutically acceptable carrier, a compound according to claim 1 or a pharmaceutically acceptable salt or prodrug form thereof, and a cytostatic or cytotoxic agent.

38. A method of treating a cell proliferative disease associated with CDK activity in a patient in need thereof, comprising administrering to said patient a pharmaceutically effective amount of a compound according to claim 1, or a pharmaceutically acceptable salt or prodrug form thereof, wherein the proliferative diseases is selected from the group consisting of: Alzheimer's disease, viral infections, autoimmune diseases, fungal disease, cancer, psoriasis, vascular smooth cell proliferation associated with atherosclerosis, pulmonary fibrosis, arthritis glomerulonephritis, neurodegenerative disorders and post-surgical stenosis and restenosis.

39. A method of treating cancer associated with CDK activity in a patient in need thereof, comprising administrering to said patient a pharmaceutically effective amount of a compound according to claim 1, or a pharmaceutically acceptable salt or prodrug form thereof, wherein the cancer is selected from the group consisting of: carcinoma; hematopoietic tumors of lymphoid lineage; hematopoietic tumors of myeloid lineage; tumors of mesenchymal origin, tumors of the central and peripheral nervous system, melanoma, seminoma, teratocarcinoma, osteosarcoma, xenoderoma pigmentosum, keratoctanthoma, thyroid follicular cancer and Kaposi's sarcoma.

40. A method of treating a disease associated with apoptosis in a patient in need thereof, comprising administrering to said patient a pharmaceutically effective amount of a compound according to claim 1, or a pharmaceutically acceptable salt or prodrug form thereof, wherein the disease associated with apoptosis is selected from the group consisting of: cancer, viral infections, autoimmune diseases and neurodegenerative disorder.

41. A method of inhibiting tumor angiogenesis and metastasis in a patient in need thereof, comprising administrering to said patient a pharmaceutically effective amount of a compound according to claim 1, or a pharmaceutically acceptable salt or prodrug form thereof.

42. A method of modulating the level of cellular RNA and DNA synthesis in a patient in need thereof, comprising administering to said patient a CDK inhibitory effective amount of a compound according to claim 1, or a pharmaceutically acceptable salt or prodrug form thereof.

43. A method of treating viral infections in a patient in need thereof, comprising administering to said patient a CDK inhibitory effective amount of a compound according to claim 1, or a pharmaceutically acceptable salt or prodrug form thereof, wherein the viral infections is selected from the group consiting of HIV, human papilloma virus, herpesvirus, poxyirus, Epstein-Barr virus, Sindbis virus and adenovirus.

44. A method of chemopreventing cancer in a patient, comprising administering to said patient in need thereof, a CDK inhibitory effective amount of a compound according to claim 1, or a pharmaceutically acceptable salt or prodrug form thereof.

45. A method of inhibiting CDK activity comprising combining an effective amount of a compound according to claim 1, with a composition containing CDK.

46. A method of treating cancer associated with CDK activity in a patient in need thereof, comprising administrering to said patient a pharmaceutically effective amount of a compound according to claim 1, or a pharmaceutically acceptable salt or prodrug form thereof, in combination (administered together or sequentially) with known anti-cancer treatments.

47. A method treating cell proliferative diseases associated with CDK activity in a patient in need thereof, comprising administrering to said patient a pharmaceutically effective amount of a compound according to claim 1, or a pharmaceutically acceptable salt or prodrug form thereof, in combination (administered together or sequentially) with known anti-proliferating agents selected from the group consisting of:, altretamine, busulfan, chlorambucil, cyclophosphamide, ifosfamide, mechlorethamine, melphalan, thiotepa, cladribine, fluorouracil, floxuridine, gemcitabine, thioguanine, pentostatin, methotrexate, 6-mercaptopurine, cytarabine, carmustine, lomustine, streptozotocin, carboplatin, cisplatin, oxaliplatin, iproplatin, tetraplatin, lobaplatin, JM216, JM335, fludarabine, aminoglutethimide, flutamide, goserelin, leuprolide, megestrol acetate, cyproterone acetate, tamoxifen, anastrozole, bicalutamide, dexamethasone, diethylstilbestrol, prednisone, bleomycin, dactinomycin, daunorubicin, doxirubicin, idarubicin, mitoxantrone, losoxantrone, mitomycin-c, plicamycin, paclitaxel, docetaxel, CPT-11, epothilones, topotecan, irinotecan, 9-amino camptothecan, 9-nitro camptothecan, GS-211, etoposide, teniposide, vinblastine, vincristine, vinorelbine, procarbazine, asparaginase, pegaspargase, methoxtrexate, octreotide, estramustine, and hydroxyurea.

48. A method of inhibiting CDK1 activity, comprising adminsitering to a patient in need thereof an efective CDK1 inhibitory amount of a compound according to claim 1, or a pharmaceutically acceptable salt or prodrug form thereof.

49. A method of inhibiting CDK2 activity, comprising adminsitering to a patient in need thereof an efective CDK2 inhibitory amount of a compound according to claim 1, or a pharmaceutically acceptable salt or prodrug form thereof.

50. A method of inhibiting CDK3 activity, comprising adminsitering to a patient in need thereof an efective CDK3 inhibitory amount of a compound according to claim 1, or a pharmaceutically acceptable salt or prodrug form thereof.

51. A method of inhibiting CDK4 activity, comprising adminsitering to a patient in need thereof an efective CDK4 inhibitory amount of a compound according to claim 1, or a pharmaceutically acceptable salt or prodrug form thereof.

52. A method of inhibiting CDK5 activity, comprising adminsitering to a patient in need thereof an efective CDK5 inhibitory amount of a compound according to claim 1, or a pharmaceutically acceptable salt or prodrug form thereof.

53. A method of inhibiting CDK6 activity, comprising adminsitering to a patient in need thereof an efective CDK6 inhibitory amount of a compound according to claim 1, or a pharmaceutically acceptable salt or prodrug form thereof.

54. A method of inhibiting CDK7 activity, comprising adminsitering to a patient in need thereof an efective CDK7 inhibitory amount of a compound according to claim 1, or a pharmaceutically acceptable salt or prodrug form thereof.

55. A method of inhibiting CDK8 activity, comprising adminsitering to a patient in need thereof, an efective CDK8 inhibitory amount of a compound according to claim 1, or a pharmaceutically acceptable salt or prodrug form thereof.

56. A method of inhibiting CDK9 activity, comprising adminsitering to a patient in need thereof an efective CDK9 inhibitory amount of a compound according to claim 1, or a pharmaceutically acceptable salt or prodrug form thereof.

57. A pharmaceutical kit for treating a cell proliferative disease associated with CDK activity, said kit comprising a plurality of separate containers, wherein at least one of said containers contains a compound accordig to claim 1, or a pharmaceutically acceptable salt or prodrug form thereof, and at least another of said containers contains one or more compounds selected from the group consisting of cytostatic or cytotoxic agents; topoisomerase II inhibitors; topoisomerase I inhibitors tubulin interacting agents; hormonal agents; thymidilate synthase inhibitors; and antimetabolites, and said containers optionally contain a pharmaceutical carrier, which kit may be effectively utilized for carrying out combination therapies according to the invention.

* * * * *